United States Patent
Jenkins

(10) Patent No.: US 11,154,549 B2
(45) Date of Patent: *Oct. 26, 2021

(54) OPIOID COMPOSITIONS RESISTANT TO OVERDOSE AND ABUSE

(71) Applicant: Elysium Therapeutics, Inc., Danville, CA (US)

(72) Inventor: Thomas E. Jenkins, Half Moon Bay, CA (US)

(73) Assignee: ELYSIUM THERAPEUTICS, INC., Danville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/386,671

(22) Filed: Apr. 17, 2019

(65) Prior Publication Data

US 2020/0093817 A1 Mar. 26, 2020

Related U.S. Application Data

(60) Division of application No. 15/795,126, filed on Oct. 26, 2017, now Pat. No. 10,335,406, which is a continuation-in-part of application No. 15/683,356, filed on Aug. 22, 2017, now Pat. No. 10,251,878, which is a continuation of application No. 15/284,269, filed on Oct. 3, 2016, now Pat. No. 9,808,452.

(60) Provisional application No. 62/413,913, filed on Oct. 27, 2016, provisional application No. 62/236,048, filed on Oct. 1, 2015.

(51) Int. Cl.
| | |
|---|---|
| *A61K 31/485* | (2006.01) |
| *A61K 47/64* | (2017.01) |
| *A61K 47/61* | (2017.01) |
| *A61K 47/55* | (2017.01) |
| *A61K 45/06* | (2006.01) |

(52) U.S. Cl.
CPC ............ *A61K 31/485* (2013.01); *A61K 45/06* (2013.01); *A61K 47/55* (2017.08); *A61K 47/61* (2017.08); *A61K 47/64* (2017.08)

(58) Field of Classification Search
CPC ...... A61K 31/485; A61K 45/06; A61K 47/55; A61K 47/61; A61K 47/64
See application file for complete search history.

(56) References Cited

U.S. PATENT DOCUMENTS

| | | |
|---|---|---|
| 2,996,431 A | 8/1961 | Barry |
| 3,139,383 A | 6/1964 | Neville, Jr. |
| 3,402,240 A | 9/1968 | Cain et al. |
| 3,811,444 A | 5/1974 | Heller et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien et al. |
| 4,063,064 A | 12/1977 | Saunders et al. |
| 4,066,747 A | 1/1978 | Capozza |
| 4,070,347 A | 1/1978 | Schmitt |
| 4,079,038 A | 3/1978 | Choi et al. |
| 4,083,949 A | 4/1978 | Benedikt |
| 4,088,864 A | 5/1978 | Theeuwes et al. |
| 4,093,709 A | 6/1978 | Choi et al. |
| 4,200,098 A | 4/1980 | Ayer et al. |
| 4,285,987 A | 8/1981 | Ayer et al. |
| 4,421,736 A | 12/1983 | Walters |
| 4,434,153 A | 2/1984 | Urquhart et al. |
| 4,507,466 A | 3/1985 | Tomalia et al. |
| 4,631,337 A | 12/1986 | Tomalia et al. |
| 4,721,613 A | 1/1988 | Urquhart et al. |
| 4,752,470 A | 6/1988 | Mehta |
| 4,765,539 A | 8/1988 | Noakes et al. |
| 4,816,263 A | 3/1989 | Ayer et al. |
| 4,820,523 A | 4/1989 | Shtohryn et al. |
| 4,853,229 A | 8/1989 | Theeuwes |
| 4,962,885 A | 10/1990 | Coffee |
| 5,041,516 A | 8/1991 | Frechet et al. |
| 5,112,598 A | 5/1992 | Biesalski |
| 5,159,081 A | 10/1992 | Cantrell et al. |
| 5,177,059 A | 1/1993 | Handley et al. |
| 5,250,542 A | 10/1993 | Cantrell et al. |

(Continued)

FOREIGN PATENT DOCUMENTS

| | | |
|---|---|---|
| WO | WO-9412285 A2 | 6/1994 |
| WO | WO-9414543 A2 | 7/1994 |

(Continued)

OTHER PUBLICATIONS

Aoyama, et al. Synthesis and structure-activity study of protease inhibitors. IV. Amidinonaphthols and related acyl derivatives. Chem Pharm Bull (Tokyo). Apr. 1985;33(4):1458-71.

EP16852850.3 The Extended European Search report dated Mar. 21, 2019.

Kitayama, et al. A synthetic route to ultra-high molecular weight polystyrene ( 10 6) with narrow molecular weight distribution by emulsifier-free, emulsion organotellurium-mediated living radical polymerization (emulsion TERP). Polymer Chemistry 7.14 (2016): 2573-2580.

PCT/US2018/022986 International Search Report dated May 31, 2018.

Sekizaki, et al. Synthesis and tryptic hydrolysis of p-guanidinophenyl esters derived from amino acids and peptides. Chem Pharm Bull (Tokyo). Aug. 1996;44(8):1577-9.

(Continued)

*Primary Examiner* — Dennis Heyer

(74) *Attorney, Agent, or Firm* — Wilson Sonsini Goodrich & Rosati

(57) ABSTRACT

The invention provides pharmaceutical compositions comprising macromolecular gastrointestinal enzyme-labile opioid prodrugs, co-formulated with small-molecule and/or macromolecular gastrointestinal enzyme inhibitors. The macromolecular constructs are minimally absorbed from the GI tract, and can produce non-linear pharmacokinetic profiles of the delivered opioid agonist following oral ingestion. An optional macromolecular opioid antagonist may also be present in compositions of the invention to discourage tampering by potential abusers.

14 Claims, No Drawings

(56) References Cited

U.S. PATENT DOCUMENTS

| | | | |
|---|---|---|---|
| 5,270,328 | A | 12/1993 | Cantrell et al. |
| 5,434,171 | A | 7/1995 | Frank et al. |
| 5,468,574 | A | 11/1995 | Ehrenberg et al. |
| 5,530,092 | A | 6/1996 | Meijer et al. |
| 5,556,611 | A | 9/1996 | Biesalski |
| 5,698,155 | A | 12/1997 | Grosswald et al. |
| 5,824,701 | A | 10/1998 | Greenwald et al. |
| 5,840,387 | A | 11/1998 | Berlowitz-Tarrant et al. |
| 5,880,131 | A | 3/1999 | Greenwald et al. |
| 5,932,462 | A | 8/1999 | Harris et al. |
| 5,950,619 | A | 9/1999 | Van et al. |
| 5,954,047 | A | 9/1999 | Armer et al. |
| 5,970,974 | A | 10/1999 | Van et al. |
| 6,171,615 | B1 | 1/2001 | Roussin et al. |
| 6,375,987 | B1 | 4/2002 | Farah et al. |
| 6,379,700 | B2 | 4/2002 | Joachim et al. |
| 6,545,097 | B2 | 4/2003 | Pinchuk et al. |
| 6,664,331 | B2 | 12/2003 | Harris et al. |
| 6,716,821 | B2 | 4/2004 | Zhao et al. |
| 7,060,290 | B1 | 6/2006 | Morimoto et al. |
| 7,338,939 | B2 | 3/2008 | Mickle et al. |
| 7,375,082 | B2 | 5/2008 | Mickle et al. |
| 8,101,661 | B2 | 1/2012 | Mickle |
| 8,133,881 | B2 | 3/2012 | Mickle et al. |
| 8,163,701 | B2 | 4/2012 | Jenkins |
| 8,217,005 | B2 | 7/2012 | Jenkins et al. |
| 8,497,237 | B2 | 7/2013 | Jenkins et al. |
| 8,569,228 | B2 | 10/2013 | Jenkins et al. |
| 8,685,916 | B2 | 4/2014 | Jenkins et al. |
| 8,802,681 | B2 | 8/2014 | Jenkins et al. |
| 9,040,032 | B2 | 5/2015 | Jenkins et al. |
| 9,095,627 | B2 | 8/2015 | Jenkins et al. |
| 9,139,612 | B2 | 9/2015 | Jenkins et al. |
| 9,217,005 | B2 | 12/2015 | Touge et al. |
| 9,499,581 | B2 | 11/2016 | Jenkins et al. |
| 9,808,452 | B2 | 11/2017 | Jenkins |
| 10,251,878 | B2 | 4/2019 | Jenkins |
| 10,335,406 | B2 | 7/2019 | Jenkins |
| 2004/0043030 | A1 | 3/2004 | Griffiths et al. |
| 2005/0037059 | A1 | 2/2005 | Miller et al. |
| 2005/0176644 | A1 | 8/2005 | Mickle et al. |
| 2009/0136980 | A1 | 5/2009 | Bebbington et al. |
| 2009/0137618 | A1 | 5/2009 | Jenkins |
| 2009/0209569 | A1 | 8/2009 | Arnelle et al. |
| 2010/0080797 | A1 | 4/2010 | Yeomans et al. |
| 2011/0262359 | A1 | 10/2011 | Jenkins et al. |
| 2011/0262360 | A1 | 10/2011 | Jenkins et al. |
| 2011/0281886 | A1* | 11/2011 | Jenkins ............. A61K 31/485 514/253.02 |
| 2012/0142718 | A1 | 6/2012 | Jenkins et al. |
| 2012/0178773 | A1 | 7/2012 | Jenkins et al. |
| 2014/0016935 | A1 | 1/2014 | Uhlhorn et al. |
| 2017/0100390 | A1 | 4/2017 | Jenkins |
| 2018/0085366 | A1 | 3/2018 | Jenkins |
| 2019/0183884 | A1 | 6/2019 | Jenkins |
| 2020/0101166 | A1 | 4/2020 | Jenkins et al. |

FOREIGN PATENT DOCUMENTS

| | | |
|---|---|---|
| WO | WO-9526234 A1 | 10/1995 |
| WO | WO-9526235 A1 | 10/1995 |
| WO | WO-9532807 A1 | 12/1995 |
| WO | WO-2004041324 A2 | 5/2004 |
| WO | WO-2004062614 A2 | 7/2004 |
| WO | WO-2004082620 A2 | 9/2004 |
| WO | WO-2006073396 A1 | 7/2006 |
| WO | WO-2007120864 A2 | 10/2007 |
| WO | WO-2007140272 A2 | 12/2007 |
| WO | WO-2008101187 A2 | 8/2008 |
| WO | WO-2009092073 A2 | 7/2009 |
| WO | WO-2010045599 A1 | 4/2010 |
| WO | WO-2011002991 A1 | 1/2011 |
| WO | WO-2011002995 A1 | 1/2011 |
| WO | WO-2011133150 A1 | 10/2011 |
| WO | WO-2012109445 A1 | 8/2012 |
| WO | WO-2012122420 A2 | 9/2012 |
| WO | WO-2017059459 A1 | 4/2017 |
| WO | WO-2018170465 A1 | 9/2018 |

OTHER PUBLICATIONS

Sekizaki, et al. Trypsin-catalyzed peptide synthesis and various p-guanidinophenyl esters as acyl donors. Chem Pharm Bull (Tokyo). Aug. 1996;44(8):1585-7.

Thormann, et al. Protease-catalyzed hydrolysis of substrate mimetics (inverse substrates): A new approach reveals a new mechanism. Biochemistry. May 11, 1999;38(19):6056-62.

U.S. Appl. No. 16/572,408 Office Action dated Jun. 15, 2020.

U.S. Appl. No. 15/683,356 Notice of Allowance dated Feb. 8, 2019.

Worthington Enzyme Manual, Trypsin Inhibitors—Worthington Enzyme Manual, available online at http://worthington-biochem.com/TI/default.html, accessed on Jun. 8, 2020. (Year: 2020).

Alderman, et al. A review of cellulose ethers in hydrophilic matrices for oral controlled-release dosage forms. Int. J. Pharm. Tech. Prod. Mfr 5.3 (1984): 1-9.

Bak, et al. Acyloxyalkoxy-based Cyclic Prodrugs of Opioid Peptides: Evaluation of the Chemical and Enzymatic Stability as well as Their Transport Properties Across Caco-2 Cell Monolayers. Pharmaceutical Research, 1999, vol. 16, pp. 24-29.

Bamba, et al. Release mechanisms in gelforming sustained release preparations. International Journal of Pharmaceutics. Volume 2, Issues 5-6, Jun. 1979, pp. 307-315.

Birk, Y. Trypsin and chymotrypsin inhibitors from soybeans. Methods Enzymol. 1976;45:700-7.

Coleman, et al. Polymer Reviews: A Practical Guide to Polymer Miscibility. 1990, 31, 1187-1231.

Definition of "ex vivo" from thefreedictionary.com, accessed Oct. 7, 2014.

During, et al. Controlled release of dopamine from a polymeric brain implant: in vivo characterization. Ann Neurol. Apr. 1989;25(4):351-6.

FDA Center for Drug Evaluation and Research, Joint Meeting of the Anesthetic and Life Support Drugs Advisory Committee and the Drug Safety and Risk Management Advisory Committee, Meeting Transcript, Jul. 23-4, 2010.

Fincher, JH. Particle size of drugs and its relationship to absorption and activity. J Pharm Sci. Nov. 1968;57(11):1825-35.

Geratz, et al. Novel Bis(benzamidine) Compounds with an Aromatic Central Link. Inhibitors of Thrombin, Pancreatic Kallkrein, I Trypsin, and Compliment. J. Medicinal Chemistry, 1976, vol. 19, pp. 634-639.

Goodson. Medical Applications of Controlled Release. vol. 2, pp. 115-138, 1984.

Gotoh, et al. The Advantages of the Ussing Chamber in Drug Absorption Studies. Journal of Biomolecular Screening 10(5), pp. 517-523, 2005.

Gunatillake, et al. Thermal polymerization of a 2-(carboxyalkyl)-2-oxazoline. Macromolecules, 1988, 21 (6), pp. 1556-1562.

Hawker, et al. One-step synthesis of hyperbranched dendritic polyesters. J. Am. Chem. Soc., 1991, 113 (12), pp. 4583-4588.

Howard, et al. Intracerebral drug delivery in rats with lesion-induced memory deficits. J Neurosurg. Jul. 1989;71(1):105-12.

International Search Report with Opinion dated Dec. 23, 2016 for PCT/US16/55231.

Ito, et al. A medium-term rat liver bioassay for rapid in vivo detection of carcinogenic potential of chemicals. Cancer Sci. Jan. 2003;94(1):3-8.

Kaneda, et al. The use of PVP as a polymeric carrier to improve the plasma half-life of drugs. Biomaterials. Jul. 2004;25(16):3259-66.

Langer, et al. Chemical and Physical Structure of Polymers as Carriers for Controlled Release of Bioactive Agents: A Review. J Macromol. Sci. Rev. Macromol. Chem. 1983, 23:61-126.

Langer, R. New methods of drug delivery. Science. Sep. 28, 1990;249(4976):1527-33.

Leong, et al. Polymeric controlled drug delivery. Advanced Drug Delivery Reviews, vol. 1, Issue 3, Sep. 1988, pp. 199-233.

(56) References Cited

OTHER PUBLICATIONS

Levy, et al. Inhibition of calcification of bioprosthetic heart valves by local controlled-release diphosphonate. Science. Apr. 12, 1985;228(4696):190-2.

Lin, et al. The 0.25-nm X-ray structure of the Bowman-Birk-type inhibitor from mun gean in ternary complex with porcine trypsin. Eur. J. Biochem, 1993, vol. 212, pp. 549-555.

Lu, et al. Dimensionless presentation for drug release from a coated pure drug bead: 2. Experiment. Int. J. Pharm. 1994, 112, 117-124.

Markwardt, et al. Comparative Studies on the Inhibition of Trypsin, Plasmin, and Thrombin, by Derivatives of Benzylamine and Benzylamidine. Eur. J. Biochem, 1968, vol. 6, pp. 502-506.

Notice of allowance dated Aug. 17, 2017 for U.S. Appl. No. 15/284,269.

Ozawa, et al. The reactive site of trypsin inhibitors. J Biol Chem. Sep. 10, 1966;241(17):3955-61.

Raleigh, et al. American Association for Cancer Research Anuual Meeting. 1999, 40, 397.

Roerdink, et al. Drug Carrier Systems 1989, vol. 9, chapter 3, pp. 57-109.

Rosoff. Controlled Release of Drugs. Chapter 2, pp. 53-95, 1989.

Saudek, et al. A preliminary trial of the programmable implantable medication system for insulin delivery. N Engl J Med. Aug. 31, 1989;321(9):574-9.

Schanker, et al. Absorption of drugs from the rat small intestine. Journal of Pharmacology and Experimental Therapeutics 123.1 (1958): 81-88.

Sefton, MV. Implantable pumps. Crit Rev Biomed Eng. 1987;14(3):201-40.

Sekizaki et al. "The Structural Requirements for an Inverse Substrate for Enzymatic Peptide Synthesis: Position Isomers of Guanidononaphthyl Esters as the Acyl Donor Component", Chem. Pharm. Bull. 1999. vol. 47(1), pp. 104-110.

U.S. Appl. No. 15/683,356 Notice of Allowance dated Jan. 3, 2019.

U.S. Appl. No. 15/683,356 Notice of Allowance dated Nov. 26, 2018.

Thanou, et al. Polymer-protein and polymer-drug conjugates in cancer therapy. Curr Opin Investig Drugs. Jun. 2003;4(6):701-9.

Tomalia, et al. Discovery of dendrimers and dendritic polymers: A brief historical perspective. Journal of Polymer Science Part A: Polymer Chemistry. vol. 40, Issue 16, pp. 2719-2728, Aug. 15, 2002.

Umezawa, H. Structures and activities of protease inhibitors of microbial origin. Methods Enzymol. 1976;45:678-95.

U.S. Appl. No. 15/683,356 Notice of Allowance dated Jan. 9, 2019.

U.S. Appl. No. 15/683,356 Office Action dated Aug. 16, 2018.

U.S. Appl. No. 15/795,126 Notice of Allowance dated Jan. 17, 2019.

U.S. Appl. No. 15/795,126 Notice of Allowance dated Jan. 31, 2019.

U.S. Appl. No. 15/795,126 Office Action dated Jun. 22, 2018.

Van Gelder, et al. Drug Metabolism and Disposition 30 (8) p. 924-930, 2002.

Verma, et al. Osmotically controlled oral drug delivery. Drug Dev Ind Pharm. Jul. 2000;26(7):695-708.

Veronese, et al. Bioconjugation in pharmaceutical chemistry. Farmaco. Aug. 30, 1999;54(8):497-516.

Verschoyle, et al. British J. Cancer, 1999, 80, Suppl. 2, 96. Poster Presentations.

U.S. Appl. No. 16/286,096 Office Action dated Aug. 18, 2020.

EP18766937.9 The Extended European Search Report dated Dec. 14, 2020.

U.S. Appl. No. 16/286,096 Notice of Allowance dated Feb. 11, 2021.

U.S. Appl. No. 16/572,408 Notice of Allowance dated Jan. 19, 2021.

\* cited by examiner

OPIOID COMPOSITIONS RESISTANT TO OVERDOSE AND ABUSE

CROSS-REFERENCE

This application is a division of U.S. patent application Ser. No. 15/795,126, filed Oct. 26, 2017, now U.S. Pat. No. 10,335,406; which claims the benefit of U.S. Provisional Application Ser. No. 62/413,913, filed Oct. 27, 2016; and U.S. patent application Ser. No. 15/795,126 is also a continuation-in-part of U.S. patent application Ser. No. 15/683,356, filed Aug. 22, 2017, now U.S. Pat. No. 10,251,878; which is a continuation of U.S. patent application Ser. No. 15/284,269, filed Oct. 3, 2016, now U.S. Pat. No. 9,808,452; which claims the benefit of U.S. Provisional Application Ser. No. 62/236,048, filed Oct. 1, 2015; all of which are incorporated herein by reference in their entirety and to which applications we claim priority under 35 USC § 120.

STATEMENT AS TO FEDERALLY SPONSORED RESEARCH

This invention was made with the support of the United States government under SBIR Grant number 1R44DA037900 by the National Institute on Drug Abuse (NIDA), one of the National Institutes of Health (NIH) in the U.S. Department of Health and Human Services.

INTRODUCTION

The present invention relates to compounds, methods and formulations for the prevention and/or treatment of pain. More particularly, the invention relates to pharmaceutical agents that interact with analgesic receptors, methods of preparing these agents, and their use for analgesia, pain, overdose protection, and other conditions.

The class of drugs exhibiting opium or morphine-like properties are referred to as opioid agonists, or opioids, and they interact with opioid receptors in the brain, the peripheral nervous system and other tissues. The three major opioid receptor subtypes are mu, delta, and kappa. Each of these receptors has a unique anatomical distribution in the central nervous system, the peripheral nervous system and the gastrointestinal tract. Most of the clinically-used opioids exert their desired therapeutic action (i.e. analgesia) at the mu-receptor subtype.

Opioids include morphine, codeine, oxycodone, hydrocodone, hydromorphone, and the like. Examples of marketed opioids in the United States include OxyContin®, Vicodin®, and Percocet®. The opioids have diverse effects, including analgesia, euphoria, drowsiness, changes in mood and alterations of the endocrine and autonomic nervous systems. Opioid analgesics comprise the major class of drugs used in the management of moderate to severe pain. As a class, opioids are among the most prescribed drugs in the U.S. Pharmacologically, opioid agonists represent an important class of agents for the management of pain.

The high abuse- and addiction-liability of opioid agonists often limits their use in the treatment of patients, and results in severe social and financial cost. The U.S. Food and Drug Administration has recently described prescription opioid analgesics as being at the center of a major public health crisis of addiction, misuse, abuse, overdose, and death (FDA/Center for Drug Evaluation and Research, Joint Meeting of the Anesthetic and Life Support Drugs Advisory Committee and the Drug Safety and Risk Management Advisory Committee, Meeting Transcript, Jul. 23-4, 2010).

SUMMARY

Typically, opioids pass rapidly through the blood-brain-barrier (BBB) and rapidly reach peak concentrations that produce the "highs" experienced by opioid abusers. Current strategies to reduce abuse have focused on formulation or alternative delivery strategies, such as orally administered extended-release formulations and transdermal patches. Unfortunately, these "tamper-resistant" formulations can often be easily defeated by crushing, chewing, or dissolving the formulation in commonly available household solvents, enabling the abuser to achieve the desired pharmacokinetic profile for achieving the high.

The present disclosure provides compositions and methods of treatment that can effectively be used to treat opioid addiction without the risk of diversion. Some of the advantages of the compositions of the disclosure include:

The compositions of the disclosure comprise prodrugs that are designed not to be orally bioavailable. The compositions of the disclosure may only convert to active opioid in the presence of digestive enzymes in the lumen of the small intestine, and not in the systemic circulation.

Further, the compositions of the disclosure provide diminished oral absorption of enzyme-labile opioid prodrugs and small molecule trypsin inhibitors. Oral absorption of unmodified enzyme-labile opioid prodrugs and small molecule trypsin inhibitors may result in undesired systemic exposures of the opioid prodrug and/or the trypsin inhibitor and their derived metabolites. Ingestion of these bioavailable molecules can produce high systemic exposures, especially in an overdose scenario. The compounds of the disclosure solve this challenge by limiting the oral absorption of the polymer modified prodrugs and inhibitors described herein.

Additionally, oral absorption of unmodified small molecule trypsin inhibitors reduces its effective concentration in its intended "effect-site" within the body (i.e. the lumen of the small intestine). This results in transient, and diminishing overdose protection in vivo. The effective attenuation of opioid exposures following ingestion of multi-pill overdoses is temporally limited, whereby high systemic opioid exposures resulting from overdoses are merely delayed with little reduction in magnitude. This problem is especially concerning as individuals who intentionally overdose and experience little or none of the desired opioid effects over an initial transient time period will be motivated to further ingest more pills, eventually resulting in delayed and significant opioid exposures with toxic and/or potentially deadly consequences. The compounds of the disclosure are absorbed in the lumen of the small intestine and limit the oral absorption of unmodified small molecule trypsin inhibitors.

The small molecule prodrugs and trypsin inhibitors employed in the art have divergent molecular weights and physicochemical properties. This can result in differential interactions with fluids, surfaces, and tissues present in the gastrointestinal tract. These differential interactions can result in the effective partitioning or separation of the prodrug molecules and the trypsin inhibitors during transport along the small intestine. This can dramatically reduce the effective concentration of the trypsin inhibitor molecules local to the prodrug molecules resulting in greatly diminished trypsin inhibition effects focal to the prodrug molecules. This further results in effective cleavage of the opioid agonist from the opioid prodrug molecules in the small intestine that is unimpeded by the partitioned trypsin inhibitor molecules. Consequently, the intended reduction in opioid exposure (i.e. overdose protection) by inhibiting the trypsin-mediated release of the opioid agonist from the prodrug is undermined. In contrast, the compounds of the disclosure have similar molecular weights and physicochemical properties and may not partition or separate from prodrug molecules and trypsin inhibitors during transport along the small intestine.

The present disclosure provides formulations of digestive enzyme-labile opioid prodrugs with novel digestive enzyme inhibitors, that provide unique and effective solutions to the critical shortcomings of previously published strategies.

In the broadest sense, the invention described herein provides compositions comprising a macromolecular GI enzyme-labile opioid agonist prodrug, and/or a macromolecular GI enzyme inhibitor. The macromolecular enzyme-labile opioid prodrug comprising an opioid agonist covalently bonded to a promoiety comprising a gastrointestinal (GI) enzyme-cleavable moiety and a macromolecular addend. The GI enzyme activates the release of the opioid agonist from the GI enzyme-labile opioid promoiety within the GI tract for the treatment of pain, while the macromolecular GI enzyme inhibitor modulates the activity of the same enzyme within the GI tract that mediates the release of the opioid agonist from the enzyme-labile opioid prodrug to prevent oral overdose or abuse of the composition.

In contrast to existing treatments, the current disclosure provides enzyme-labile opioid prodrugs and the GI enzyme inhibitors that are covalently modified with a macromolecular addend. The macromolecular addend is chosen to limit or prevent the oral absorption of the enzyme-labile opioid prodrug, and/or the enzyme inhibitor from the gastrointestinal tract following ingestion while permitting absorption of the drug in the lumen of the small intestine. In some instances, the macromolecular addend is a polymer. Further, the macromolecular addends can be installed on the enzyme-labile opioid prodrug and/or the enzyme inhibitor to create physicochemical parity between the enzyme-labile opioid prodrug and the enzyme inhibitor to prevent/minimize the undesired partitioning of the enzyme-labile opioid prodrug and the enzyme inhibitor during their transit through the GI tract, specifically the small intestine. In some embodiments, the macromolecular addends can be judiciously attached to the GI enzyme-labile opioid prodrug and/or the GI enzyme inhibitor so as to also prevent or minimize absorption of metabolites derived from the enzyme-labile opioid prodrug and/or the enzyme inhibitor. In other embodiments, some of the aforementioned issues are addressed by formulating all or some of the GI enzyme inhibitor component in a controlled-delivery matrix or device. The above unique aspects of the disclosure serve to prevent or limit systematic exposures (and potential safety risks) of the enzyme-labile opioid prodrug and/or the enzyme inhibitor and their resulting metabolites, as well as dramatically improving the efficiency of both the opioid delivery, and overdose protection mechanisms.

In one aspect, the disclosure provides a pharmaceutical composition comprising a GI enzyme-labile opioid agonist prodrug, and a macromolecular GI enzyme inhibitor. The opioid agonist is selected from the group consisting of morphine, hydromorphone, hydrocodone, oxycodone, codeine, levorphanol, meperidine, methadone, oxymorphone, dihydrocodeine, tramadol, pharmaceutically acceptable salts thereof, and mixtures thereof.

In another aspect, the disclosure provides a pharmaceutical composition comprising a macromolecular GI enzyme-labile opioid agonist prodrug, and a GI enzyme inhibitor. The opioid is selected from the group consisting of morphine, hydromorphone, hydrocodone, oxycodone, codeine, levorphanol, meperidine, methadone, oxymorphone, dihydrocodeine, tramadol, pharmaceutically acceptable salts thereof, and mixtures thereof.

In another aspect, the disclosure provides a pharmaceutical composition comprising a macromolecular GI enzyme-labile opioid agonist prodrug, and a macromolecular GI enzyme inhibitor. The opioid agonist is selected from the group consisting of morphine, hydromorphone, hydrocodone, oxycodone, codeine, levorphanol, meperidine, methadone, oxymorphone, dihydrocodeine, tramadol, pharmaceutically acceptable salts thereof, and mixtures thereof.

In another aspect, the disclosure provides a pharmaceutical composition comprising a GI enzyme-labile opioid agonist prodrug, and a GI enzyme inhibitor whereby all or some of the GI enzyme-labile opioid agonist prodrug and/or all or some of the GI enzyme inhibitor is formulated in a controlled-delivery matrix or device. The opioid agonist is selected from the group consisting of morphine, hydromorphone, hydrocodone, oxycodone, codeine, levorphanol, meperidine, methadone, oxymorphone, dihydrocodeine, tramadol, pharmaceutically acceptable salts thereof, and mixtures thereof.

In another aspect, the disclosure provides a pharmaceutical composition comprising a macromolecular GI enzyme-labile opioid agonist prodrug, and a GI enzyme inhibitor whereby all or some of the GI enzyme inhibitor and/or the macromolecular GI enzyme-labile opioid agonist prodrug are/is formulated in a controlled-delivery matrix or device. The opioid agonist is selected from the group consisting of morphine, hydromorphone, hydrocodone, oxycodone, codeine, levorphanol, meperidine, methadone, oxymorphone, dihydrocodeine, tramadol, pharmaceutically acceptable salts thereof, and mixtures thereof.

In another aspect, the disclosure provides a pharmaceutical composition comprising a macromolecular GI enzyme-labile opioid agonist prodrug, and a macromolecular GI enzyme inhibitor whereby all or some of the macromolecular GI enzyme inhibitor and/or the macromolecular gastrointestinal enzyme-labile opioid agonist prodrug are/is formulated in a controlled-delivery matrix or device. The opioid agonist is selected from the group consisting of morphine, hydromorphone, hydrocodone, oxycodone, codeine, levorphanol, meperidine, methadone, oxymorphone, dihydrocodeine, tramadol, pharmaceutically acceptable salts thereof, and mixtures thereof.

In another aspect, any or all of the embodiments described above may optionally contain a macromolecular opioid antagonist polymer conjugate. The macromolecular opioid antagonist polymer conjugate is designed to not be absorbed from, and remain intact in, the GI tract. The opioid antagonist polymer conjugate is further designed to release a monomeric FDA-approved opioid antagonist drug when dose forms of the invention are subjected to chemical tampering by potential abusers. The opioid antagonist is selected from the group consisting of buprenorphine, cyclazocine, cyclorphan, naloxone, naltrexone, nalmephene, 6-amino-6-desoxo-naloxone, levallorphan, nalbuphine, naltrendol, naltrindole, nalorphine, nor-binaltorphimine, oxilorphan, pentazocine, piperidine-N-alkylcarboxylate opioid antagonists such as those described in U.S. Pat. Nos. 5,159,081, 5,250,542, 5,270,328, and 5,434,171, and derivatives, mixtures, salts, polymorphs, or prodrugs thereof.

In some instances, the disclosure provides a macromolecule of formula:

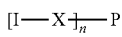

wherein:
I is a gastrointestinal enzyme inhibitor;
X is independently at each occurrence a cleavable or non-cleavable linker that joins I to a polymer P, wherein P is selected to provide less than 20% absorption of the macromolecule from the gastrointestinal tract of a subject following oral administration; and
n is an integer from 1 to 1000.

In some instances, the macromolecule is formulated in an extended release matrix or in an immediate release matrix. The gastrointestinal enzyme can be trypsin. The gastrointestinal enzyme inhibitor can be a trypsin inverse substrate.

The trypsin inverse substrate can be selected from the group consisting of:

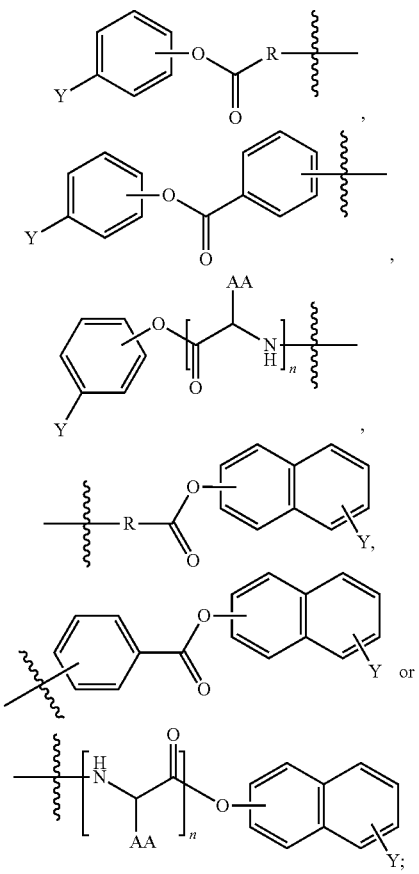

AA is a side chain of a natural or an unnatural amino acid;
R is aryl, substituted aryl, heteroaryl, substituted heteroaryl, cinnamyl, substituted cinnamyl, acrylate, substituted acrylate, styryl, or substituted styryl;
Y is H, halogen, an electron withdrawing group, an electron donating group,

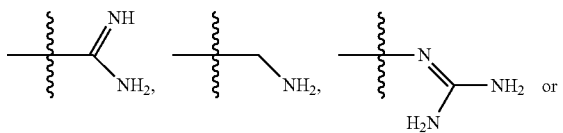

-continued

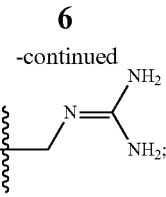

and
n is an integer from 1 to 1000.
The trypsin inverse substrate can comprise a compound selected from the group consisting of:

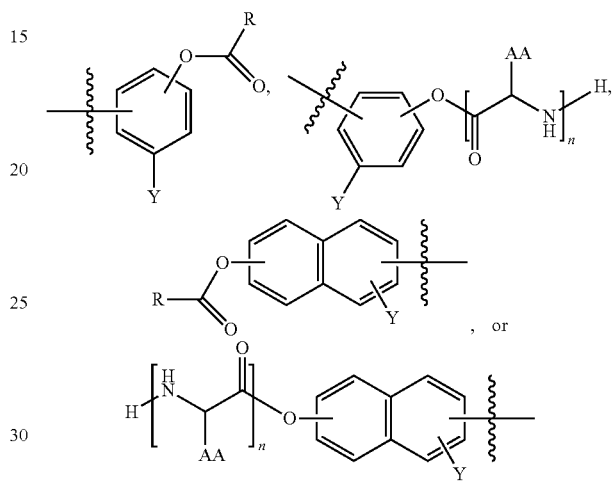

where R is an aryl, substituted aryl, heteroaryl, substituted heteroaryl, cinnamyl, substituted cinnamyl, acrylate, substituted acrylate, styryl, or substituted styryl;
Y is H, halogen, an electron withdrawing group, an electron donating group,

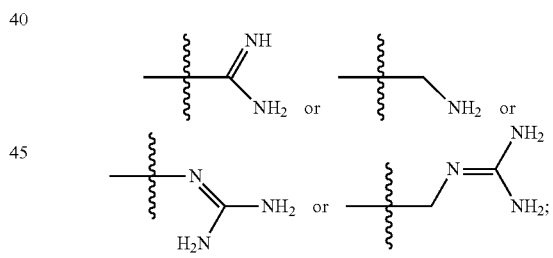

and
n is an integer between 1 and 1000. In some instances, the R—C(=O)—O— ester group is derived from benzoic acid, salicylic acid, aspirin, 3-hydroxybenzoic acid, 4-hydroxybenzoic acid, galic acid, 2,3,4-trihydroxybenzoic acid, 2,3,6-trihydroxybenzoic acid, 2,4,5-trihydroxy benzoic acid, 6-methylsalicylic acid, o-cresotinic acid, (alkyl)-anacardic acids, o-thymotic acid, 3-O-methylgallic acid, 4-O-methylgallic acid, syringic acid, 3,4,5-trimethoxybenzoic acid, diflusinal, p-anisic acid, 2,3-dihydroxybenzoic acid, alpha-resorcylic acid, anthranilic acid, 3-aminobenzoic acid, 4,5-dimethylanthranilic acid, N-methylanthranilic acid, protocatechuic acid, gentisic acid, piperonylic acid, 3-methoxysalicylic acid, fenamic acid, toifenamic acid, mefenamic acid, flufenamic acid, vanillic acid, isovanillic acid, veratric acid, 3,5-dimethoxybenzoic acid, 2,4-diaminobenzoic acid, N-acetylanthranilic acid, 2-acetylamino-4- aminobenzoic acid, 2,4-diacetylaminobenzoic acid, 4-aminosalicylic acid, 3-hydroxyanthranilic acid, 3-methoxyanthranilic acid, nicotinic acid, isonicotinic acids, and cinnamic acids.

The trypsin inverse substrate can be selected from the group consisting of:

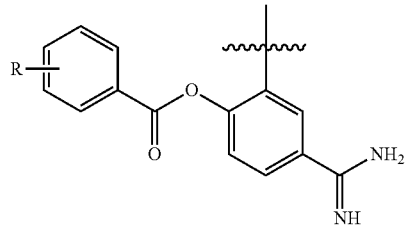

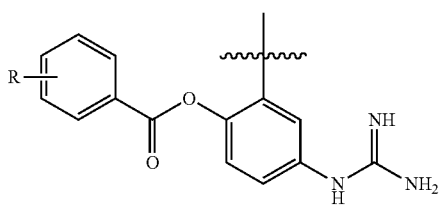

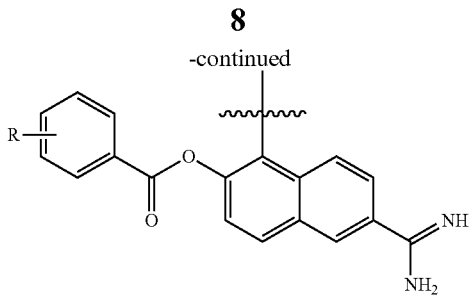

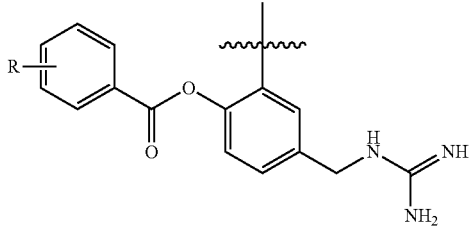

where R can be hydrogen, alkyl, substituted alkyl, aryl, substituted aryl, hydroxy, amino, cyano, halogen, alkoxy, alkylamino, acyloxy, acylamino, benzyloxy, benzylamino, substituted benzyloxy, substituted benzylamino, —COOH, an ester, a heterocycle, a natural or an unnatural amino acid, or a polypeptide consisting of from 2 to 10 natural and/or unnatural amino acids.

In some instances, X can be an ester, a thioester, an amide, an amine, a carbamate, a carbonate, an ether, a thioether, or a urea. In some instances, the macromolecule can be selected from the group consisting of:

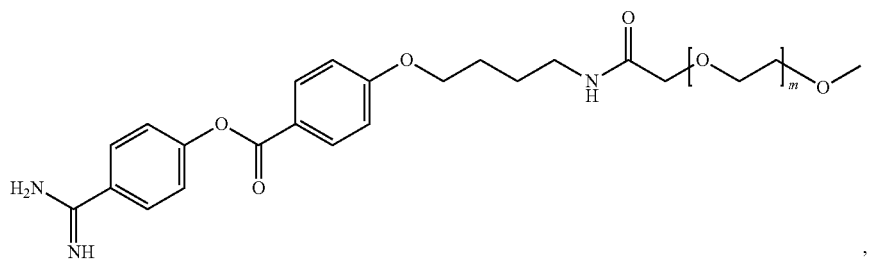

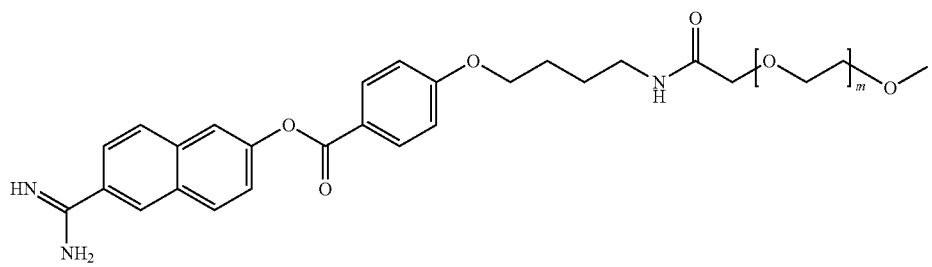

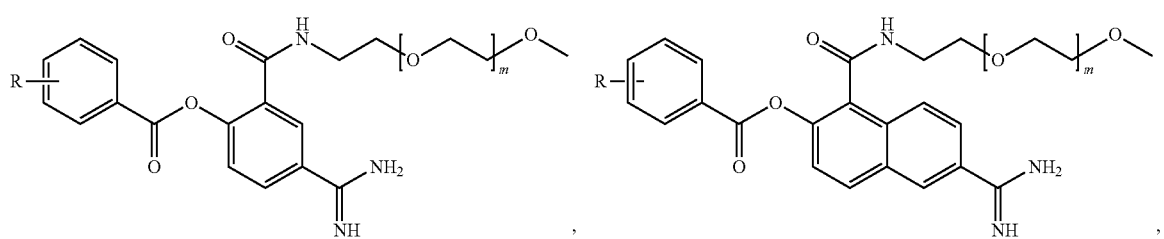

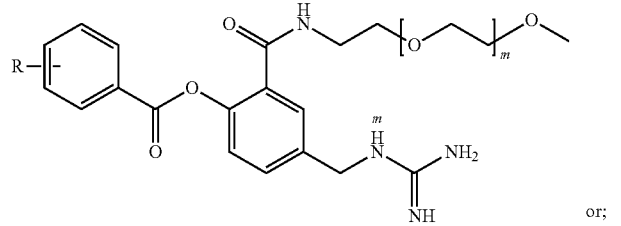

or;

m is an integer between 2 and 1000; and and R is hydrogen, alkyl, substituted alkyl, aryl, substituted aryl, hydroxy, amino, cyano, halogen, alkoxy, alkylamino, acyloxy, acylamino, benzyloxy, benzylamino, substituted benzyloxy, substituted benzylamino, —COOH, an ester, a heterocycle, a natural or an unnatural amino acid, or a polypeptide consisting of from 2 to 10 natural and/or unnatural amino acids.

The polymer can be selected from the group consisting of poly-D-lysine, poly-L-lysine, poly-D-(α-N-methyl)lysine, poly-L-(α-N-methyl)lysine, poly-D-(ε-N-methyl)lysine, poly-L-(ε-N-methyl)lysine, polyglutamic acid, cellulose, modified cellulose, chitosan, modified chitosan, or polyalkylene glycol. The polymer can be polyethylene glycol.

In some instances, the disclosure provides a macromolecule of formula:

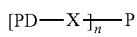

wherein:

PD is a gastrointestinal enzyme-labile opioid agonist prodrug;

X is a linker group that covalently joins PD to a polymer;

P is a polymer; and n is an integer between 1 and 1000.

P is selected to provide fewer than 20% of absorption of the macromolecule from the gastrointestinal tract of a subject following oral administration. The macromolecule can be formulated in an immediate release matrix or in an extended release matrix. The gastrointestinal enzyme can release an opioid from PD. In some instances PD can comprises an opioid, and the opioid can be selected from the group consisting of morphine, hydromorphone, hydrocodone, oxycodone, codeine, levorphanol, meperidine, methadone, oxymorphone, dihydrocodeine, tramadol, pharmaceutically acceptable salts thereof, prodrugs thereof, and mixtures thereof. The polymer can be selected from the group consisting of poly-D-lysine, poly-L-lysine, poly-D-(α-N-methyl)lysine, poly-L-(α-N-methyl)lysine, poly-D-(ε-N-methyl)lysine, poly-L-(ε-N-methyl)lysine, polyglutamic acid, cellulose, modified cellulose, chitosan, modified chitosan, or polyalkylene glycol. The polymer can be polyethylene glycol.

In some instances the gastrointestinal enzyme-labile opioid agonist prodrug is:

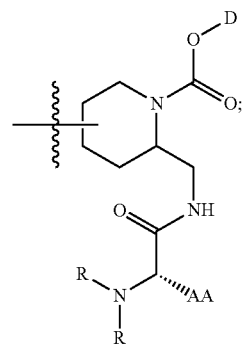

wherein D is an opioid agonist;

AA is a natural or an unnatural amino acid side-chain that is recognized by a digestive enzyme; and R is independently hydrogen, methyl, ethyl, substituted alkyl, substituted aryl, a natural or an unnatural amino acid, or a polypeptide consisting of from 2 to 10 natural and/or unnatural amino acids; wherein, adjacent R groups can be joined to form a ring.

In some instances the gastrointestinal enzyme-labile opioid agonist prodrug is:

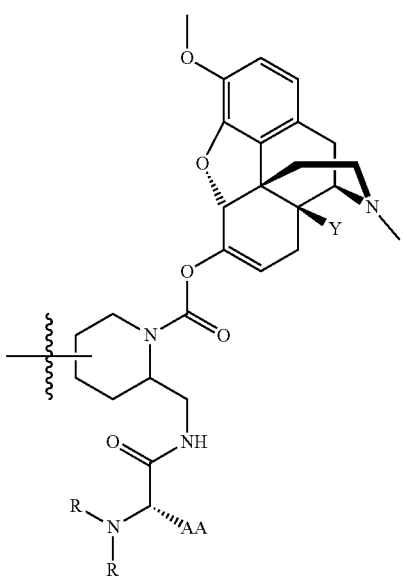

or

-continued

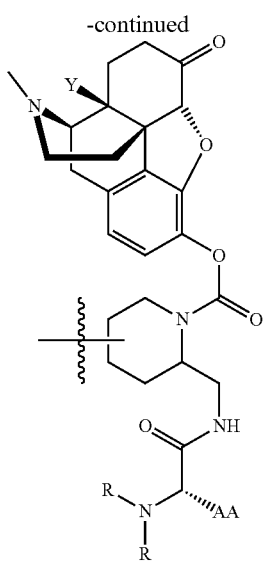

where Y is H or OH;

AA is a natural or unnatural amino acid side chain that is recognized by a digestive enzyme; and R is independently hydrogen, methyl, ethyl, substituted alkyl, or substituted aryl, or a natural or unnatural amino acid, or a polypeptide comprising up to 10 natural and/or unnatural amino acids; adjacent R groups can be joined to form a ring.

In some instances the disclosure provides a composition comprising a macromolecule of formula

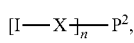

and a therapeutically-effective amount of a macromolecule of formula:

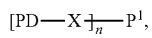

wherein:
PD is a gastrointestinal enzyme-labile opioid against prodrug;
I is a gastrointestinal enzyme inhibitor;
X is independently at each occurrence absent or a cleavable or non-cleavable linker that joins I and PD to a polymer;
$P^1$ and $P^2$ are a polymer, wherein each $P^1$ and $P^2$ is independently selected to provide less than 20% absorption of the macromolecule from the gastrointestinal tract of a subject following oral administration; and
n is an integer from 1 to 1000.

The gastrointestinal enzyme inhibitor can be a trypsin inverse substrate. In some instances, $P^1$ and $P^2$ are identical. In some instances, $P^1$ and $P^2$ have an equal or functionally equivalent number of hydrogen bond donating groups. In some instances, $P^1$ and $P^2$ have an equal or functionally equivalent number of hydrogen bond accepting groups. In some instances, $P^1$ and $P^2$ have an equal or functionally equivalent molecular composition. In some instances, $P^1$ and $P^2$ have an equal or functionally equivalent similar charge state. In some instances, $P^1$ and $P^2$ have an equal or functionally equivalent polar surface area. In some instances, $P^1$ and $P^2$ have an equal or functionally equivalent number of rotatable bonds. In some instances, $P^1$ and $P^2$ have an equal or an equivalent molecular weights.

In some instances, the disclosure provides a composition comprising: a gastrointestinal enzyme inhibitor; and a therapeutically-effective amount of a macromolecule of formula:

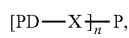

wherein the inhibitor and the therapeutically-effective amount of the macromolecule are each independently formulated in an immediate release matrix or in an extended release matrix.

In some instances, the gastrointestinal enzyme is trypsin. In other instances, the gastrointestinal enzyme inhibitor is a trypsin inverse substrate. In some cases, wherein the trypsin inverse substrate is:

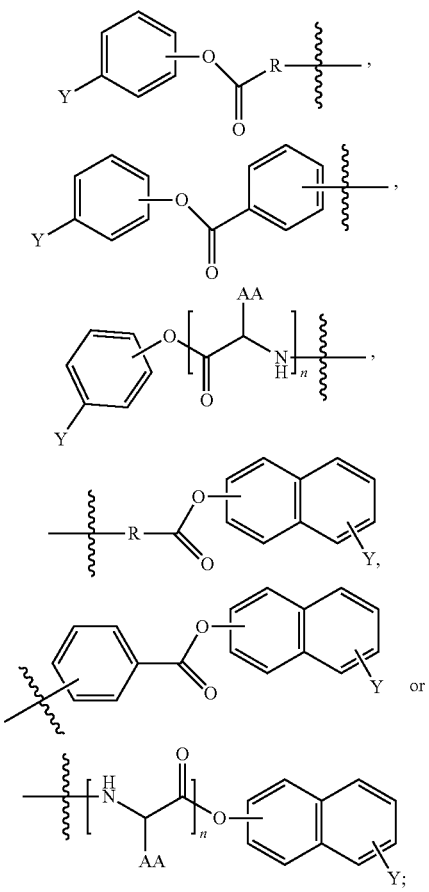

AA is a side chain of a natural or an unnatural amino acid;
R is aryl, substituted aryl, heteroaryl, substituted heteroaryl, cinnamyl, substituted cinnamyl, acrylate, substituted acrylate, styryl, or substituted styryl;
Y is H, halogen, an electron withdrawing group, an electron donating group,

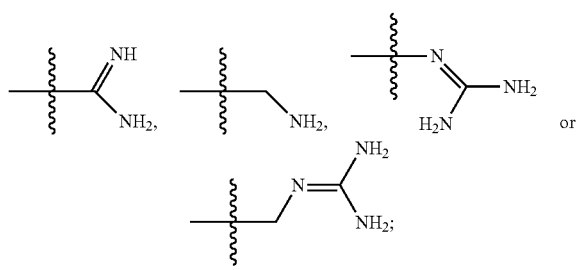

and n is an integer from 1 to 1000.

In some instances, the trypsin inverse substrate is:

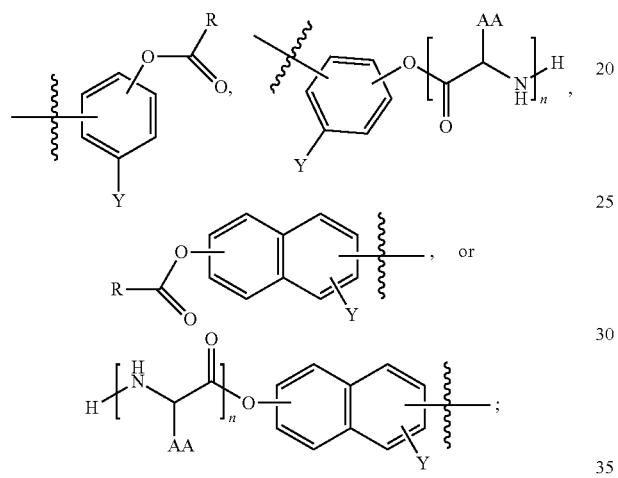

where

R is an aryl, substituted aryl, heteroaryl, substituted heteroaryl, cinnamyl, substituted cinnamyl, acrylate, substituted acrylate, styryl, or substituted styryl;

Y is H, halogen, an electron withdrawing group, an electron donating group,

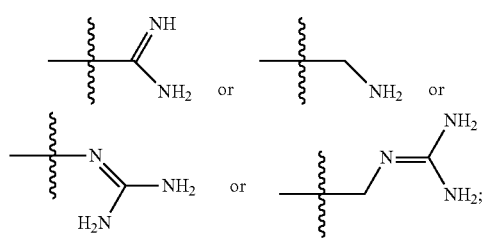

and n is an integer between 1 and 1000.

In some instances, the R—C(=O)—O— ester group is derived from benzoic acid, salicylic acid, aspirin, 3-hydroxybenzoic acid, 4-hydroxybenzoic acid, galic acid, 2,3,4-trihydroxybenzoic acid, 2,3,6-trihydroxybenzoic acid, 2,4,5-trihydroxy benzoic acid, 6-methylsalicylic acid, o-cresotinic acid, (alkyl)-anacardic acids, o-thymotic acid, 3-O-methylgallic acid, 4-O-methylgallic acid, syringic acid, 3,4,5-trimethoxybenzoic acid, diflusinal, p-anisic acid, 2,3-dihydroxybenzoic acid, alpha-resorcylic acid, anthranilic acid, 3-aminobenzoic acid, 4,5-dimethylanthranilic acid, N-methylanthranilic acid, protocatechuic acid, gentisic acid, piperonylic acid, 3-methoxysalicylic acid, fenamic acid, toifenamic acid, mefenamic acid, flufenamic acid, vanillic acid, isovanillic acid, veratric acid, 3,5-dimethoxybenzoic acid, 2,4-diaminobenzoic acid, N-acetylanthranilic acid, 2-acetylamino-4-aminobenzoic acid, 2,4-diacetylaminobenzoic acid, 4-aminosalicylic acid, 3-hydroxyanthranilic acid, 3-methoxyanthranilic acid, nicotinic acid, isonicotinic acids, and cinnamic acids.

In some instances, the trypsin inverse substrate is:

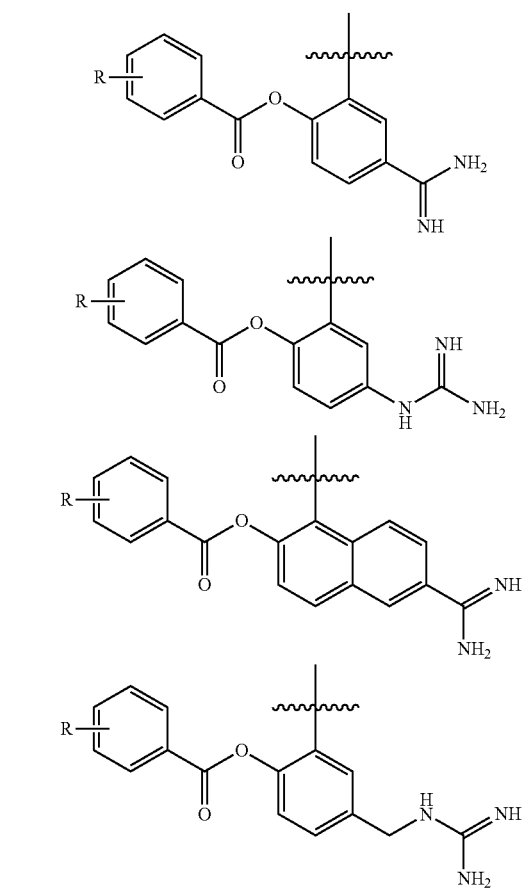

and R is hydrogen, alkyl, substituted alkyl, aryl, substituted aryl, hydroxy, amino, cyano, halogen, alkoxy, alkylamino, acyloxy, acylamino, benzyloxy, benzylamino, substituted benzyloxy, substituted benzylamino, —COOH, an ester, a heterocycle, a natural or an unnatural amino acid, or a polypeptide consisting of from 2 to 10 natural and/or unnatural amino acids.

In some instances, X is an ester, a thioester, an amide, an amine, a carbamate, a carbonate, an ether, a thioether, or a urea.

In some instances, the disclosure provides a method for treating a condition, the method comprising administering to a subject in need thereof a therapeutically-effective amount of a macromolecule of formula

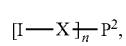

and a macromolecule of formula:

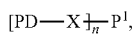

$$[PD-X]_n-P^1,$$

wherein:
PD is a gastrointestinal enzyme-labile opioid against prodrug;
I is a gastrointestinal enzyme inverse substrate;
X is a linker group that covalently joins I to a polymer;
$P^1$ and $P^2$ are a polymer, wherein each $P^1$ and $P^2$ is independently selected to provide less than 20% absorption of the macromolecule from the gastrointestinal tract of a subject following oral administration; and
n is an integer from 1 to 1000.

Terms

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2004) "Advanced Organic Chemistry $4^{rd}$ Ed." Vols. A and B, Springer, New York. The practice of the present invention will employ, unless otherwise indicated, conventional methods of mass spectroscopy, protein chemistry, biochemistry, and pharmacology, within the skill of the art. Any undefined terms have their art recognized meanings.

"Alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or un-branched saturated hydrocarbon chain, usually having from 1 to 40 carbon atoms, more usually 1 to 10 carbon atoms and even more usually 1 to 6 carbon atoms. This term is exemplified by methylene, ethylene, the propylene isomers and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis- or trans-conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R', where R' is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

"Acylamino" refers to the groups —NR'C(O) alkyl, —NR'C(O)substituted alkyl, NR'C(O)cycloalkyl, —NR'C(O)substituted cycloalkyl, —NR'C(O)cycloalk-enyl, —NR'C(O)substituted cycloalkenyl, —NR' C(O) alkenyl, —NR'C(O)substituted alkenyl, —NR'C(O)alkynyl, —NR'C(O)substituted alkynyl, NR' C(O)aryl, —NR' C(O)substituted aryl, —NR'C(O)heteroaryl, —NR'C(O)substituted heteroaryl, —NR'C(O)heterocyclic, and —NR'C(O)substituted heterocyclic, wherein R' is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Aminoacyl" refers to the group-C(O)NR'R, wherein R' and R" independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —OR' where R' represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR' where R' represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, asindacene, sindacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or sp3 carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is (C7-C30) arylalkyl, e.g., the alkanyl, alkenyl or alkynyl moiety of the arylalkyl group is (C1-C10) and the aryl moiety is (C6-C20). In certain embodiments, an arylalkyl group is (C7-C20) arylalkyl, e.g., the alkanyl, alkenyl or alkynyl moiety of the arylalkyl group is (C1-C8) and the aryl moiety is (C6-C12).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenylnapthyl, binaphthyl, biphenylnapthyl, and the like. When the number of carbon atoms in an arylaryl group is specified, the numbers refer to the carbon atoms comprising each aromatic ring. For example, (C5-C14) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a (C5-C14) aromatic. In certain embodiments, each aromatic ring system of an arylaryl group is independently a (C5-C10) aromatic. In certain embodiments, each aromatic ring system is identical, e.g., biphenyl, triphenyl, binaphthyl, trinaphthyl, etc.

"Carboxyl," "carboxy" or "carboxylate" refers to —CO2H or salt thereof.

"Cyano" or "nitrile" refers to the group —CN.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is (C3-C10) cycloalkyl. In certain embodiments, the cycloalkyl group is (C3-C7) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NRR', =N—N=, PR', P(O)2R, —O—P(O)2-, —S—O—, —S(O)—, —SO2-, SNRR', and the like where R, R' are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazme.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heteroarylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalky 1 group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Heterocycle," "heterocyclic," "heterocycloalkyl," and "heterocyclyl" refer to a saturated or unsaturated group having a single ring or multiple condensed rings, including fused bridged and spiro-ring systems, and having from 3 to 15 ring atoms, including 1 to 4 heteroatoms. These heteroatoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

"Aromatic Ring System" by itself or as part of another substituent, refers to an unsaturated cyclic or polycyclic ring system having a conjugated π-electron system. Specifically included within the definition of "aromatic ring system" are fused ring systems in which one or more of the rings are aromatic, and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, asindacene, sindacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —R, —O—, =O, —OR, —SR, —S—, =S, —NRR', —NHR, =NR, —CF$_3$, —CN, —OCN, —SCN, —NO, —NO$_2$, =N$_2$, —N$_3$, —S(O)O—, —S(O)$_2$O H, —S(O)$_2$R, —OS(O)$_2$R, —P(O)O$_2$, —C(O)R, —C(O)OR, —C(S)OR, —C(O)NRR', —NRC(O)—, C(=NH)NRR', where M is halogen; R, and R' are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R and R' together with the nitrogen atom to which they are bonded form a cycloheteroalkyl or substituted cycloheteroalkyl ring.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

"Dose unit" as used herein refers to a combination of a macromolecular GI enzyme-cleavable prodrug (e.g., trypsin-cleavable prodrug) and a macromolecular or small molecule GI enzyme inhibitor (e.g., a trypsin inhibitor).

An "intended dose" is a dose that provides a therapeutically effective amount of drug (i.e., a sufficient amount of drug to effect a therapeutic effect, e.g., a dose within the respective drug's therapeutic window, or therapeutic range).

"Multiple dose units" or "multiples of a dose unit" or a "multiple of a dose unit" refers to at least two or more single dose units.

"Gastrointestinal enzyme" or "GI enzyme" refers to an enzyme located in the gastrointestinal (GI) tract, which encompasses the anatomical sites from mouth to anus. Trypsin is an example of a GI enzyme.

"Gastrointestinal enzyme-cleavable moiety" or "GI enzyme-cleavable moiety" refers to a group comprising a site susceptible to cleavage by a GI enzyme. For example, a "trypsin-cleavable moiety" refers to a group comprising a site susceptible to cleavage by trypsin.

"Gastrointestinal enzyme inhibitor" or "GI enzyme inhibitor" refers to any agent capable of inhibiting the action of a gastrointestinal enzyme on a substrate. The term also encompasses salts of gastrointestinal enzyme inhibitors. For example, a "trypsin inhibitor" refers to any agent capable of inhibiting the action of trypsin on a substrate.

The term "gastrointestinal enzyme inverse substrate" or "IS" refers to any agent capable of acting as an inverse substrate for a digestive enzyme. Inverse substrates are designed to bind to, and be hydrolyzed by, enzymes in a manner that is "inverse" to "normal" substrates. With "normal" substrates, the amino acid (or amino acid mimic) recognized by the enzyme is directly connected to the C-terminus of carbonyl containing group to be hydrolyzed (e.g. amide, ester, etc.), which is further connected to a leaving group (e.g. amine or alcohol, etc.). In contrast, inverse substrates have the amino acid (or amino acid mimic) recognized by the enzyme directly connected to the leaving group of the carbonyl group undergoing hydrolysis by the enzyme. The term also encompasses salts of gastrointestinal enzyme inverse substrates. For example, a "trypsin inverse substrate" refers to any agent capable of acting as an inverse substrate for trypsin.

"Patient" or "Subject" includes humans, and also other mammals, such as livestock, zoo animals, and companion animals, such as a cat, dog, or horse.

"Pharmaceutical composition" refers to a combination of compounds described herein and can further comprise a pharmaceutically acceptable carrier, with which the compound is administered to a patient.

"Pharmacodynamic (PD) profile" refers to a profile of the efficacy of a drug in a patient (or subject or user), which is characterized by PD parameters such as analgesia.

"PD parameters" include "drug Emax" (the maximum drug efficacy), "drug EC50" (the concentration of drug at 50% of the Emax) and side effects.

"PK parameter" refers to a measure of drug concentration in blood or plasma of a subject, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

"PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile"). A PK profile is characterized by PK parameters.

"Preventing" or "prevention" or "prophylaxis" refers to a reduction in risk of occurrence of a condition, such as pain.

"Prodrug" refers to a derivative of an active agent that requires a transformation within the body to release the active agent. In certain embodiments, the transformation is an enzymatic transformation. In certain embodiments, the transformation involves a cyclization-release transformation. In certain embodiments, the transformation is a combination of an enzymatic transformation and a cyclization-release transformation. Prodrugs are frequently, although not necessarily, pharmacologically inactive until converted to the active agent.

"Promoiety" refers to a chemical moiety that is attached to a chemical functionality on an active agent, thereby converting the active agent into a prodrug. Typically, the promoiety will be attached to the drug via bond(s) that are cleaved directly, or indirectly, by enzymatic or non-enzymatic means in vivo.

"Solvate" as used herein refers to a complex or aggregate formed by one or more molecules of a solute, e.g. a prodrug or a pharmaceutically acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Therapeutically effective amount" means the amount of a compound (e.g., prodrug) that, when administered to a patient for preventing or treating a condition such as pain, is sufficient to effect such treatment. The "therapeutically effective amount" will vary depending on the compound, the condition and its severity and the age, weight, etc. of the patient.

The term "agonist" means a molecule such as a compound, a drug, an enzyme activator or a hormone that enhances the activity of another molecule or the activity of the target receptor. The term "agonist" as used herein includes all biochemically functional variants of agonists such as full agonists, partial agonists, inverse agonists, biased agonists, and the like.

The term "amino acid" refers to either natural and/or unnatural or synthetic amino acids, and both the D or L optical isomers, the N-acyl and N-methyl derivatives thereof, and amino acid analogs and peptidomimetics. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine, and methyl sulfonium. Such analogs have modified side-chains, such as norleucine, homoarginine, homolysine, N-methyl lysine, ornithine, and the like, or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. For example, the unnatural amino acid L-(7-hydroxycoumarin-4-yl)ethylglycine (or 7-hydroxycoumarin-ethylglycine) finds use with the invention.

The term "amino-acid side-chain" as used herein refers to the side-chains that emanate from the alpha-carbon of natural or non-natural amino acids, and any amide, peptide, or polypeptide derivatives thereof. Examples of naturally occurring amino acid side-chains can include: —$CH_3$, —$CH_2SH$, —$CH_2COOH$, —$CH_2CH_2COOH$, —$CH_2C_6H_5$, —H, —$CH_2$—$C_3H_3N_2$, —$CH(CH_3)CH_2CH_3$, —$(CH_2)_4NH_2$, —$CH_2CH(CH_3)_2$, —$CH_2CH_2SCH_3$, —$CH_2CONH_2$, —$(CH_2)_4NHCOC_4H_5NCH_3$, —$CH_2CH_2CH_2$—, —$CH_2CH_2CONH_2$, —$(CH_2)_3NH$—$C(NH)NH_2$, —$CH_2OH$, —$CH(OH)CH_3$, —$CH_2SeH$, —$CH(CH_3)_2$, —$CH_2C_8H_6N$, —$CH_2$—$C_6H_4OH$. Examples of non-natural amino acid side chains can include alkylamines, arylamines, bicycloalkylamines, benzamidine, alkybenzamidine, alkylamidines, alkylguanidines, arylguanidines, alkylarylguanidines, or any suitable analog bearing a basic nitrogen capable of being recognized by trypsin.

The term "linker" as used herein defines an assembly of covalently linked atoms that serve to conjoin elements of the invention. Functionally, linkers are used to covalently connect GI enzyme-labile opioid prodrug moieties to macromolecular polymers, and also to covalently connect GI enzyme inhibitors to macromolecular polymers. Structurally, linkers can be characterized as homobifunctional or heterobifunctional with respect to the functionalities present on their termini. Homobifunctional linkers possess identical functional groups on their termini, and heterobifunctional linkers possess different chemical functionalities on their termini. Non-limiting examples of homobifunctional linkers can be derived from suitably protected or activated forms of diamines, dicarboxylic acids, diols, bis-isocyanates, bis-carbamoylchlorides, bischloroformates, dihalo, and the like. Non-limiting examples of heterobifunctional linkers can be derived from suitably protected or activated forms of amino acids, amino alcohols, hydroxy acids, halo amines, halo acids, halo alcohols, and the like. Covalent attachment strategies between linkers and the elements of the invention to which they are attached commonly involve, but are not limited to, the formation of amides, ureas, esters, ethers, carbamates, thioesters, thioethers, amines, and the like. It is intended that the intervening atoms disposed between the terminal chemical functionalities of linker molecules are of very broad scope. Non-limiting examples can include alkyl, aryl, alkoxy, aryloxy, alkenyl, alkynyl, alkylester, alkylether, alkylamide, heterocycles, substituted heterocycles, and the like. If desirable, the linker moiety may bear substituents. The specific molecular structure of linkers that find use within the scope of the invention may be further defined based on commercial availability, cost, ease of synthesis, and the complimentary nature between the functional groups present on the termini of the linker and the chemical functionalities present on the specific elements of the invention which they conjoin.

The term "small molecule" as used herein refers to molecules that are not covalently attached to a macromolecular entity such as a polyalkylene glycol, a polypeptide, a polysaccharide, a polyester, a polyamide, a biopolymer, a polymer, etc. and the like.

An "enzymatically degradable linkage" means a linkage that is subject to degradation by one or more enzymes under ordinary physiological conditions.

The term "halogen" as used herein refers to fluoro, bromo, chloro and/or iodo.

The term "modulator" means a molecule that interacts with a target. The interactions include, but are not limited to, agonist, antagonist, and the like, as defined herein.

The term "macromolecular" refers to the overall size of a molecular entity. This can relate to the molecular weight a molecule containing a very large number of atoms, such as a protein, nucleic acid, or natural or synthetic polymer. However, other molecular features such as charge state, conformational rigidity, hydration sphere radius, radius of gyration, etc. can also be considered to impart macromolecularity.

The term "biopolymer" as used herein refers to polymers produced by living organisms; in other words, they are polymeric biomolecules. Biopolymers contain monomeric units that are covalently bonded to form larger structures. There are three main classes of biopolymers, classified according to the monomeric units used and the structure of the biopolymer formed: polynucleotides (RNA and DNA), which are long polymers composed of 13 or more nucleotide monomers; polypeptides, which are polymers of amino acids; and polysaccharides, which are often linear bonded polymeric carbohydrate structures.

The term "opioid" means a substance, whether agonist, antagonist, or mixed agonist-antagonist, which reacts with one or more receptor sites bound by endogenous opioid peptides such as the enkephalins, endorphins and the dynorphins.

The terms "opioid agonist", "opioid analgesic" or "opioids" mean a diverse group of drugs, of natural, synthetic, or semi-synthetic origin, that displays opium or morphine-like properties. Opioids agonists encompasses full-, partial-, mixed-, inverse- or biased-agonists, and the like. They can include, without limitation, morphine, heroin, hydromorphone, oxymorphone, buprenorphine, levorphanol, butorphanol, codeine, dihydrocodeine, hydrocodone, oxycodone, meperidine, methadone, nalbulphine, opium, pentazocine, propoxyphene, as well as less widely employed compounds such as alfentanil, allylprodine, alphaprodine, anileridine, benzylmorphine, bezitramide, clonitazene, cyclazocine, desomorphine, dextromoramide, dezocine, diampromide, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydroxypethidine, isomethadone, ketobemidone, levallorphan, levophenacylmorphan, lofentanil, meptazinol, metazocine, metopon, myrophine, narceine, nicomorphine, norpipanone, papvretum, phenadoxone, phenomorphan, phenazocine, phenoperidine, piminodine, propiram, sufentanil, tapentadol, tramadol, tilidine, PZMO21 and analogs thereof, TRY130 and analogs thereof, BU08028 and analogs thereof, as well as salts, prodrugs and mixtures thereof.

The term "optional" or "optionally" means that the subsequently described event or circumstance may or may not occur, and that the description includes instances where the event or circumstance occurs and instances where it does not.

"PEG" or "polyalkyleneglycol" or "polyethylene glycol," as used herein, is meant to encompass any water-soluble poly(akylene oxide). Typically, PEG oligomers for use in the present invention can be —$(CH_2CH_2O)_n$— or —$(CH_2CH_2O)_n$—$CH_2CH_2$—, but can also include polyalkylene glycols including, but not limited to polypropylene- or polybutylene glycols where n can be from about 2 to 400, preferably from about 10 to about 200.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts, for example, include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like;

(2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

As used herein, the terms "treat" or "treatment" are used interchangeably and are meant to indicate a postponement of development of diseases and/or a reduction in the severity of such symptoms that will or are expected to develop. The terms further include ameliorating existing symptoms, preventing additional symptoms, and ameliorating or preventing the underlying symptoms.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

DETAILED DESCRIPTION

Before the present invention is further described, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

It should also be understood that as used herein, the term "a entity" or "an entity" refers to one or more of that entity. For example, a compound refers to one or more compounds. Similarly the terms "comprising", "including" and "having" can be used interchangeably.

The publications discussed herein are provided solely for their disclosure prior to the filing date of the present application. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

The compositions and pharmaceutical formulations of the present invention are described below. Also included are non-limiting descriptions of the optional and preferred embodiments useful in the practice of the present invention.

In one aspect of the invention, compositions comprising a macromolecular GI enzyme-labile opioid agonist prodrug and a macromolecular GI enzyme inhibitor are administered to a patient for the prevention and/or treatment of pain. The opioid and/or the GI enzyme inhibitor can each be covalently linked either directly, or via suitable linkers, onto suitably functionalized macromolecules such as oligomeric or polymer addends. Preferably, the covalent link is not susceptible to cleavage within the GI tract. The macromolecular GI enzyme-labile opioid prodrug and/or the macromolecular GI enzyme inhibitor, and/or a small-molecule GI enzyme inhibitor can be formulated in a controlled-delivery matrix or device.

In another aspect, any or all of the embodiments of the invention may optionally contain a non-bioavailable macromolecular opioid antagonist polymer conjugate to discourage chemical tampering by potential abusers.

The opioid agonist can be hydrocodone, hydromorphone, morphine, oxycodone, oxymorphone, and/or salts or prodrugs thereof, and the GI inhibitor or GI inverse substrate is a trypsin inhibitor and can be an arginine-based inhibitor, a lysine-based inhibitor, an arginine mimic-based inhibitor, a lysine mimic-based inhibitor, and salts thereof. The inhibition can operate via a reversible, or an irreversible, or an "inverse substrate" mechanism. The opioid and/or the GI enzyme inhibitor are preferably covalently attached to a "non-absorbable", water soluble polymer, such as polyamino acid, poly-D-amino acid, poly N-methyl (D-, or L-) amino acid, a "biopolymer", or polyalkylene glycol (e.g. PEG).

The disclosure provides a macromolecular GI enzyme-labile opioid prodrug that provides controlled release of an opioid. The disclosure provides a promoiety that is attached to an opioid through any chemical moiety on the opioid, where the structural moiety has a reactive group. Examples of reactive groups on an opioid include, but are not limited to ketone, phenol, and amide. It is contemplated that opioids useful for the treatment of pain in subjects bearing at least some of the functionalities described herein will be developed in the future (e.g. biased opioid agonists); such opioids are included as part of the scope of this disclosure.

Any drug, therapeutically acceptable drug salt, drug derivative, drug analog, drug homologue, polymorph or prodrug can be used in the present invention. In one aspect of the invention, the drug can be orally administered. In another aspect of the invention, drugs susceptible to abuse are used. Drugs commonly susceptible to abuse include analgesics and psychoactive drugs, including but not limited to opioids and amphetamines. In another aspect of the invention, orally administered drugs with narrow therapeutic indices can be used.

The compositions of the invention have the advantages that the macromolecular GI enzyme-labile opioid agonist prodrugs and the macromolecular GI enzyme inhibitors, and their resulting metabolites, are not significantly absorbed from the GI tract. Thus, in contrast to the small molecule variants described in the prior art, the subject will not be exposed to high systemic concentrations of opioid prodrugs, opioid prodrug metabolites, enzyme inhibitors, and/or metabolites of enzyme inhibitors with uncharacterized safety profiles. In further contrast to the prior art, macromolecular variants of the GI enzyme-labile opioid agonist prodrug and the GI enzyme inhibitor will not be removed from the small intestine via absorption so that the GI enzyme-mediated opioid delivery efficiency, and overdose protection effects are maximized in vivo. Further, the compositions of the invention prevent overdose via the oral route. If multiple pharmaceutical oral dosage forms of the invention are co-ingested, the resulting concentration of the macromolecular GI-enzyme inhibitor reaches a high enough level in the small intestine so that the GI enzyme-mediated release of the opioid is inhibited. Importantly, this resulting inhibition of the digestive enzyme mediated release of the opioid will be sustained due to the non-absorbability of the macromolecular GI-enzyme inhibitor and/or the controlled release of the GI enzyme inhibitor from a controlled release matrix or device. Thus, intentional ingestion of multiple pills of the invention will not enable abusers to achieve the desired pharmacokinetic profile for achieving a "high" or euphoric state. Furthermore, accidental co-ingestion of multiple pills by young children, the elderly, or the subjects will be less likely to produce toxic or lethal effects.

Opioid Agonist

In one aspect of the invention, the opioid is an opioid agonist. The class of drugs exhibiting opium or morphine-like properties are referred to as opioid agonists, or opioids, and they interact with opioid receptors in the brain, the peripheral nervous system and other tissues. The three major opioid receptor subtypes are mu, delta, and kappa. Each of these receptors has a unique anatomical distribution in the central nervous system, the peripheral nervous system and the gastrointestinal tract. Most of the clinically used opioids exert their desired therapeutic action (i.e. analgesia) at the mu receptor subtype.

In one aspect of the invention, opioid agonists useful in the present invention include, but are not limited to full-, partial-, inverse-, or biased-agonists such as, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, tramadol, PZM021 and analogs thereof, TRY130 and analogs thereof, BU08028 and analogs thereof, as well as mixtures of any of the foregoing, salts thereof, prodrugs thereof, and derivatives, analogs, homologues, and polymorphs thereof.

In certain embodiments, the amount of the delivered opioid agonist can be from about 1 ng to about 1000 mg.

In one aspect of the invention, a pharmaceutical composition of the present invention includes one or more opioids such as hydrocodone, hydromorphone, morphine, oxycodone, oxymorphone, and/or salts or prodrugs thereof, as the therapeutically active ingredient. Prodrugs of opioids include such as those described in U.S. Pat. No. 8,217,005 to Jenkins et al., U.S. Pat. No. 8,101,661 to Mickle, and U.S. Pat. Nos. 8,133,881, 7,375,082 and 7,338,939 all to Mickle et al., prodrugs described in U.S. Publication Nos. 20120178773, 20120142718, 20110281886, 20110262360, and 20110262359, and those described in PCT publication Nos. WO 2011/002995 and WO 2011/002991. Typically in a suitable dosage form, as described in more detail below, the opioid agonist can be present in such dosage forms in an amount normally prescribed, typically about 0.5 to about 50 percent on a dry weight basis, based on the total weight of the formulation.

In a unit dose form, the amount of the delivered opioid agonist can be about 1 mg, about 5 mg, about 10 mg, about 15 mg, about 25 mg, about 50 mg, about 75 mg, about 100 mg, about 125 mg, about 150 mg, about 175 mg or about 200 mg. More typically, the drug can be present in an amount from about 1 mg to about 500 mg, preferably about 1 mg to 200 mg. As will be understood by one of skill in the art, a dosage form preferably contains an appropriate amount of drug to provide a therapeutic effect.

Polymers

Polymers suitable for conjugation to a GI enzyme labile opioid prodrug and a GI enzyme inhibitor include, but are not limited to, linear, branched, brush (or comb), or dendrimeric polymers. In one aspect of the invention, the polymer can be polycationic or polyanionic materials including natural and/or unnatural polyamino acids having net positive or negative charge at neutral pH, positively or negatively charged polysaccharides, and positively or negatively charged synthetic polymers. The polymers can be prepared from monomers including, N-vinylpyrrolidone, acrylamide, N,N-dimethylacrylamide, vinyl acetate, dextran, L-glutamic acid, L-aspartic acid, L-lysine, L-threonine, L-tyrosine, D-glutamic acid, D-aspartic acid, D-lysine, D-threonine, D-tyrosine, styrene, maleic anhydride, N-(2-hydroxypropyl) methacrylamide, N-(2-hydroxyethyl)methacryalte, N-(2-hydroxyethyl)methacrylamide, ethylene glycol, ethylene oxide, propylene glycol, propylene oxide, tetrahydrofuran, butylene glycol, tetrahydropyran, ethyl vinyl ether, nonpeptide polyamines such as poly(aminostyrene), poly(aminoacrylate), poly (N-methyl aminoacrylate), poly (N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly (methyacrylamidopropyltrimethyl ammonium chloride), and natural or synthetic polysaccharides such as chitosan, and copolymers of the previous, including random, alternating, block, multi-block linear copolymers, and star polymers. The polymers may be isotactic, syndiotactic, or atactic as appropriate. Methods for synthesis of biopolymers and for conjugating them to biological materials are well known in the art (see, for example, published U.S. Patent Application 20040043030; U.S. Pat. Nos. 5,177,059; 6,716,821; 5,824,701; 6,664,331; 5,880,131; Kameda, Y. et al., Biomaterials 25: 3259-3266, 2004; Thanou, M. et al, Current Opinion in Investigational Drugs 4(6): 701-709, 2003; Veronese, F. M., et al., Il Farmaco 54: 497-516, 1999).

In addition, dendritic polymers may be used for preparation of macromolecular embodiments of the invention. Appropriate dendrimers include, but are not limited to, polyamido amine (PAMAM) (Gunatillake et al., Macromolecules, 1988, 21, 1556; U.S. Pat. No. 4,507,466), polyethyleneimine (U.S. Pat. No. 4,631,337), polypropyleneimine (U.S. Pat. No. 5,530,092), and Frechet-type dendrimers (U.S. Pat. No. 5,041,516; Hawker et al., J. Am. Chem. Soc., 1991, 113, 4583) terminated with amines, alcohols, or carboxylic acid surface groups. A recent review on dendrimer synthesis is Tomalia et al., J. Polym. Sci., Part A: Polym. Chem., 2002, 40, 2719. The polymers can be prepared by methods known in the art, or they can be obtained from commercial sources.

In one aspect of the invention, the molecular weight of the scaffold polymer portion of a polymer conjugate of the invention is greater than about 500 Daltons (Da), and more preferably is greater than about 1,000 Da. In another aspect of the invention, the polymer has a molecular weight of about 1,000 Da to about 250,000 Da. Thus, the ranges of molecular weights for the polymer portion of the conjugate can be from about 500 Da to about 200,000 Da, preferably about 1,000 Da to about 50,000 Da, more preferably about 2,000 Da to about 50,000 Da, or from about 1,500 Da to about 50,000 Da. The polymer backbones having an average molecular weight of about 1,000 Da, 2,000 Da, 5,000 Da, about 7,000 Da, about 10,000, about 15,000 Da and about 17,500 Da, about 20,000 Da, about 30,000 Da, about 35,000 Da, about 40,000 Da, about 45,000 Da, and about 50,000 Da are particularly preferred.

Commercially available polymers suitable for use in the invention include, but are not limited to those available commercially, such as monofunctionalized mPEG-NH$_2$ ($M_w$~1 kDa, ~20 kDa), mPEG-OH ($M_w$~1 kDa, 2 kDa, ~3 kDa, ~5 kDa, ~10 kDa, ~12 kDa, ~20 kDa), or di-functionalized NH$_2$—PEG-NH$_2$ ($M_w$~1 kDa, 2 kDa, ~3 kDa, ~5 kDa, ~10 kDa, ~12 kDa, ~20 kDa), HO-PEG-OH ($M_w$~1 kDa, 2 kDa, ~3 kDa, ~5 kDa, ~10 kDa, ~12 kDa, ~20 kDa), 3-arm PEG-triol ($M_w$~1 kDa glycerol core, 2 kDa glycerol core, ~5 kDa glycerol core), 4-arm PEG-tetrol ($M_w$~2 kDa pentaerythritol core, ~5 kDa pentaerythritol core, ~10 kDa pentaerythritol core, ~15 kDa pentaerythritol core, ~20 kDa pentaerythritol core), 8-arm PEG-octol ($M_w$~2 kDa hexaglycerine, ~10 kDa hexaglycerine, ~15 kDa hexaglycerine, ~20 kDa hexaglycerine, ~40 kDa hexaglycerine); available from Polysciences (Warrington, Pa.), such as Poly(acrylic acid), $M_w$~5 kDa, Poly(l-glycerol methacrylate), Poly(acrylamide-co-acrylic acid), Poly(ethylene oxide-block-propylene oxide), Poly(L-lysine) hydrobromide, Poly(styrenesulfonic acid), Poly(vinyl alcohol), Poly(vinyl amine) hydrochloride, poly(caprolactone) diol; available from Sigma-Aldrich (Milwaukee, Wis.), and Dendritech products (Midland, Mich.), 0,0'-bis(2-carboxyethyl)dodecaethylene glycol, Poly(allyl amine), Poly(antholesulfonic acid, sodium salt), Poly(caprolactone) triol 1,1,1-tris(hydroxymethyl)propane core, Poly(di(ethylene glycol) phthalate) diol, Poly(di(ethylene glycol)/trimethylolpropane-alt-adipic acid), polyol, PEG-bis(3-aminopropyl) terminated, PEG-bis(carboxylic acid) ether $M_w$~1 kDa, 2 kDa, ~3 kDa, ~5 kDa, ~10 kDa, ~12 kDa, ~20 kDa, PEG-bis(carboxylic acid) ether $M_w$—600 Da, PEG-block-PPG-block-PEG diol ($M_w$~1,100 Da, ~1,900 Da, 2,000 Da, ~2,800 Da, ~2,900 Da, ~4,400 Da, ~5,800 Da, ~8,400 Da, ~14,600 Da), PEG-ran-PPG diol ($M_w$~2,500 Da, ~12,000 Da, ~970 Da, ~1,700 Da, ~3,900 Da), PEG-tetrahydrofurfuryl ether, Poly(2-hydroxyethyl methacrylate), Polyoxyethylene bis(amine) $M_w$~2,000 Da, Polyoxyethylene bis(amine) $M_w$~20,000 Da, PPG diol ($M_w$~425 Da, 725 Da, ~1,000 Da, ~2,000 Da, ~2,700 Da, ~3,500 Da), Poly(DL-lysine) hydrobromide ($M_w$~1,000-4,000 Da, ~30,000-70,000 Da, ~500-2,000 Da, ~1,000-4,000 Da, ~4,000-15,000 Da, ~15,000-30,000 Da, ~30,000-70,000 Da), Poly(D-lysine) hydrobromide ($M_w$ 1,000-4,000 Da), ~4,000-15,000 Da, ~15,000-30,000 Da, ~30,000-70,000 Da), Poly(L-tyrosine) $M_w$~10,000-40,000 Da, Poly(L-serine) $M_w$~5,000-10,000 Da, Poly(L-threonine) $M_w$~5,000-15,000 Da, PAMAM Dendrimer G(0)-NH$_2$, ethylenediamine core (surface groups: 4, 8, 16, 32, or 64), PAMAM Dendrimer G(2)-OH, ethylenediamine core (surface groups: 16, 32, 64), DAB-AM-4, polypropyleneimine tetraamine dendrimer (surface groups: 4, 8, 16, 32, 64), PAMAM-tris(hydroxymethyl)amidomethane dendrimer, Generation 2, ethylenediamine core (surface groups: 48), PAMAM-tris(hydroxymethyl)amidomethane dendrimer, Generation 3, ethylenediamine core (surface groups: 96), PAMAM-succinamic acid dendrimer, ethylenediamine core, Generation 2 (surface groups: 16), Amino-dPEG$_2$™ t-butyl ester, Amino-dPEG$_4$™ t-butyl ester, Amino-dPEG$_8$™ t-butyl ester, Amino-dPEG$_{12}$™ t-butyl ester, Amino-dPEG$_{24}$™ t-butyl ester, m-dPEG$_4$™ amine, m-dPEG$_{12}$™ amine, m-dPEG$_{24}$™ amine, Hydroxy-dPEG$_4$™ t-butyl ester, Hydroxy-dPEG$_8$™ t-butyl ester, m-dPEG$_{11}$™ alcohol, dPEG$_{12}$™ diol, Mono-N-t-boc-amido-dPEG$_3$™-amine, Mono-N-t-boc-amido-dPEG$_{11}$™-amine, Mono-N-t-CBZ-amido-dPEG$_3$™-amine, N-t-boc-amido-dPEG$_4$™ alcohol, N-t-boc-amido-dPEG$_{12}$™ alcohol, Bis-dPEG$_5$™ acid, Bis-dPEG$_7$™ acid, Bis-dPEG$_5$™ half benzyl half acid, Bis-dPEG$_9$™ half benzyl half acid, N-Fmoc-amido-dPEG$_2$™ acid, N-Fmoc-amido-dPEG$_4$™ acid, N-Fmoc-amido-dPEG$_8$™ acid, N-Fmoc-amido-dPEG$_{12}$™ acid, N-Fmoc-amido-dPEG$_{24}$™ acid, N-CBZ-amido-dPEG$_4$™-acid, N-CBZ-amido-dPEG$_8$™-acid, N-CBZ-amido-dPEG$_{12}$™-acid, N-CBZ-amido-dPEG$_{24}$™-acid, N-t-boc-amido-dPEG$_4$™-acid, and the like.

Non-limiting examples of polymers for use in the present invention also include: polyesters, polyethers, poly(orthoesters), poly(vinyl alcohols), polyamides, polycarbonates, polyacrylamides, polyalkylene glycols, polyalkylene oxides, polyalkylene terephthalates, polyolefins, polyvinyl ethers, polyvinyl esters, polyvinyl halides, polyvinylpyrrolidone, polyglycolides, polysiloxanes, polylactides, polyurethanes, polyethylenes, polyanhydrides, polyhydroxyacids, polypropylfumerates, polycaprolactones, polyacetals, polyurethanes, polyphosphazenes, polyacrylates, polymethacrylates, polycyanoacrylates, polyureas, polystyrenes, polyamines, olefinic polymers, and block- or co-polymers thereof.

Non-limiting examples of biopolymers for use in the present invention include: polyesters such as polyhyroxyalkanoates, polylactic acid and the like; proteins such as silks, collagens, gelatins, elastin, resilin, adhesives, polyamino acids, soy, zein, wheat gluten, casein, serum albumin and the like; polysaccharides such as xanthan, dextran, gellan, levan, curdian, polygalactosamine, cellulose, pullulan, elsinan, yeast glucans, starch, agar, alginate, carrageenan, pectin, konjac, and various gums (e.g. guar), chitin, chitosan, hyaluronic acid, and the like; lipids/surfactants such as acetoglycerides, waxes, emulsions, and the like; polyphenols such as lignin, tannin, humic acid and the like; specialty polymers such as shellac, poly-gamma-glutamic acid, natural rubbers, synthetic rubbers from natural fats, and the like. Also included are chemically modified versions (to enhance solubility/functionality in the drug product formulation, resist digestion/degradation, facilitate chemical modification with antagonist synthons, etc.) of the above biopolymers.

In one aspect of the invention, the polymer is a "charged polymer" wherein the polymer can have one or more charged groups. Charged polymers can include a wide range of species, including polycations and their precursors (e.g., polybases, polysalts, etc.), polyanions and their precursors (e.g., polyacids, polysalts, etc.), polymers having multiple anionic and cationic groups (e.g., polymers having multiple acidic and basic groups such as are found in various proteins), ionomers (charged polymers in which a small but significant proportion of the constitutional units carry charges), and so forth. Typically, the number of charged groups is so large that the polymers are soluble in polar solvents (particularly water) when in ionically dissociated form (also called polyions). Some charged polymers have both anionic and cationic groups (e.g., proteins) and may have a net negative charge (e.g., because the anionic groups contribute more charge than the cationic groups—referred to herein as polyanions), a net positive charge (e.g., because the cationic groups contribute more charge than the anionic groups—referred to herein as polycations), or may have a neutral net charge (e.g., because the cationic groups and anionic groups contribute equal charge). In this regard, the net charge of a particular charged polymer may change with the pH of its surrounding environment. Charged polymers containing both cationic and anionic groups may be categorized herein as either polycations or polyanions, depending on which groups predominate.

Specific examples of suitable polycations may be selected, for instance, from the following: polyamines, including polyamidoamines, poly(amino methacrylates) including poly(dialkylaminoalkyl methacrylates) such as poly(dimethylaminoethyl methacrylate) and poly(diethylaminoethyl methacrylate), polyvinylamines, polyvinylpyridines including quaternary polyvinylpyridines such as poly(N-ethyl-4-vinylpyridine), poly(vinylbenzyltrimethylamines), polyallylamines such as poly(allylamine hydrochloride) (PAH) and poly(diallyidialklylamines) such as poly(diallyidimethylammonium chloride), spermine, spermidine, hexadimethrene bromide(polybrene), polyimines including polyalkyleneimines such as polyethyleneimines, polypropyleneimines and ethoxylated polyethyleneimines, basic peptides and proteins, including histone polypeptides and homopolymer and copolymers containing lysine, arginine, ornithine and combinations thereof including poly-L-lysine, poly-D-lysine, poly-L,D-lysine, poly-L-arginine, poly-D-arginine, poly-D,L-arginine, poly-L-ornithine, poly-D-ornithine, and poly-L,D-ornithine, gelatin, albumin, protamine and protamine sulfate, and polycationic polysaccharides such as cationic starch and chitosan, as well as copolymers, derivatives and combinations of the preceding, among various others. The preferred polymers for use in the invention include poly(d-glutamic acid), poly(dl-glutamic acid), poly(l-aspartic acid), poly(d-aspartic acid), poly(dl-aspartic acid), poly(l-lysine), poly(d-lysine), poly(dl-lysine), and copolymers of the polyamino acids, and the polymers of the N-methyl derivatives of the amino acids. Other preferred polymers include polyethylene glycol (PEG), as well as poly(2-hydroxyethyl 1-glutamine), chitosan, carboxymethyl dextran, hyaluronic acid, human serum albumin and alginic acid.

Specific examples of suitable polyanions may be selected, for instance, from the following: polysulfonates such as polyvinylsulfonates, poly(styrenesulfonates) such as poly(sodium styrenesulfonate) (PSS), sulfonated poly(tetrafluoroethylene), sulfonated polymers such as those described in U.S. Pat. No. 5,840,387, including sulfonated styrene-ethylene/butylene-styrene triblock copolymers, sulfonated styrenic homopolymers and copolymers such as a sulfonated versions of the polystyrene-polyolefin copolymers described in U.S. Pat. No. 6,545,097 to Pinchuk et al., which polymers may be sulfonated, for example, using the processes described in U.S. Pat. Nos. 5,840,387 and 5,468,574, as well as sulfonated versions of various other homopolymers and copolymers, polysulfates such as polyvinylsulfates, sulfated and non-sulfated glycosaminoglycans as well as certain proteoglycans, for example, heparin, heparin sulfate, chondroitin sulfate, keratan sulfate, dermatan sulfate, polycarboxylates such as acrylic acid polymers and salts thereof (e.g., ammonium, potassium, sodium, etc.), for instance, those available from Atofina and Polysciences Inc., methacrylic acid polymers and salts thereof (e.g., EUDRAGIT, a methacrylic acid and ethyl acrylate copolymer), carboxymethylcellulose, carboxymethylamylose and carboxylic acid derivatives of various other polymers, polyanionic peptides and proteins such as glutamic acid polymers and copolymers, aspartic acid polymers and copolymers, polymers and copolymers of uronic acids such as mannuronic acid, galacturonic acid and guluronic acid, and their salts, alginic acid and sodium alginate, hyaluronic acid, gelatin, and carrageenan, polyphosphates such as phosphoric acid derivatives of various polymers, polyphosphonates such as polyvinylphosphonates, polysulfates such as polyvinylsulfates, as well as copolymers, derivatives and combinations of the preceding, among various others.

Non-limiting examples of polysaccharides and biopolymers for use in the present invention include amylose, amylopectin, glycogen, cellulose, hyaluronic acid, chondroitin sulfate, heparin, dextrin, inulin, mannan, chitin, galactose, guar gum, carrageenan, agar, furcellaran, xanthan gum, other hydrocolloid gums, pectic acid and pectin, locust bean gum, acacia, ghatti gum, pentosan, arabinogalactan, alginates and alginate derivatives, gellan, gellan gum, glucose, collagen (and gelatin), cellulose, carboxymethylcellulose, hydroxymethylcellulose, hydroxypropylmethylcellulose, methylcellulose, and methoxycellulose, fibrin, xanthan and xanthan gum, agarose, chitosan (polycationic polysaccharide polymers), albumin, human gamma globulin, pullulan, carrageenan (polyanionic polysaccharide polymers), dextrin, dextran, dextran sulfate, keratin, inulin, dextrose, amylose, glycogen, amylopectin, polylysine and other polyamino acids, and copolymers, graft copolymers, synthetic derivatives, blends and other mixtures of the above.

Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, silks, collagen, elastin, resilin, polyamino acids, soy, wheat gluten, and casein.

Non-limiting examples of polyesters include polylactic acid, polyglycolic acid, poly(lactide-co-glycolide), poly(e-caprolactone), polydioxanone, poly(ethylene terephthalate), poly(malic acid), poly(tartronic acid), polyphosphazenes, poly(orthoester), poly(valeric acid), poly(buteric acid), polyhydroxybutyrate, polyhydroxyvalerate, polyanhydride, and copolymers of the monomers used to synthesize any of the above-mentioned polymers, e.g., poly(lactic-co-glycolic acid) (PLGA) or the copolymer of polyhydroxy butyrate with hydroxyvaleric acid.

Polyethers and poly(orthoesters) can also be used in preparing the polymer conjugate for use in the present invention. These polymers can be incorporated into multi-blocks resulting in block polymers having diverse degradation rates, mechanical strengths, porosities, diffusivities, and inherent viscosities. Examples of polyethers include polyethylene glycol and polypropylene glycol. An example of a multi-block copolymer is poly(ether ester amide). Additionally, tri-block copolymers of poly(orthoesters) with various poly(ethylene glycol) contents are useful for their stability in water/oil (w/o) emulsions. Other useful block copolymers include diblock copolymers of poly (lactic-co-glycolic acid) and poly(ethylene glycol) (PEG), triblock copolymers of PEG-PLGA-PEG, copolymers of PLGA and polylysine, and poly (ester ether) block copolymers.

In one aspect of the invention, the polymer is poly (ethylene glycol) (PEG) or a related poly(alkylene glycol). The term PEG includes poly(ethylene glycol) in any its forms, including linear forms (e.g., alkoxy PEG or bifunctional PEG), branched or multi-arm forms (e.g., forked PEG or PEG attached to a polyol core), pendant PEG, and the like. The general formula of PEG is —$CH_2CH_2O$—($CH_2CH_2O)_n$—$CH_2CH_2$— wherein n is from about 0 to about 500, typically from about 2 to about 200. Similar polymers can also be derived from polypropylene glycol and related poly(alkylene) glycols.

Multi-armed or branched PEG molecules, such as those described in U.S. Pat. No. 5,932,462 can also be used as the PEG polymer. Generally speaking, a multi-armed, branched, or star or dendrimeric polymers possess two or more polymer arms extending from a central branch point that is covalently attached, either directly or indirectly via intervening connecting atoms, to one or more active moieties such as an opioid agonist, antagonist, or digestive enzyme inhibitor. It is understood by those skilled in the art that the term poly(ethylene glycol) or PEG represents or includes all the above forms of PEG or poly(alkylene glycols).

GI Enzyme Inhibitors

The disclosure provides for a compositions comprising a gastrointestinal enzyme inhibitor (I). Such an inhibitor can inhibit at least one of any of the GI enzymes disclosed herein. The GI enzyme can be, for example, pepsin, trypsin, chymotrypsin, colipase, elastase, aminopeptidases, dipeptidylaminopeptidase IV, tripeptidase, enteropeptidases, carboxypeptidases, dipeptidal aminopeptidases, pteroyl polyglutamate hydrolyase, gamma-glutamyl transferase, aminoaspartate aminopeptidases, amino-oligopeptidase, membrane Gly-Leu peptidase, and zinc stable Asp-Lys peptidase).

An example of a GI enzyme inhibitor is a protease inhibitor, such as a trypsin inhibitor, or a chymotrypsin inhibitor.

As used herein, the term "trypsin inhibitor" refers to any agent capable of inhibiting the action of trypsin on a substrate, and includes prodrugs and salts of trypsin inhibitors. The inhibitor may be a small molecule, or a macromolecule designed to not be absorbed from the gastrointestinal tract following ingestion. The ability of an agent to inhibit trypsin can be measured using assays well known in the art. For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241, 3955 and Y. Birk, 1976, Meth. Enzymol. 45, 700. In certain instances, a trypsin inhibitor can interact with an active site of trypsin, such as the 51 pocket and the S3/4 pocket. The 51 pocket has an aspartate residue which has affinity for a positively charged moiety. The S3/4 pocket is a hydrophobic pocket. The disclosure provides for specific trypsin inhibitors and non-specific serine protease inhibitors.

There are many trypsin inhibitors known in the art, and include inhibitors that are specific to trypsin and those that inhibit trypsin and other proteases such as chymotrypsin. The disclosure provides for trypsin inhibitors that are proteins, peptides, and small molecules. The disclosure provides for trypsin inhibitors that are irreversible inhibitors, inverse substrates, or reversible inhibitors. The disclosure provides for trypsin inhibitors that are competitive inhibitors, non-competitive inhibitors, or uncompetitive inhibitors. The disclosure provides for natural, synthetic or semi-synthetic trypsin inhibitors. The disclosure also provides for salts of natural, synthetic or semi-synthetic trypsin inhibitors.

Trypsin inhibitors can be derived from a variety of animal or vegetable sources: for example, soybean, corn, lima and other beans, squash, sunflower, bovine and other animal pancreas and lung, chicken and turkey egg white, soy-based infant formula, and mammalian blood. Trypsin inhibitors can also be of microbial origin: for example, antipain; see, for example, H. Umezawa, 1976, Meth. Enzymol. 45, 678.

In one aspect of the invention, the trypsin inhibitor is derived from soybean. Trypsin inhibitors derived from soybean (*Glycine max*) are readily available and are considered to be safe for human consumption. They include, but are not limited to, SBTI, which inhibits trypsin, and Bowman-Birk inhibitor, which inhibits trypsin and chymotrypsin. Such trypsin inhibitors are available, for example from Sigma-Aldrich, St. Louis, Mo., USA.

A trypsin inhibitor can be an arginine mimic or lysine mimic, either natural or synthetic compound. In certain embodiments, the trypsin inhibitor is an arginine mimic or a lysine mimic, wherein the arginine mimic or lysine mimic is a synthetic compound. As used herein, an arginine mimic or lysine mimic can include a compound capable of binding to the 51 pocket of trypsin and/or interfering with trypsin active site function. The arginine or lysine mimic can be a cleavable or non-cleavable substrate.

Examples of trypsin inhibitors, which are arginine mimics and/or lysine mimics, include, but not limited to, arylguanidines, benzamidines, 3,4-dichloroisocoumarin, diisopropylfluorophosphate, benzyl amines, gabexate mesylate, and phenylmethanesulfonyl fluoride, or substituted versions or analogs thereof. In certain embodiments, trypsin inhibitors comprise a covalently modifiable group, such as a chloroketone moiety, an aldehyde moiety, or an epoxide moiety. Other examples of trypsin inhibitors are 4-amidinophenylpyruvate (p-APPA), 3-amidinophenyl-pyruvate (m-APPA), aprotinin, or pentamidine.

Proteases can be inhibited by naturally occurring peptide or protein inhibitors, or by naturally occurring small molecule, or synthetic, inhibitors. Examples of protein or peptide inhibitors that are protease inhibitors include, but are not limited to, A1-anti-trypsin from human plasma, aprotinin, trypsin inhibitor from soybean (SBTI), Bowman-Birk Inhibitor from soybean (BBSI), trypsin inhibitor from egg white (ovomucoid), chromostatin, and potato-derived carboxypeptidase inhibitor. Examples of small molecule irreversible inhibitors that are protease inhibitors include, but are not limited to, TPCK (1-chloro-3-tosylamido-4-phenyl-2-butanone), TLCK(1-chloro-3-tosylamido-7-amino-2-heptone), and PMSF (phenylmethyl sulfonyl fluoride). Examples of small molecule inhibitors that are protease inhibitors include, but are not limited to benzamidine, apixaban, camostat, 3,4 dichloroisocoumarin, E-aminocaprionic acid, amastatin, lysianadioic acid, 1,10-phenanthroline, cysteamine, and bestatin. Other examples of small molecule inhibitors are Compound I-1, Compound I-2, Compound I-3, Compound I-4, Compound I-5, Compound I-6, Compound I-7, Compound I-8, Compound I-9 and Compound I-10, Compound I-11, Compound I-12, or Compound I-13. The following table shows examples of gastrointestinal (GI) proteases, examples of their corresponding substrate specificities, and examples of corresponding inhibitors.

TABLE 1

Table of GI Enzymes, Corresponding Substrate Specificities, and Inhibitors

| GI Enzyme | Substrate specificities | Inhibitors |
| --- | --- | --- |
| Trypsin | Arg, Lys, positively charged residues | TLCK, Benzamidine, Bowman-Birk, SBTI |
| Chymotrypsin | Phe, Tyr, Trp, bulky hydrophobic residues | ☐-Aminocaprionic TPCK, Bowman-Birk |
| Pepsin | Leu, Phe, Trp, Tyr | Pepstatin, PMSF |
| Carboxypeptidase A | Not Arg, Lys | Potato-derived inhibitor, 1,10-phenanthroline |
| Carboxypeptidase B | Arg, Lys | Potato-derived inhibitor, Lysianadioic acid, |
| Elastase | Ala, Gly, Ser, small neutral residues | A1-antitrypsin, 3,4-dichlorocoumarin |
| Aminopeptidase | Free N-terminal Amino Acid residues | Bestatin, Amastatin |

Examples of trypsin inhibitors, which are arginine mimics and/or lysine mimics, include, but not limited to, arylguanidine, benzamidine, 3,4-dichloroisocoumarin, diisopropylfluorophosphate, gabexate mesylate, and phenyl-methanesulfonyl fluoride, or substituted versions or analogs thereof. In certain embodiments, trypsin inhibitors comprise a covalently modifiable group, such as a chloroketone moiety, an aldehyde moiety, or an epoxide moiety. Other examples of trypsin inhibitors are aprotinin, nafamostat, camostat and pentamidine.

Other examples of trypsin inhibitors include compounds of formula:

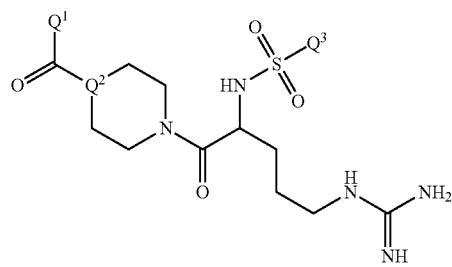

Wherein: $Q^1$ is selected from —O-$Q^4$ or -$Q^4$-$CO_2H$, where $Q^4$ is $C_1$-$C_4$ alkyl; $Q^2$ is N or CH; and $Q^3$ is aryl or substituted aryl.

Other examples of trypsin inhibitors include compounds of formula:

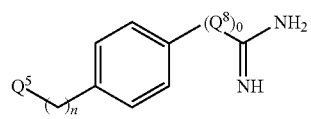

Wherein: $Q^5$ is —C(O)—$CO_2H$ or —NH-$Q^6$-$Q^7$-SO2-Aryl, where $Q^6$ is —$(CH_2)_p$—$CO_2H$; $Q^7$ is —$(CH_2)_r$—$C_6H_5$; $Q^8$ is NH; n is a number from zero to two; o is zero or one; p is an integer from one to three; and r is an integer from one to three.

Other examples of trypsin inhibitors include compounds of formula:

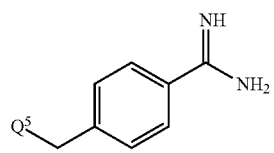

Wherein: $Q^5$ is —C(O)—$CO_2H$ or —NH-$Q^6$-$Q^7$-$SO_2$-Aryl, where $Q^6$ is —$(CH_2)_p$—$CO_2H$; $Q^7$ is —$(CH_2)_r$—$CO_2H$; p is an integer from one to three; r is an integer from one to three.

Other examples of trypsin inhibitors include compounds of formula:

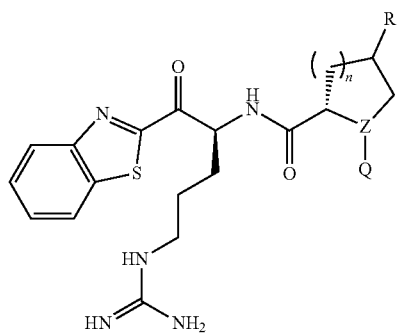

Wherein: Q is acetyl, —$S(O)_2$-Me, Benzyl, hydrogen or alkyl, or amino acid(s); R is —OH, =O, or hydrogen, and n is an integer from zero to 2.

Other examples of trypsin inhibitors include compounds of formulae:

Compound I-1
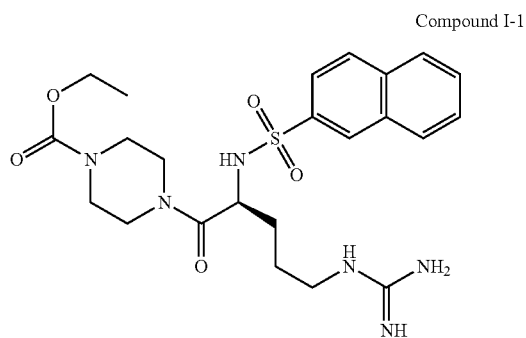
Compound I-2
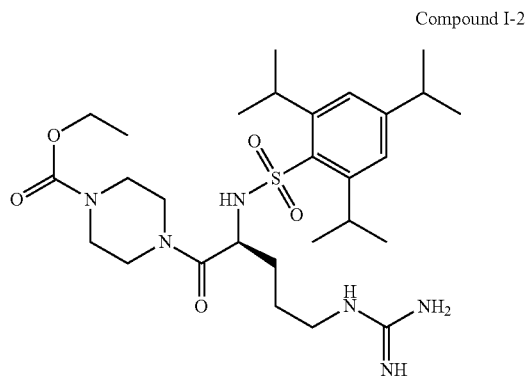
Compouund I-3
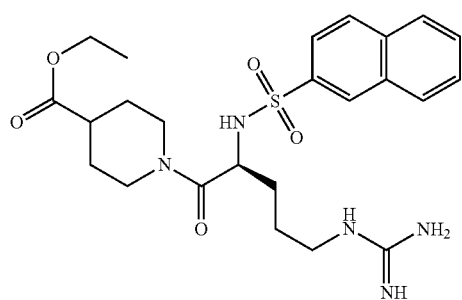
Compound I-4
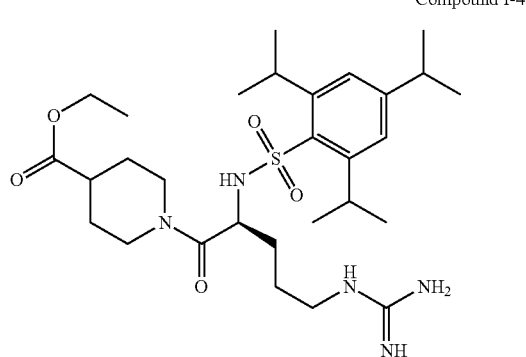
Compound I-5
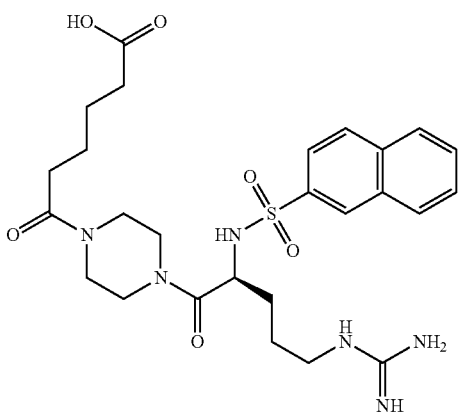
Compound I-6
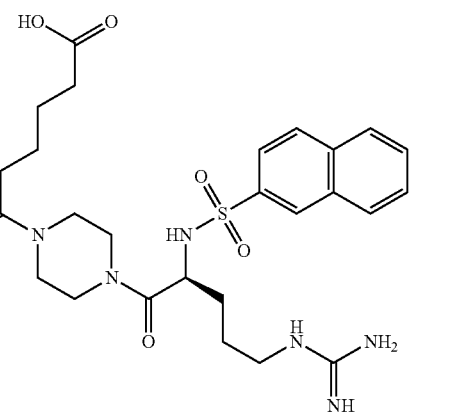
Compound I-7
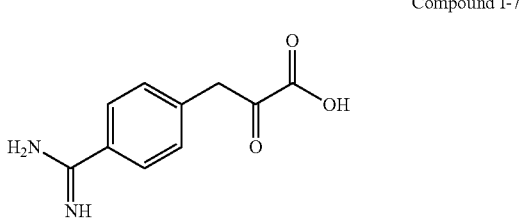
Compound I-8
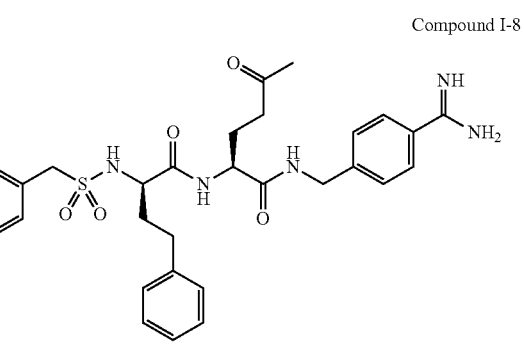
Compound I-9
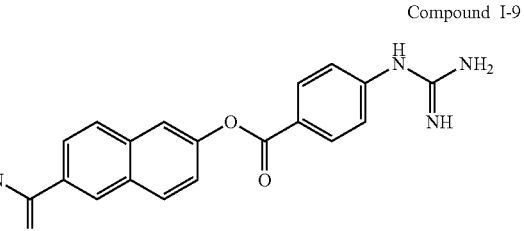
Compound I-10
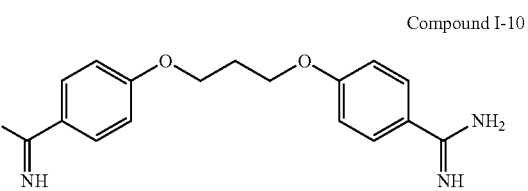

-continued

Compound I-11

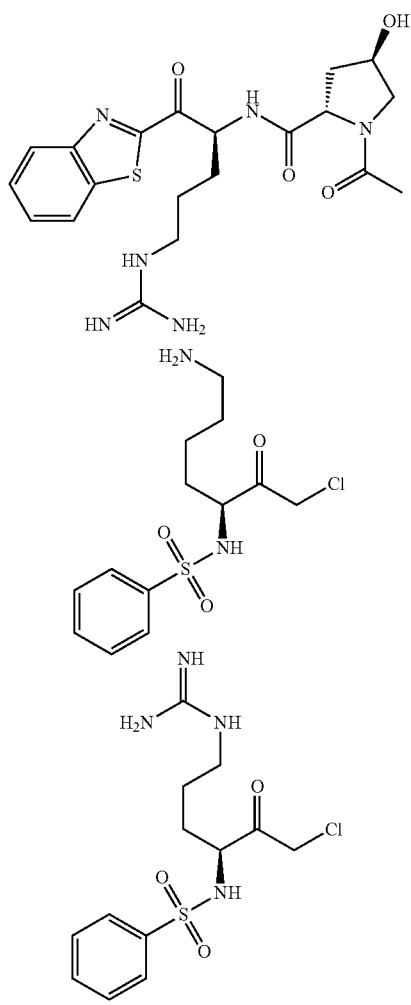

Compound I-12

Compound I-13

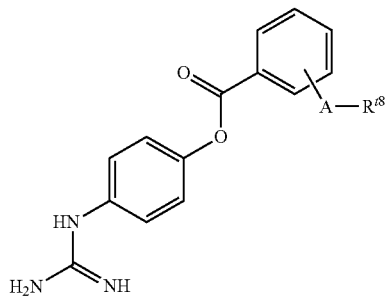

A description of methods to prepare Compound I-1, Compound I-2, Compound I-3, Compound I-4, Compound I-5, Compound I-7, and Compound I-8 is provided in PCT International Publication Number WO 2010/045599A1, published 22 Apr. 2010, which is hereby incorporated by reference in its entirety. The synthesis used to make compound I-11 is provided in J. Med. Chem. 2003, Vol. 46, No. 18, 3865. Compounds I-6, I-7, I-9, I-10, I-12, and I-13 can be obtained commercially (Sigma-Aldrich, St. Louis, Mo., USA.). In certain embodiments, the trypsin inhibitor is SBTI, BBSI, Compound I-1, Compound I-6, Compound I-8, Compound I-9, or Compound I-10. In certain embodiments, the trypsin inhibitor is camostat.

In some embodiments the trypsin inhibitor is:

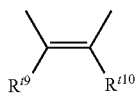

Wherein A represents a group of the following formula:

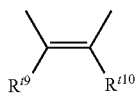

where $R^{r9}$ and $R^{r10}$ each represent independently a hydrogen atom or $C_{1-4}$ alkyl group; $R^{r8}$ represents a group from the following formulae:

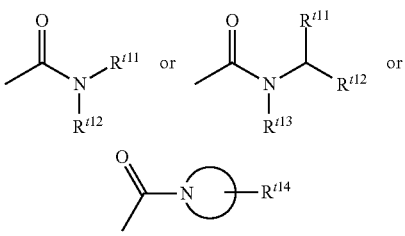

wherein each $R^{r11}$, $R^{r12}$, and $R^{r13}$ each represent independently a hydrogen atom, a phenyl group, a $C_{1-4}$ alkyl group substituted by a phenyl group, a $C_{1-10}$ alkyl group, a $C_{1-10}$ alkoxyl group, a $C_{1-10}$ alkenyl group having one to three double bonds, a $C_{1-10}$ alkynyl group having one to two triple bonds, a group of formula $R^{r15}$—C(O)$XR^{r16}$, wherein $R^{r15}$ represents a single bond or a $C_{1-8}$ alkylene group, X represents an oxygen atom or a NH— group, and $R^{r16}$ represents a hydrogen atom, a $C_{1-4}$ alkyl group substituted by a phenyl group, or a $C_{3-7}$ cycloalkyl group represented by

with the structure representing a 4-7 membered monocyclic heterocycle containing 1 to 2 nitrogen atoms; $R^{r14}$ represents a hydrogen atom, a $C_{1-4}$ alkyl group substituted by a phenyl group provided that $R^{r11}$, $R^{r12}$, and $R^{r13}$ do not simultaneously represent hydrogen atoms, or non-toxic salts, addition acid salts, hydrates, or solvates thereof.

In certain embodiments, the trypsin inhibitor is a compound selected from the following:

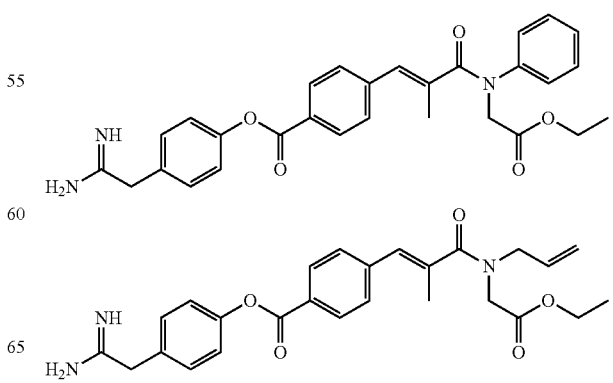

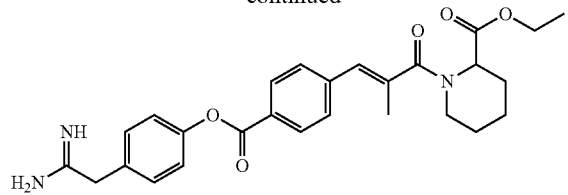

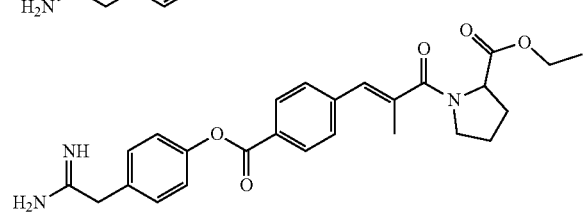

In other embodiments, the trypsin inhibitor is of the formula:

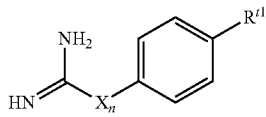

Wherein: X is NH; n is zero or one; and $R^{t1}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —$(CH_2)_m$—C(O)—O—$(CH_2)_m$—C(O)—N—$R^{n1}R^{n2}$, wherein each m is independently zero to 2; and $R^{n1}$ and $R^{n2}$ are independently selected from hydrogen and $C_{1-4}$ alkyl. In certain embodiments, in $R^{t1}$ is guanidino or amidino. In certain embodiments, $R^{t1}$ is —$(CH_2)_m$—C(O)—O—$(cH_2)_m$—C(O)—N—$R^{n1}R^{n2}$ wherein m is one and $R^{n1}$ and $R^{n2}$ are methyl.

In other embodiments, the trypsin inhibitor is of the formula:

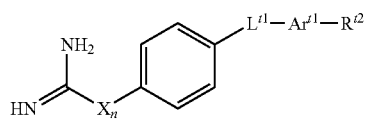

Wherein: X is NH, n is zero or one, $L^{t1}$ is selected from —C(O)—O—; —OC(O)—; O—$(CH_2)_m$—O—; —C(O)—$NR^{t3}$—; —$NR^{t3}$—C(O)—; $R^{t3}$ is selected from hydrogen, $C_{1-6}$ alkyl, and substituted $C_{1-6}$ alkyl; $Ar^{t1}$ and $Ar^{t2}$ are independently a substituted or unsubstituted aryl group; m is a number from 1 to 3; and $R^{t2}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano, and —$(CH_2)_m$—C(O)—O—$(CH_2)_m$—C(O)—N—$R^{n1}R^{n2}$, wherein each m is independently zero to 2; and $R^{n1}$ and $R^{n2}$ are independently selected from hydrogen and $C_{1-4}$ alkyl.

In certain embodiments, $R^{t2}$ is guanidine or amidino.

In certain embodiments $R^{t2}$ is —$(CH_2)_m$—C(O)—O—$(CH_2)_m$—C(O)—N—$R^{n1}R^{n2}$, wherein m is one and $R^{n1}$ and $R^{n2}$ are methyl.

In certain embodiments, the trypsin inhibitor is a compound of formula:

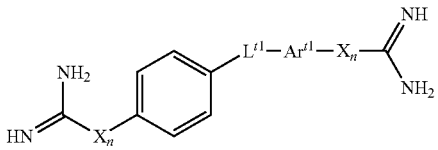

wherein each X is NH; each n is independently zero or one; $L'1$ is selected from —C(O)—O—; —O—C(O)—, —O—$(CH_2)_m$—O—, —$OCH_2$—$Ar^{t2}$—$CH_2$—O—, —C(O)—$NR^{t3}$—; —$NR^{t3}$—C(O)—; $R^{t3}$ is selected from hydrogen, $C_{1-6}$ alkyl, and substituted $C_{1-6}$ alkyl; $Ar^{t1}$ and $Ar^{t2}$ are independently a substituted or unsubstituted aryl group, and m is an integer from 1 to 3. In certain embodiments $Ar^{t1}$ or $Ar^{t2}$ is phenyl. In other embodiments $Ar^{t1}$ or $Ar^{t2}$ is naphthyl.

In certain embodiments the trypsin inhibitor is compound I-9.

In certain embodiments the trypsin inhibitor is:

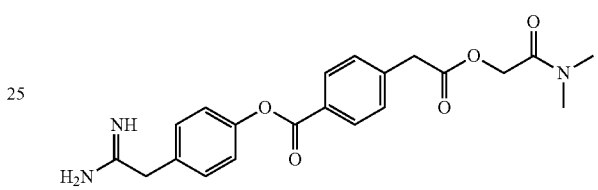

In certain embodiments the trypsin inhibitor is compound I-10 or a bis-arylamidine variant thereof (see, for example J. D. Geratz, M. C.-F. Cheng and R. R. Tidwell (1976) J. Med. Chem. 19, 634-639.

It will be appreciated that the pharmaceutical composition according to the embodiments may further comprise one or more additional trypsin inhibitors.

It is to be appreciated that the invention also includes inhibitors of other enzymes involved in protein assimilation that can be used in combination with a prodrug disclosed herein comprising an amino acid of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine or amino acid variants or mimics thereof.

In another aspect of the invention, the GI enzyme inhibitor can be covalently attached to a macromolecular entity (i.e. polymer). Without limitation, the inhibitor and the polymer can be conjoined via ester, thioester, amide, amine, carbamate, carbonate, ether, thioether, and urea linkages, and the like. The particular linkage and linkage chemistry employed are intended to be of very broad scope and can be readily determined by one skilled in the art based upon the guidance presented herein and will depend upon the subject inhibitor, functional groups within the molecules available either for attachment to a polymer or conversion to a suitable attachment site, and the presence of additional functional groups within the inhibitor molecule. The effects of the attachment of a macromolecular entity, such as the polymers described herein, to trypsin inhibitors on the desired trypsin inhibitory properties can be evaluated using in vitro assays well known to the skilled artisan. Particular examples of trypsin inhibitors attached to polymers are disclosed herein.

The macromolecular GI enzyme inhibitors of the invention preferably have inhibitory activity against the target GI enzyme. Thus, in one aspect of the invention, a macromolecular GI enzyme inhibitor in accordance with the invention will retain from about 30% to about 100% of the specific activity of the unmodified small-molecule parent inhibitor. Such activity may be determined using suitable in-vivo, or in-vitro assays, depending upon the known activity of the particular inhibitor. Thus, an inhibitor-polymer conjugate of the invention will possess a specific activity of about 30%, 40%, 50%, 60%, 70%, 75%, 80%, 85%, 90%, 95%, or 100% relative to that of the unmodified small molecule parent inhibitor, when measured in a suitable assay, such as those well known in the art.

In another aspect of the invention, the macromolecular GI enzyme inhibitors of the invention are not required to be absorbed from the GI tract, and preferably are not absorbed from the GI tract following oral ingestion. Thus, in one aspect of the invention, macromolecular GI enzyme inhibitors in accordance with the invention will demonstrate only about 0% to about 30% absorption from the GI tract into the systemic circulation. Absorption from the GI can be evaluated using suitable in-vivo or in-vitro assays. Thus, an inhibitor-polymer conjugates or the IS-polymer conjugates of the invention will possess GI absorption percentages of about 0%, 0.25%, 0.5%, 0.75%, 1% 2%, 5%, 10%, 15%, 25%, or 30%, when measured in a suitable assay, such as those well known in the art.

In some cases, the disclosure provides a macromolecule of formula:

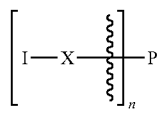

wherein:

I is a gastrointestinal enzyme inhibitor;

X is a linker group that covalently joins I to a polymer;

P is a polymer; and n is an integer between 1 and 1000, wherein P is selected to provide fewer than 0.25%, fewer than 0.5%, fewer than 0.75%, fewer than 1%, fewer than 2%, fewer than 5%, fewer than 10%, fewer than 15%, fewer than 25%, or fewer than 30% of absorption of the macromolecule from the gastrointestinal tract of a subject following oral administration.

In one aspect of the invention, the macromolecular GI inhibitor is represented by the formula below:

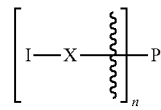

where I is the inhibitor; X is a "linker" that links the inhibitor to a polymer P, and n is an integer between 1 and 1000. The polymer P can be any of the polymers described above, such as, for example, PEG, polypeptides, polysaccharides and biopolymers and the like.

The inhibitor can be derived from amidinophenylpyruvate (APPA) including, but not limited to:

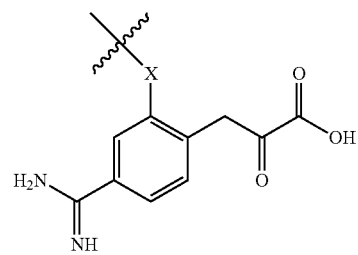

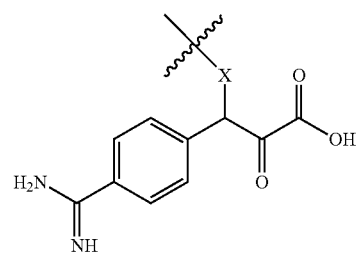

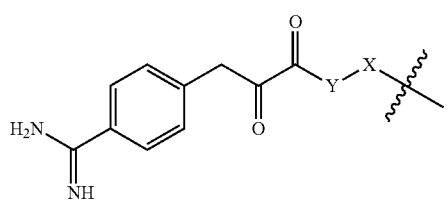

where Y can be O, NH, NR or S; X is as defined above, and it links APPA to another moiety, such as a polymer. For example, APPA can be attached to a polymer as shown in the non-limiting examples below:

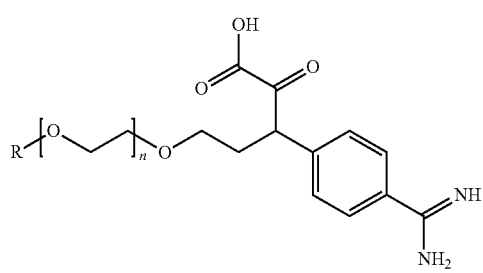

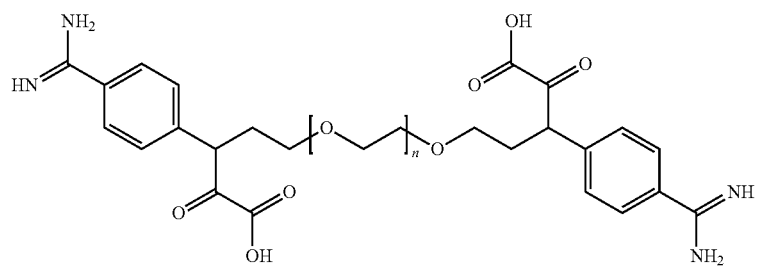
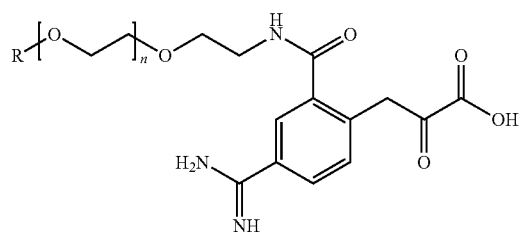
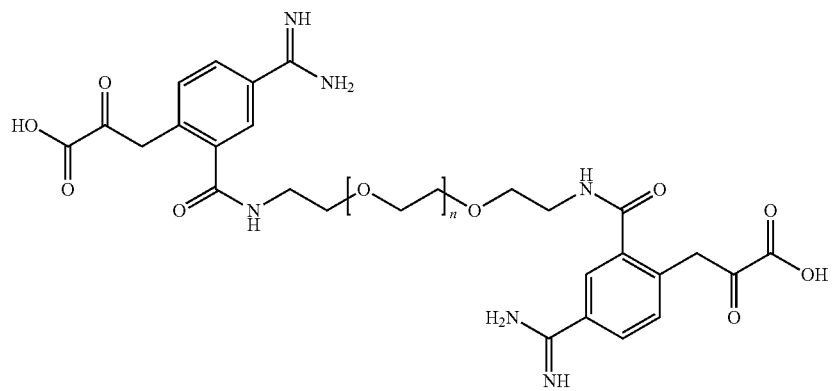
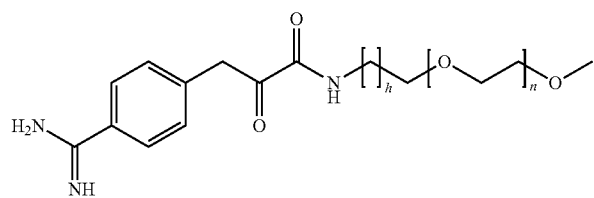
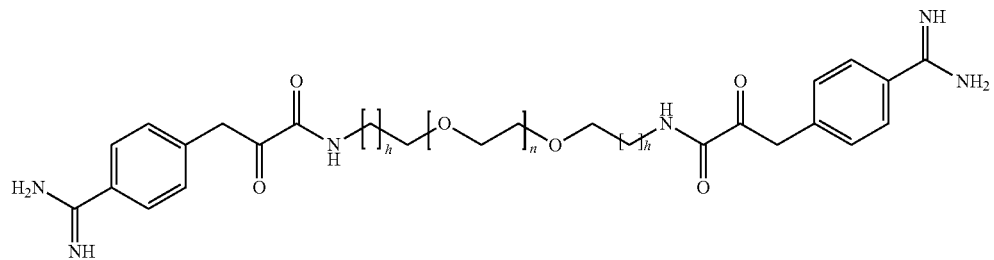

-continued
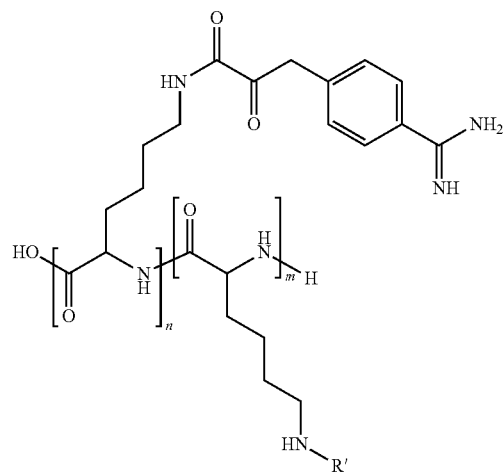
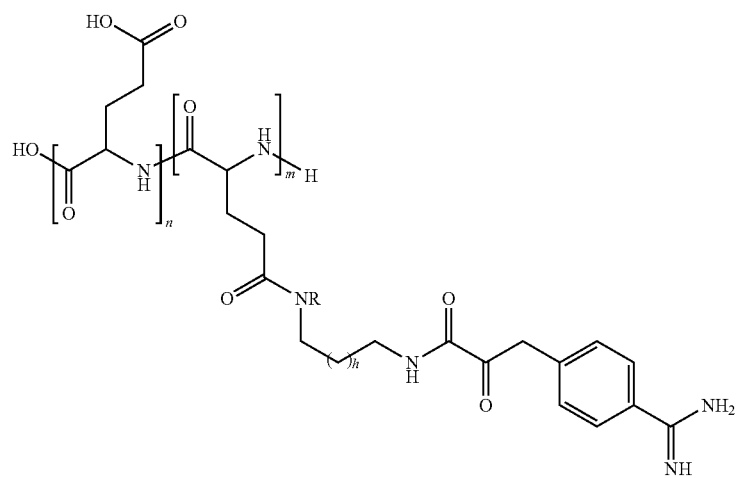
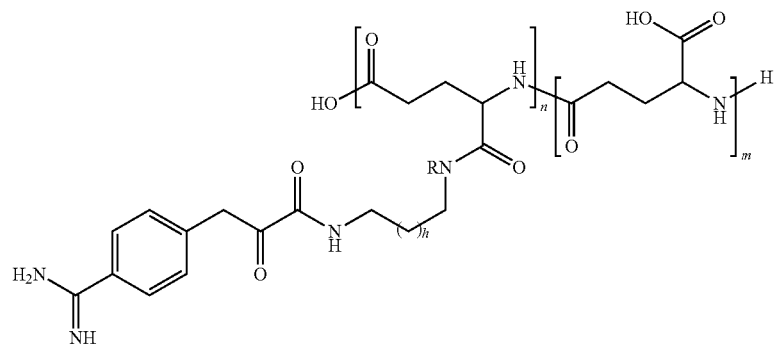

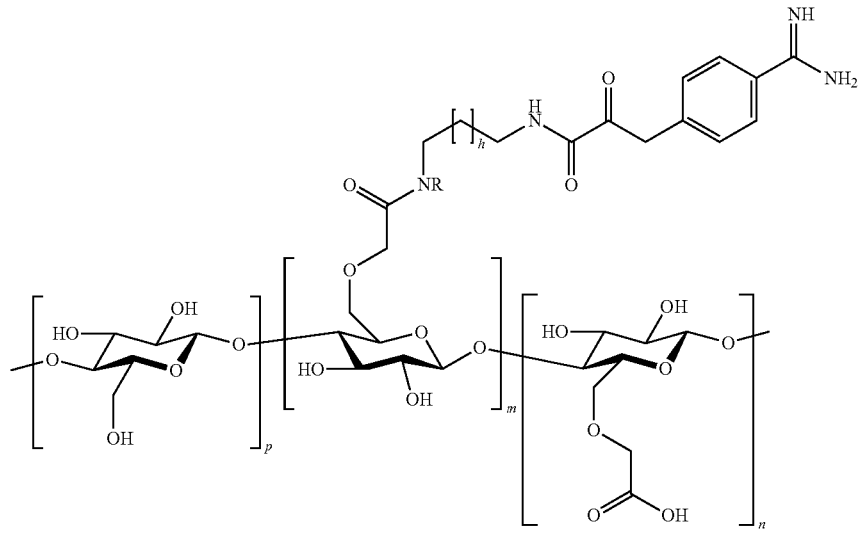

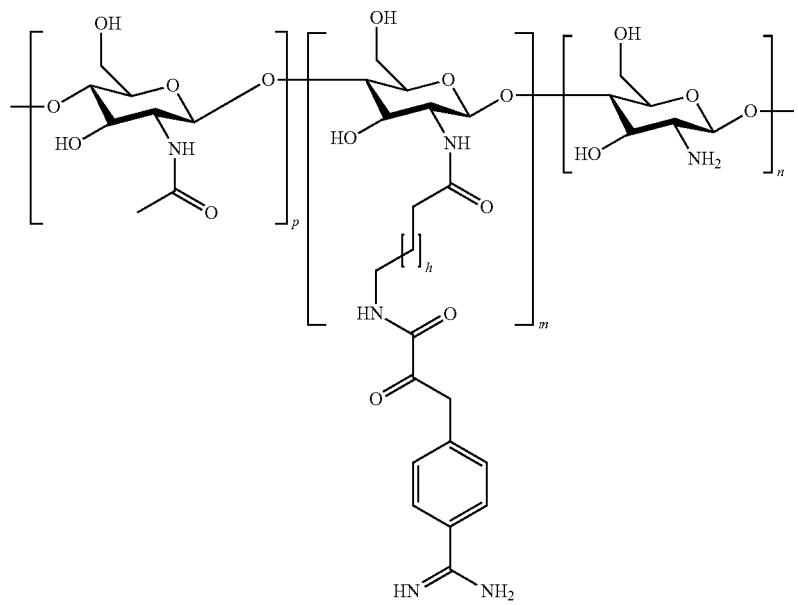

Where n, m, and p can independently be an integer from zero to 1,000; h represents a number of substituted or unsubstituted methylene units and can be an integer from zero to ten. R is independently hydrogen, methyl, ethyl, substituted alkyl, or substituted aryl. Each R' can independently be hydrogen, methyl, ethyl, substituted alkyl, or substituted aryl, acyl, or substituted acyl.

In another aspect of the invention, the inhibitor can be derived from an activated ketone derivative, including, but not limited to the following:

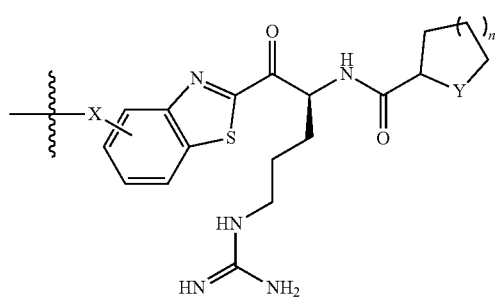

51
-continued
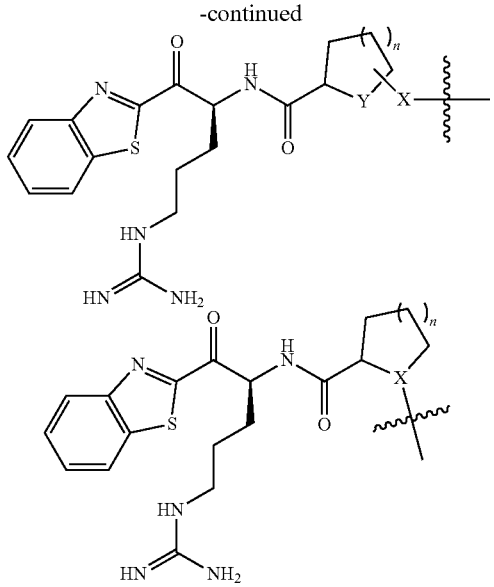
52
-continued
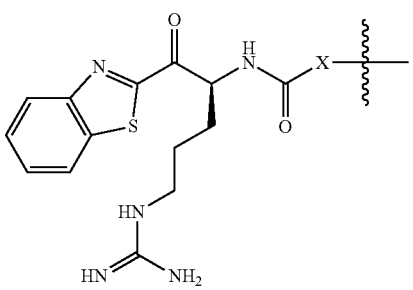
and can include lysine-mimic or arginine mimic side-chain variants. For example, an activated ketone derivative inhibitor can be attached to a polymer as shown in the non-limiting examples below:
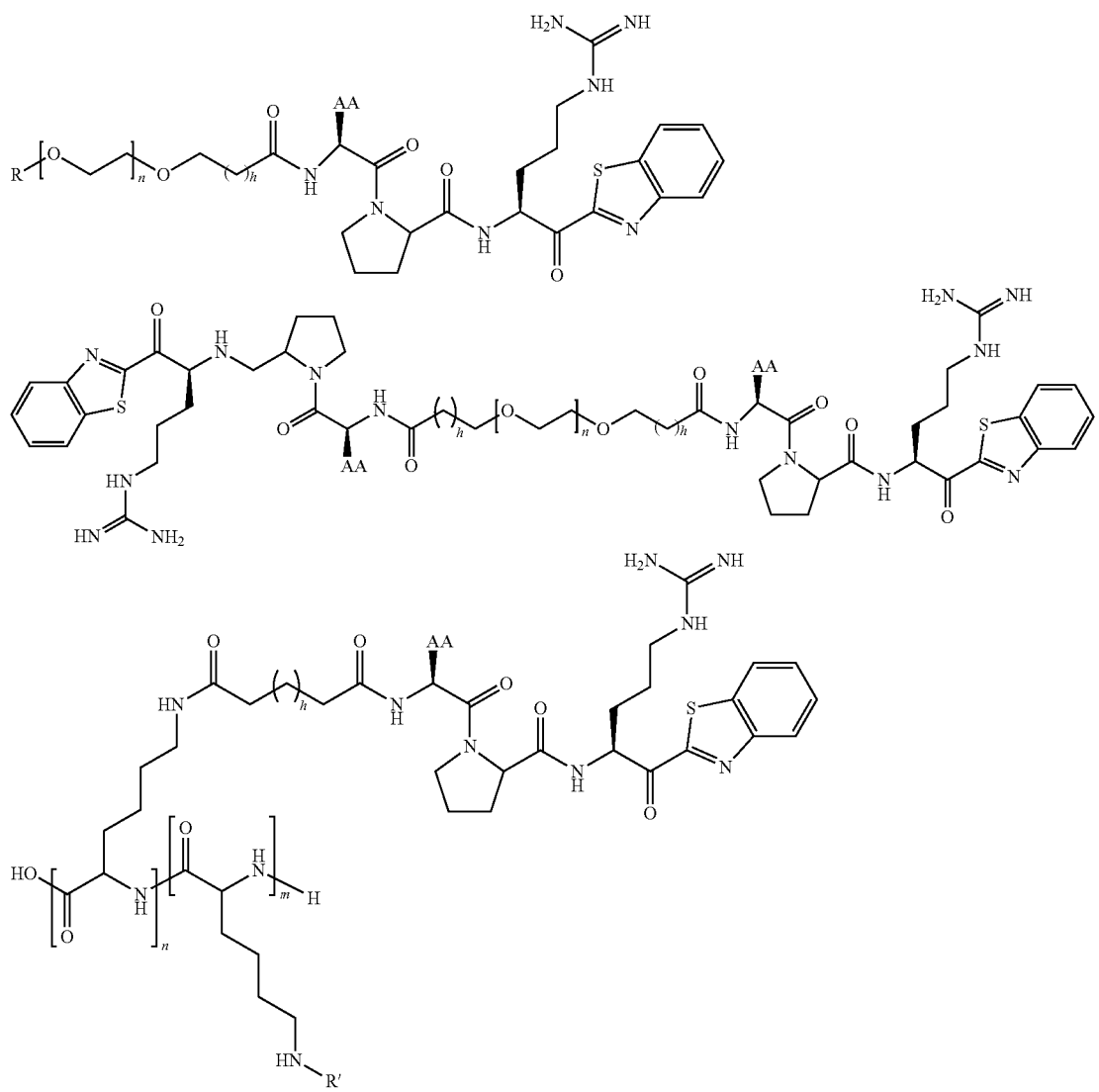

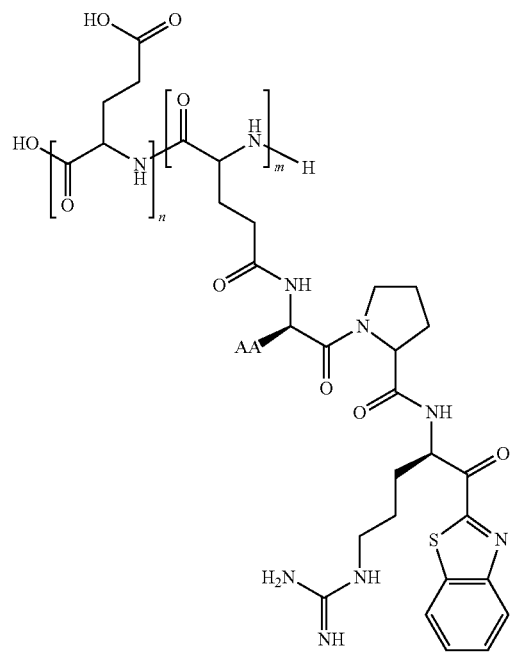
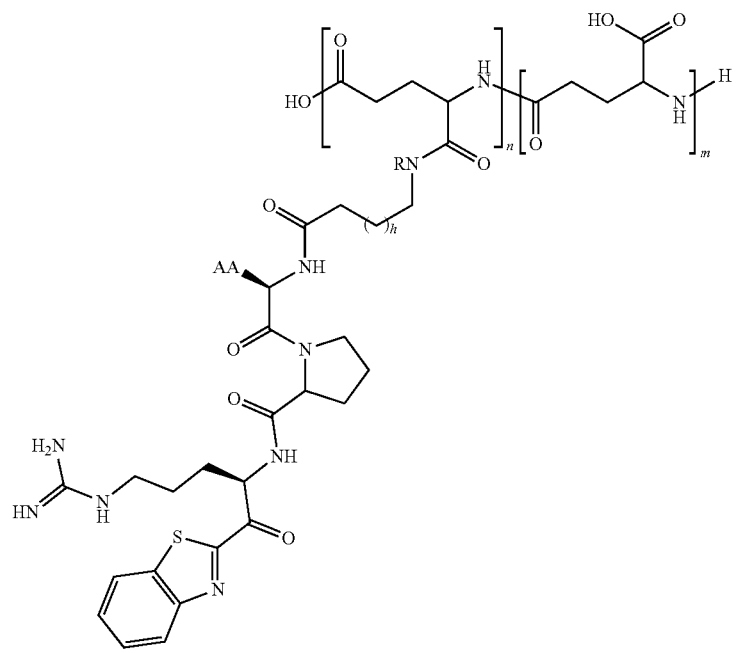

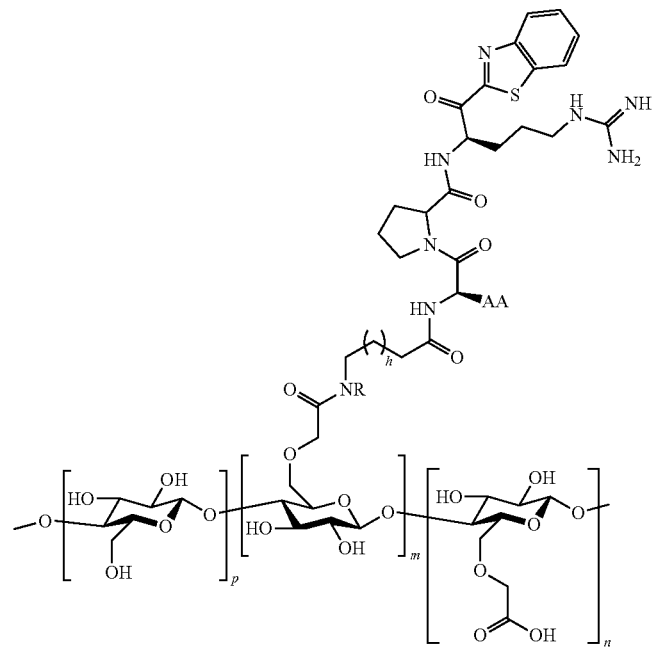
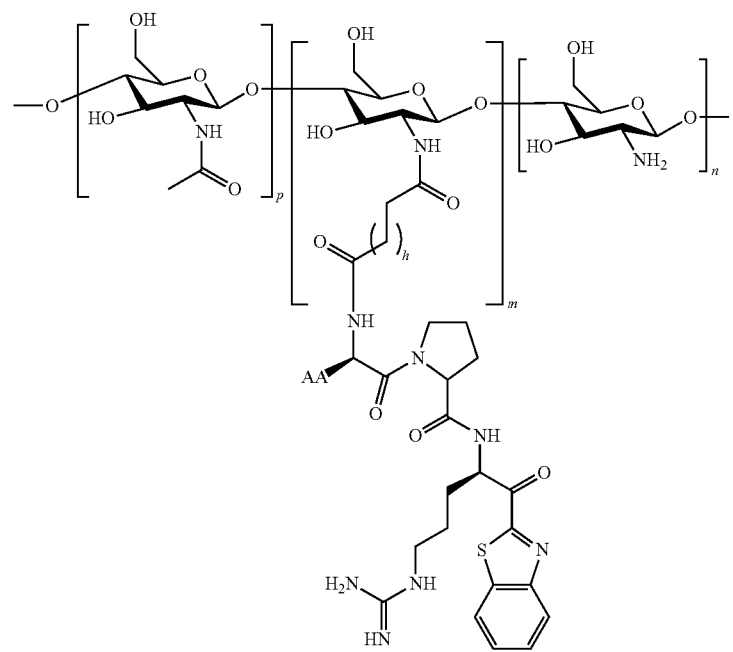

Where n, m and p can independently be an integer from zero to 1,000; h represents a number of substituted or unsubstituted methylene units and can be an integer from zero to ten. R is independently hydrogen, methyl, ethyl, substituted alkyl, or substituted aryl. Each R' can independently be hydrogen, methyl, ethyl, substituted alkyl, or substituted aryl, acetyl, acyl, or substituted acyl; AA is a natural or unnatural amino-acid side-chain as defined herein.

In another aspect of the invention, the inhibitor can be derived from chloroketone analogs as shown below:

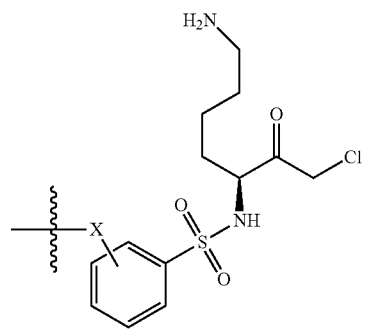

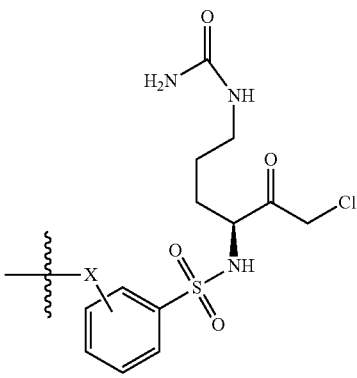

The chloroketone analogs can also include lysine-mimic or arginine mimic side-chain variants. Non-limiting examples of chloroketone analog inhibitors attached to a polymer are shown below:

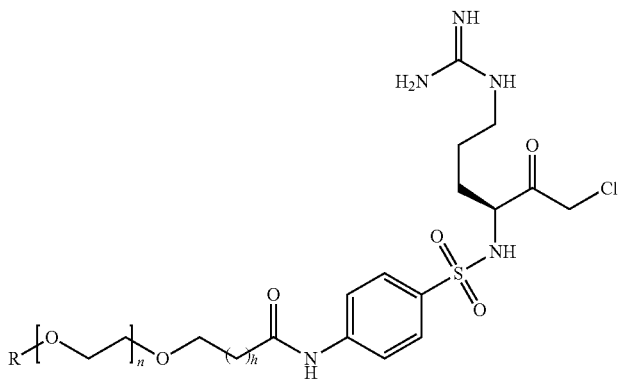

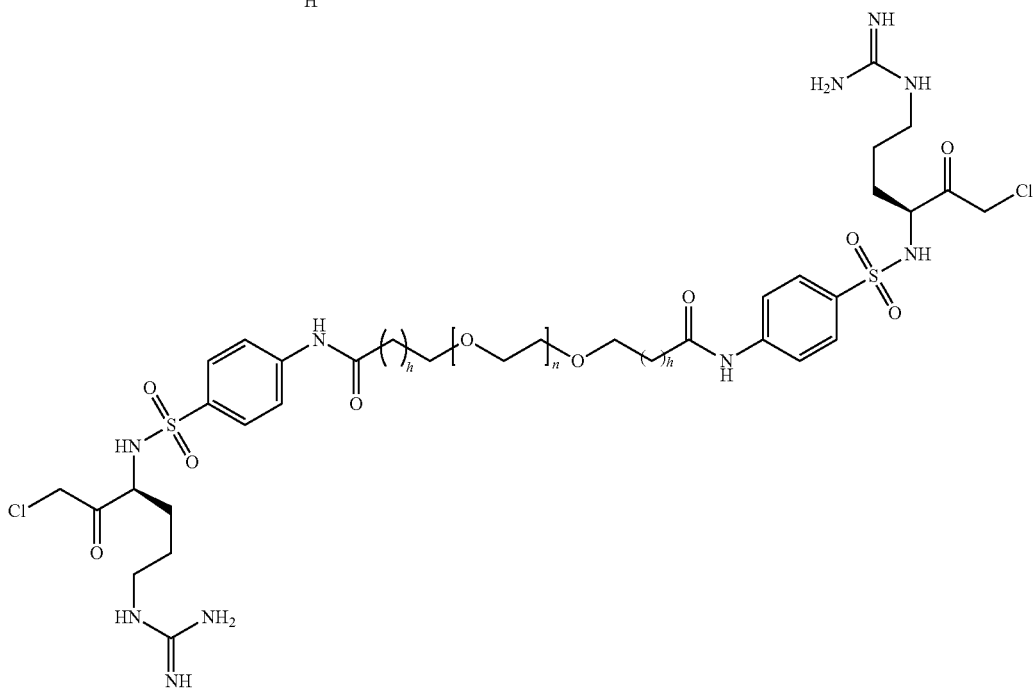

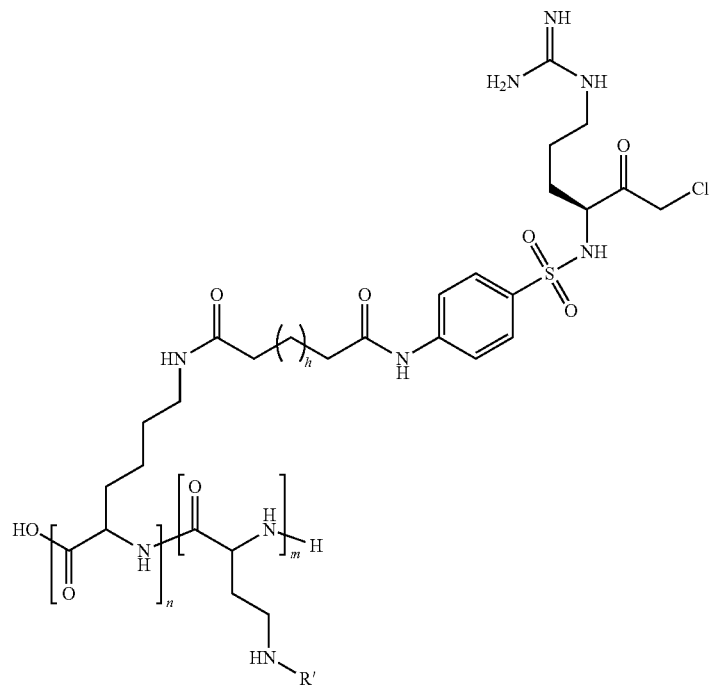
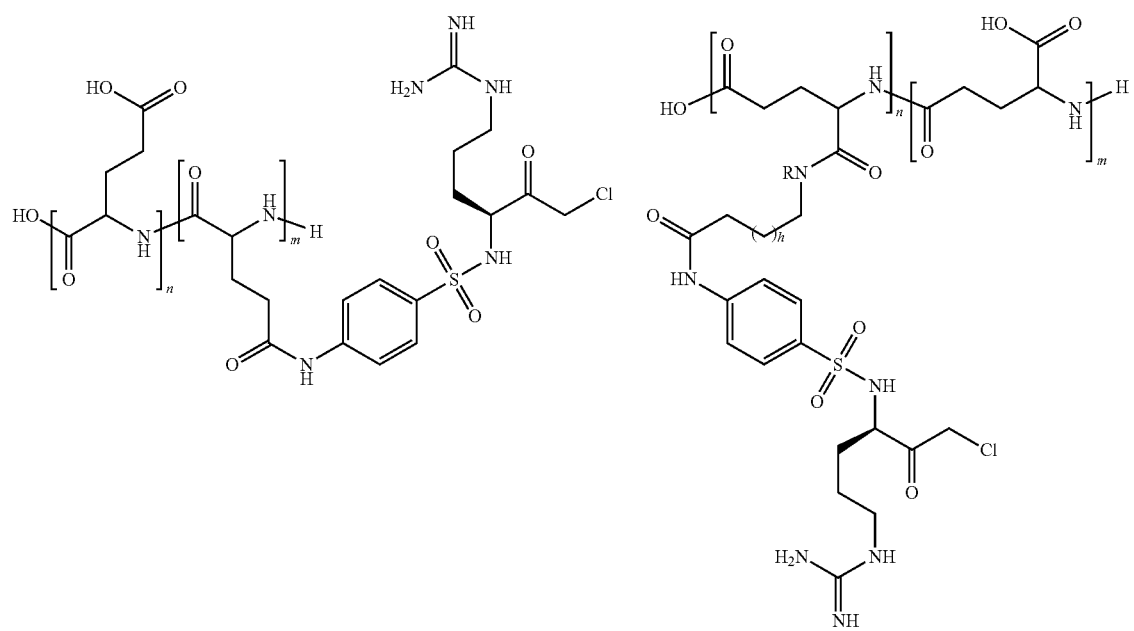

-continued

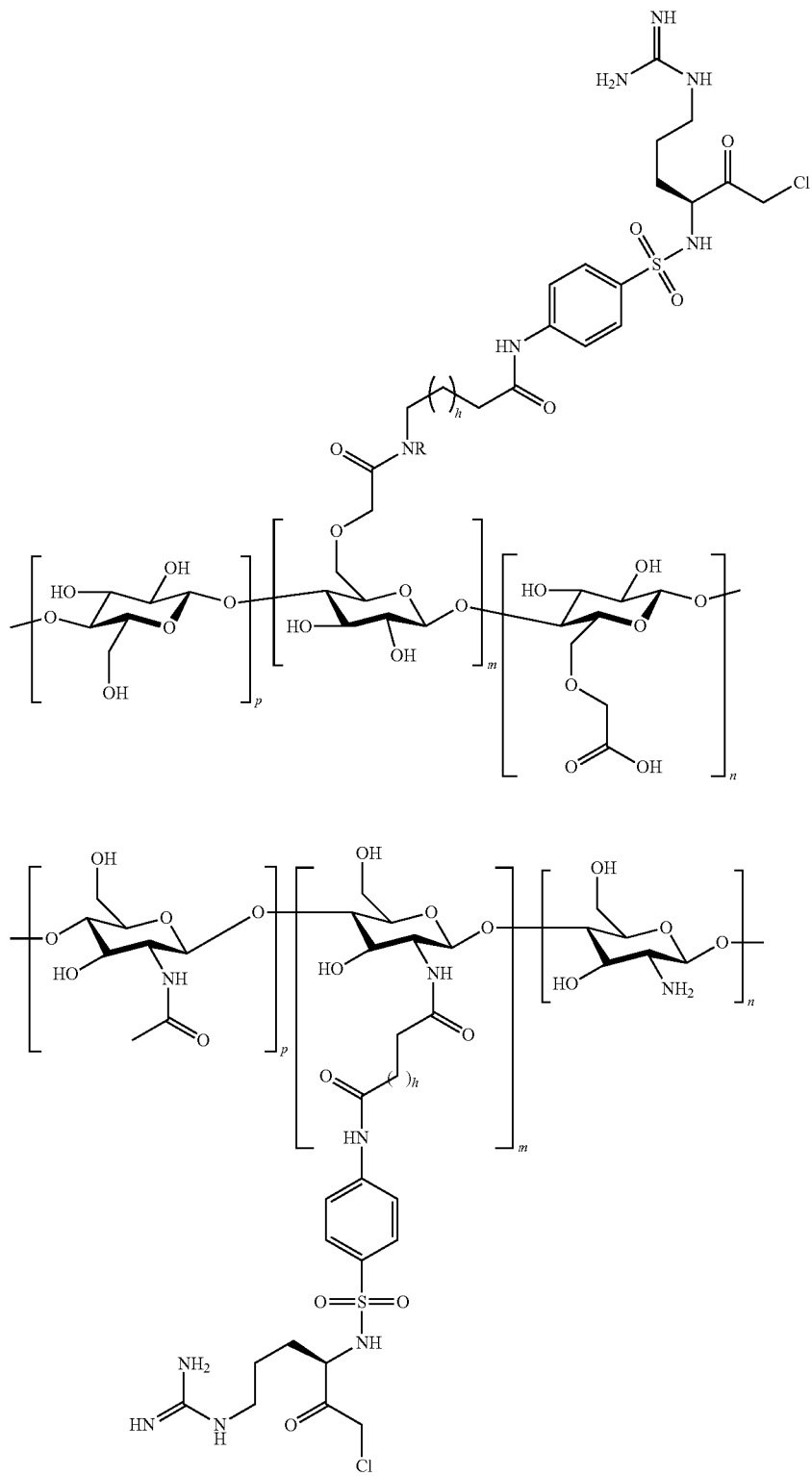

Where n, m and p can independently be an integer from zero to 1,000; h represents a number of substituted or unsubstituted methylene units and can be an integer from zero to ten. R is independently hydrogen, methyl, ethyl, substituted alkyl, or substituted aryl. Each R' can independently be hydrogen, methyl, ethyl, substituted alkyl, or substituted aryl, acetyl, acyl, or substituted acyl.

In another aspect of the invention, the inhibitor can be an aldehyde analog, including, but not limited to the following aldehyde examples:

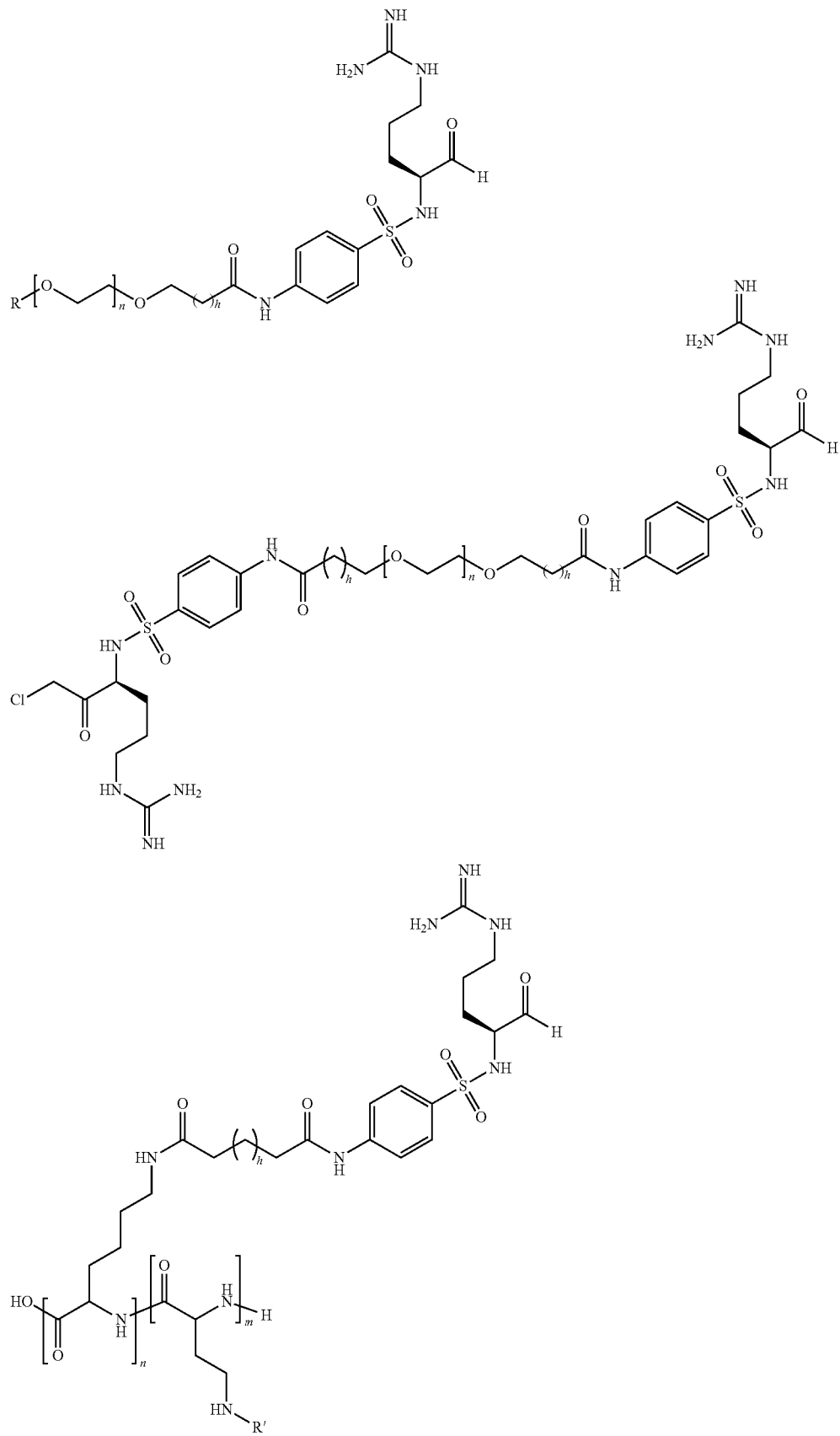

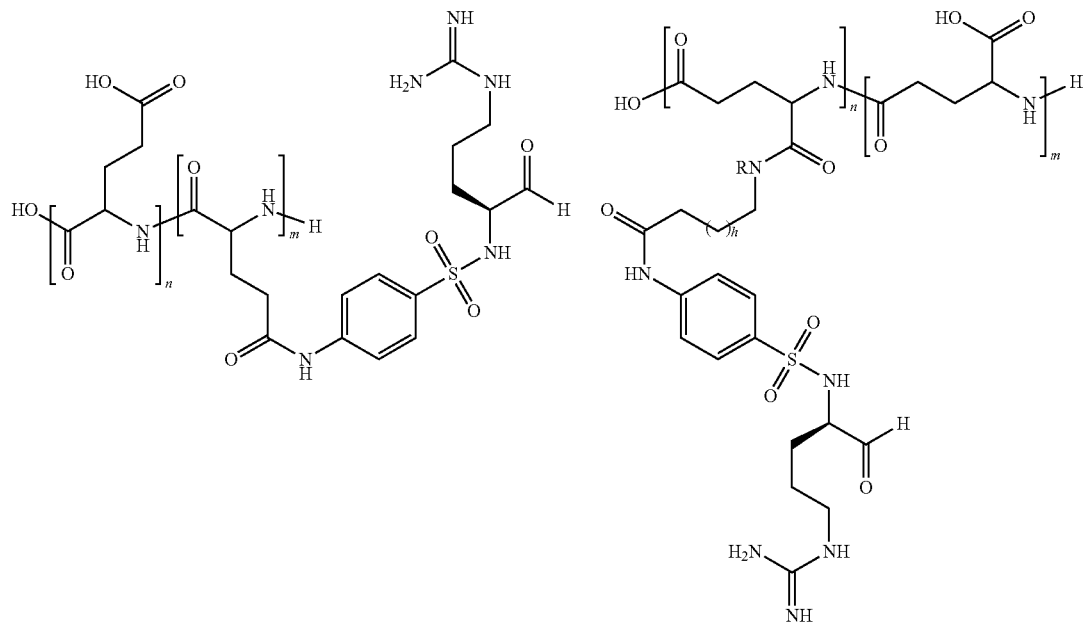
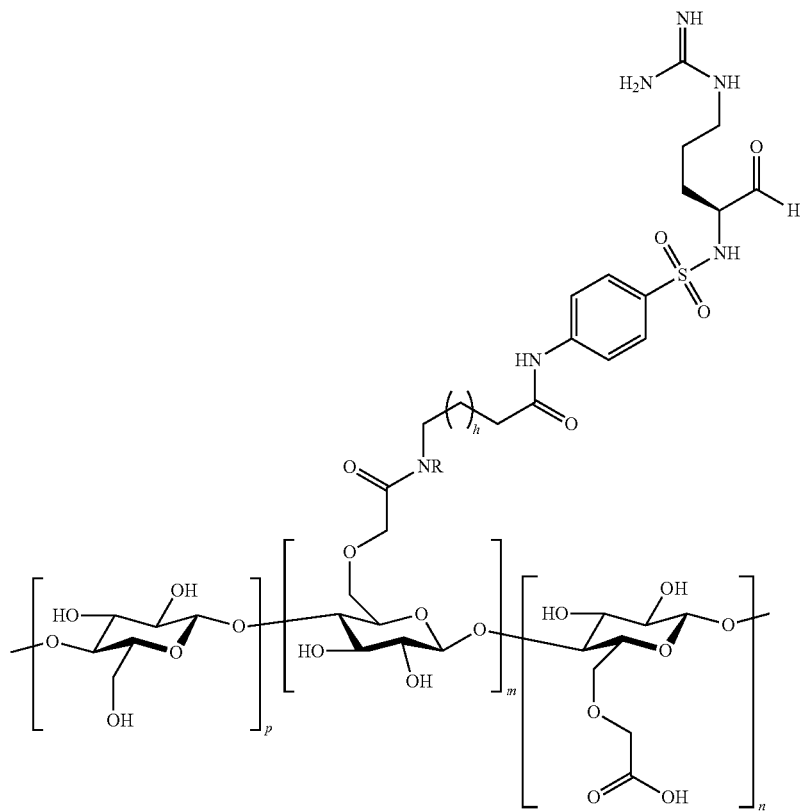

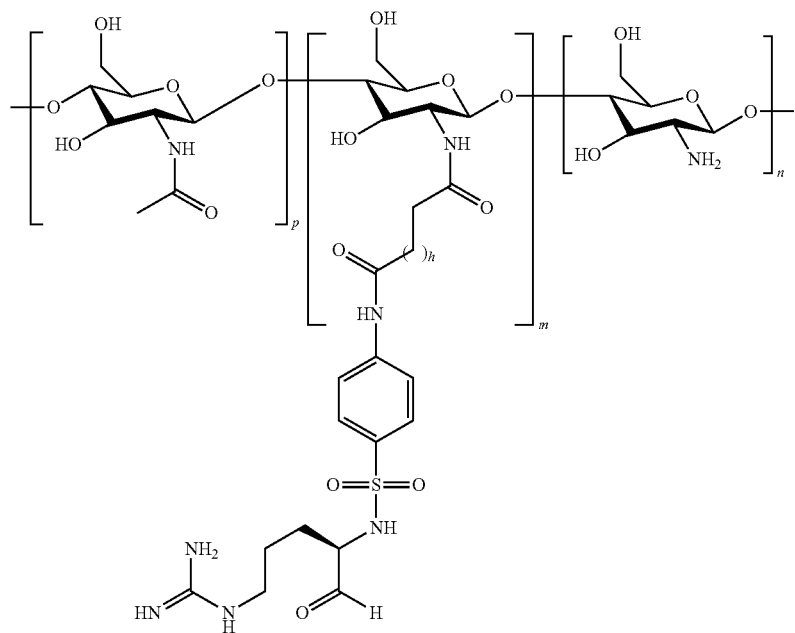

Where n, m and p can independently be an integer from zero to 1,000; h represents a number of substituted or unsubstituted methylene units and can be an integer from zero to ten. R is independently hydrogen, methyl, ethyl, substituted alkyl, or substituted aryl. Each R' can independently be hydrogen, methyl, ethyl, substituted alkyl, or substituted aryl, acetyl, acyl, or substituted acyl. The aldehyde inhibitors can have an amino-acid side-chain alpha to the aldehyde moiety.

In another non-limiting aspect of the invention, the inhibitor can have cycloheteroalkyl groups, naphthylamidines, arylguanidines, arylamidines, benzylamines, 4-guanidinopiperazines, and peptide based structures, as illustrated below:

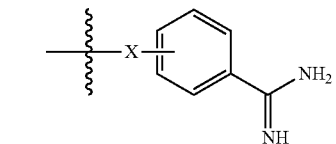

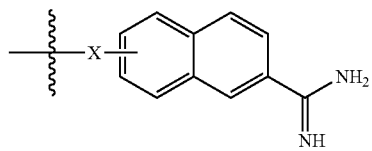

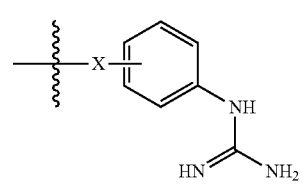

-continued

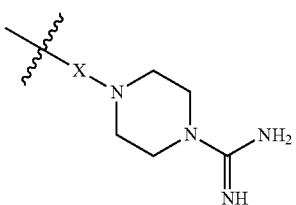

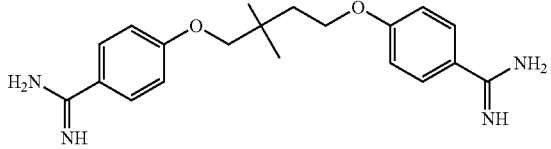

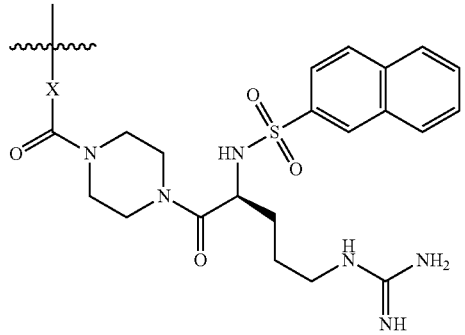

69
-continued
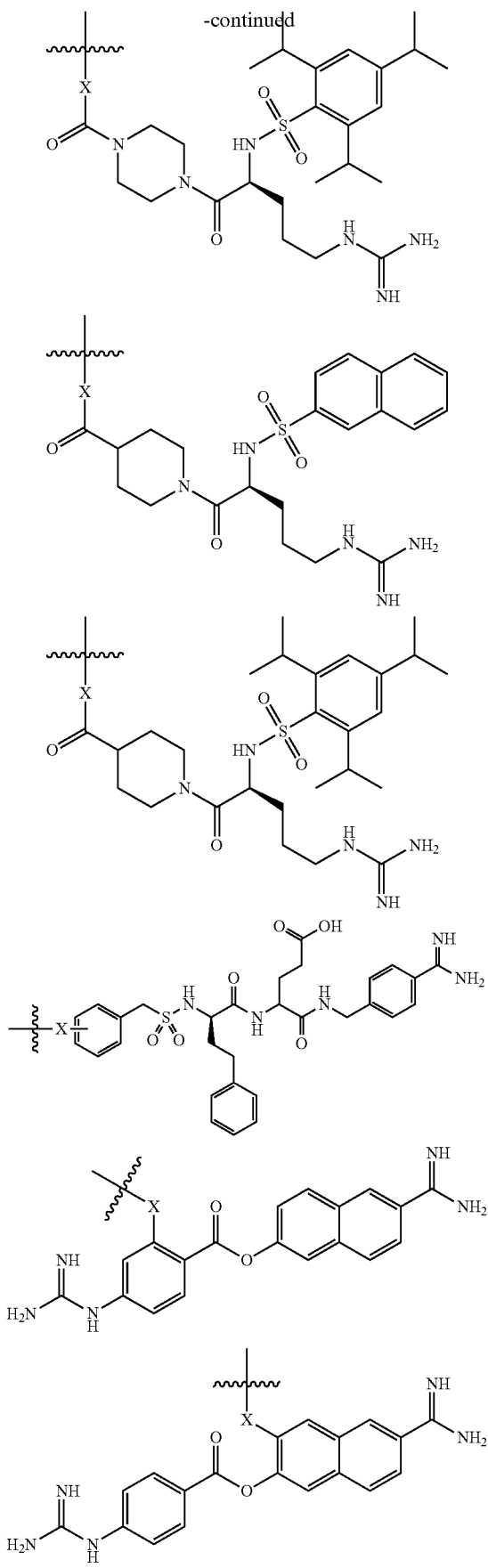
70
-continued
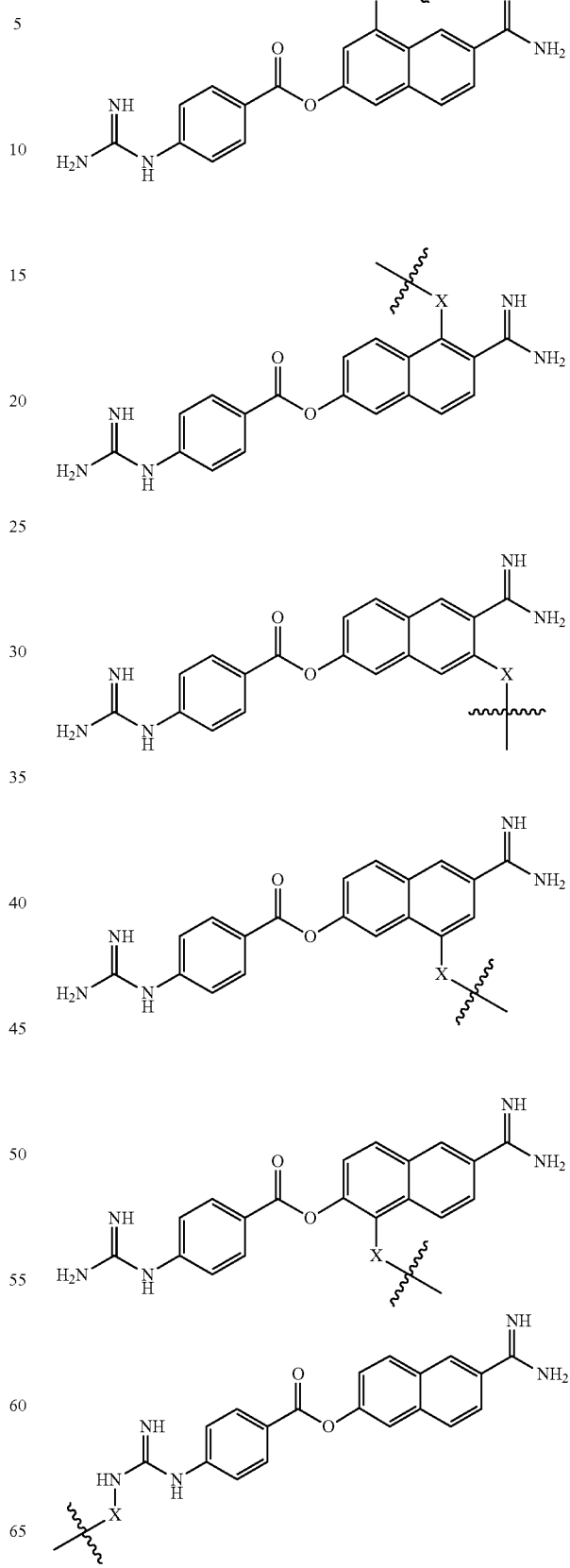

71
-continued
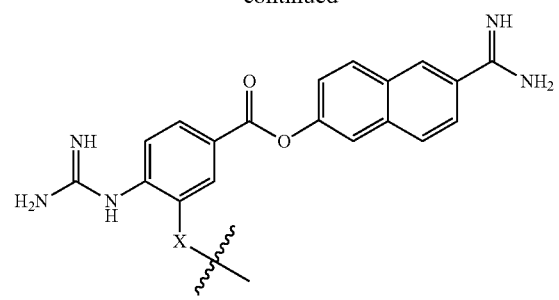
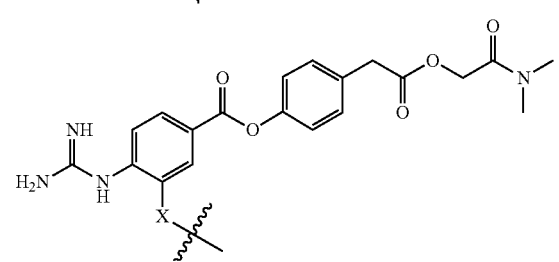
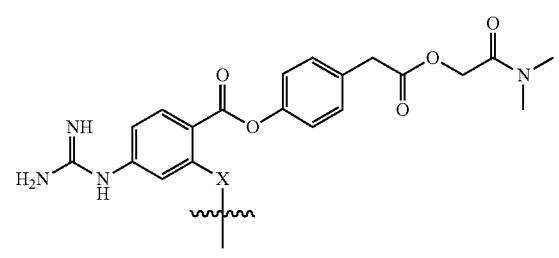
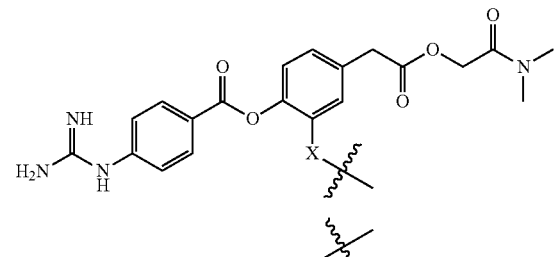
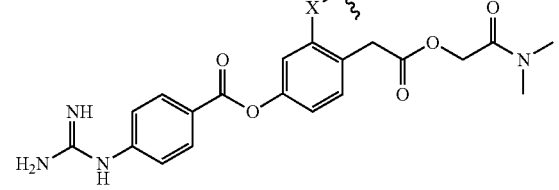
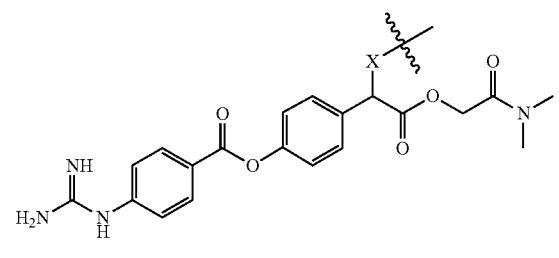
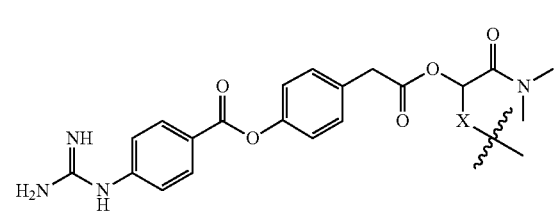
72
-continued
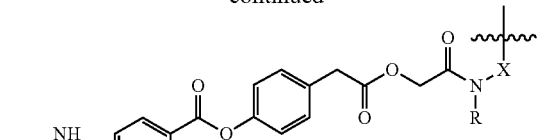
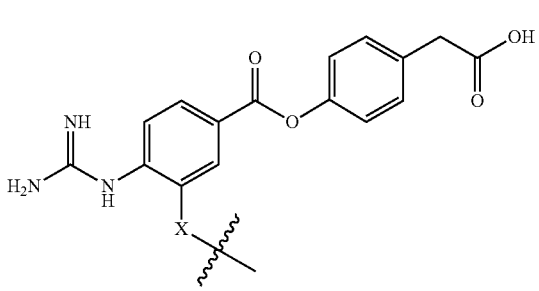
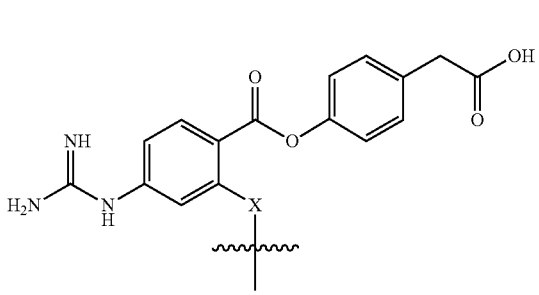
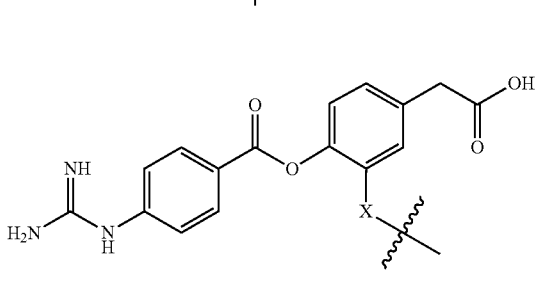
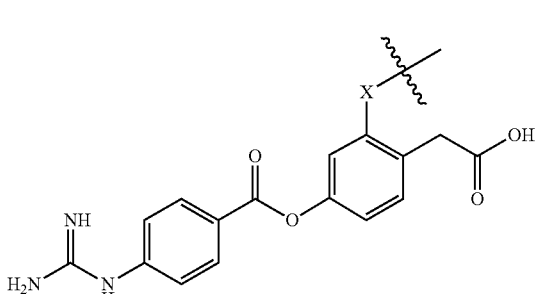
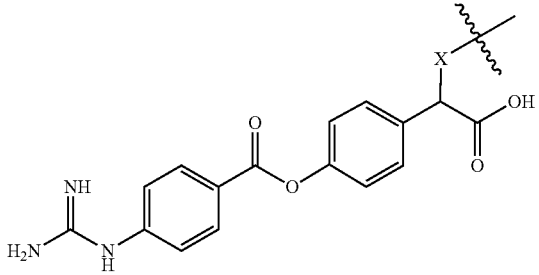

73
-continued
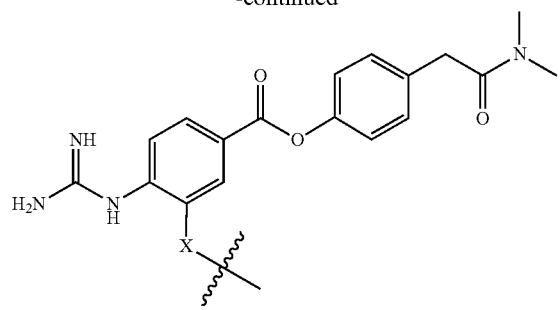
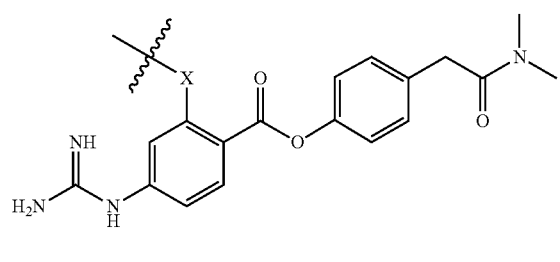
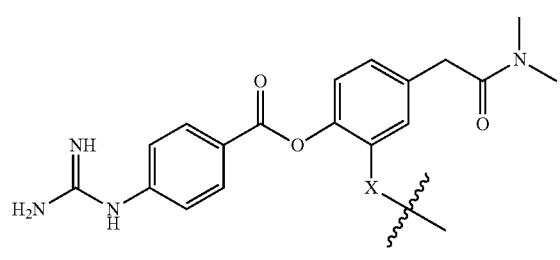
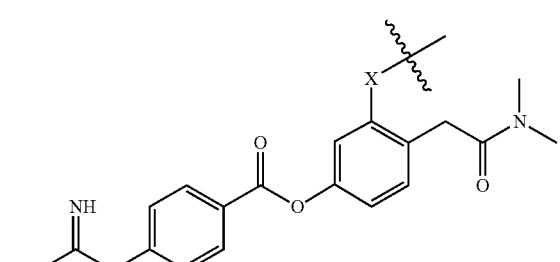
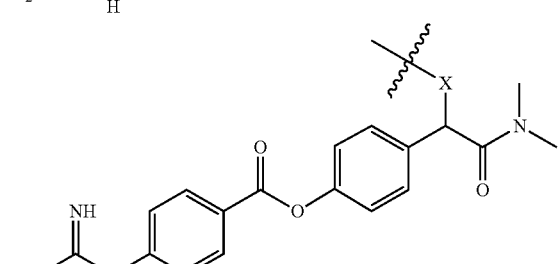
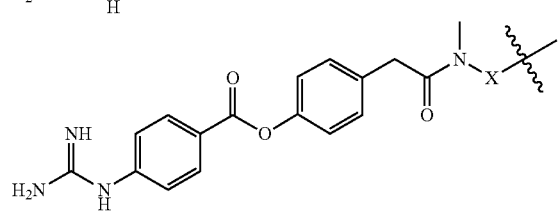
74
-continued
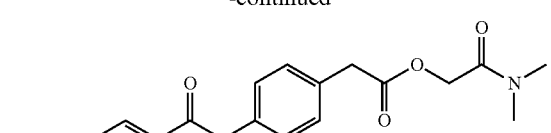
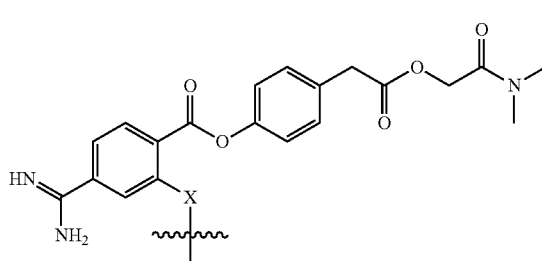
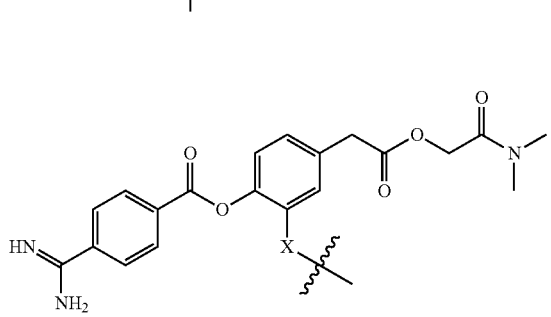
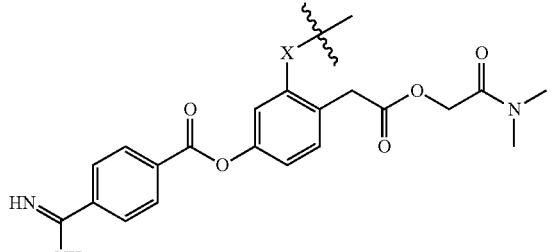
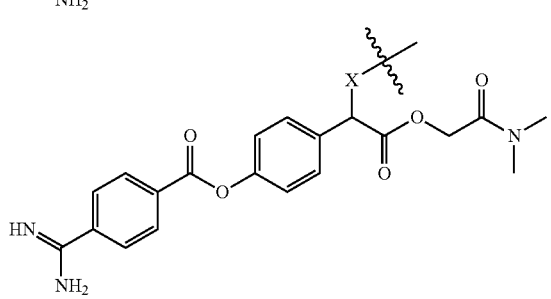
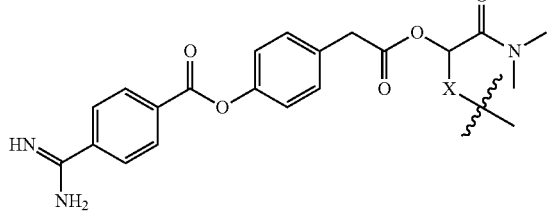

75
-continued
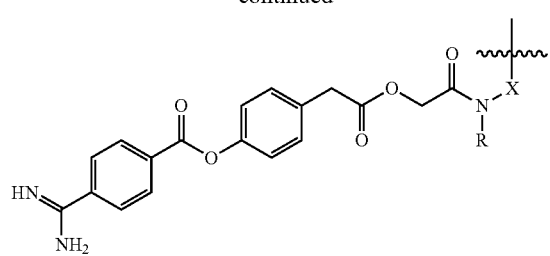
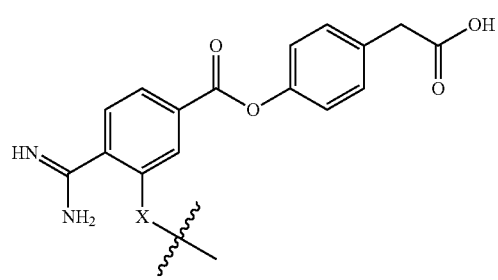
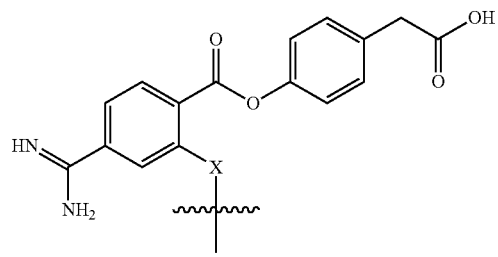
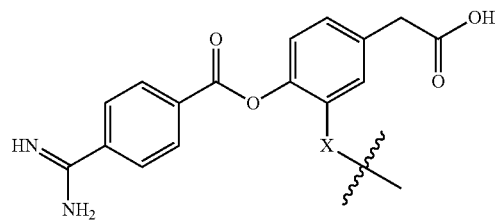
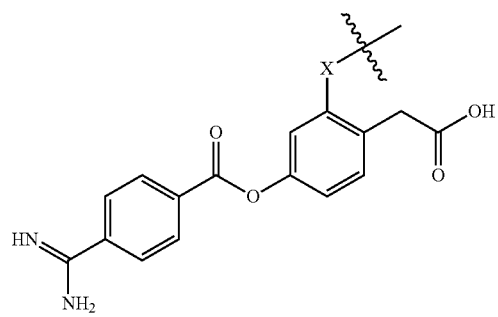
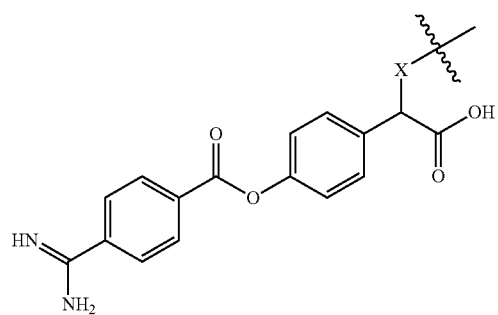
76
-continued
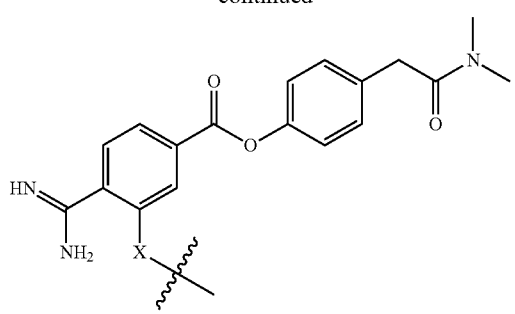
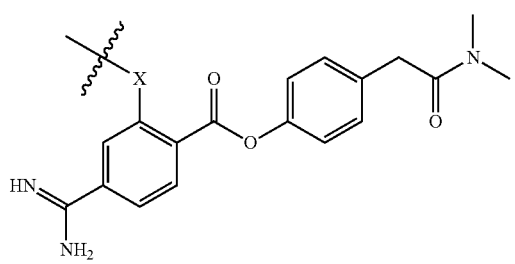
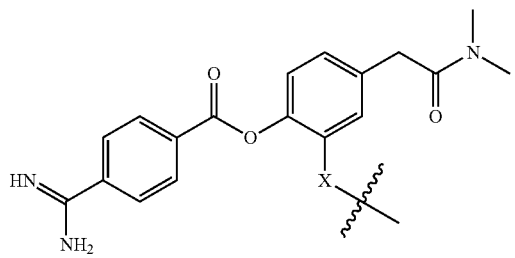
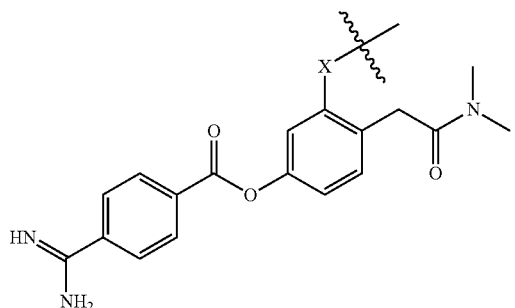
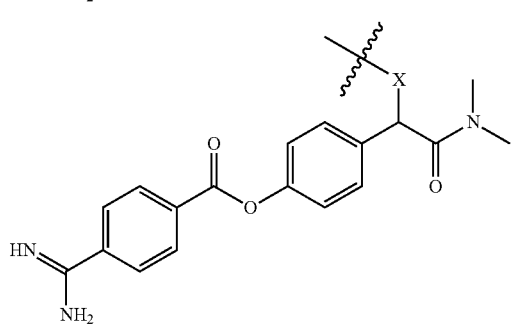
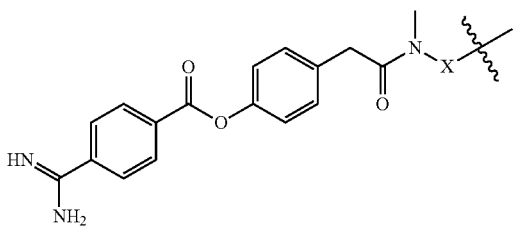

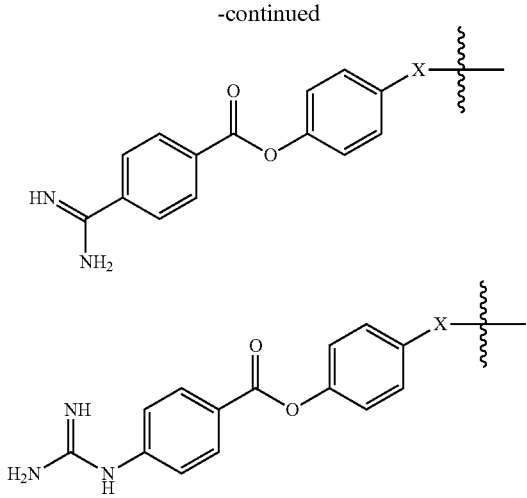 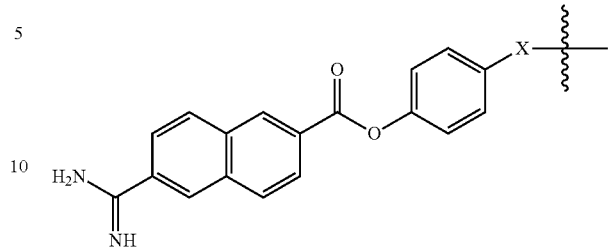
where X is a linker as defined herein, that directly or indirectly links the inhibitor to a macromolecular construct, such as a polymer. Representative structures, illustrated using 4-aminobenzamidine are shown in the non-limiting examples below:
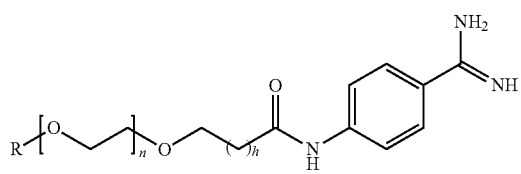
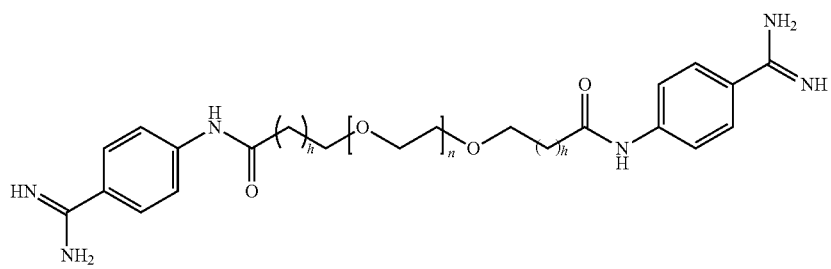
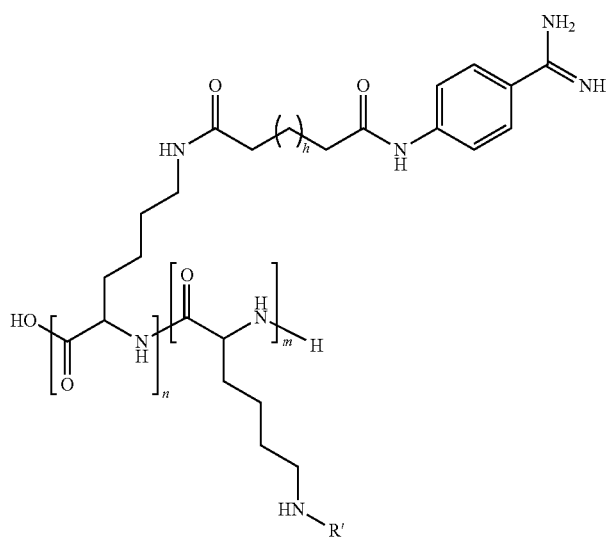 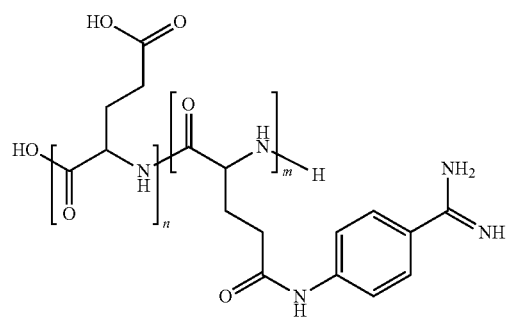

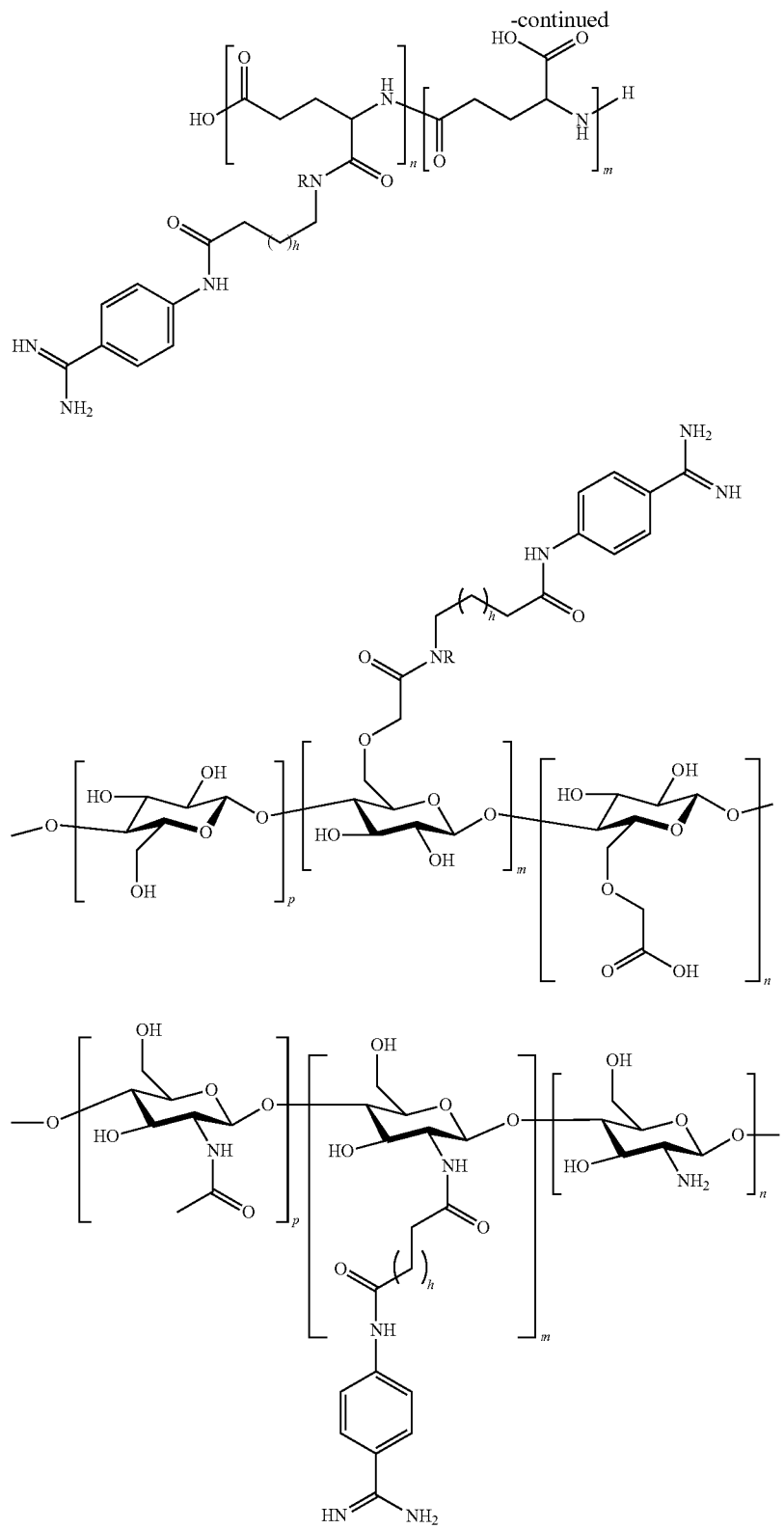

Where n, m and p can independently be an integer from zero to 1,000; h represents a number of substituted or unsubstituted methylene units and can be an integer from zero to ten. R is independently hydrogen, methyl, ethyl, substituted alkyl, or substituted aryl. Each R' can independently be hydrogen, methyl, ethyl, substituted alkyl, or substituted aryl, acetyl, acyl, or substituted acyl.

In one aspect of the invention, the compositions, pharmaceutical formulations, and methods disclosed herein comprise an inverse substrate GI enzyme inhibitor, or a macromolecular GI enzyme inhibitor, for GI enzymes, such as trypsin.

In one aspect, a polymer is attached to an inverse substrate GI enzyme inhibitor as illustrated below:

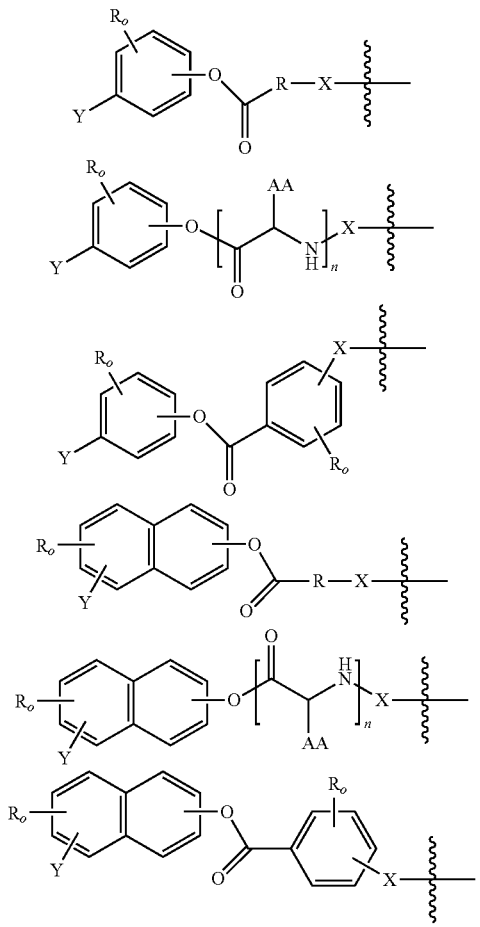

where X is a linker as defined herein that directly or indirectly links the inverse substrate GI enzyme inhibitor to a macromolecular entity (e.g. polymer); n is an integer between 1 and 10; each R is hydrogen, alkyl, substituted alkyl, acyl, substituted acyl, aryl, substituted aryl, heteroaryl, substituted heteroaryl, cinnamyl, substituted cinnamyl, acrylate, substituted acrylate, styryl, substituted styryl, alkylamino, hydroxy, methoxy, alkoxy, or amino-acid, or polypeptide; Each o is an integer from zero to 5; Y can be any functionality capable of being recognized by or interacting with a digestive enzyme. The digestive enzyme may be trypsin, whereby Y is preferably:

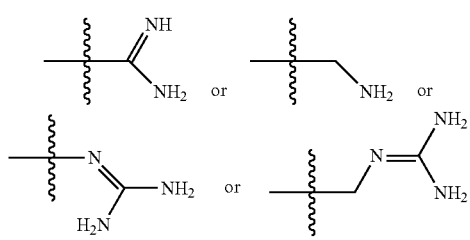

In another aspect of the invention, the inverse substrate GI enzyme inhibitor can be attached to the polymer as illustrated below:

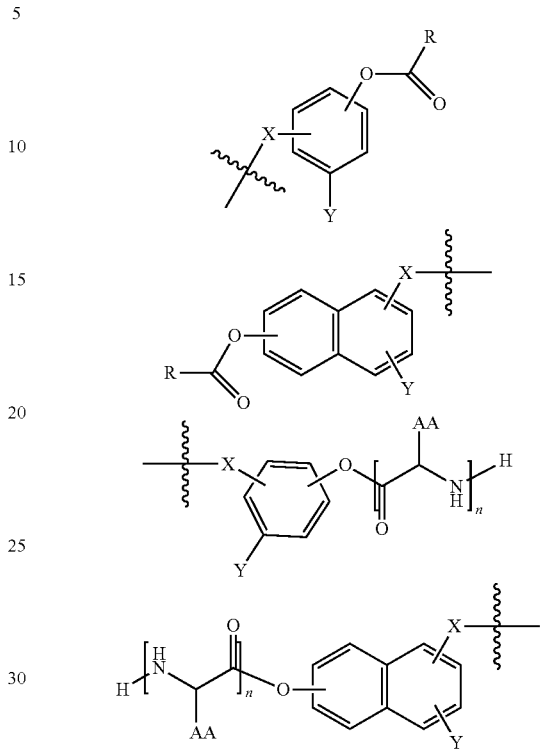

where X is a linker as defined herein that directly or indirectly links the inverse substrate GI enzyme inhibitor to a macromolecular entity (e.g. polymer); n is an integer between 1 and 10; each R can be hydrogen, alkyl, substituted alkyl, acyl, substituted acyl, carboxyl, substituted carboxyl, aryl, substituted aryl, heteroaryl, substituted heteroaryl, cinnamyl, substituted cinnamyl, acrylate, substituted acrylate, styryl, substituted styryl, alkylamino, hydroxy, methoxy, alkoxy, or amino-acid, or polypeptide; Y can be any functionality capable of being recognized by or interacting with a digestive enzyme. The digestive enzyme may be trypsin, whereby Y is preferably:

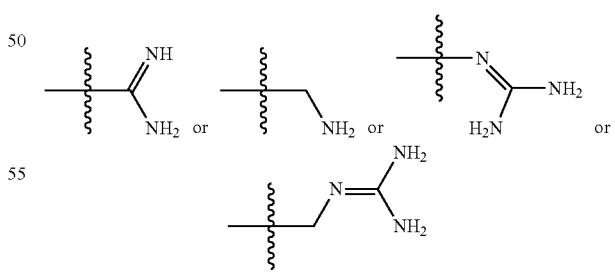

Trypsin hydrolysis of the above inverse substrate GI enzyme inhibitors will produce a benzoic acid molecule as a primary metabolite. There are many benzoic acid analogs that are generally regarded as safe (GRAS). The hydrolysis of inverse substrates by a GI enzyme to yield a GRAS benzoic acid metabolite is illustrated by the general mechanism below:

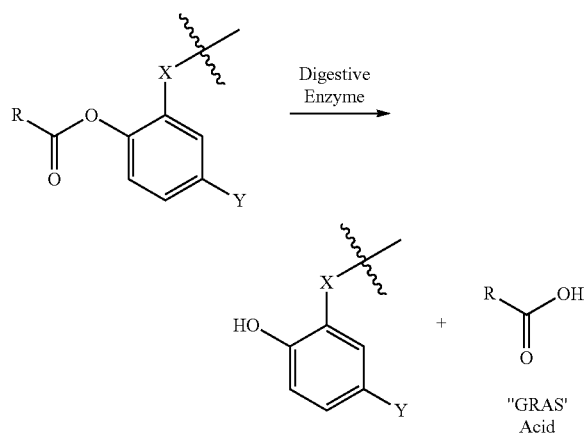

The products produced by the hydrolysis are a GRAS acid and an alcohol, such as the substituted phenol shown above, where the alcohol is still directly attached, or attached via a linker moiety "X", to a non-absorbable macromolecular entity such as a polymer. Inverse substrates derived from GRAS acids have the advantage that the liberated GRAS acids have well-characterized safety profiles. In addition, the inverse substrate GI enzyme inhibitors described above are chemically stable and are not easily hydrolyzed by the acid in the stomach, or non-specifically by digestive enzymes, of the subjects to whom they are administered. Exemplary GRAS acid metabolites include, but are not limited to: Benzoic acid, salicylic acid, aspirin, 3-hydroxybenzoic acid, 4-hydroxybenzoic acid, galic acid, 2,3,4-trihydroxybenzoic acid, 2,3,6-trihydroxybenzoic acid, 2,4,5-trihydroxy benzoic acid, 6-methylsalicylic acid, o-cresotinic acid, (alkyl)-anacardic acids, o-thymotic acid, 3-O-methylgallic acid, 4-O-methylgallic acid, syringic acid, 3,4,5-trimethoxybenzoic acid, diflusinal, p-anisic acid, 2,3-dihydroxybenzoic acid, alpha-resorcylic acid, anthranilic acid, 3-aminobenzoic acid, 4,5-dimethylanthranilic acid, N-methylanthranilic acid, protocatechuic acid, gentisic acid, piperonylic acid, 3-methoxysalicylic acid, fenamic acid, toifenamic acid, mefenamic acid, flufenamic acid, vanillic acid, isovanillic acid, veratric acid, 3,5-dimethoxybenzoic acid, 2,4-diaminobenzoic acid, N-acetylanthranilic acid, 2-acetylamino-4-aminobenzoic acid, 2,4-diacetylaminobenzoic acid, 4-aminosalicylic acid, 3-hydroxyanthranilic acid, 3-methoxyanthranilic acid, nicotinic acid, isonicotinic acids, and cinnamic acids.

In another aspect of the invention, inverse substrates for trypsin can have the inhibitor structures with linker functionalities (X) as shown below:

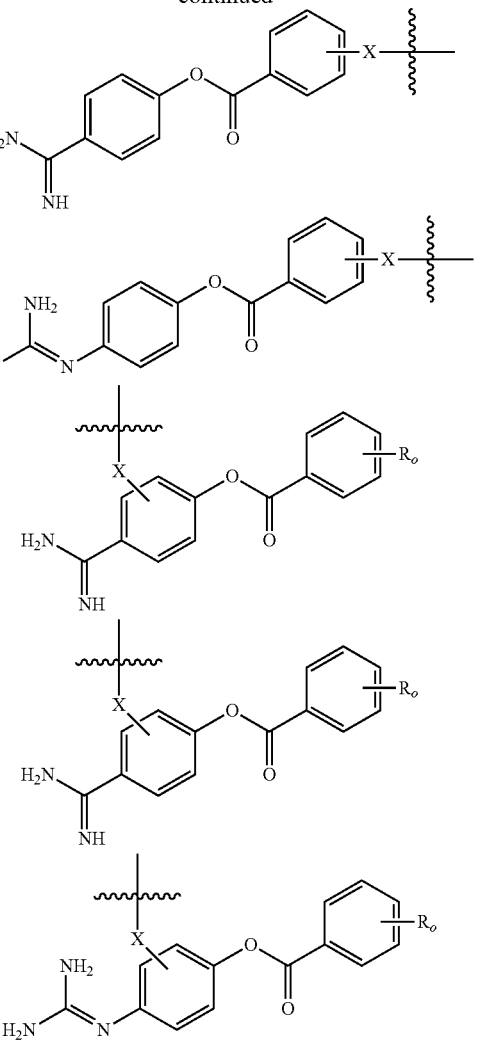

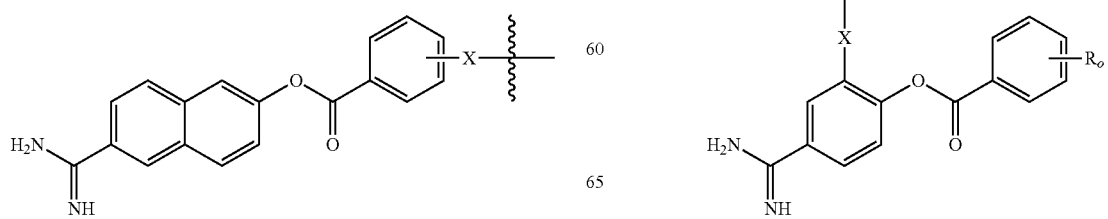

where X is a linker as defined herein that directly or indirectly links the inverse substrate GI enzyme inhibitor to a macromolecular entity (e.g. polymer); each R can be hydrogen, alkyl, substituted alkyl, acyl, substituted acyl, carboxyl, substituted carboxyl, aryl, substituted aryl, heteroaryl, substituted heteroaryl, cinnamyl, substituted cinnamyl, acrylate, substituted acrylate, styryl, substituted styryl, alkylamino, hydroxy, methoxy, alkoxy, or aminoacid, or polypeptide; each o is an integer from zero to 5.

In another aspect of the invention, inverse substrates for trypsin can have the inhibitor structures with polymer attachment functionalities (X) as shown below:

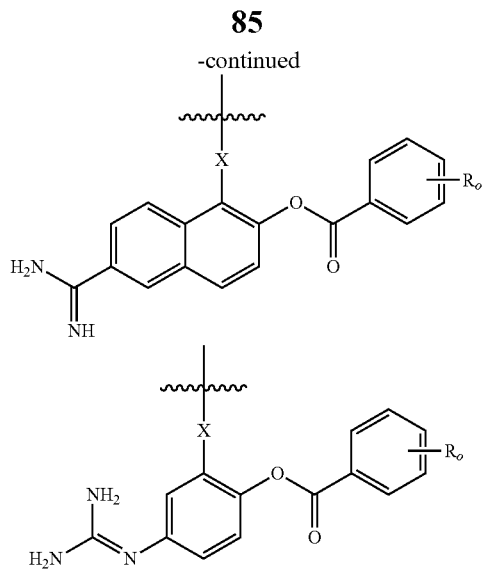

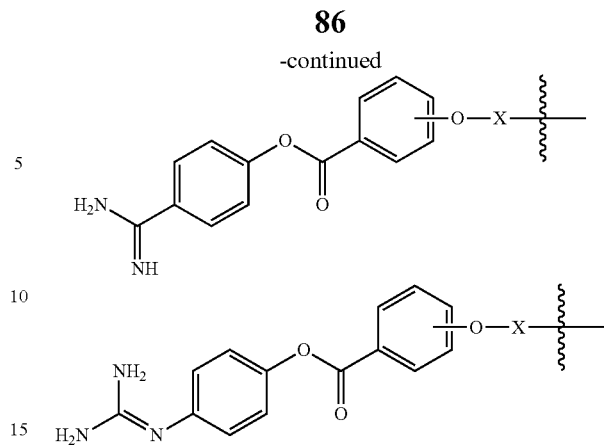

where X is a linker as defined herein that directly or indirectly links the inverse substrate GI enzyme inhibitor to a macromolecular entity (e.g. polymer); each R can be hydrogen, alkyl, substituted alkyl, acyl, substituted acyl, carboxyl, substituted carboxyl, aryl, substituted aryl, heteroaryl, substituted heteroaryl, cinnamyl, substituted cinnamyl, acrylate, substituted acrylate, styryl, substituted styryl, alkylamino, hydroxy, methoxy, alkoxy, or amino-acid, or polypeptide; each o is an integer from zero to 5.

In another aspect of the invention, inverse substrates for trypsin comprising benzoate ester moieties can have the non-limiting structures shown below where X is a linker as defined herein:

In another aspect of the invention, inverse substrates for trypsin comprising benzoate ester moieties can have the non-limiting structures shown below where X is a linker as defined herein:

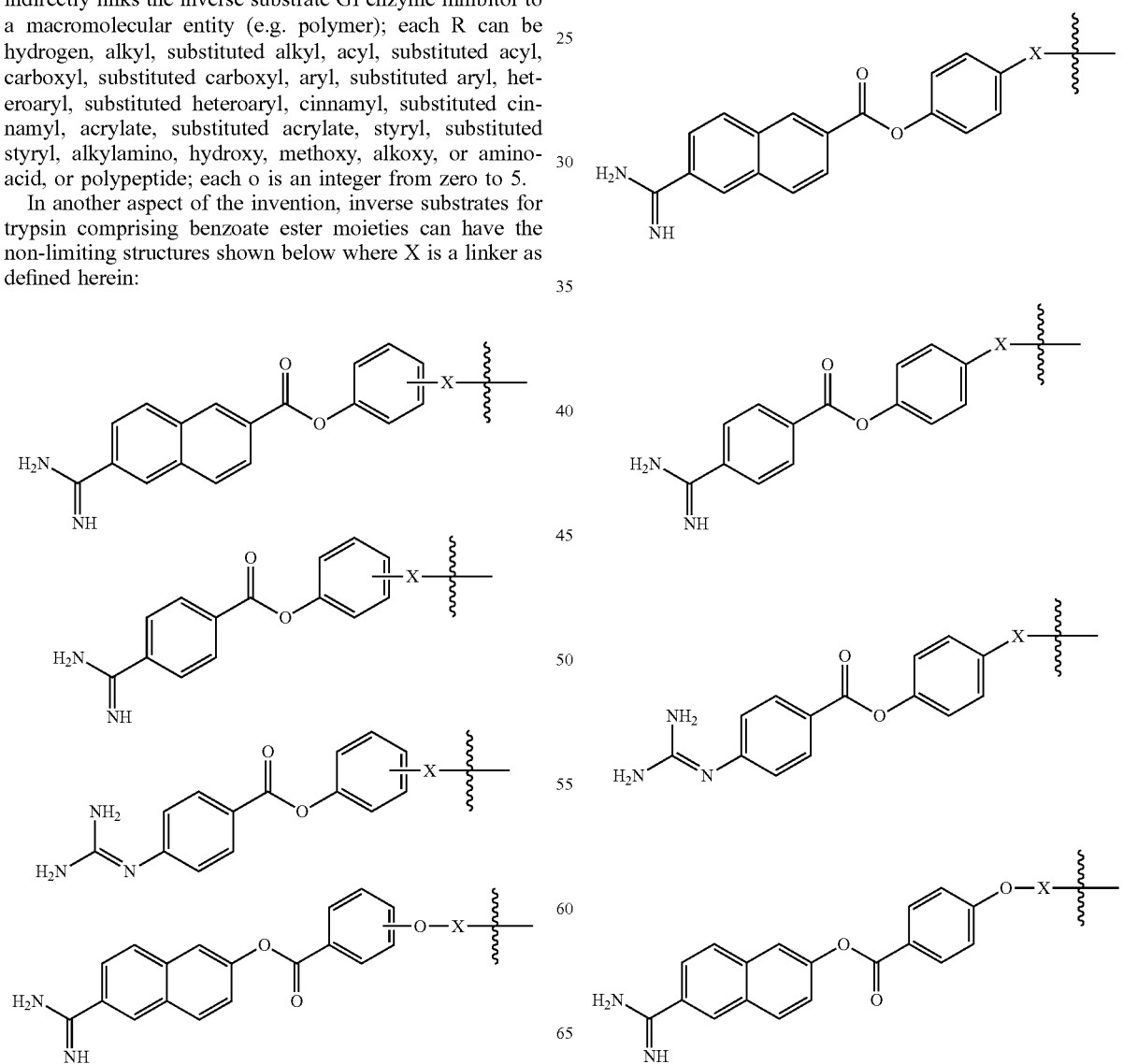

87
-continued
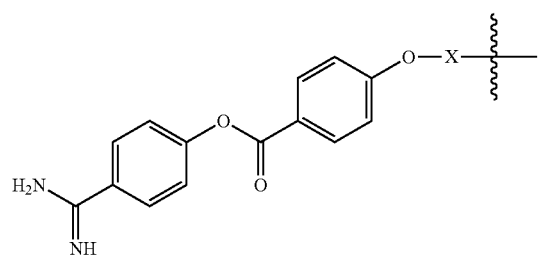
88
-continued
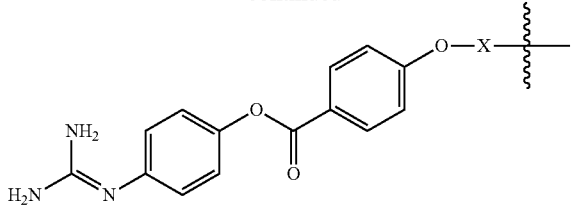
For example, inverse substrate GI enzyme inhibitors attached to PEG polymers are shown in the non-limiting examples below:
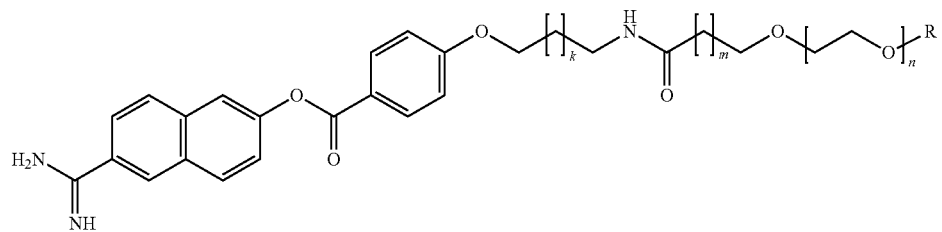
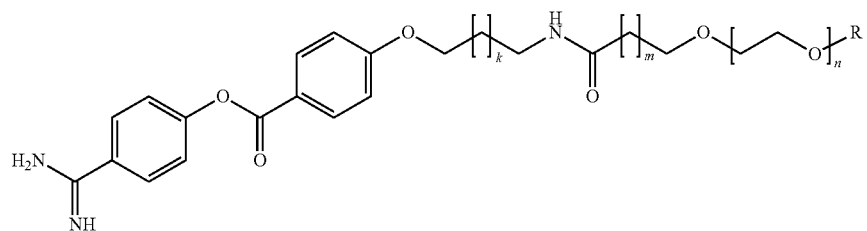
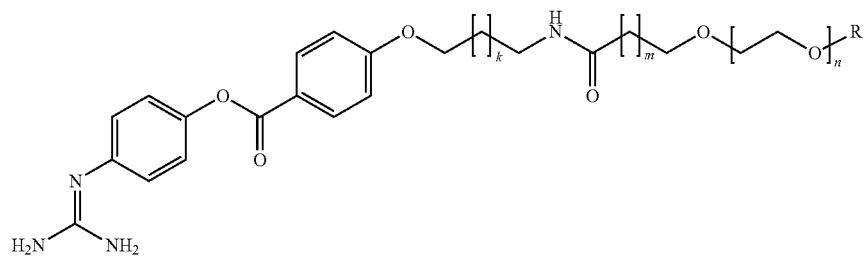
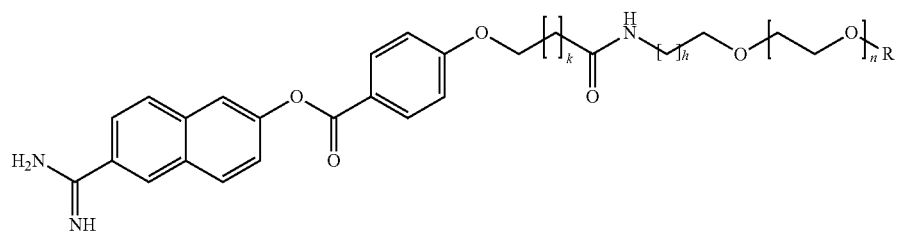
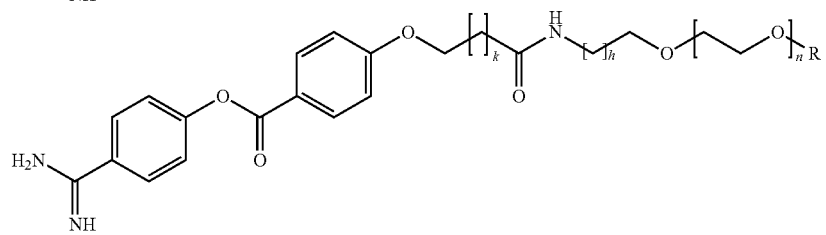

-continued
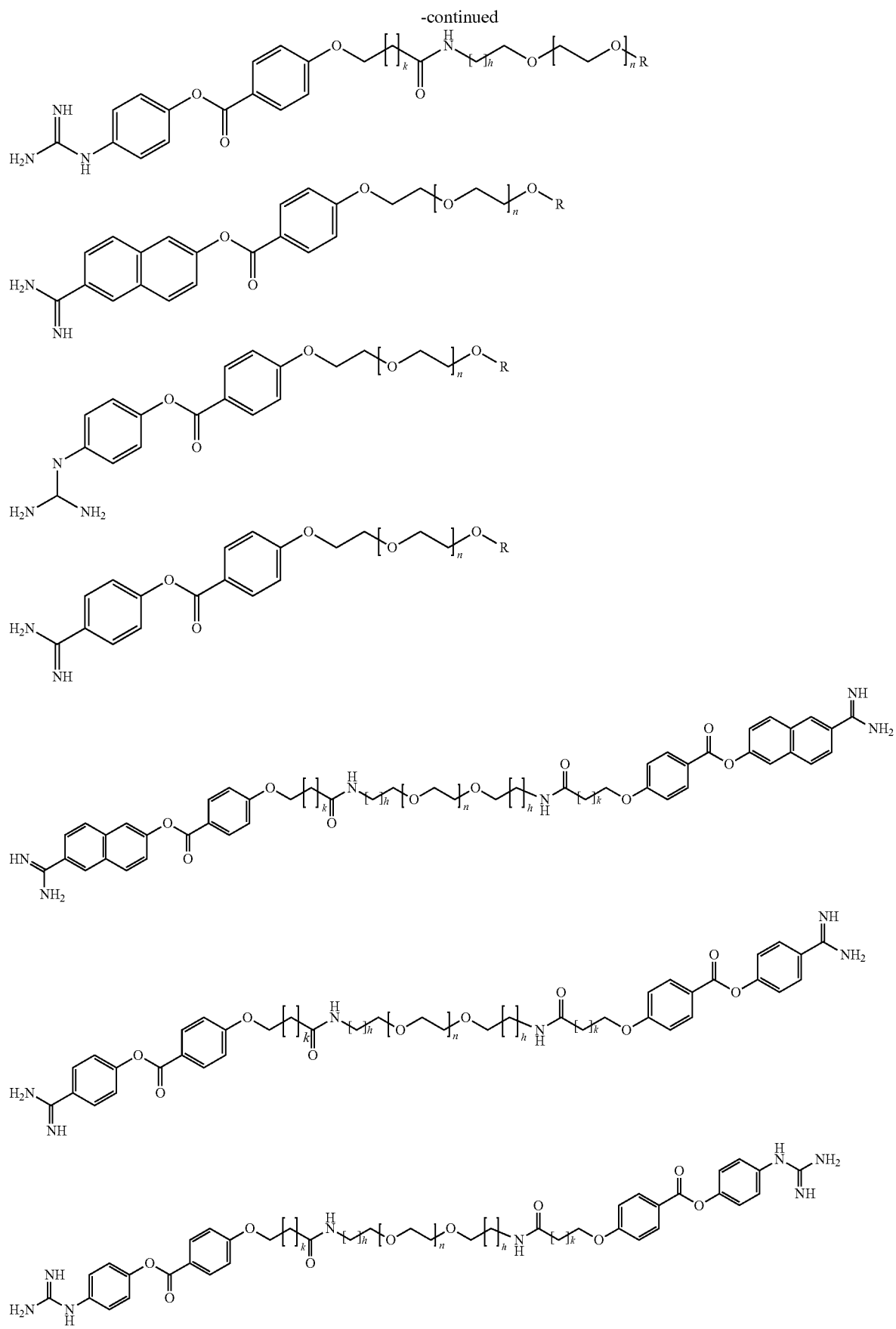

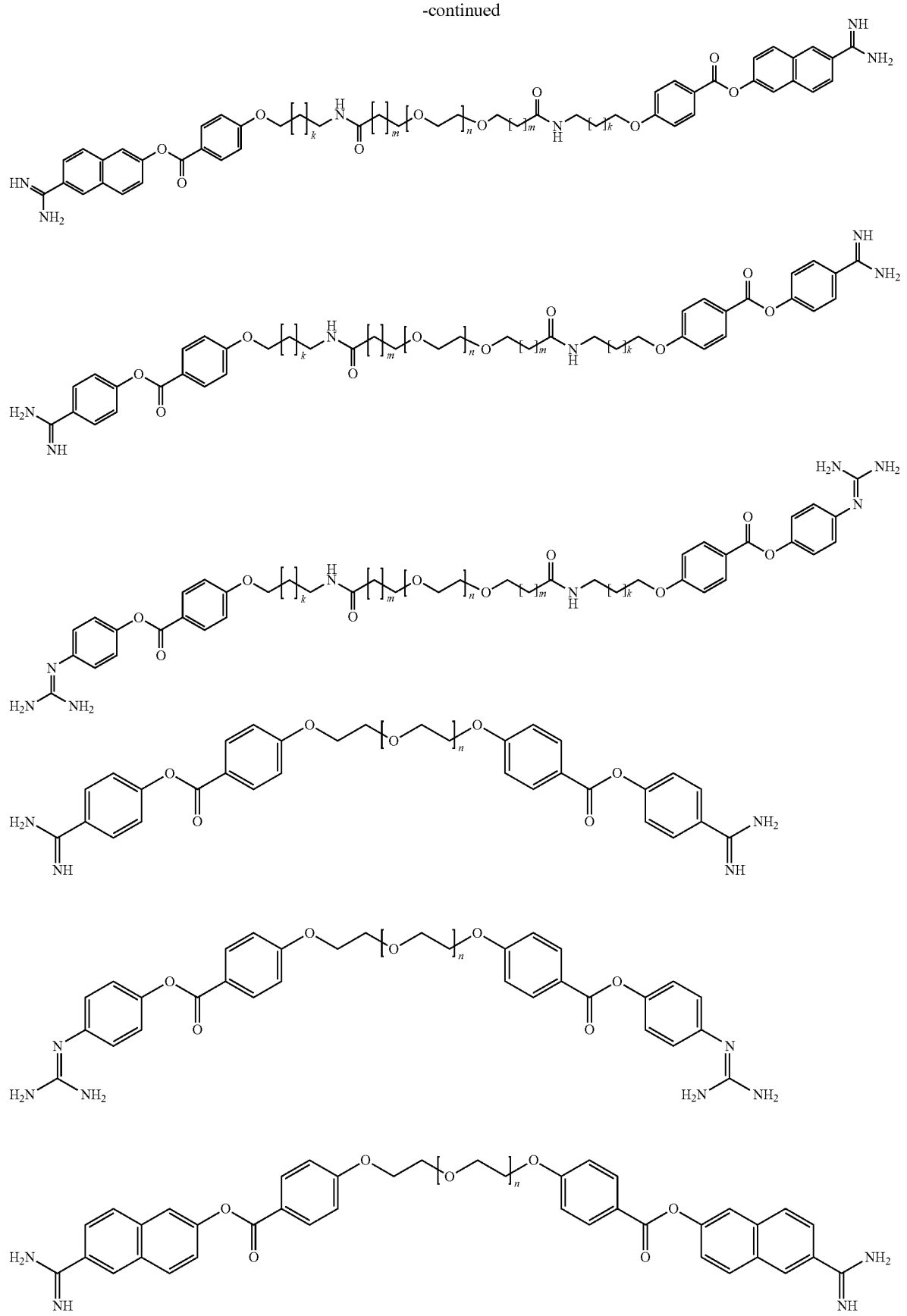

Where k, h, and m each represent a number of substituted or unsubstituted methylene units and independently can be an integer from zero to ten; n is an integer from 1 to 1,000 to 1,000; h represents a number of substituted or unsubstituted methylene units and can be an integer from zero to ten. R can be hydrogen, methyl, ethyl, substituted alkyl, or substituted aryl.

For example, inverse substrate GI enzyme inhibitors attached to macromolecular polypeptide scaffolds are shown in the examples below:

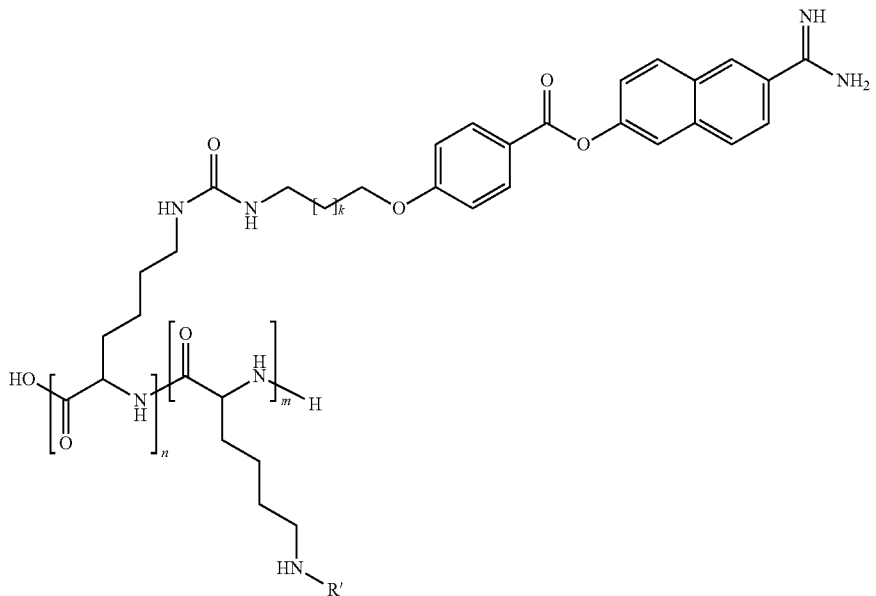

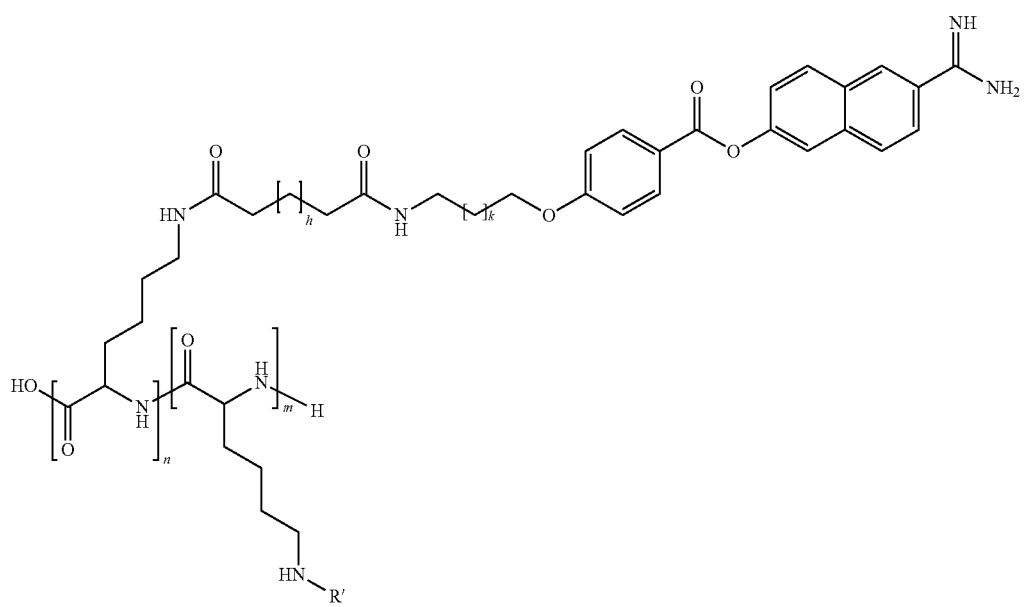

-continued
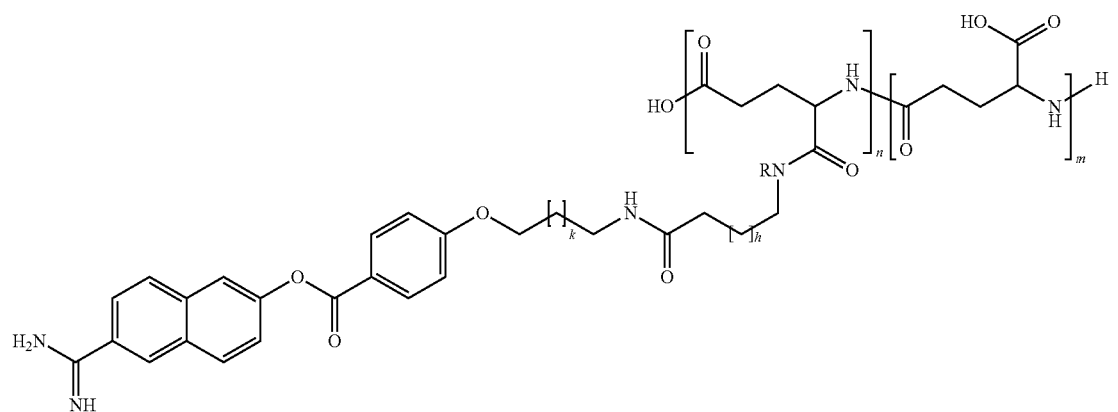
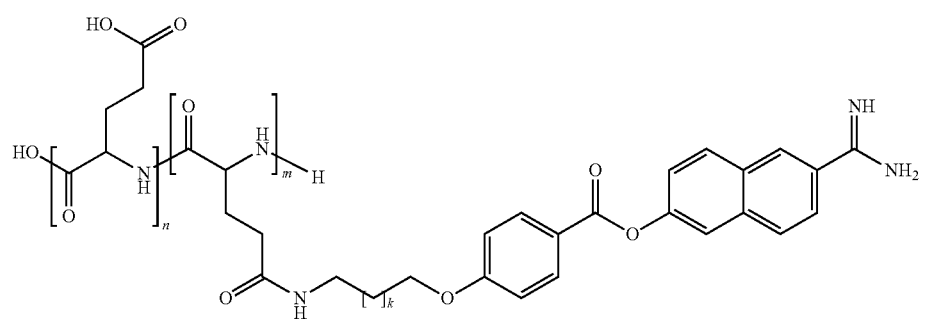
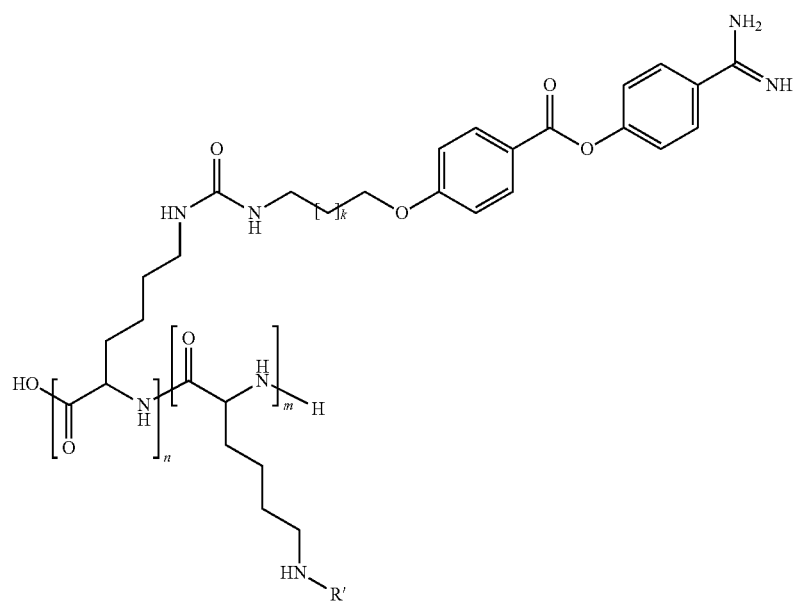

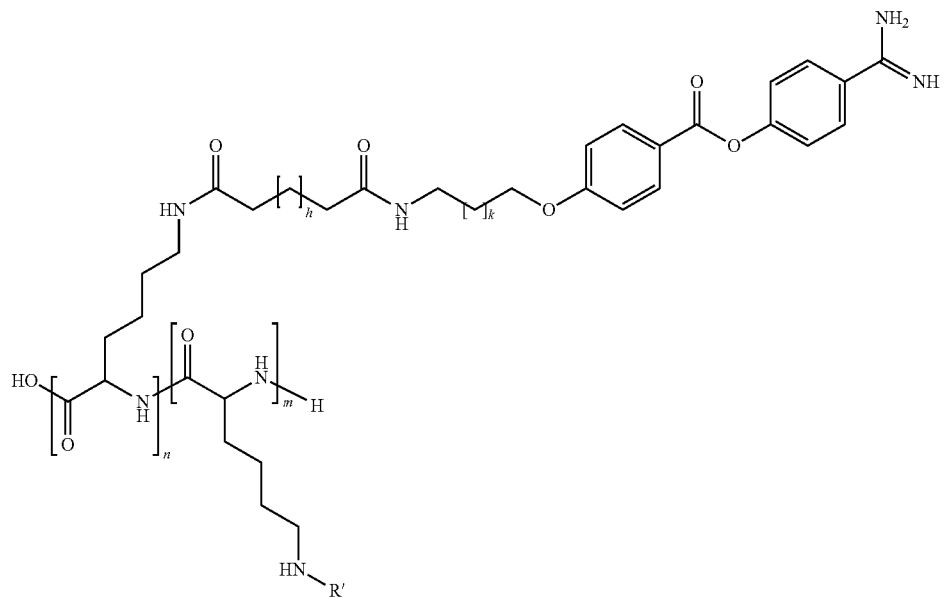
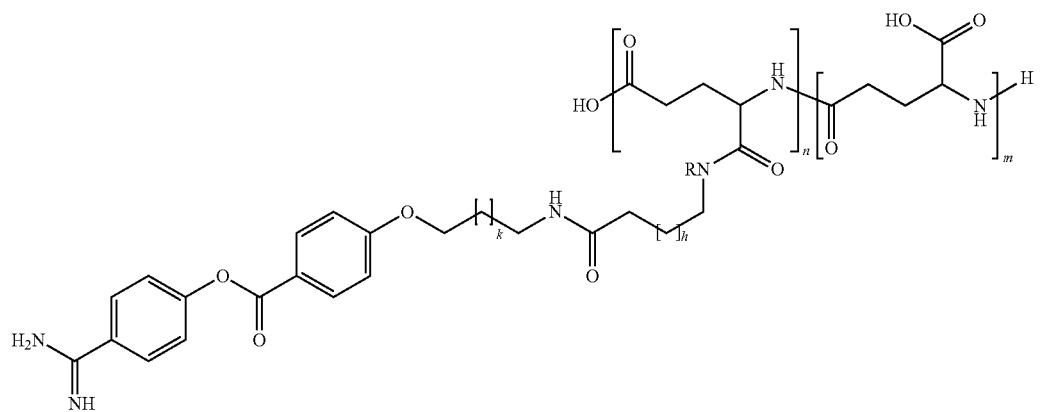
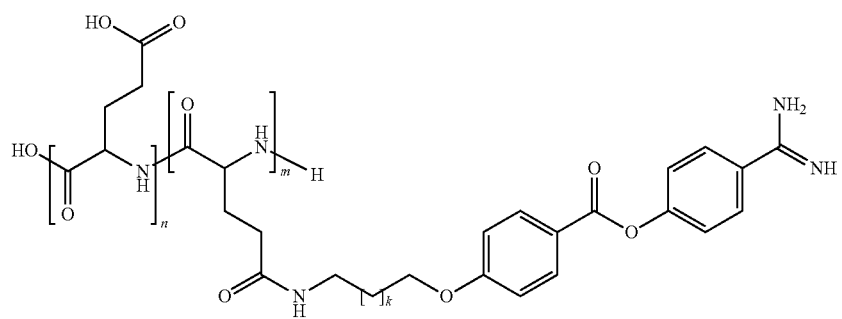

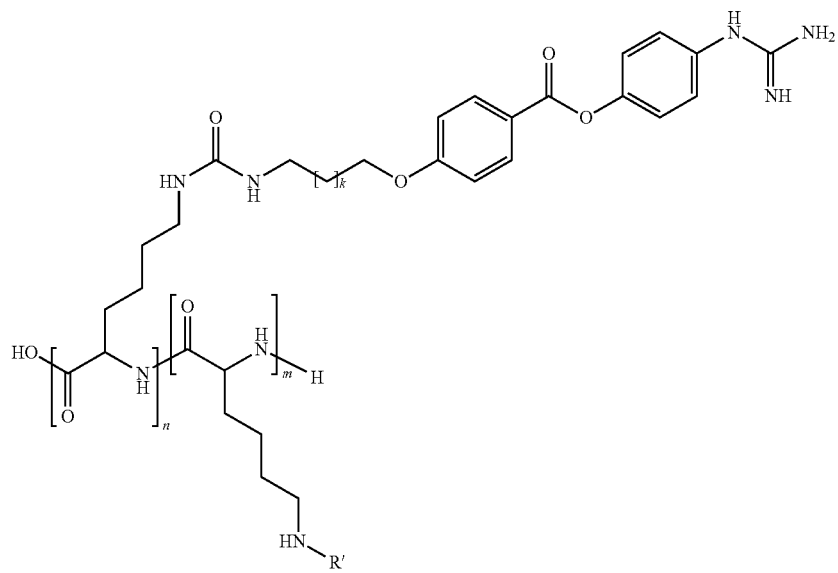
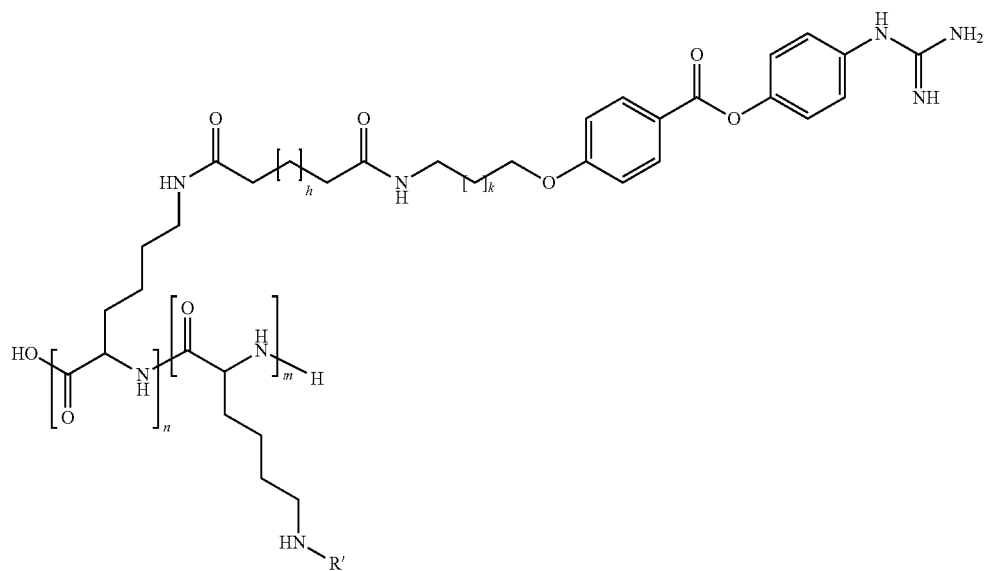
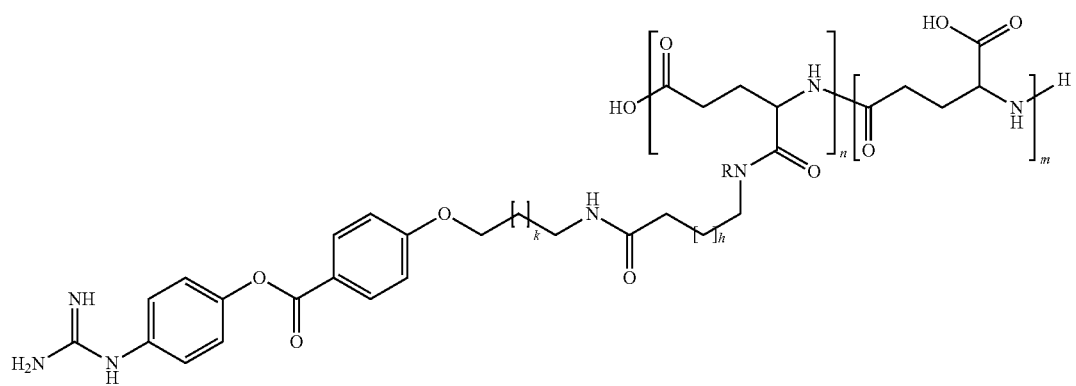

-continued
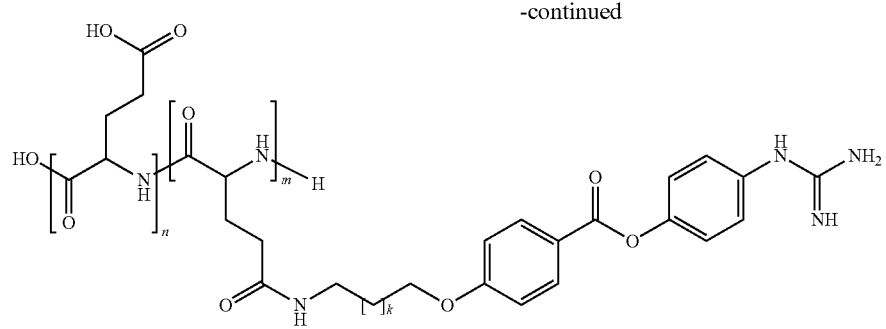
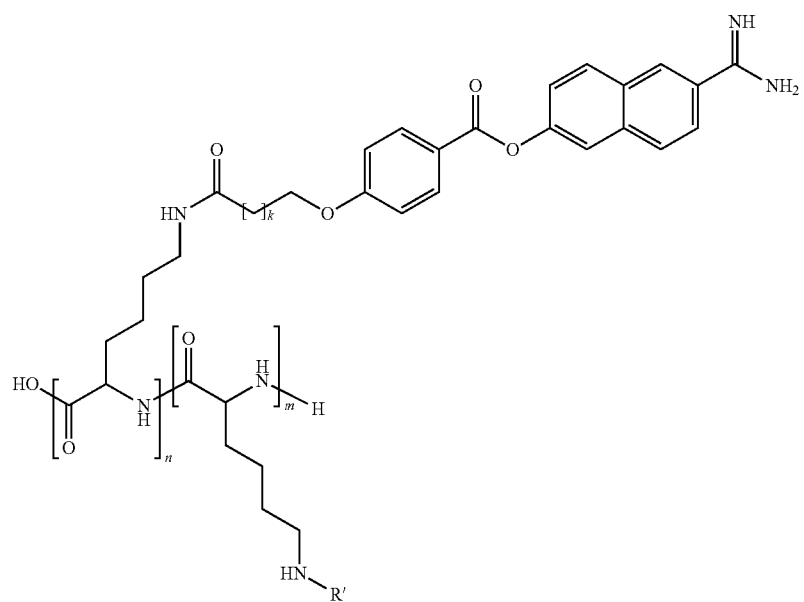
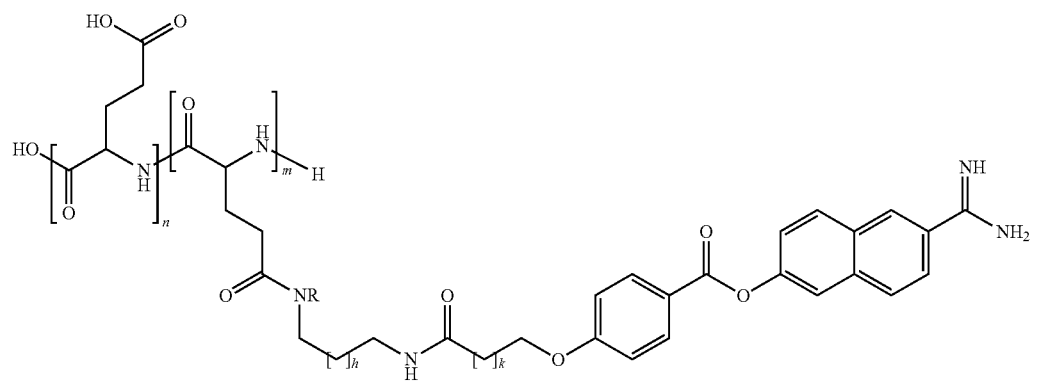
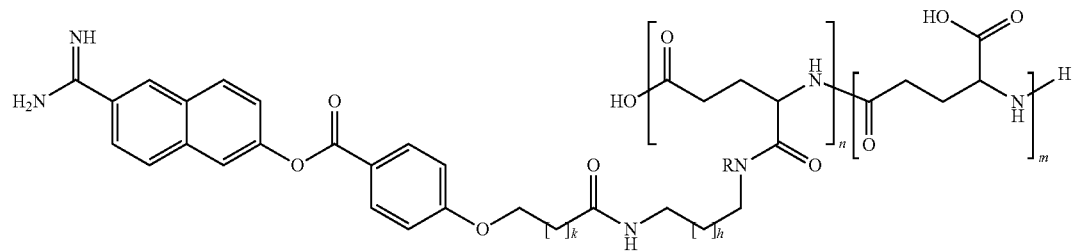

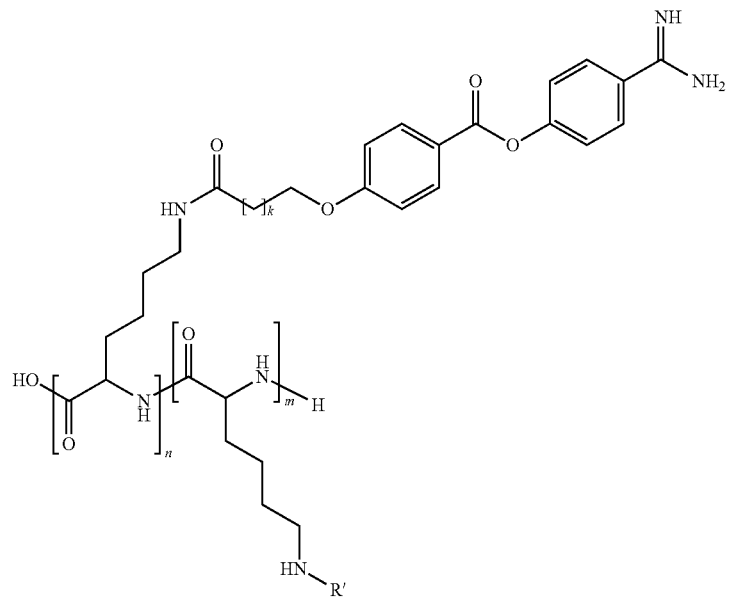
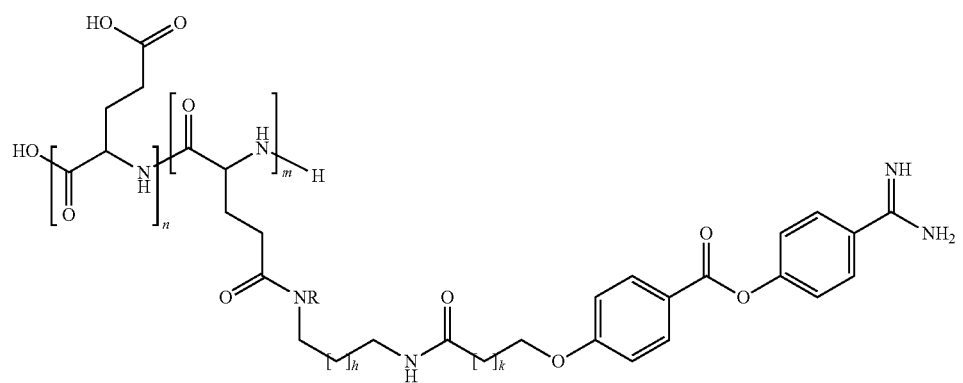
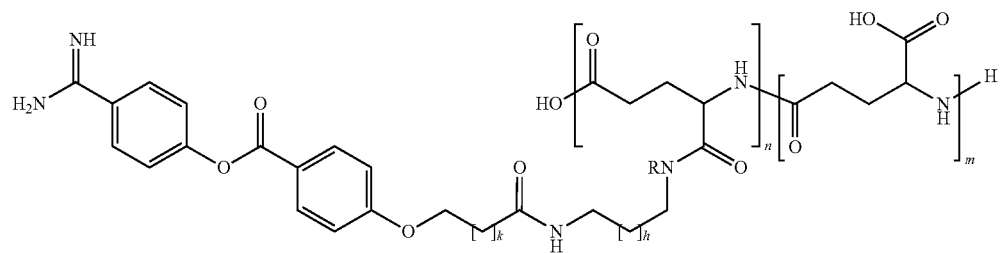

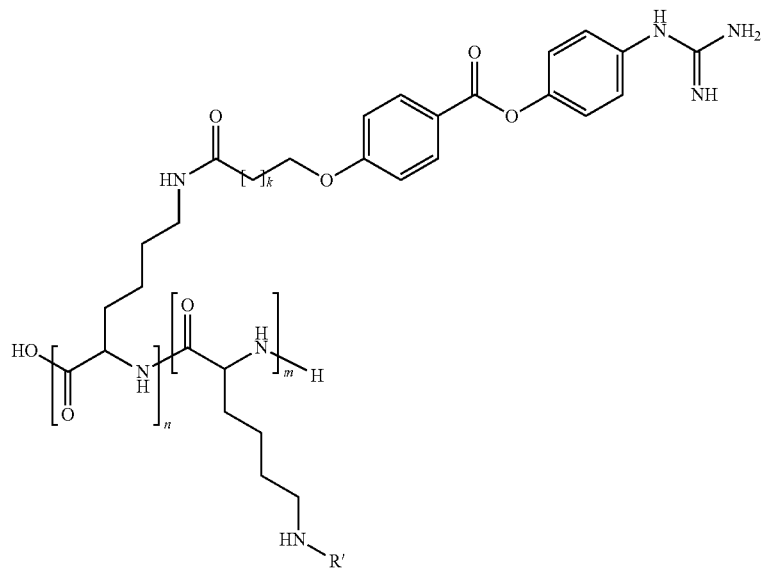

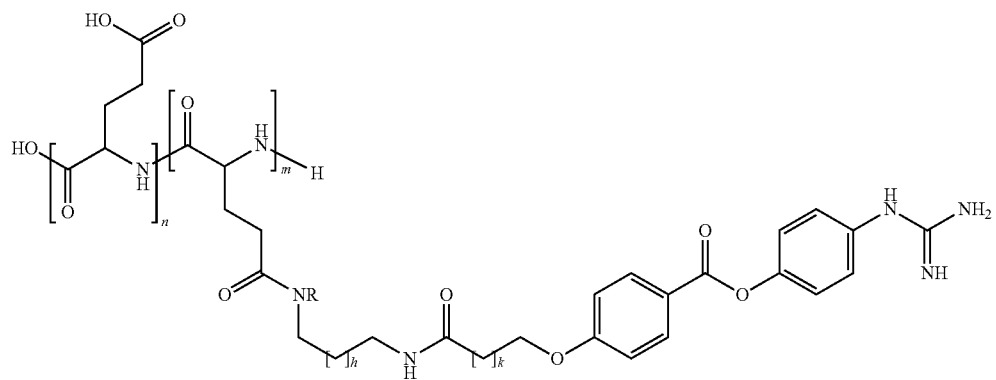

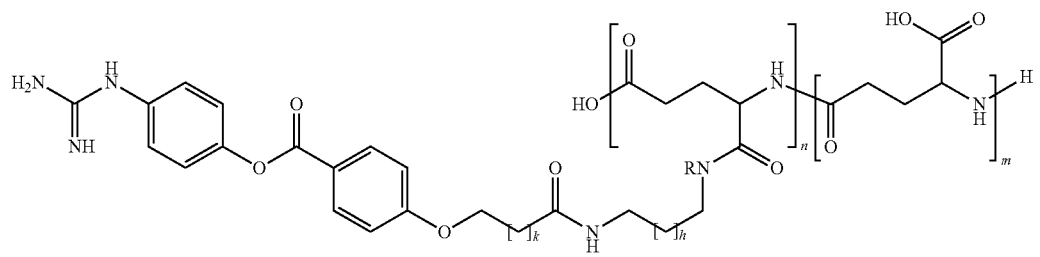

Where h and k, represent a number of substituted or unsubstituted methylene units and can independently be an integer from zero to ten; n and m can independently be an integer from zero to 1,000; h. R is independently hydrogen, methyl, ethyl, substituted alkyl, or substituted aryl. Each R' can independently be hydrogen, methyl, ethyl, substituted alkyl, or substituted aryl, acyl, or substituted acyl.

For example, inverse substrate GI enzyme inhibitors attached to representative polysaccharide polymers are shown in the examples below:

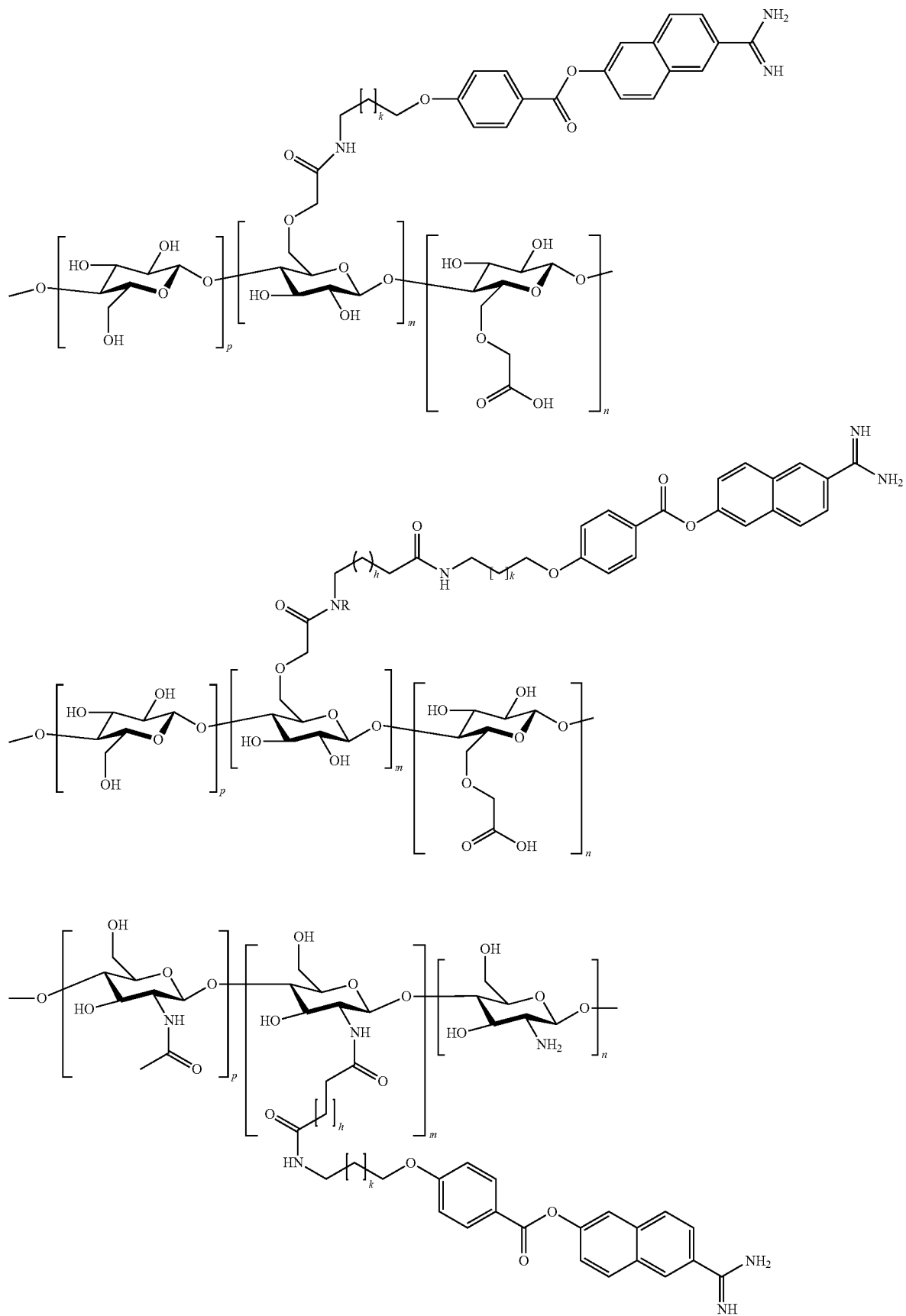

-continued
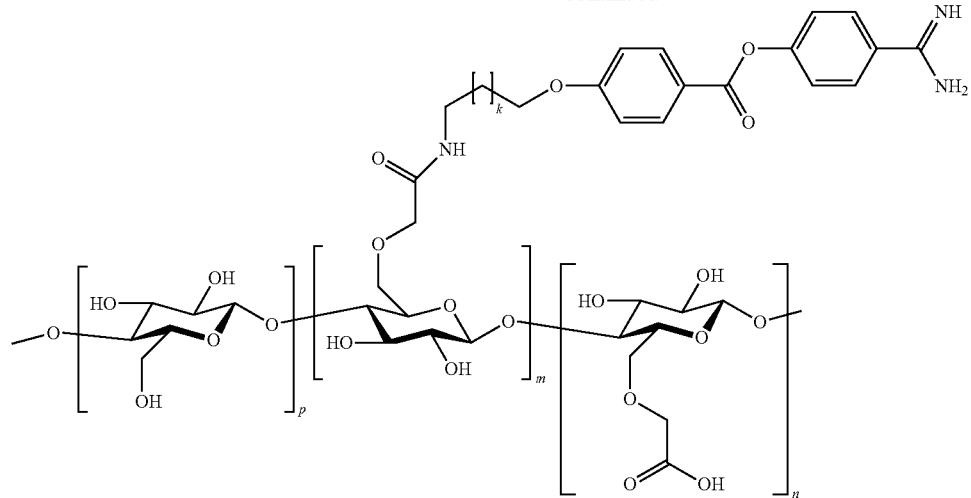
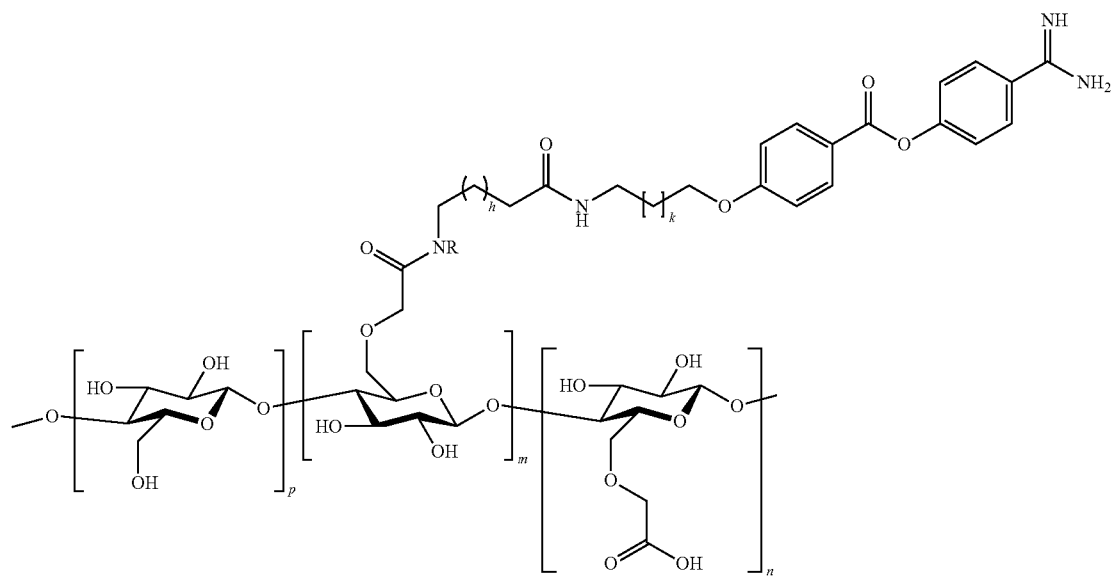
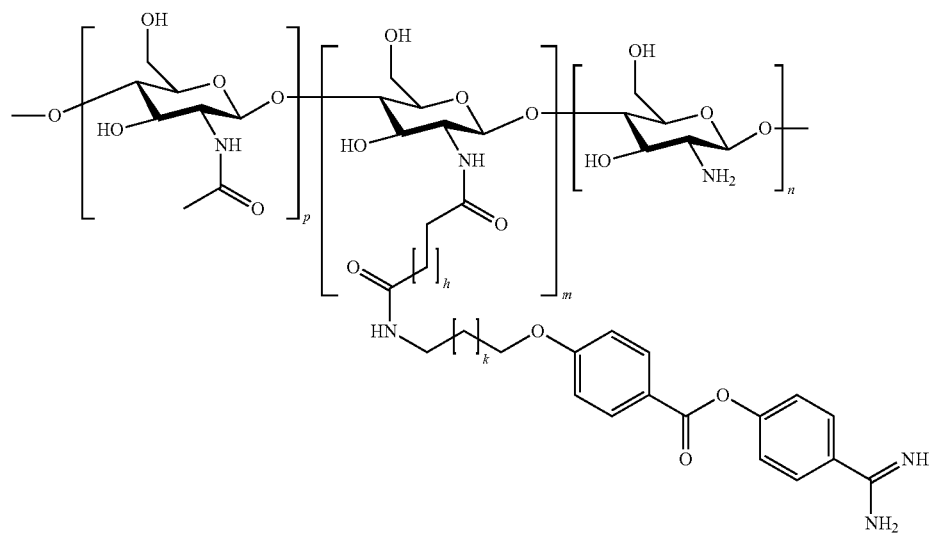

-continued

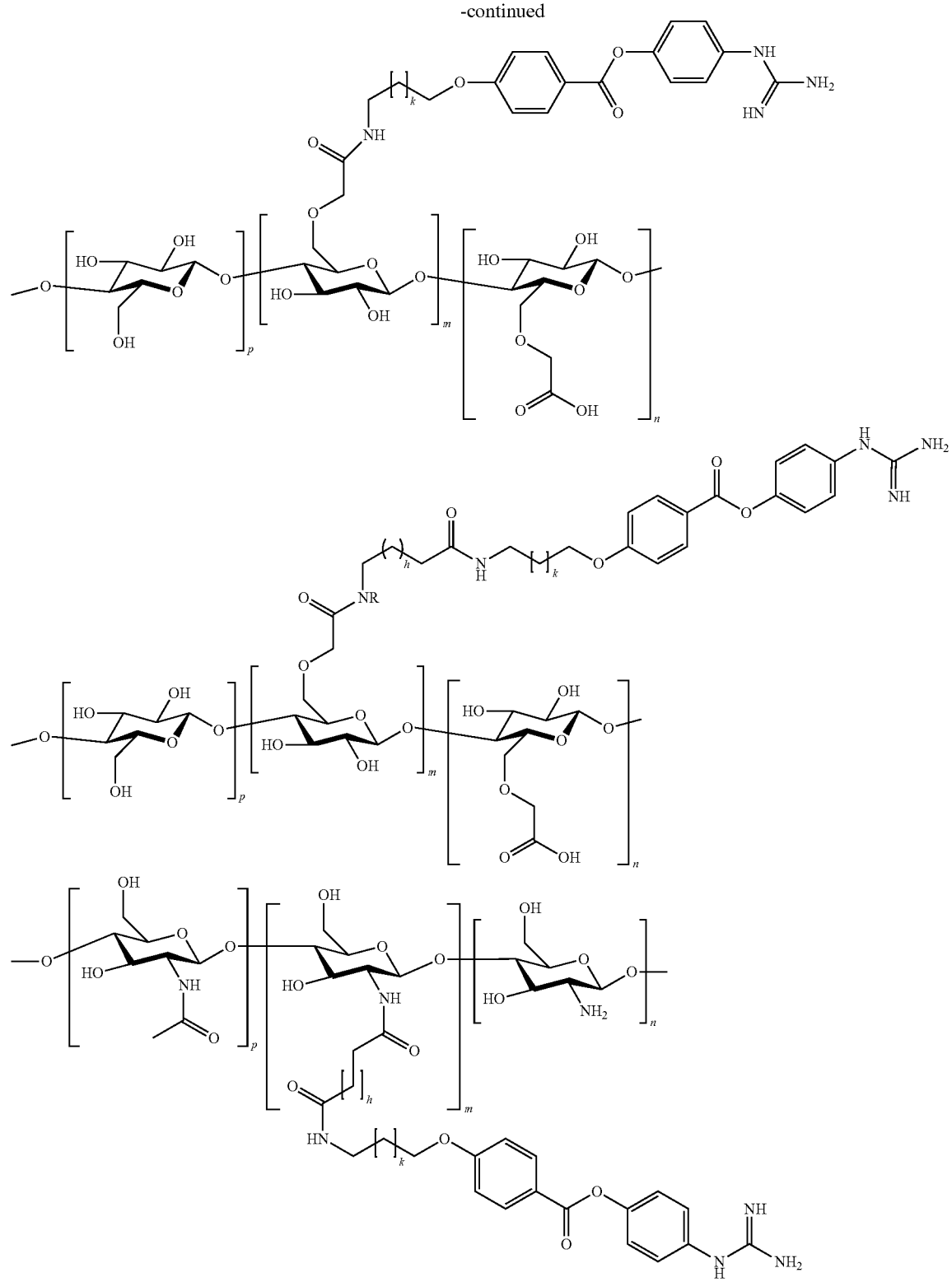

Where n, m and p can independently be an integer from zero to 1,000; h and k represent a number of substituted or unsubstituted methylene units and can be an integer from zero to ten. R is independently hydrogen, methyl, ethyl, substituted alkyl, or substituted aryl.

Non-Limiting Examples of Macromolecular GI Enzyme-Labile Opioid Prodrugs

The invention provides compositions comprising a GI enzyme-labile opioid agonist prodrug attached to a polymer having the general formula below:

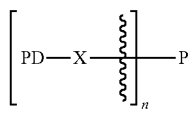

where PD is the GI enzyme-labile opioid agonist prodrug, X is a functional "linker" group as defined herein that directly, or indirectly, covalently joins PD to the polymer; n is an integer between 1 and 1000; and P is a polymer. The polymer P can be any of the polymers described above, such as, for example, PEG, polypeptides, polysaccharides and biopolymers. The polymer is selected such that when attached to the opioid or opioid prodrug it is chemically stable to the acidic conditions in the stomach, and to non-specific actions of digestive enzymes. The polymer prevents the systemic absorption of the GI enzyme labile opioid agonist prodrug and resulting non-GRAS metabolites while allowing specific GI enzymes to recognize the prodrug and mediate the release of the delivered opioid.

In some aspects the disclosure provides a macromolecule of formula:

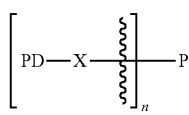

wherein:
PD is a gastrointestinal enzyme-labile opioid against prodrug;
X is a linker group that covalently joins PD to a polymer;
P is a polymer; and
n is an integer between 1 and 1000,
wherein P is selected to provide fewer than 0.25%, fewer than 0.5%, fewer than 0.75%, fewer than 1%, fewer than 2%, fewer than 5%, fewer than 10%, fewer than 15%, fewer than 25%, or fewer than 30% of absorption of the macromolecule from the gastrointestinal tract of a subject following oral administration.

The linkage between the polymer and the GI enzyme labile opioid prodrug (PD in Formulae above) is preferably stable enough under physiological conditions so that the minimal monomeric opioid or opioid prodrug is released from the polymer resulting from chemical hydrolysis or enzymatic (e.g. cleavage of linker moiety X) following administration to a patient. Thus, the linkage (X) for connecting the GI enzyme labile opioid prodrug to the polymer can include, but is not limited to, ester, thioester, amide, amine, carbamate, carbonate, ether, thioether, and urea linkages. The particular linkage and linkage chemistry employed will depend upon the subject opioid, inhibitor, functional groups within the molecules available either for attachment to a polymer or conversion to a suitable attachment functionality, the presence of additional functional groups within the molecule, and the like, and can be readily determined by one skilled in the art based upon the guidance presented herein.

The GI enzyme labile opioid prodrug can generally be hydrolyzed under specific physiological conditions. The GI enzyme labile opioid prodrug can be cleaved enzymatically, preferably by a GI enzyme. The GI enzyme is preferably trypsin or chymotrypsin.

In one aspect of the invention, a compound is provided wherein an opioid agonist is covalently linked to a GI enzyme cleavable moiety. The opioid can be morphine, a morphone or other phenol containing opioid, or a codone or other ketone containing opioids, such as illustrated by the structures below:

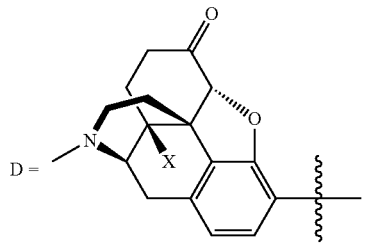

Morphones
(or other phenol containing opioids)

X = H, OH

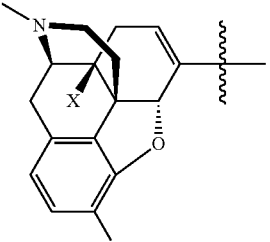

Codones
(or other ketone containing opioids)

X = H, OH

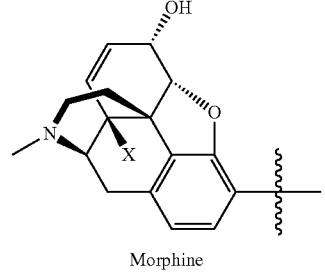

Morphine

D can be a phenolic opioid selected from buprenorphine, dihydroetorphine, diprenorphine, etorphine, hydromorphone, levorphanol, morphine, nalmefene, and oxymorphone or D is a ketone-containing opioid selected from acetylmorphone, hydrocodone, hydromorphone, oxycodone, oxymorphone, pentamorphone, ketobemidone and methadone.

According to one aspect, the invention provides pharmaceutical compositions which comprise a GI enzyme-labile opioid prodrug for controlled release of an opioid. The disclosure provides a promoiety that is attached to an opioid through any structural moiety on the opioid, where the structural moiety has a reactive group. Any type of reactive group on an opioid can provide a handle for a point of attachment to a promoiety. Examples of reactive groups on an opioid include, but are not limited to, alcohol (such as phenol), ketone, amino, and amide.

An alcohol (such as a phenol) on an opioid can provide a point of attachment to a promoiety by reaction to form a linkage, such as a carbamate, an ether, or an ester. A ketone on an opioid can provide a point of attachment to a promoiety by reaction to form a linkage, such as an enol-ester or enol-carbamate. An amino group on an opioid can provide a point of attachment to a promoiety by reaction to form an amino linkage, including quaternary salts, or an amide. An amide on an opioid can provide a point of attachment to a promoiety by reaction to form a linkage via acylation of the nitrogen atom, acylation of the enolic oxygen of the amide moiety, or acylation of the imino-alcohol tautomer of the amide moiety.

Release of the opioid is mediated by enzymatic cleavage of the promoiety from the opioid prodrug. In each case, the promoiety comprises an enzyme-cleavable moiety that is susceptible to cleavage by a GI enzyme. Such cleavage can initiate, contribute to, or effect drug release.

In one aspect of the invention, the opioid is a phenolic opioid. Accordingly, a phenoic opioid is attached through the phenolic oxygen to a linker, which is further attached to a GI enzyme cleavable moiety. Such drugs can be phenol-modified opioid agonist drugs or include phenol-modified opioid partial agonist, inverse agonists, mixed agonist-antagonist drugs, or partial antagonist drugs, and the like.

In another aspect of the invention, the disclosure provides for ketone-modified opioids. Such as ketone-modified opioid agonists, partial agonists, inverse agonists, mixed agonist-antagonists, partial antagonists, or biased-agonists and the like.

The disclosure provides for opioid prodrug polymer conjugates co-formulated with small molecule GI enzyme inhibitors, GI enzyme inhibitor-polymer conjugates or inverse substrate-polymer conjugates. In some embodiments the opioid prodrug is the prodrug of morphine, hydromorphone, hydrocodone, oxycodone, codeine, and oxymorphone. The prodrug can be attached to a polymer, such as PEG or polypeptide, as described in detail above.

In one aspect of the invention, the opioid promoiety is an enolic or phenolic ester and the release of the opioid drug molecule from the macromolecular GI enzyme-labile opioid prodrug occurs concomitant with enzyme hydrolysis. The GI enzyme recognizes the amino acid ester, and directly hydrolyzes the bond between the opioid and the amino acid, thereby releasing the opioid agonist drug molecule, as illustrated below:

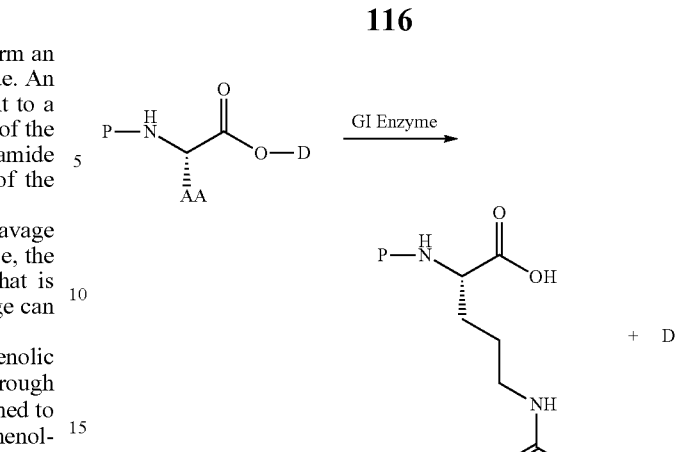

Macromolecular GI enzyme-labile opioid prodrugs that operate via this mechanism can be described by the general formula:

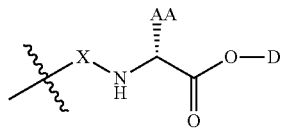

Where D is an opioid as defined above; X is a covalent bond, or functional group, or "linker" that conjoins the GI enzyme-labile opioid prodrug to a macromolecular polymer; and AA is a natural or unnatural amino acid side chain that is recognized by the GI enzyme that modulates the release of opioid D.

Non-limiting examples of macromolecular GI enzyme-labile opioid prodrugs that operate via this mechanism include the following:

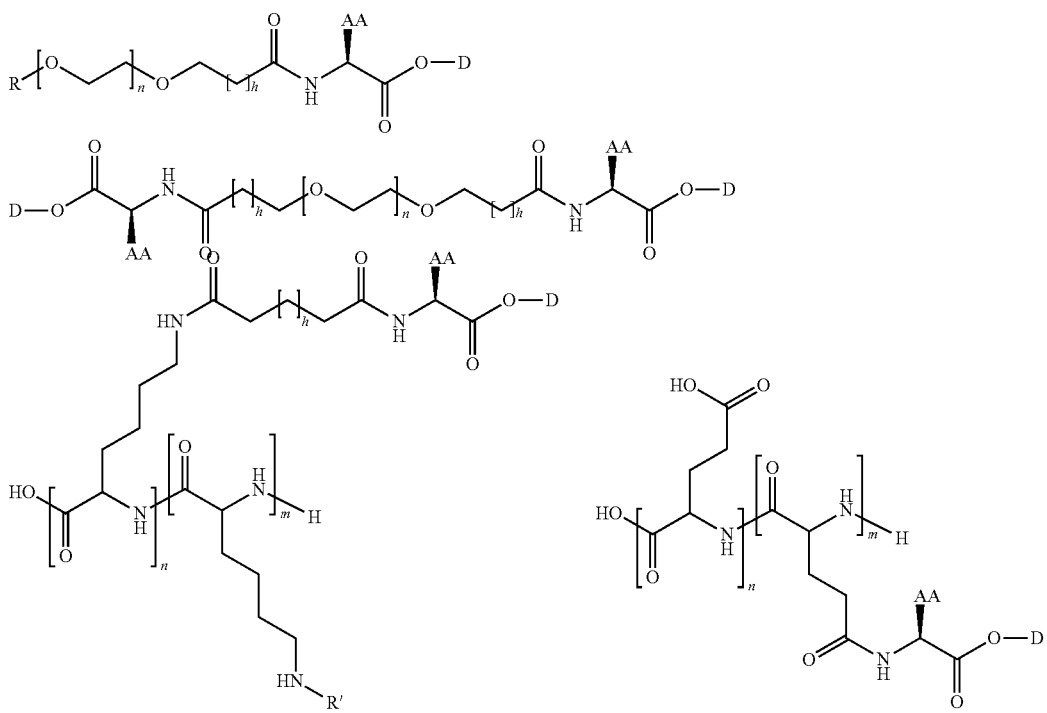

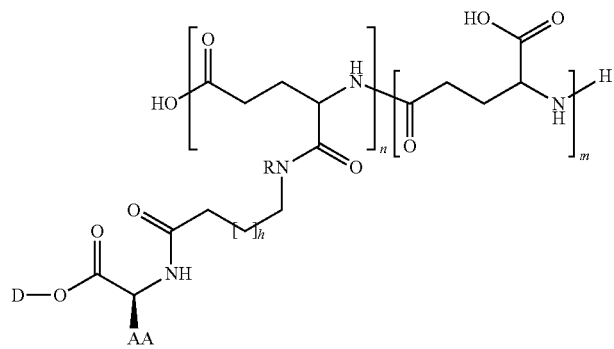

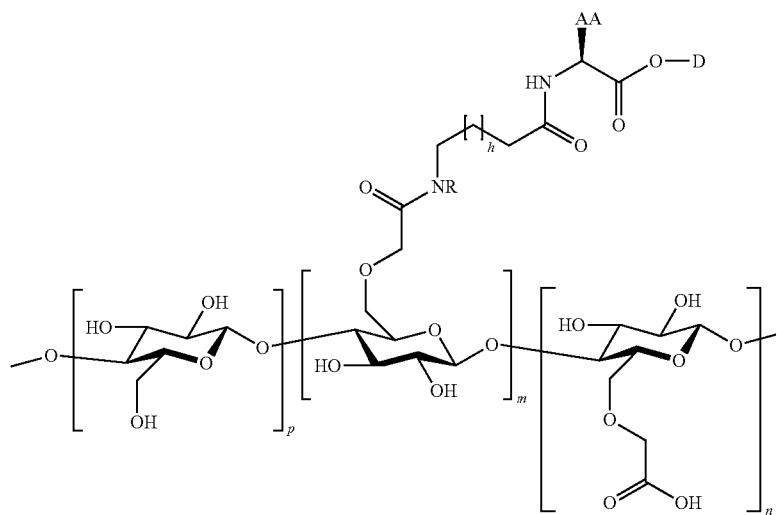

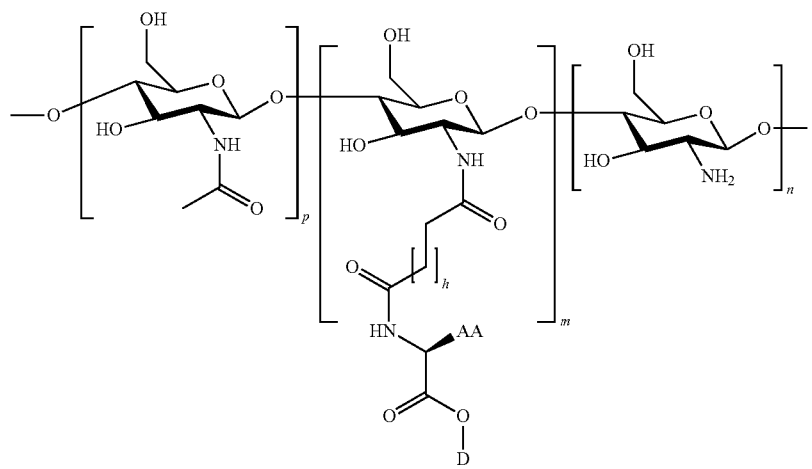

Where D is an opioid agonist as defined above; AA is a natural or unnatural amino acid side chain that is recognized by a digestive enzyme; h represents a number of substituted or unsubstituted methylene units and can be an integer from zero to ten; n, m, and p can independently be an integer from 1 to 1000; R is independently hydrogen, methyl, ethyl, substituted alkyl, or substituted aryl; Each R' can independently be hydrogen, methyl, ethyl, substituted alkyl, or substituted aryl, acyl, or substituted acyl.

Further non-limiting examples of macromolecular trypsin enzyme-labile hydrocodone, oxycodone, hydromorphone, and oxymorphone prodrugs that operate via this mechanism can include the following:

119
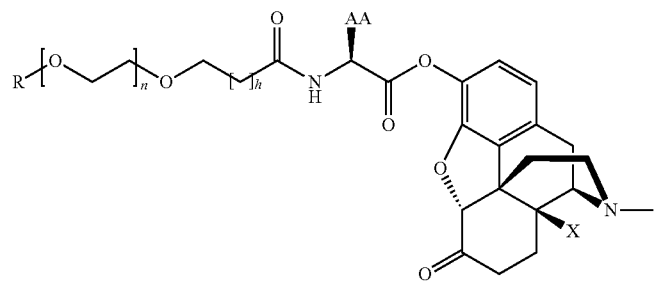
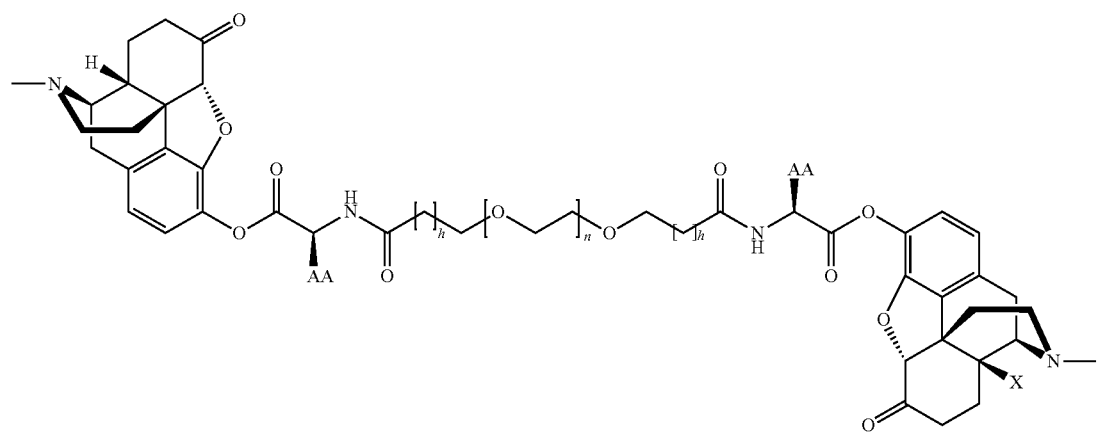
120
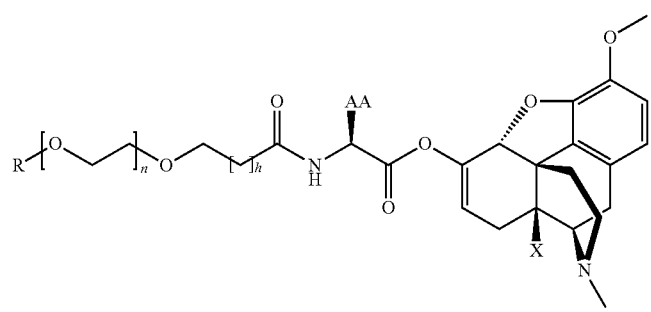
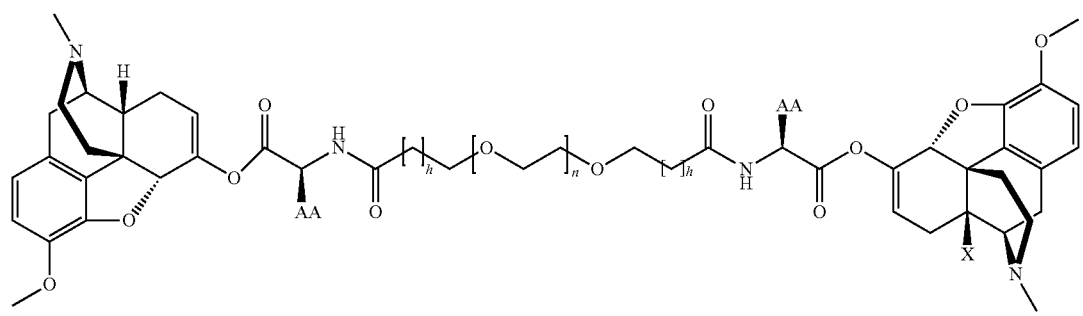

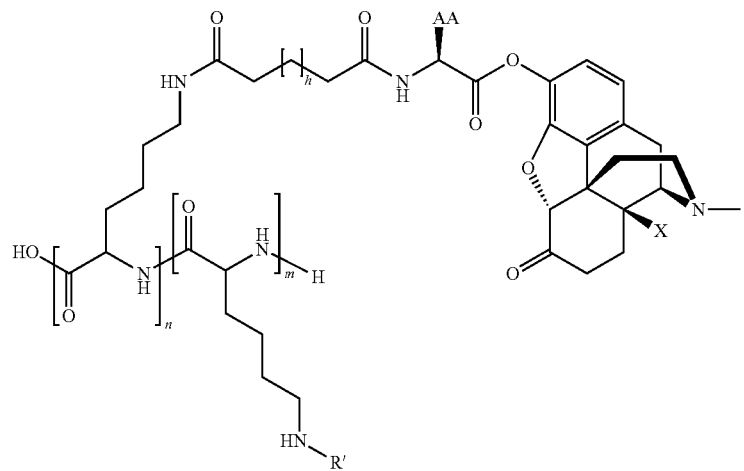
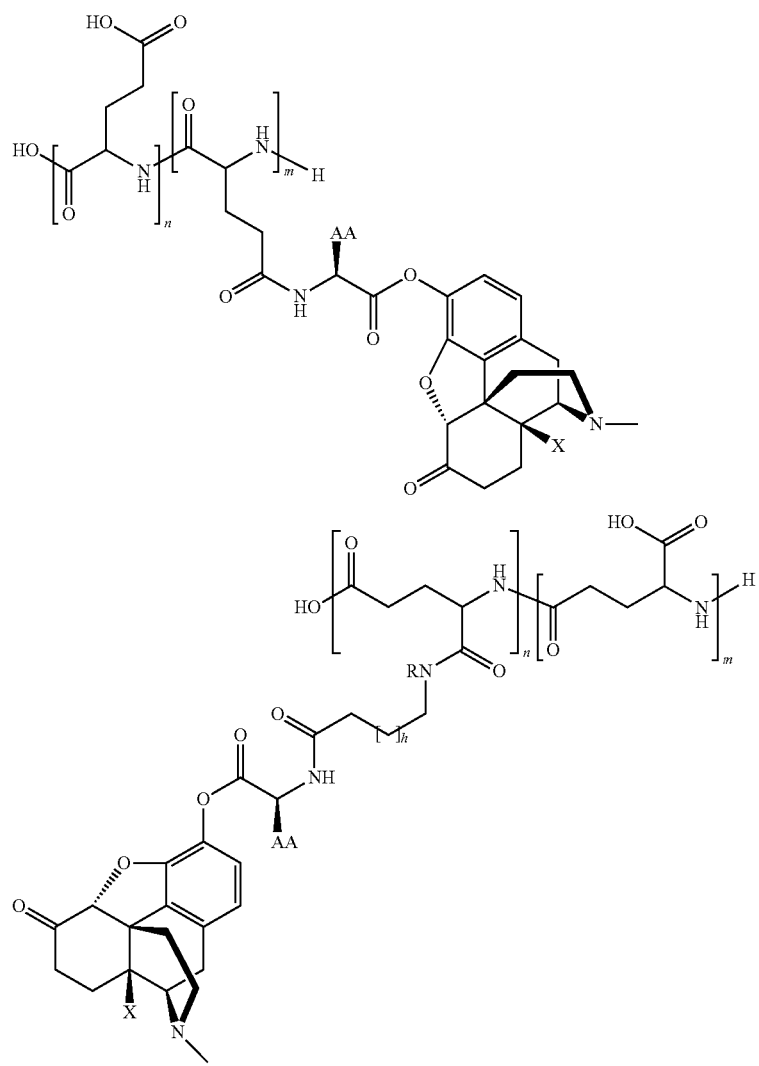

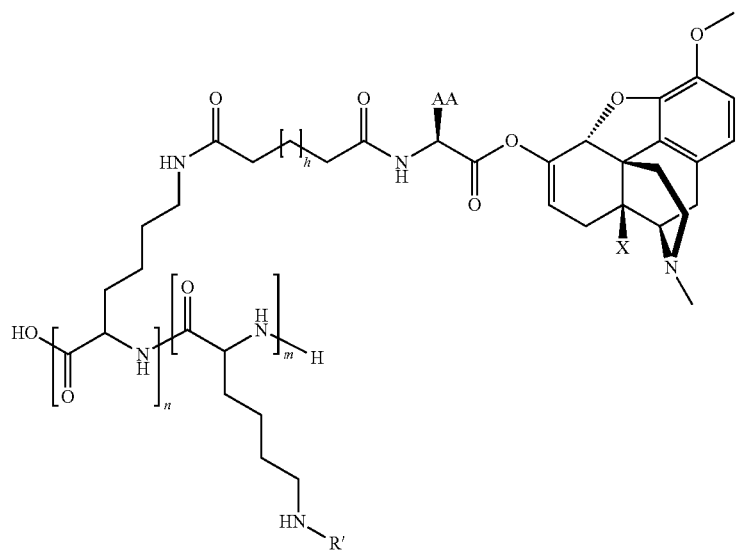
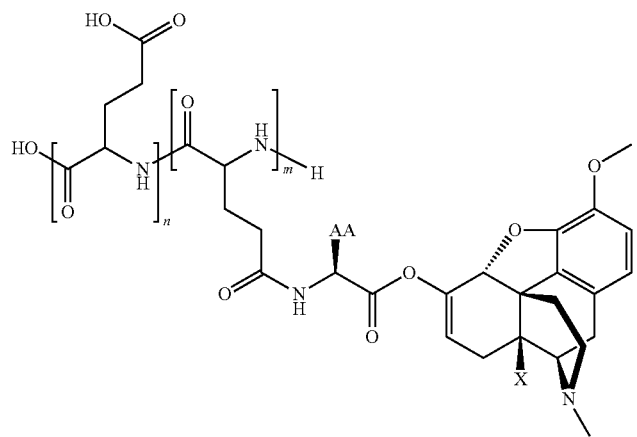
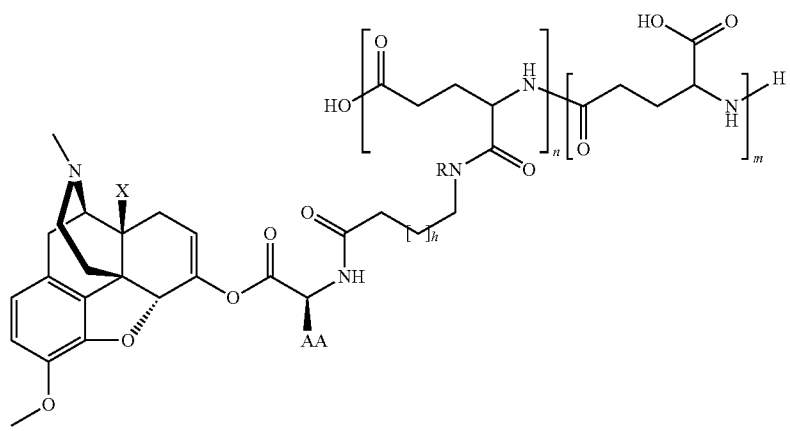

-continued
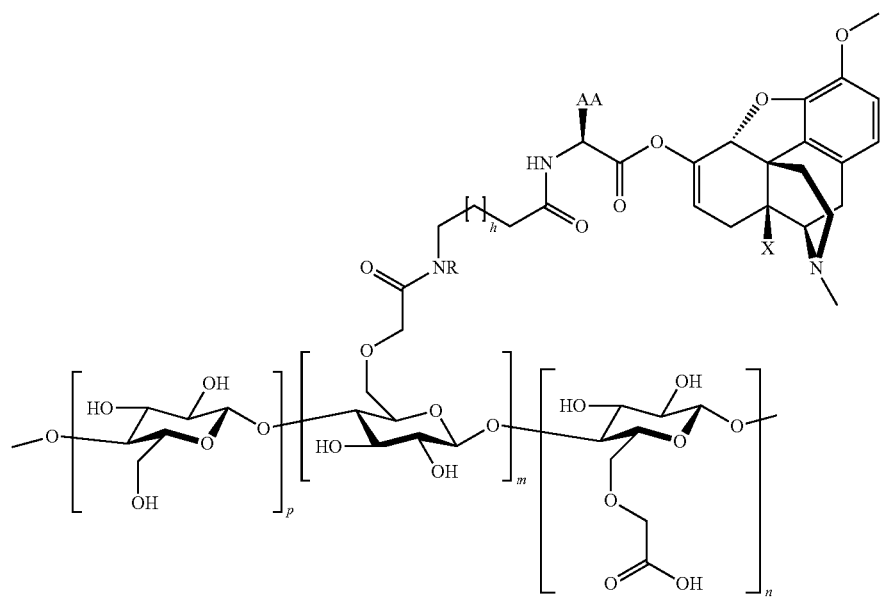
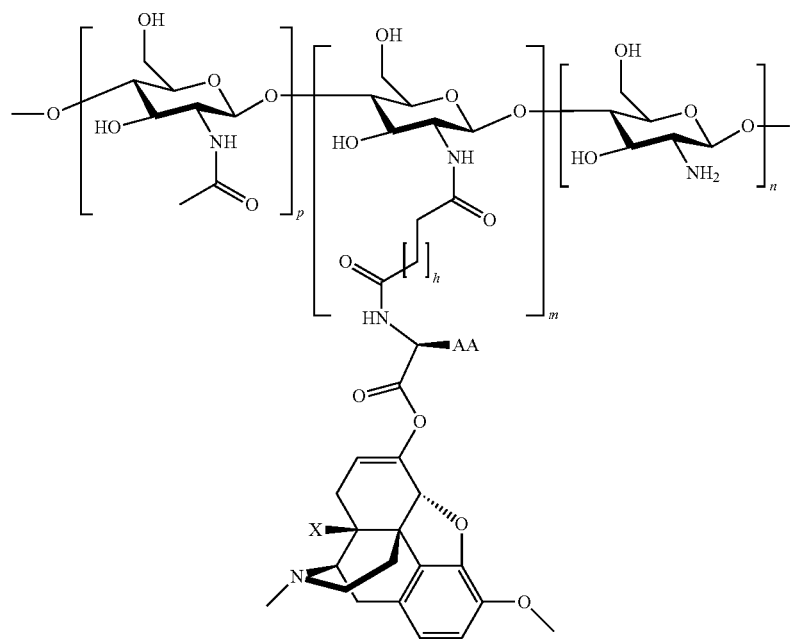

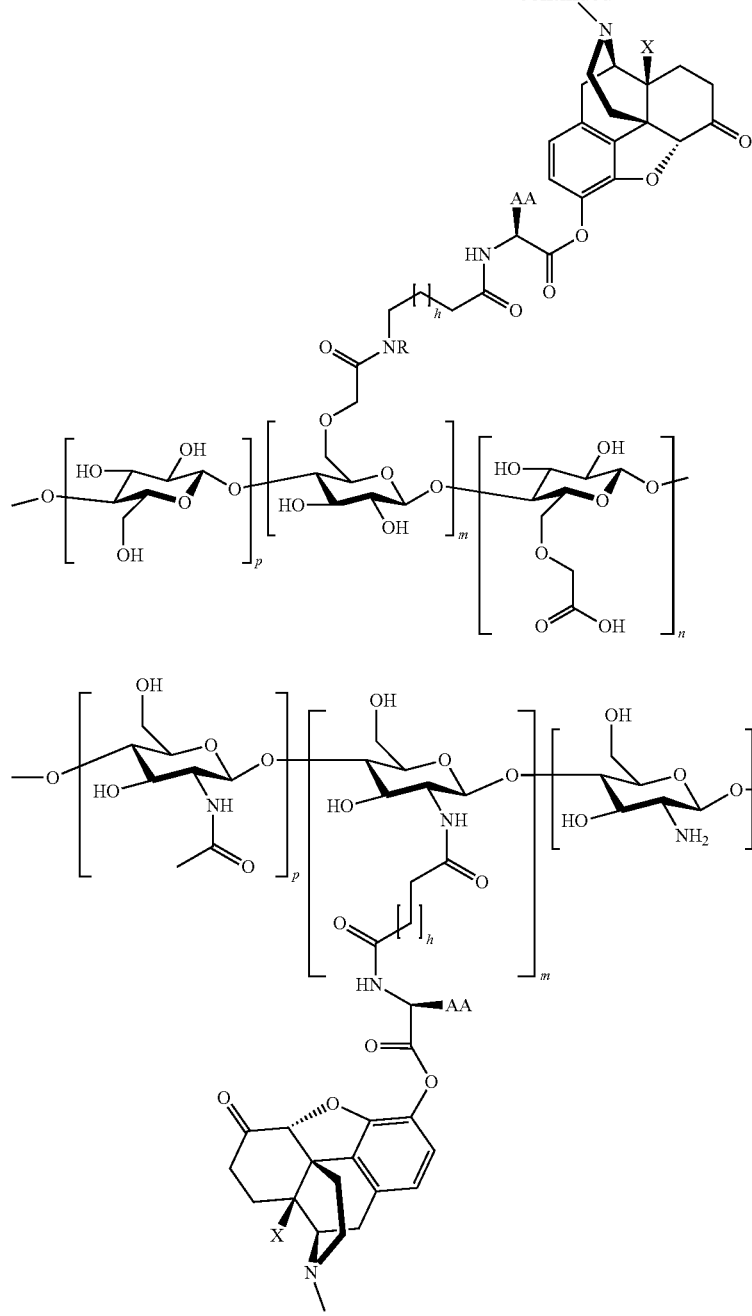

Where X can be H or OH; AA is a natural or unnatural amino acid side chain that is recognized by a digestive enzyme; h represents a number of substituted or unsubstituted methylene units and can be an integer from zero to ten; n, m, and p can independently be an integer from 1 to 1000. R is independently hydrogen, methyl, ethyl, substituted alkyl, or substituted aryl. Each R' can independently be hydrogen, methyl, ethyl, substituted alkyl, or substituted aryl, acyl, or substituted acyl.

In another aspect of the invention, the GI enzyme-labile opioid prodrug is and enolic or phenolic carbamate and the release of the opioid agonist drug molecule from the macromolecular GI enzyme-labile opioid prodrug occurs via the two-step process depicted below. The initial enzyme hydrolysis of the promoiety results in the formation of a nucleophilic oxygen nucleophile (e.g. phenolate or carboxylate) which then undergoes a rapid intramolecular cyclization-release reaction to release the opioid drug molecule, as illustrated below:

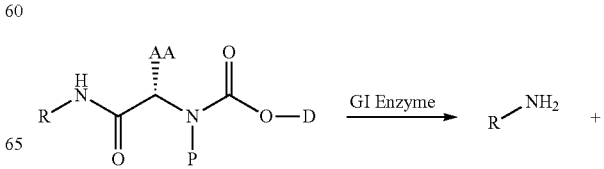

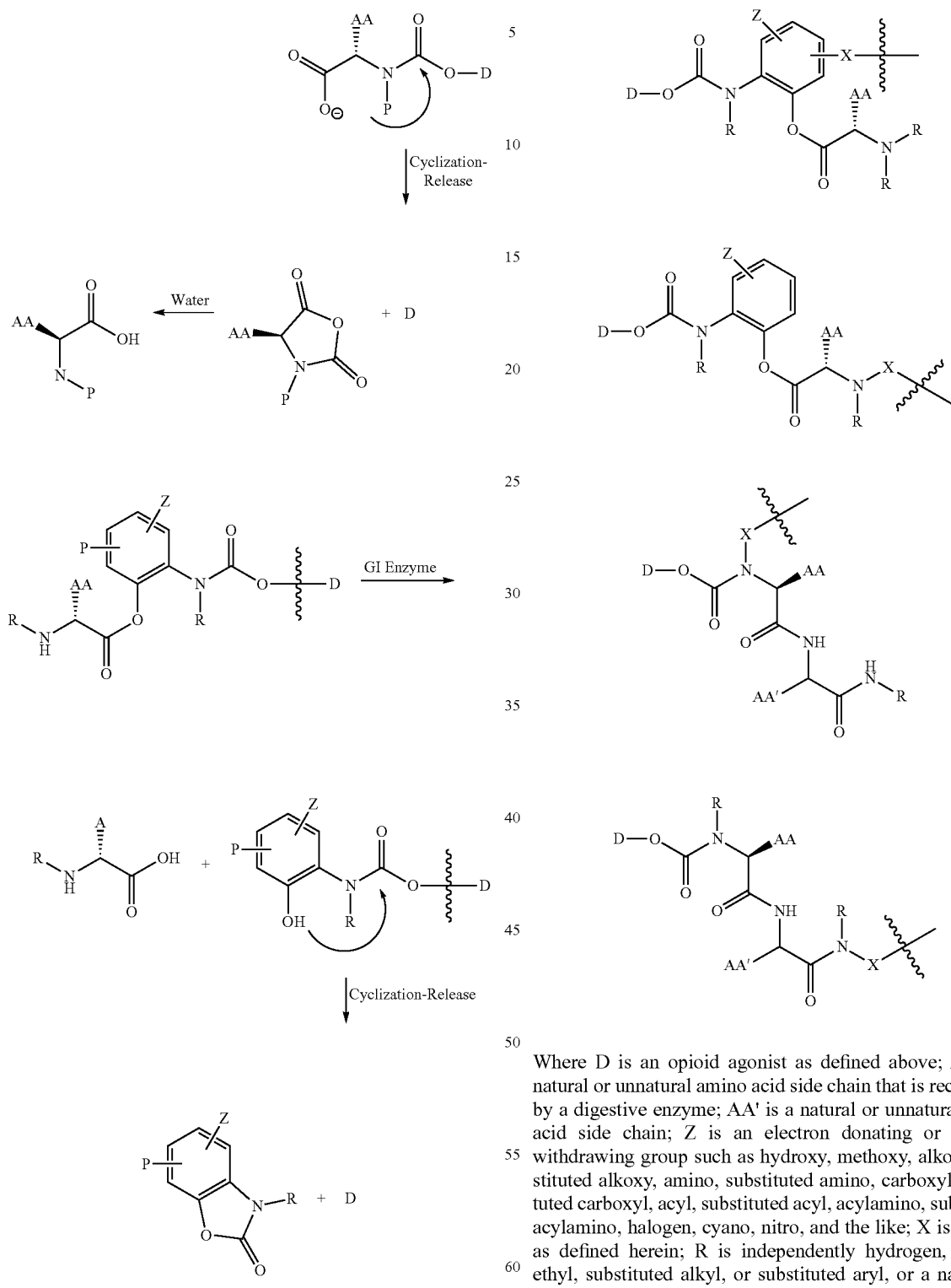

Where D is an opioid agonist as defined above; AA is a natural or unnatural amino acid side chain that is recognized by a digestive enzyme; AA' is a natural or unnatural amino acid side chain; Z is an electron donating or electron withdrawing group such as hydroxy, methoxy, alkoxy, substituted alkoxy, amino, substituted amino, carboxyl, substituted carboxyl, acyl, substituted acyl, acylamino, substituted acylamino, halogen, cyano, nitro, and the like; X is a linker as defined herein; R is independently hydrogen, methyl, ethyl, substituted alkyl, or substituted aryl, or a natural or unnatural amino acid or a polypeptide comprising up to 10 natural and/or unnatural amino acids; adjacent R groups can be joined to form a cyclic or heterocyclic structure.

Non-limiting examples of macromolecular GI enzyme-labile opioid prodrugs that operate via this mechanism include the following:

Macromolecular GI enzyme-labile opioid prodrug moieties that operate via this mechanism can be described by the general formulae:

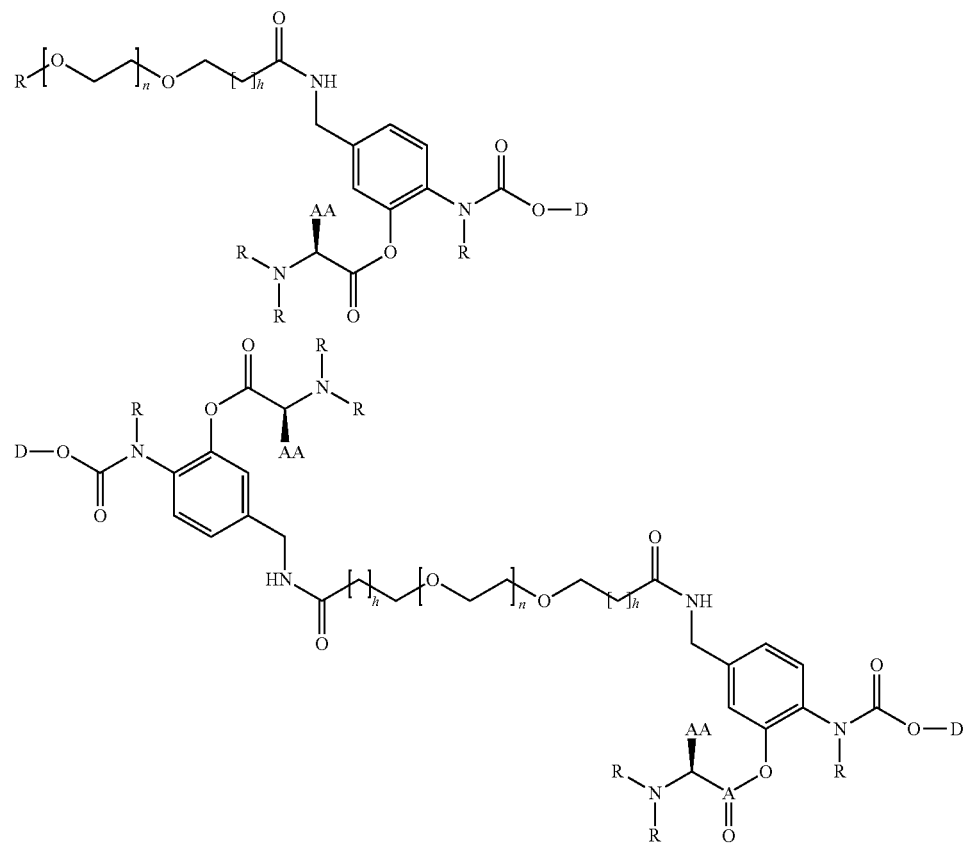
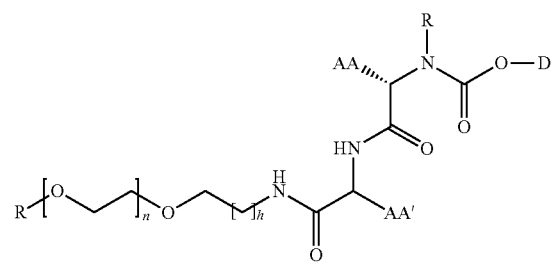
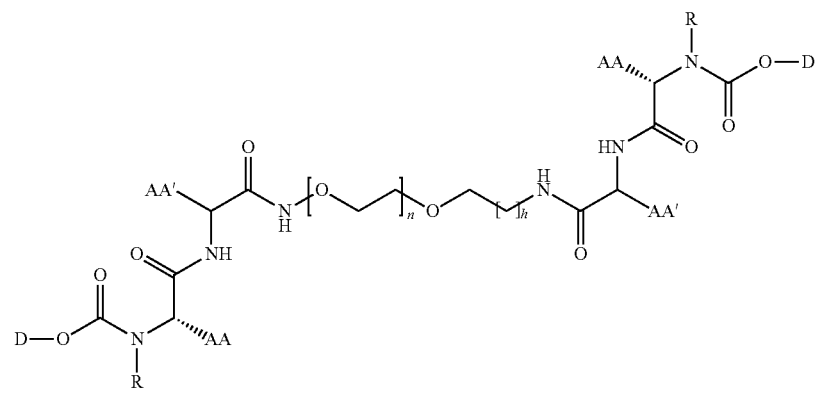

-continued
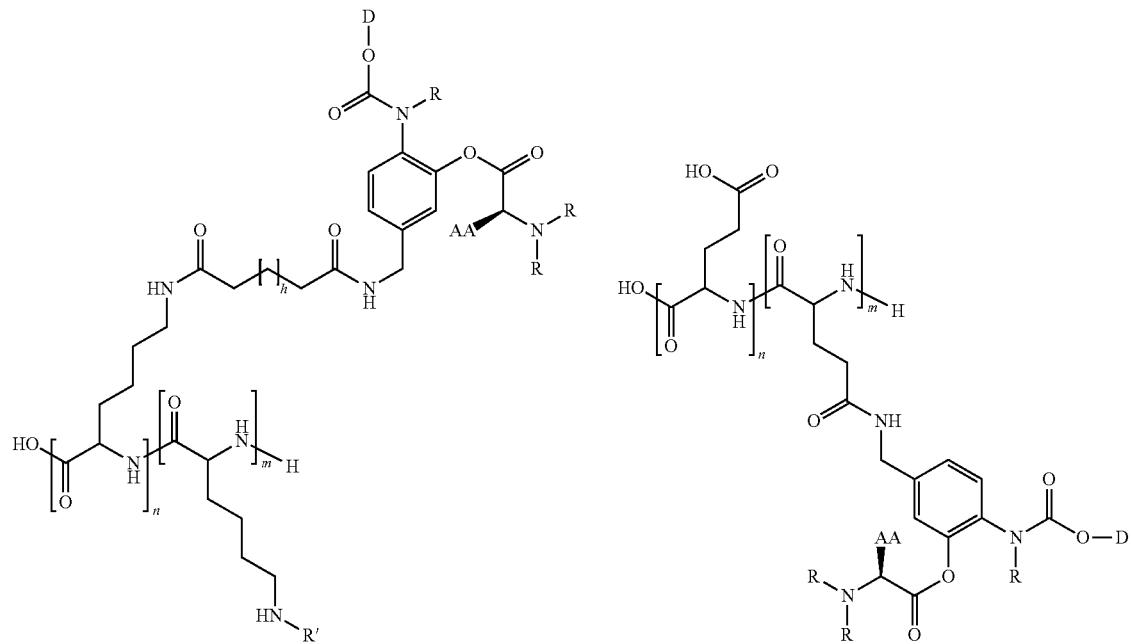
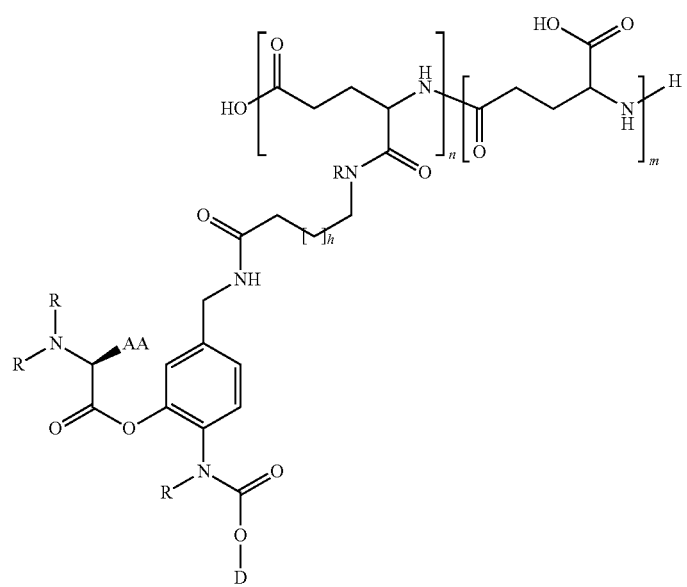

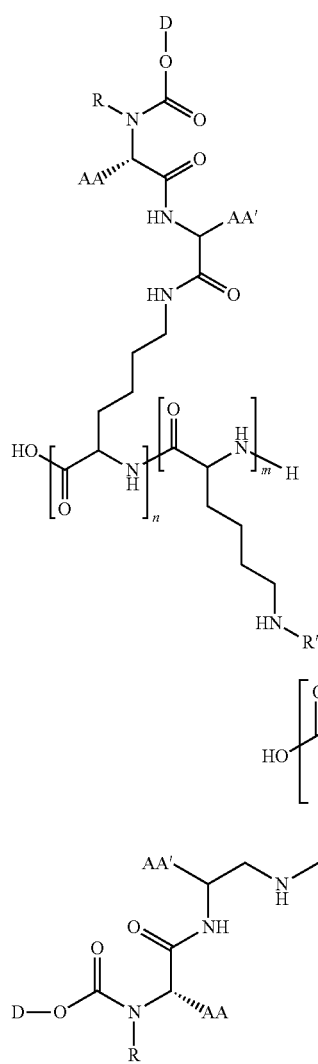
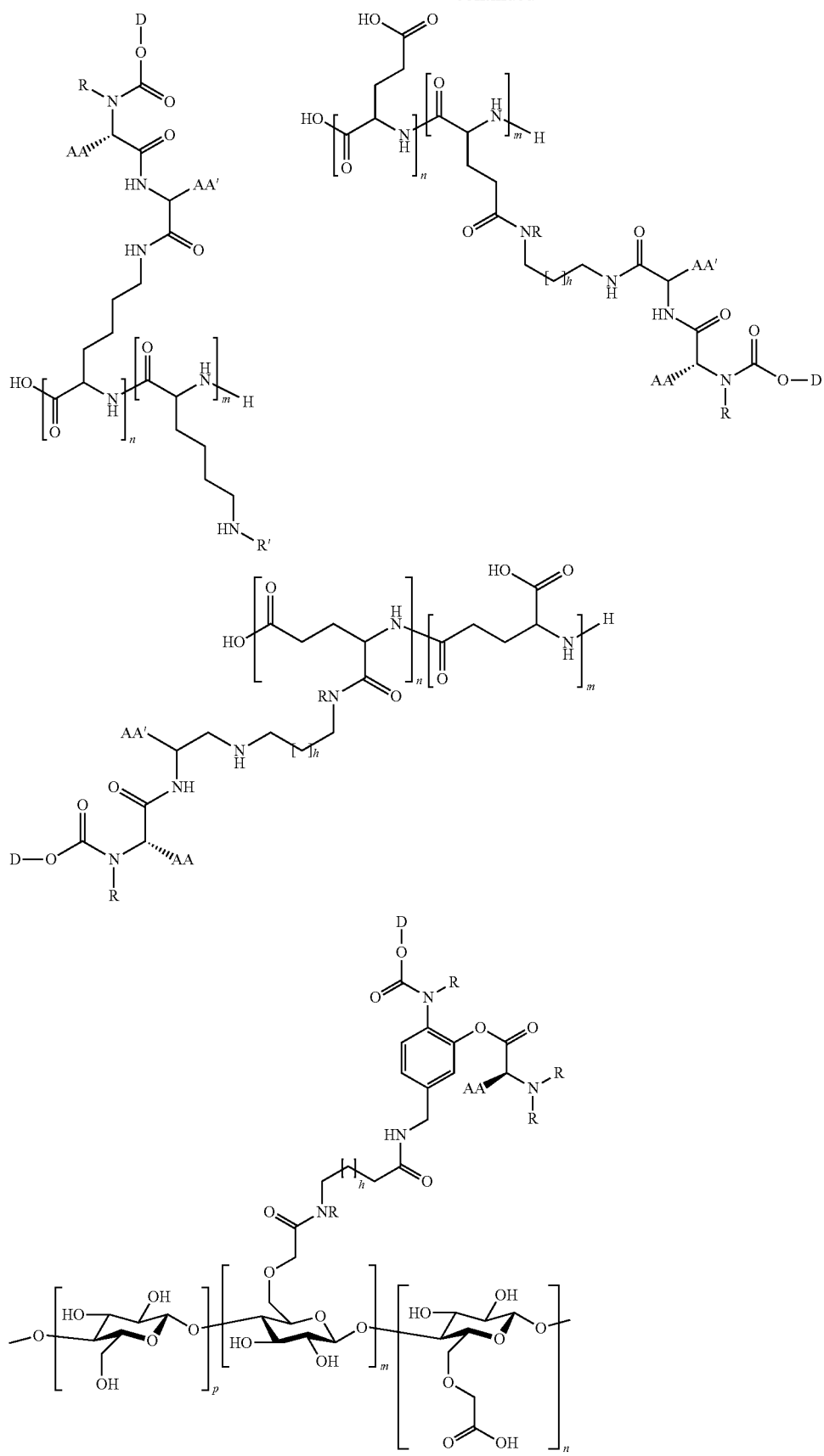

-continued
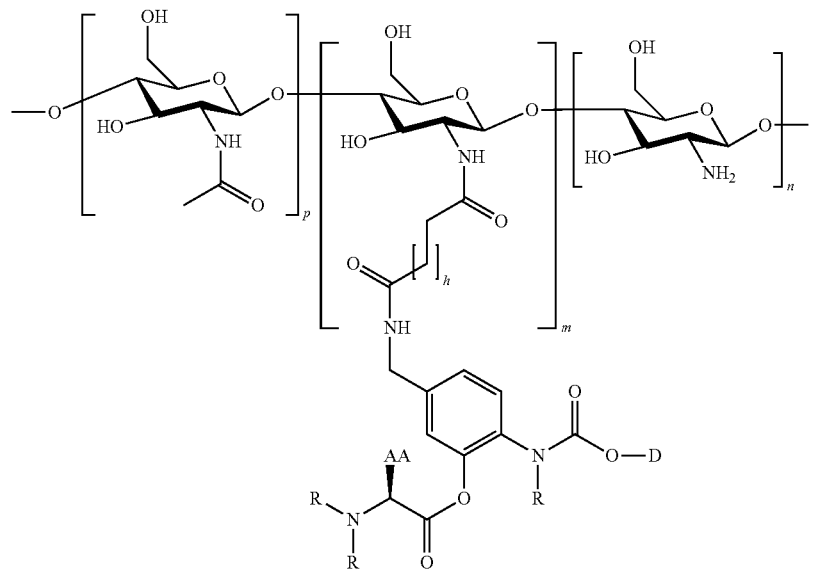
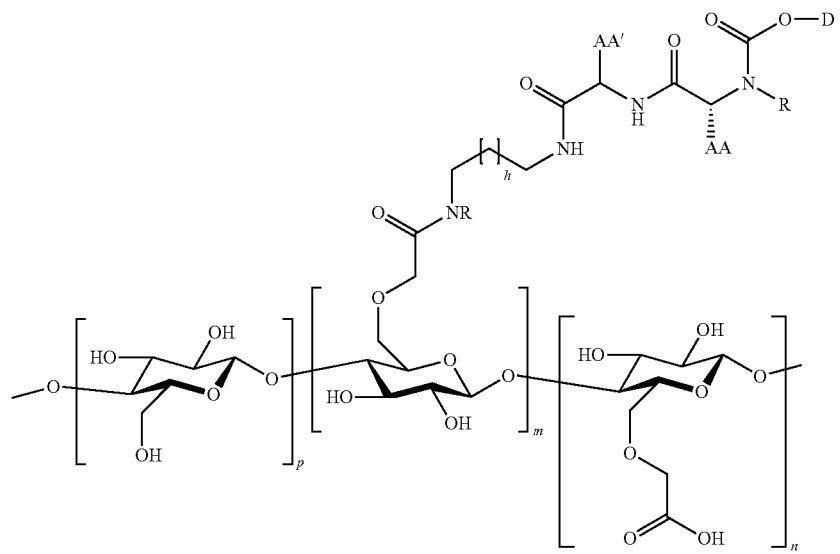

-continued

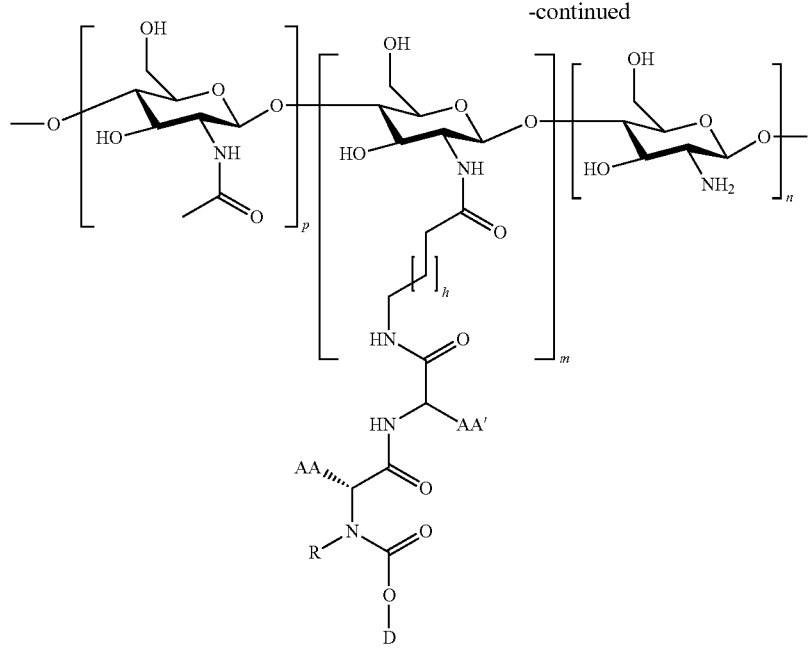

Where D is an opioid agonist as defined above; AA is a natural or unnatural amino acid side chain that is recognized by a digestive enzyme; AA' is a natural or unnatural amino acid side chain; R is independently hydrogen, methyl, ethyl, substituted alkyl, or substituted aryl, or a natural or unnatural amino acid, or a polypeptide comprising up to 10 natural and/or unnatural amino acids; adjacent R groups can be joined to form a cyclic or heterocyclic structure; h represents a number of substituted or unsubstituted methylene units and can be an integer from zero to ten; n, m, and p can independently be an integer from 1 to 1000; each R' can independently be hydrogen, methyl, ethyl, substituted alkyl, or substituted aryl, acyl, or substituted acyl.

Further non-limiting examples of macromolecular trypsin enzyme-labile hydrocodone, oxycodone, hydromorphone, and oxymorphone prodrugs that operate via this mechanism can include the following:

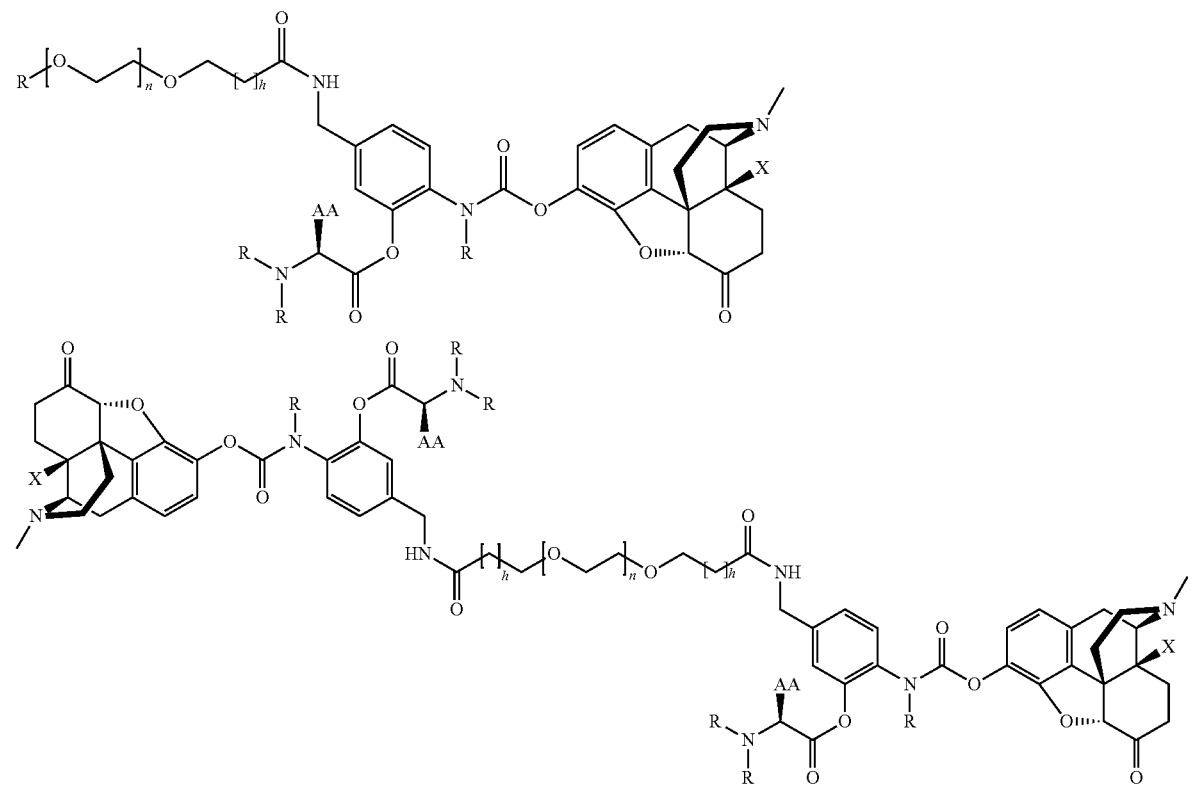

-continued
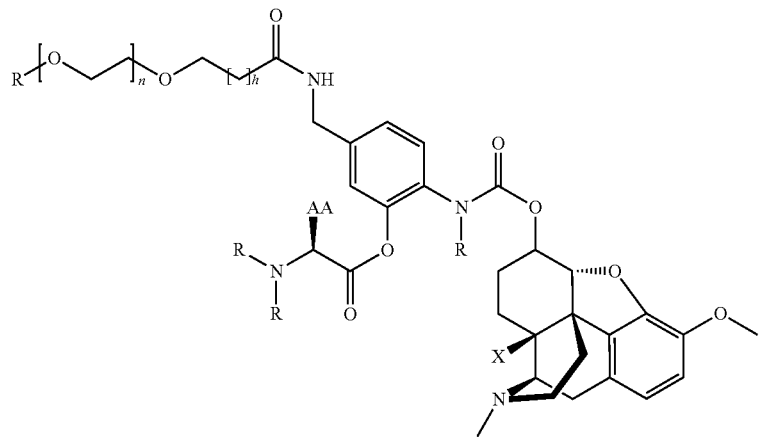
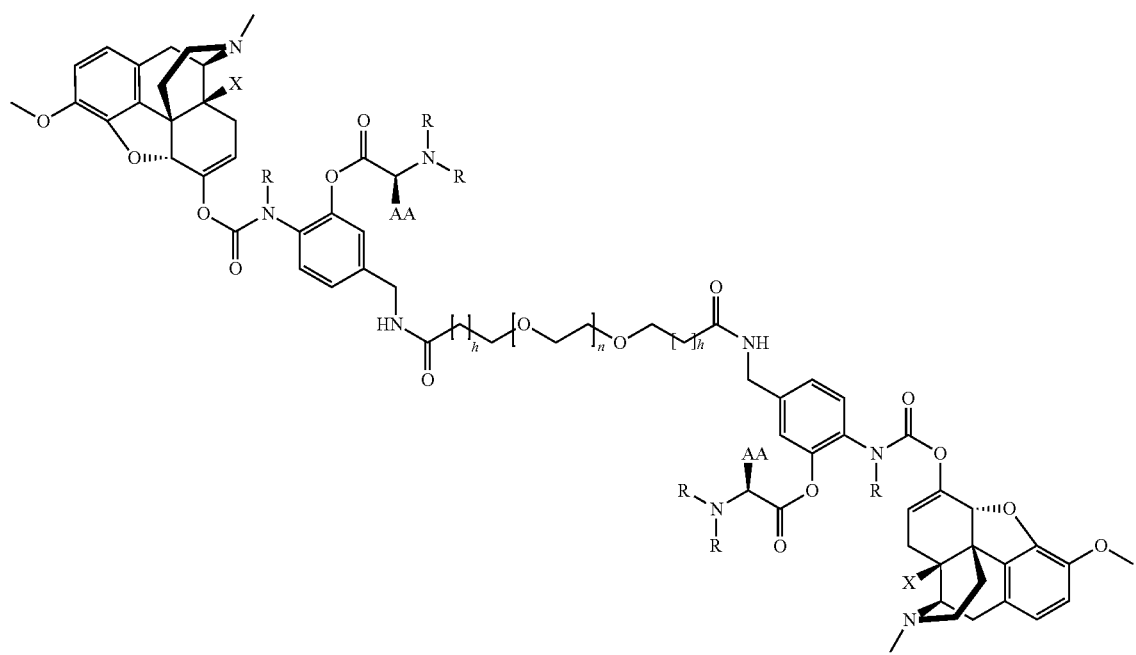
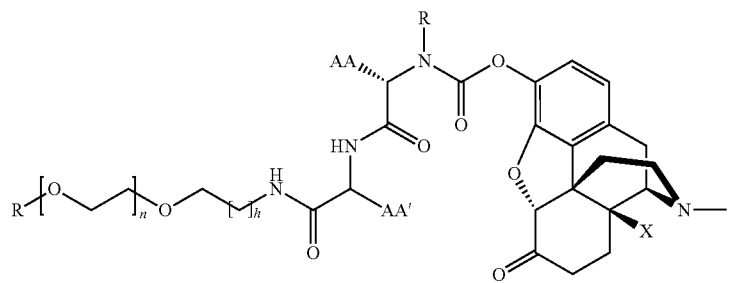

-continued
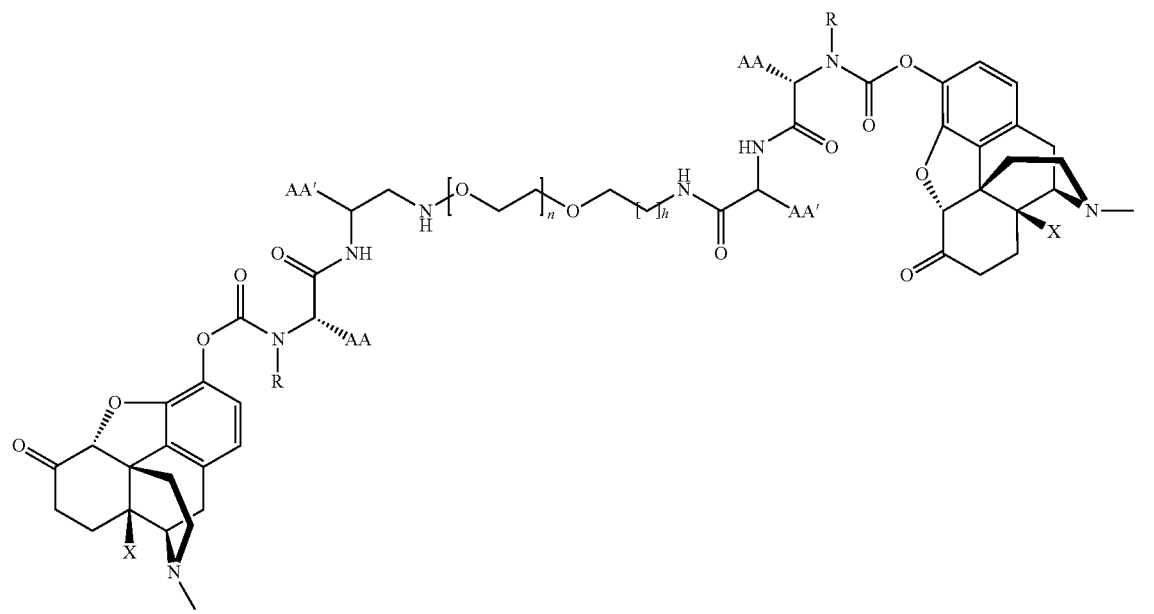
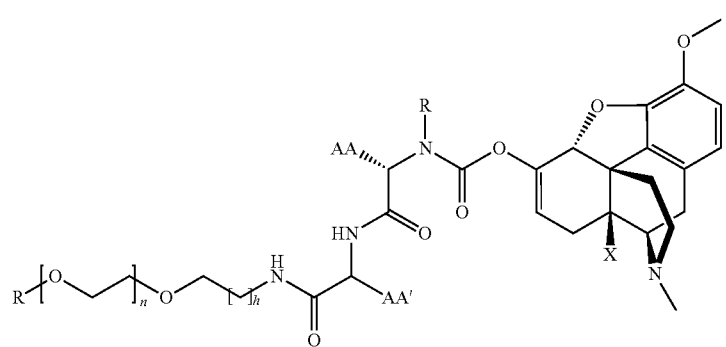
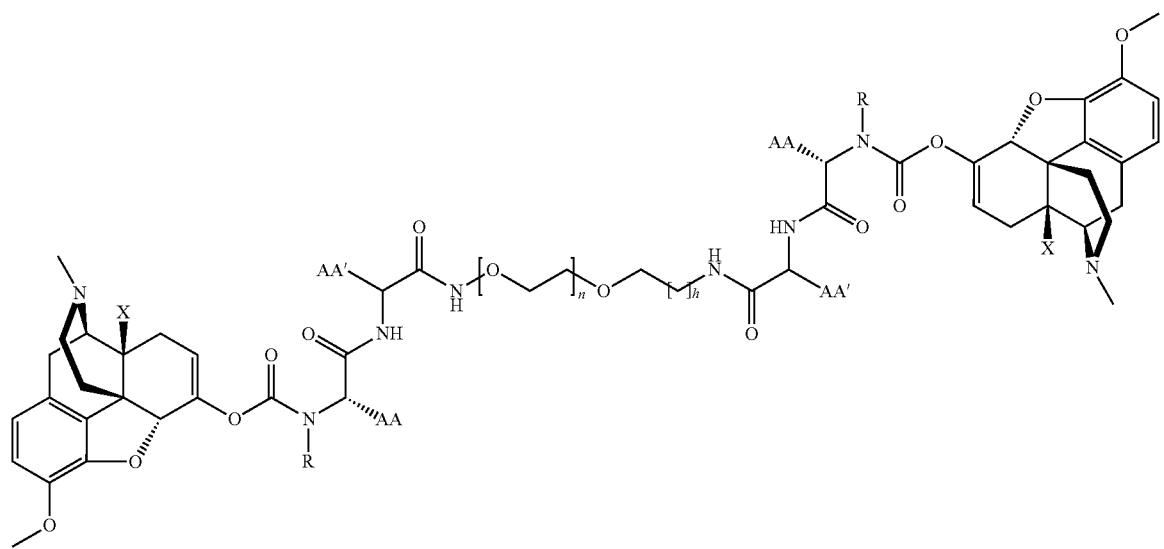

-continued
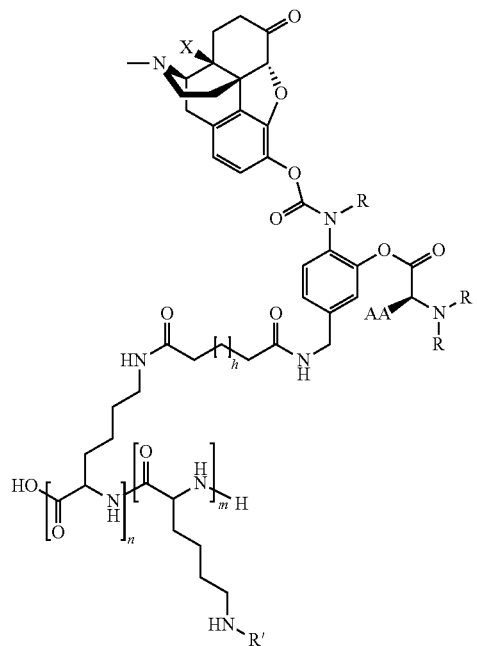
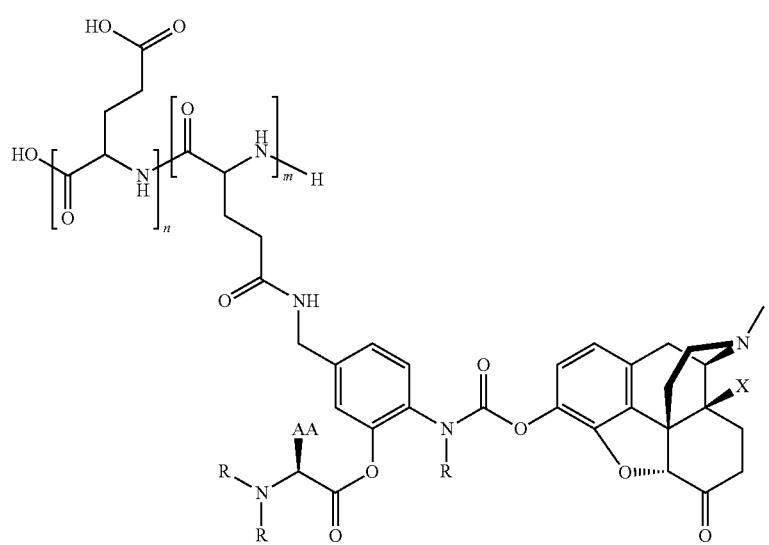

-continued
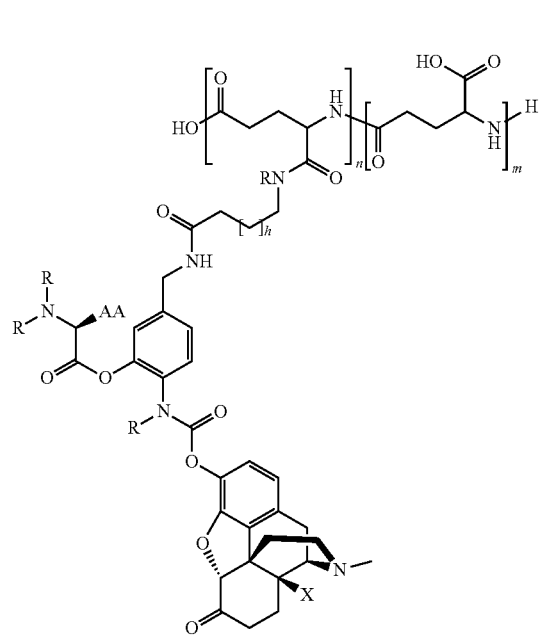
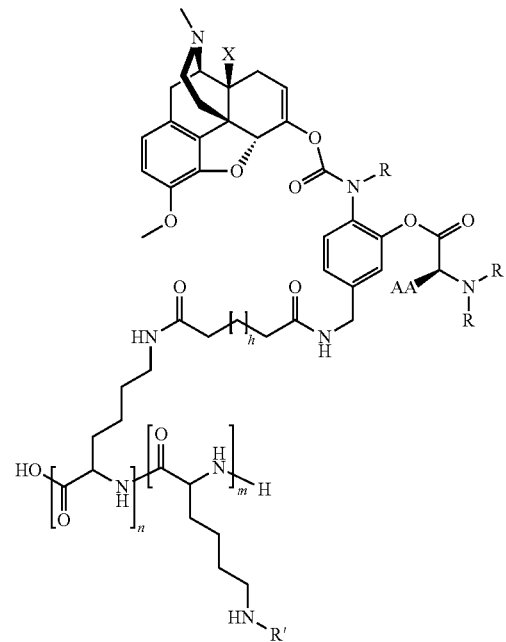
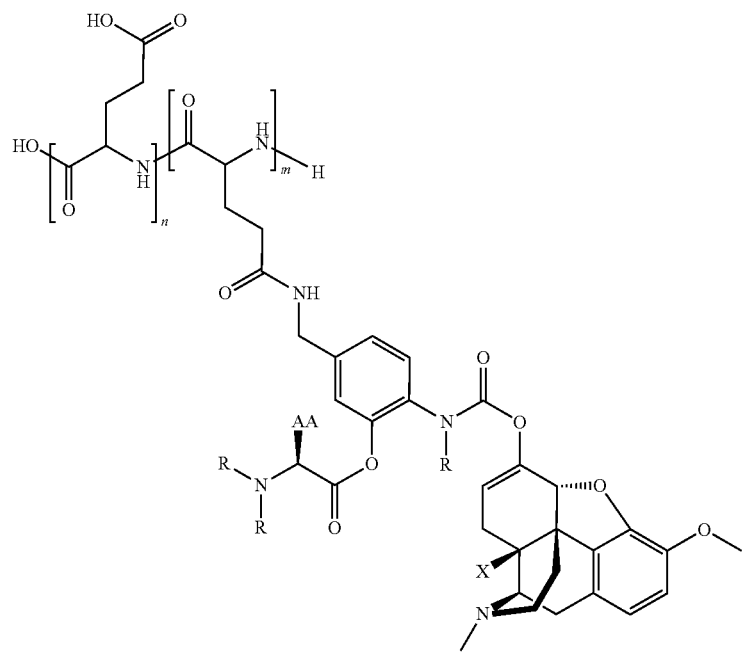

-continued
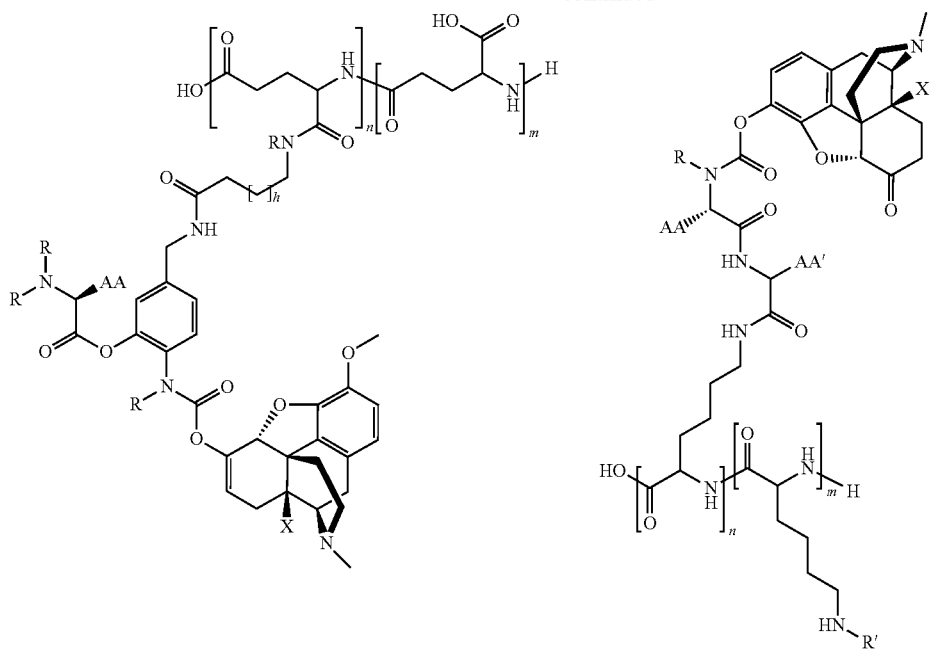
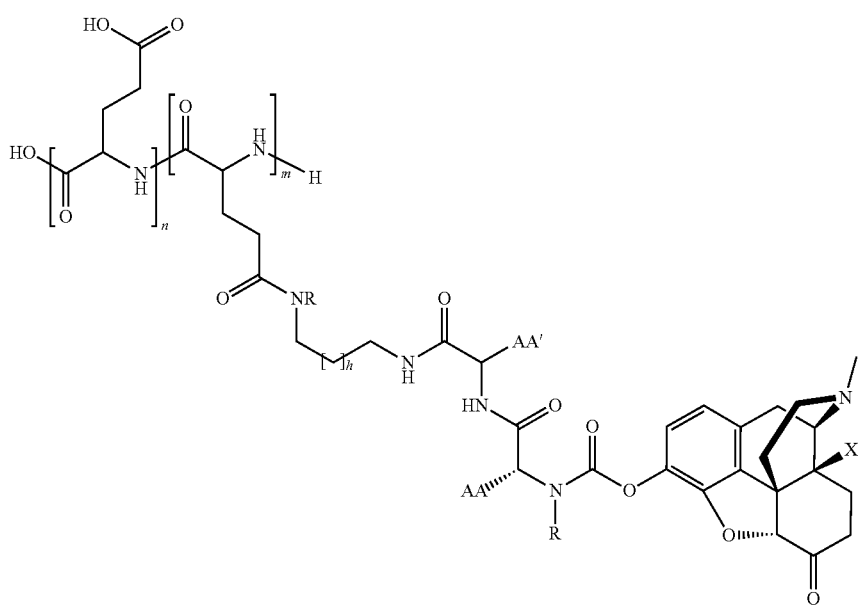
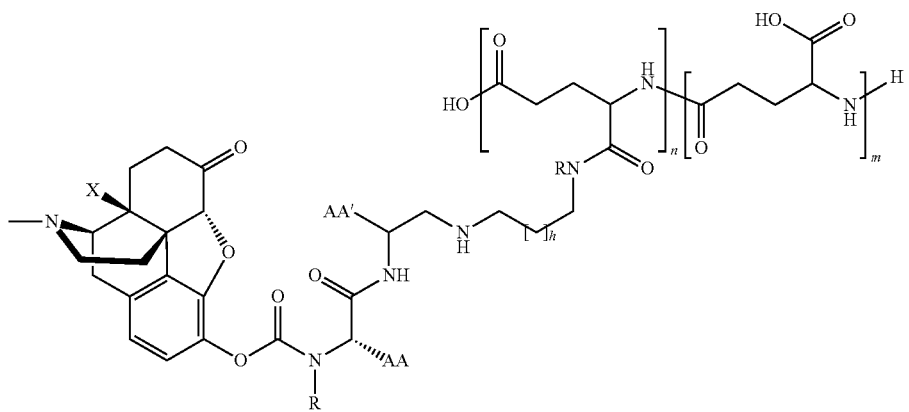

-continued
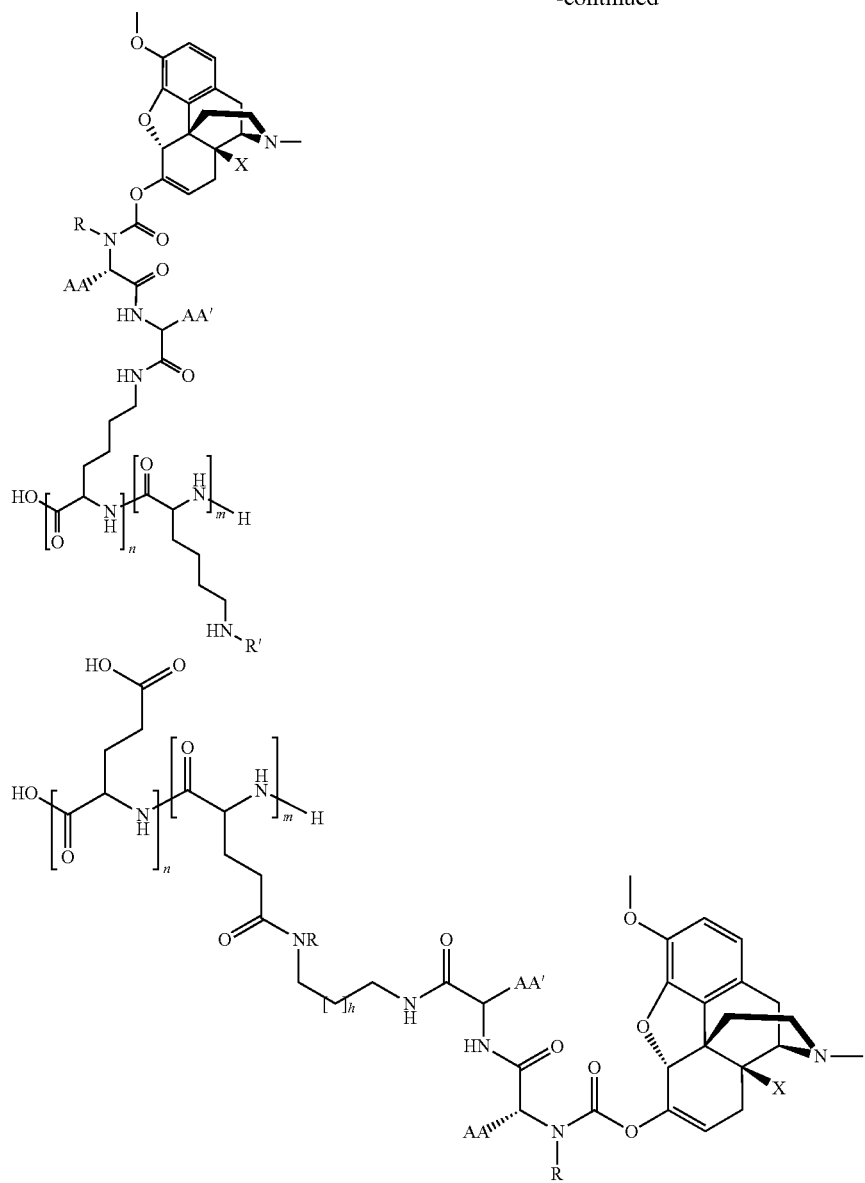
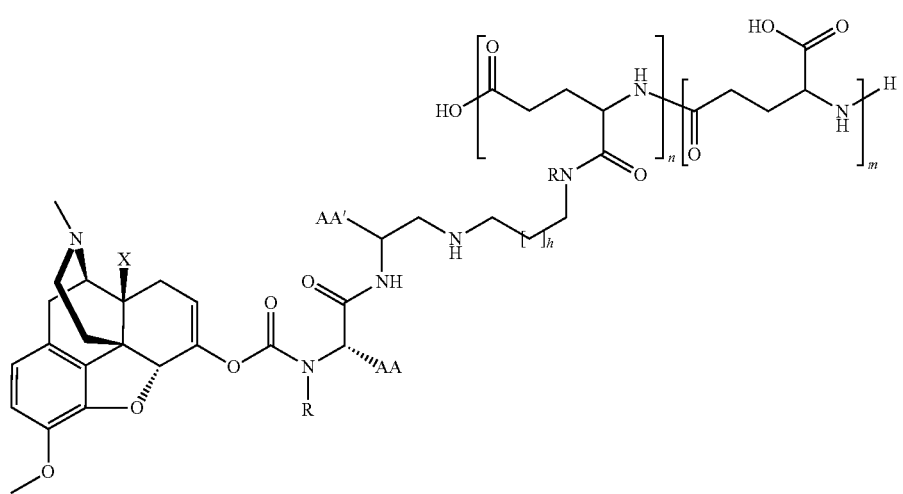

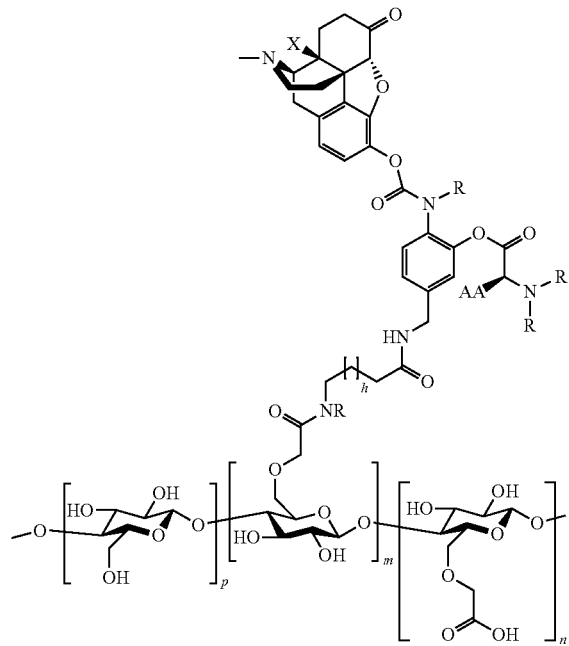
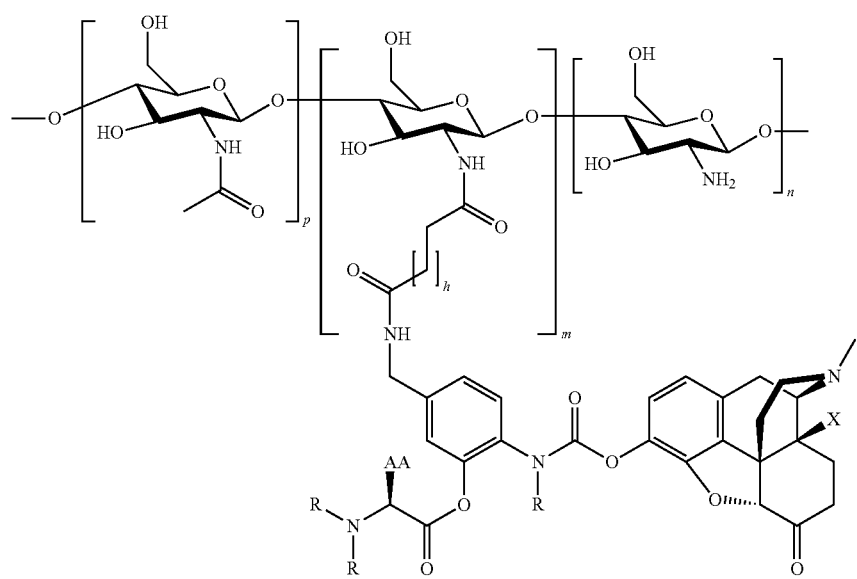

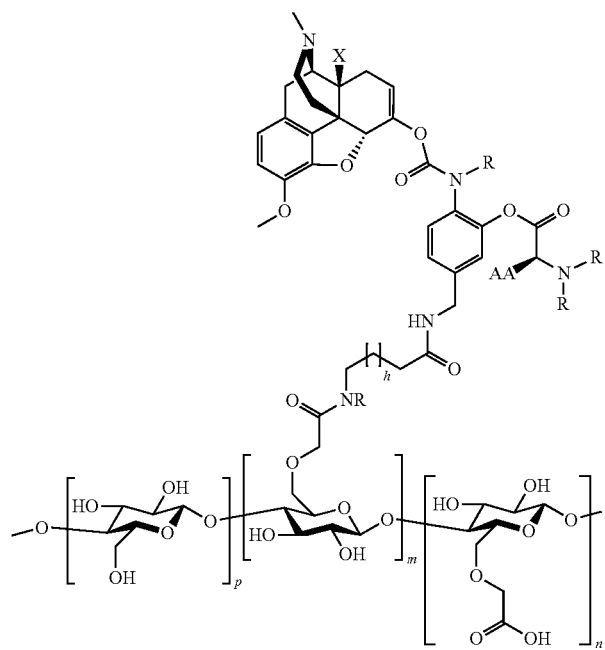
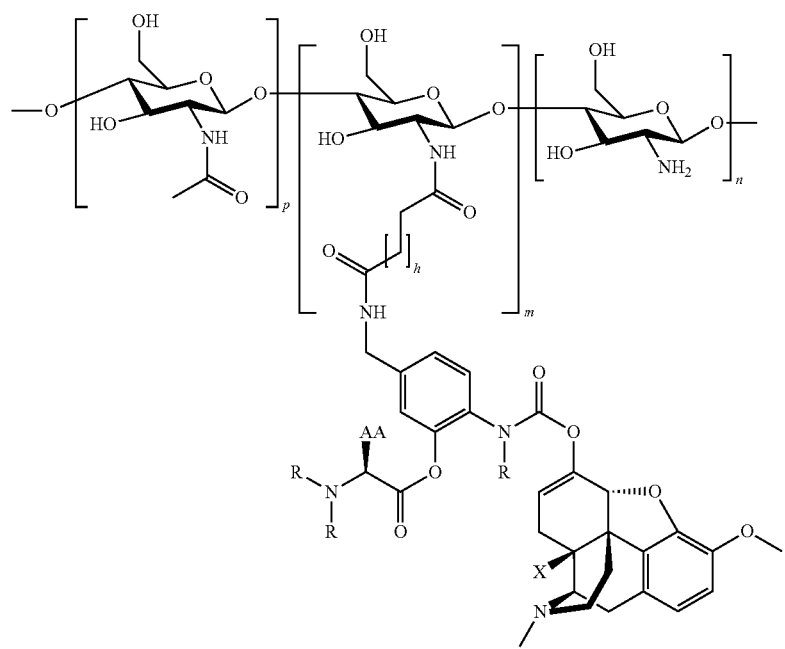

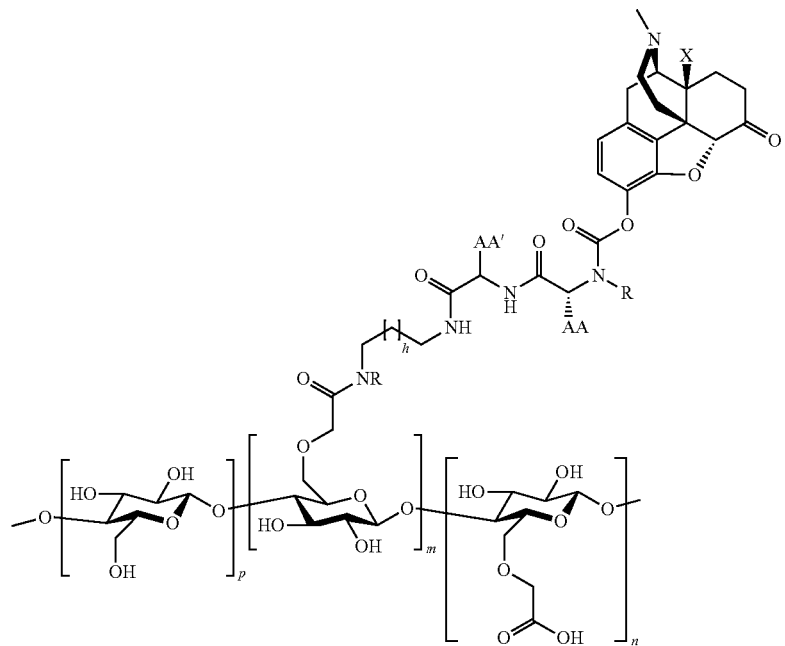
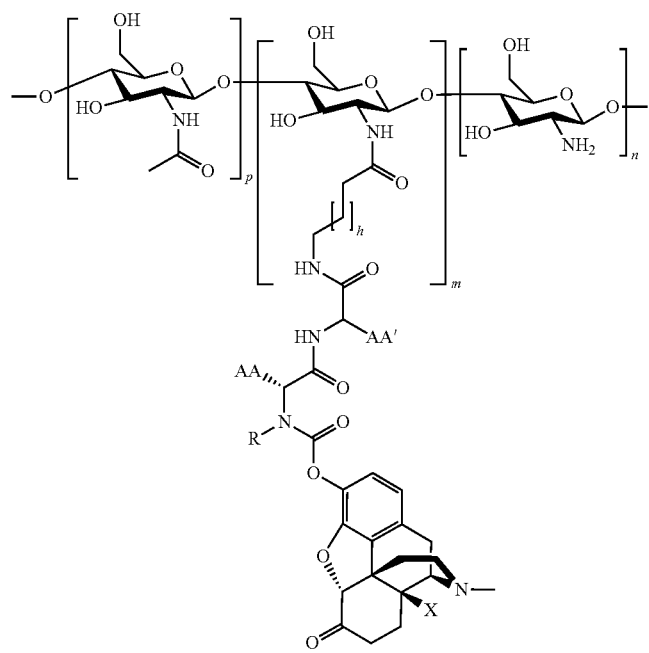

-continued

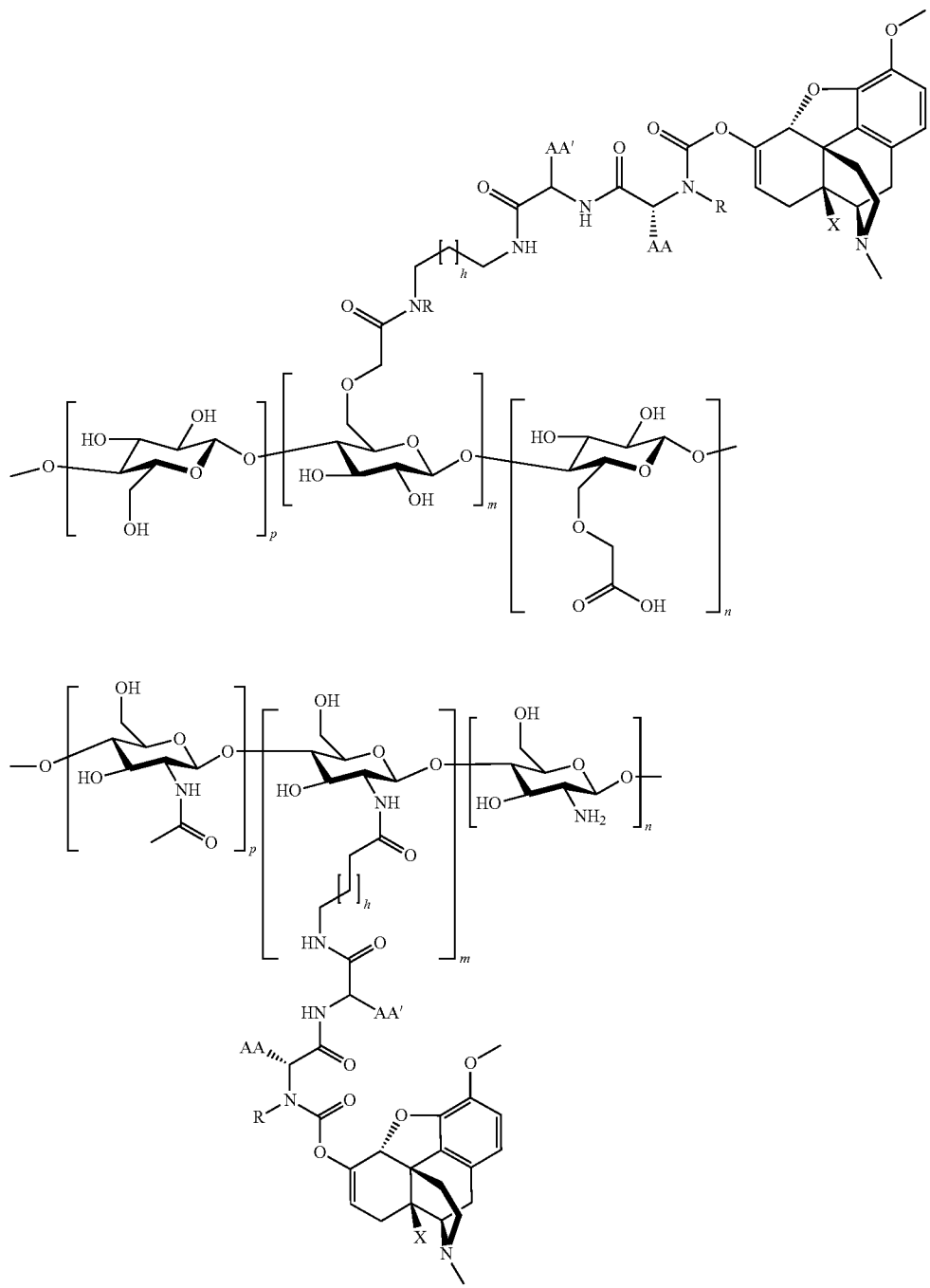

Where X can be H or OH; AA is a natural or unnatural amino acid side chain that is recognized by a digestive enzyme; AA' is a natural or unnatural amino acid side chain; R is independently hydrogen, methyl, ethyl, substituted alkyl, or substituted aryl, or a natural or unnatural amino acid, or a polypeptide comprising up to 10 natural and/or unnatural amino acids; adjacent R groups can be joined to form a cyclic or heterocyclic structure; h represents a number of substituted or unsubstituted methylene units and can be an integer from zero to ten; n, m, and p can independently be an integer from 1 to 1000; each R' can independently be hydrogen, methyl, ethyl, substituted alkyl, or substituted aryl, acyl, or substituted acyl.

In another aspect of the invention, the GI enzyme-labile opioid prodrug is an enolic or phenolic carbamate and the release of the opioid agonist drug molecule from the macromolecular GI enzyme-labile opioid prodrug occurs via the two-step process depicted below. Cleavage of the GI enzyme promoiety reveals an internal nucleophilic amine. Subsequent controlled release of the opioid drug is then mediated as the appended nucleophilic amine undergoes a rapid intramolecular cyclization-release reaction, whereby the parent phenolic or enolic opioid is released.

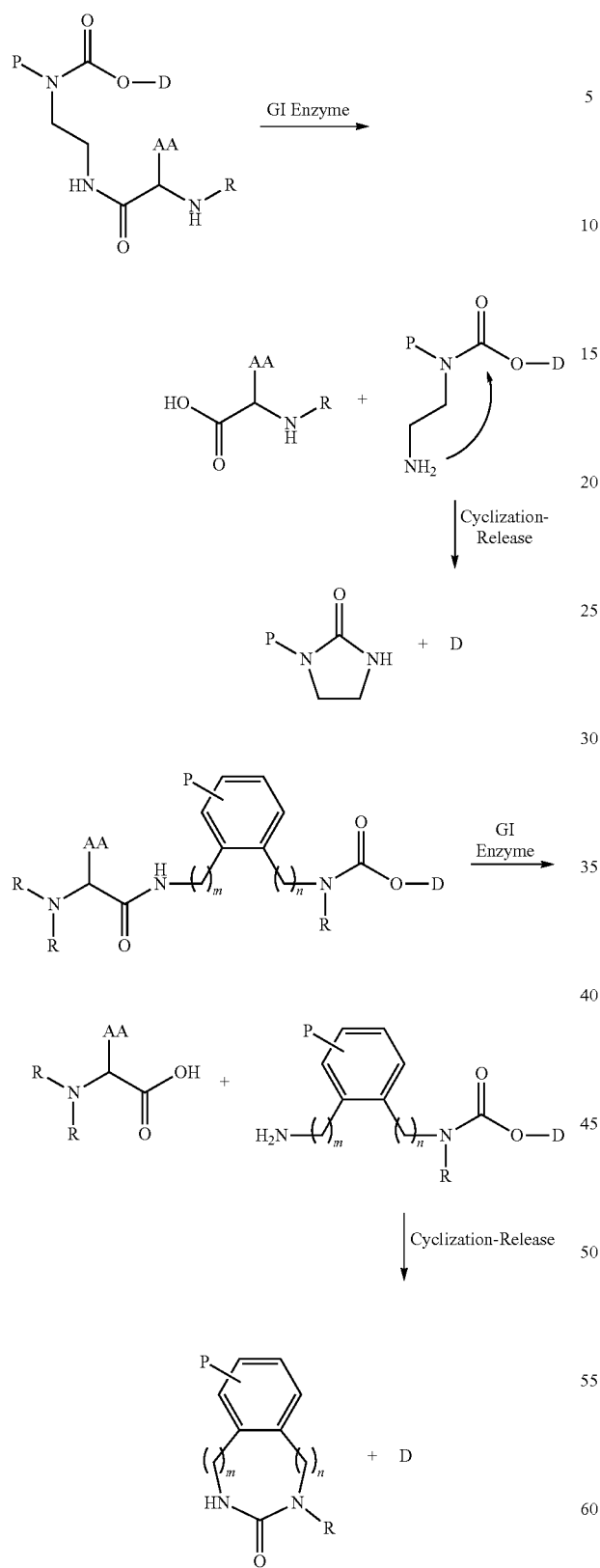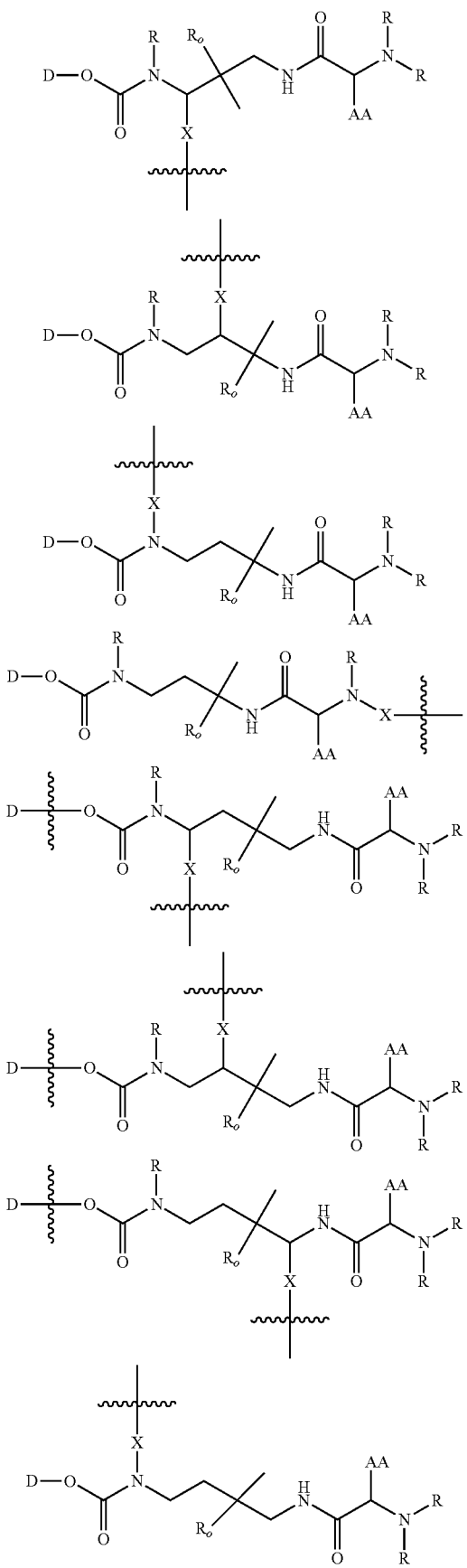
Macromolecular GI enzyme-labile opioid prodrugs that operate via this mechanism can be described by the general formulae:

163

-continued

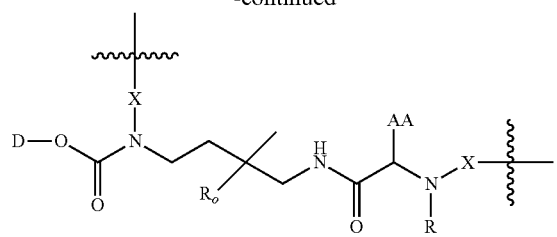

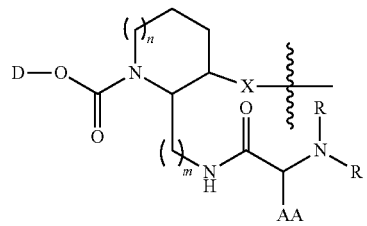

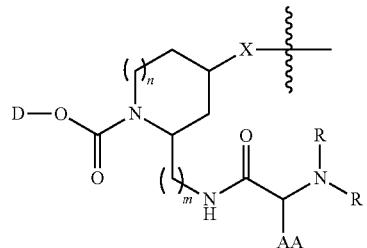

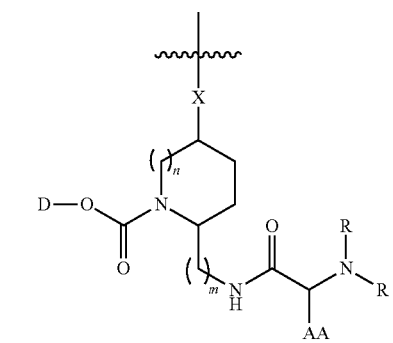

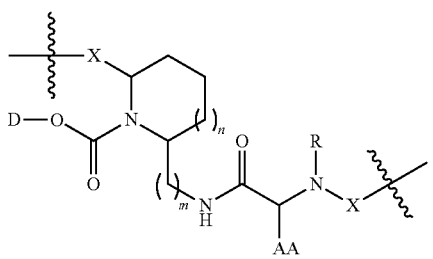

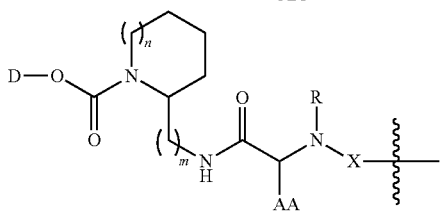

164

-continued

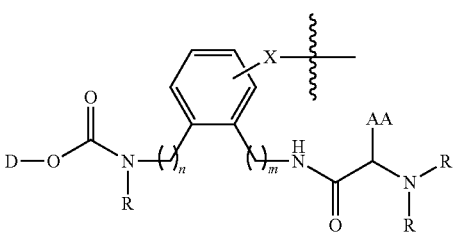

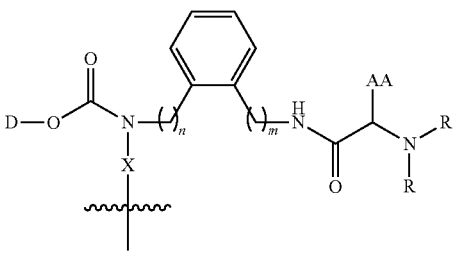

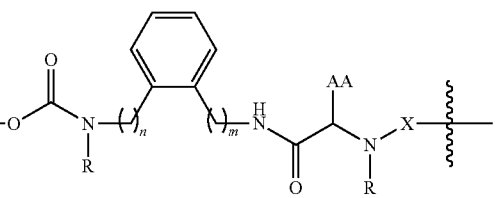

Where D is an opioid agonist as defined above; AA is a natural or unnatural amino acid side chain that is recognized by a digestive enzyme; R is independently hydrogen, methyl, ethyl, substituted alkyl, or substituted aryl, or a natural or unnatural amino acid, or a polypeptide comprising up to 10 natural and/or unnatural amino acids; adjacent R groups can be joined to form a cyclic or heterocyclic structure; m, n and o independently represent an integer from zero to six; and X is a linker as defined herein.

Further non-limiting examples of macromolecular trypsin enzyme-labile hydrocodone, oxycodone, hydromorphone, and oxymorphone prodrugs that operate via this mechanism can include the following:

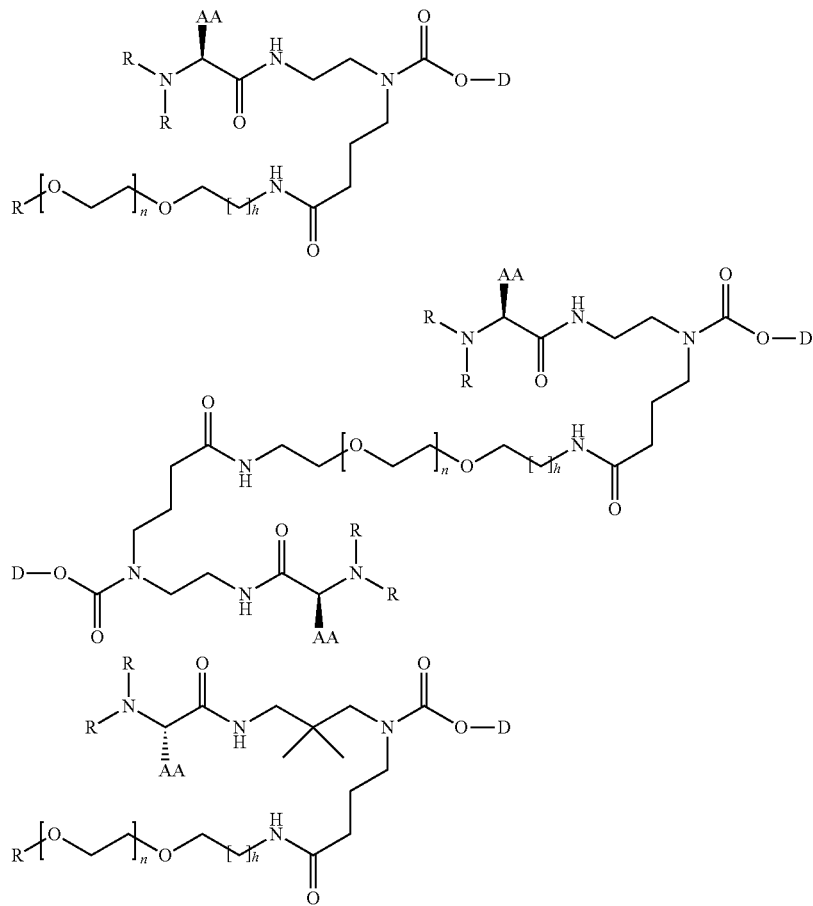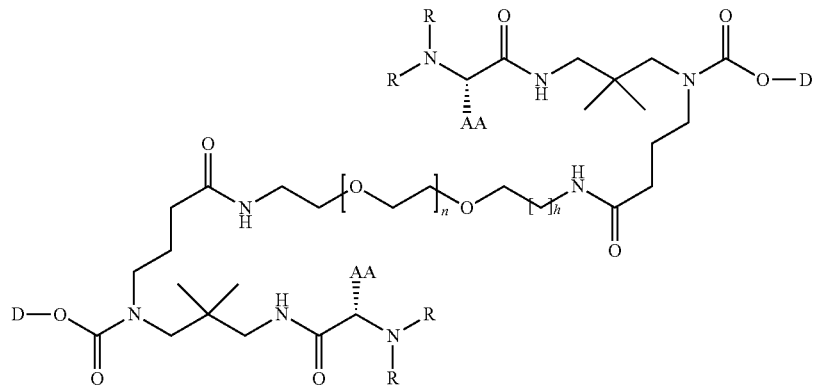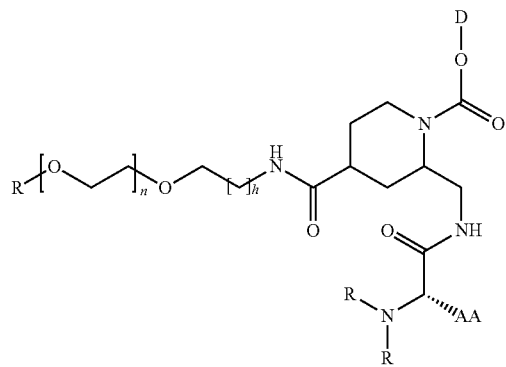

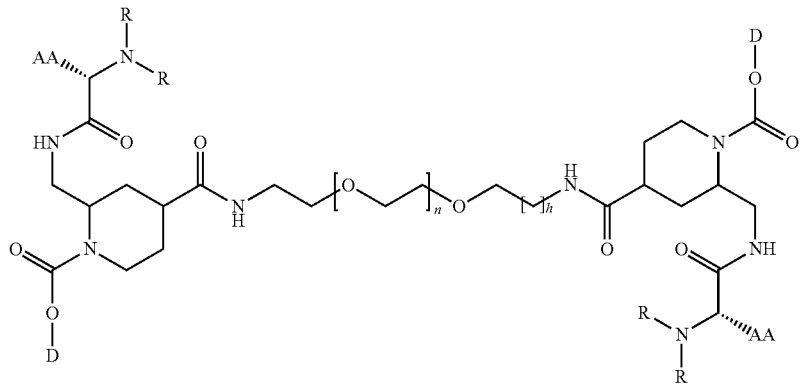
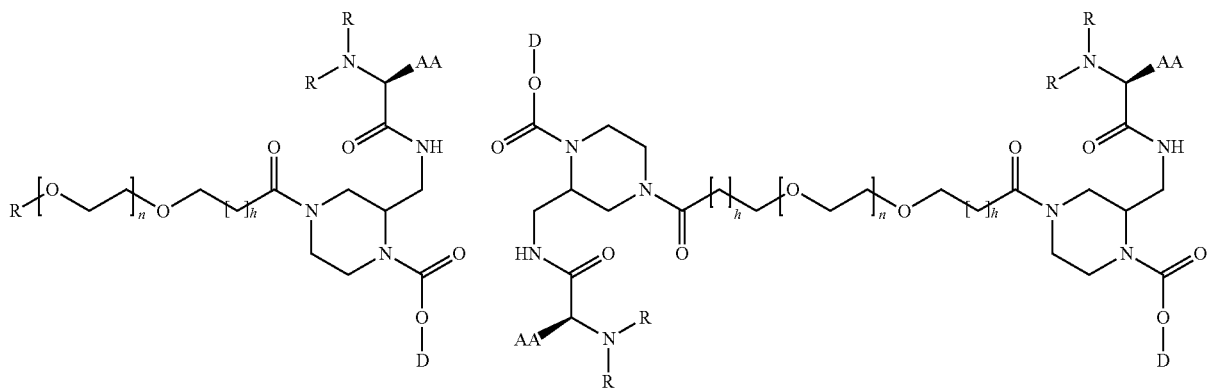
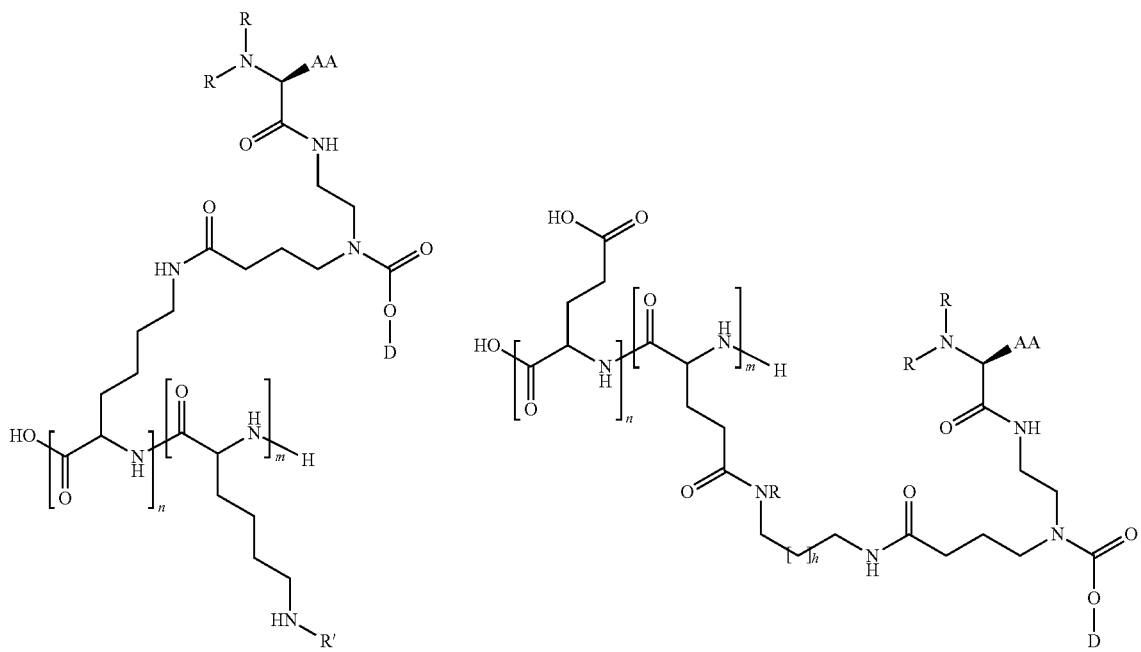

169
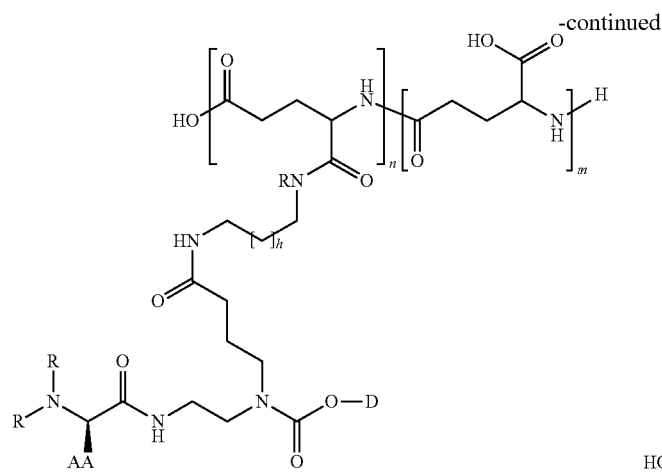
170
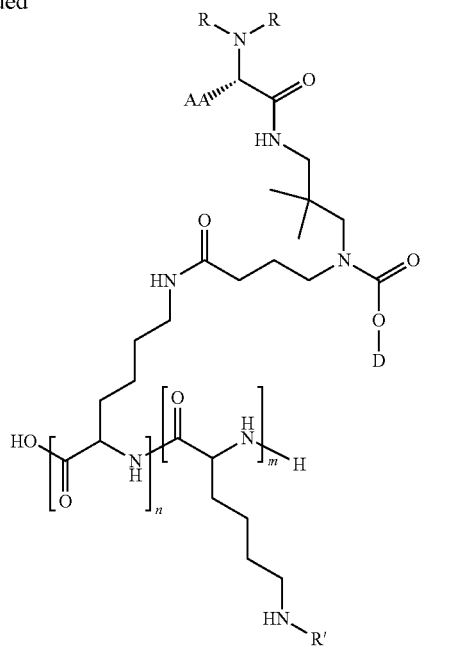
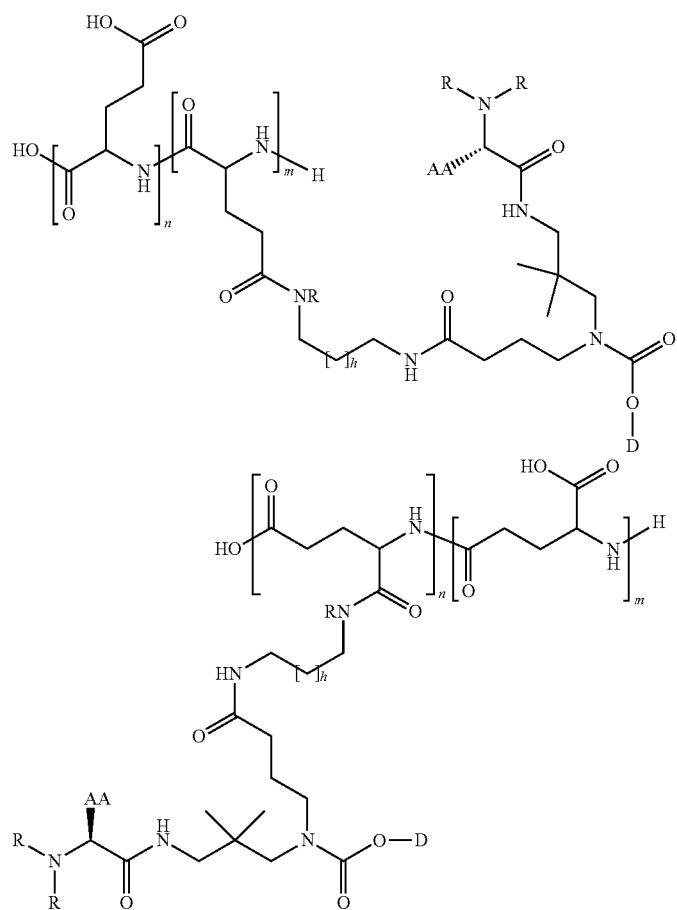
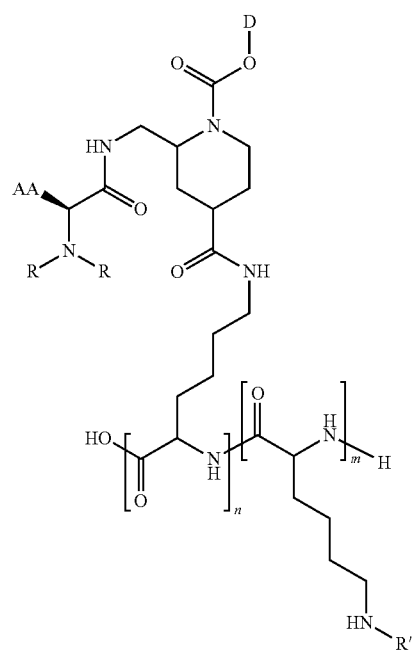

-continued
171
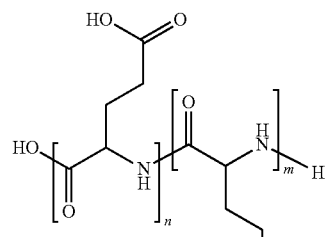
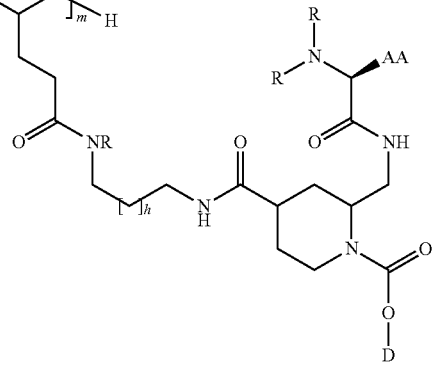
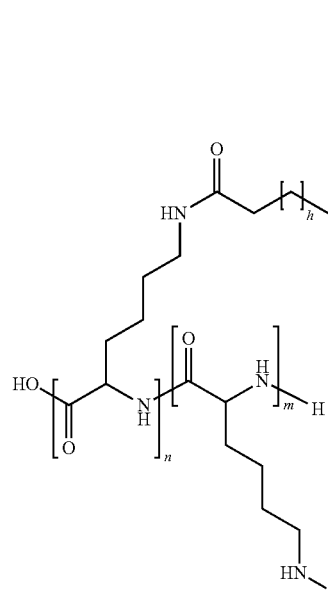
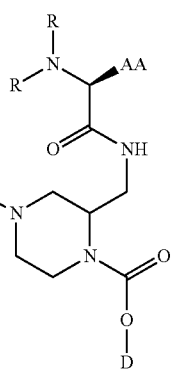
172
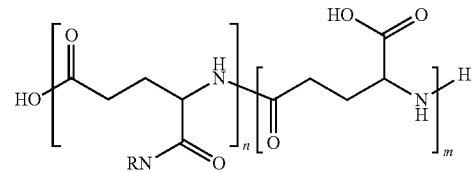
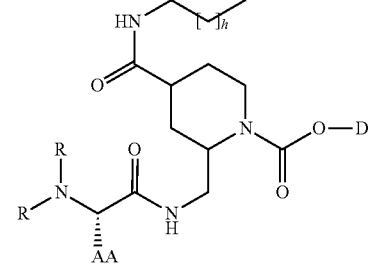
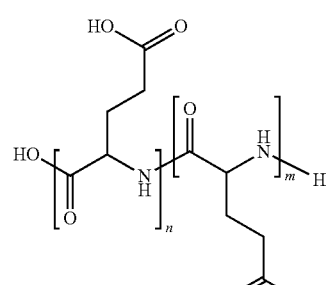
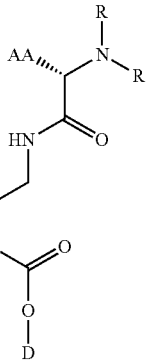
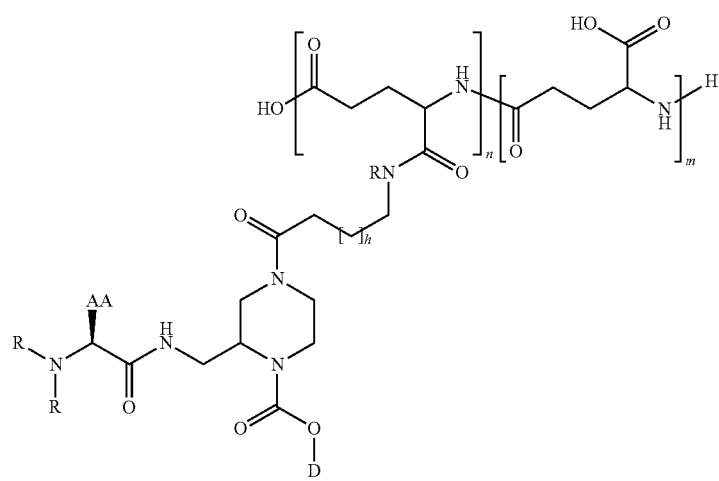

-continued
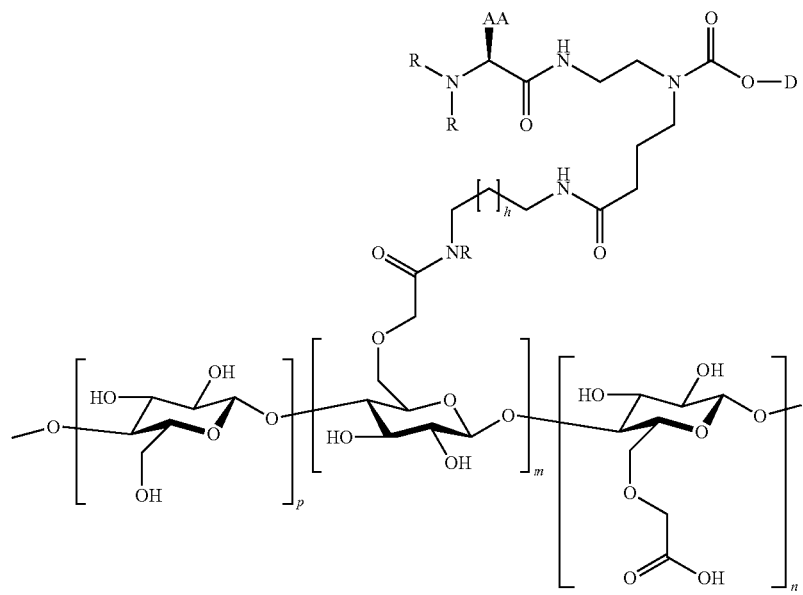
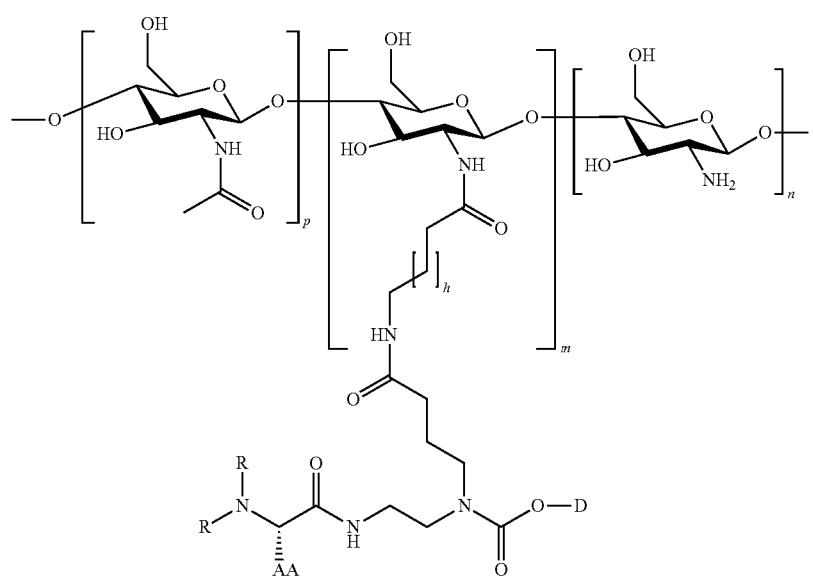

-continued
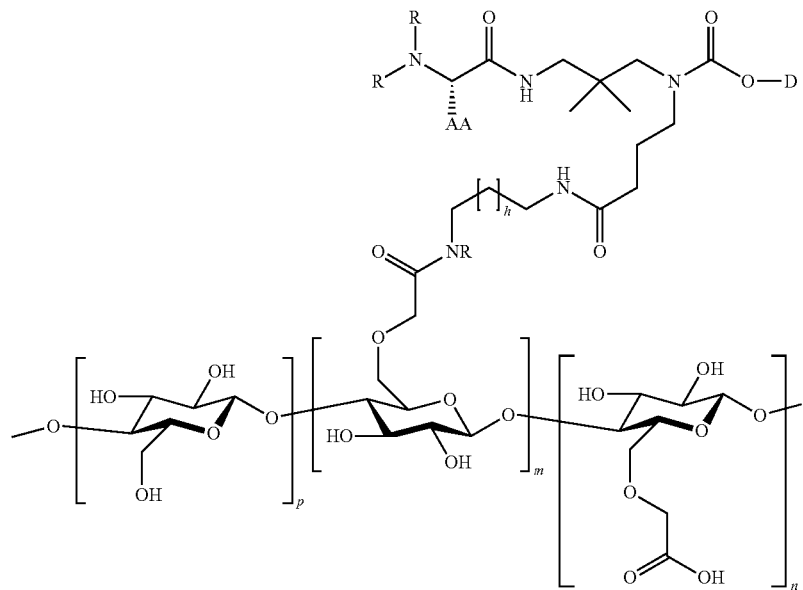
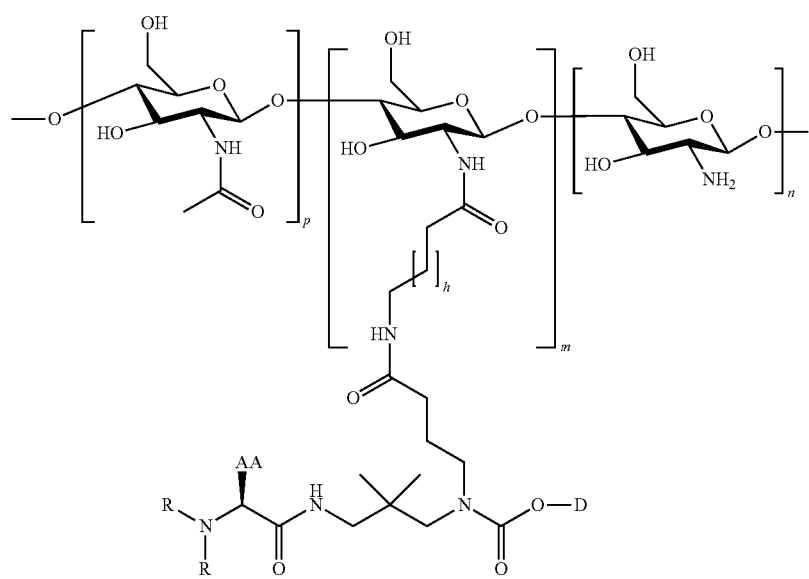

-continued
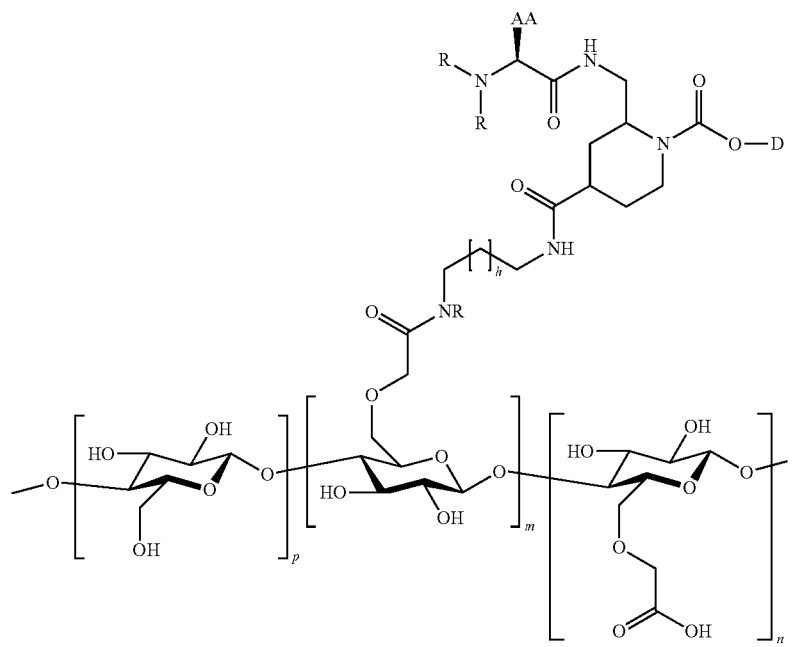
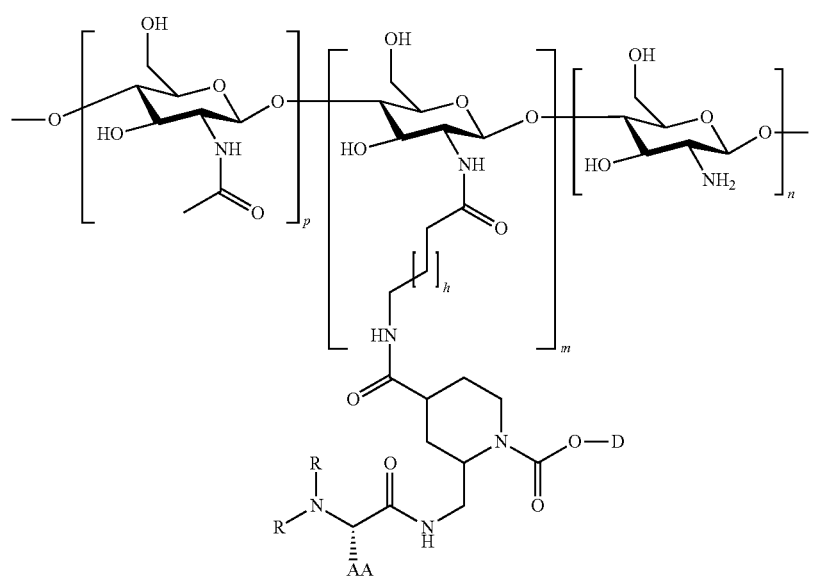

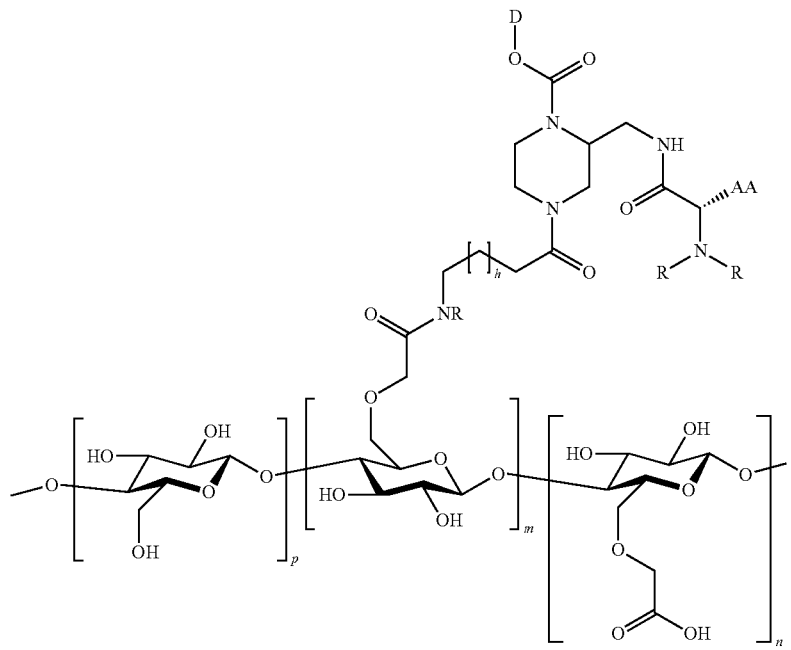

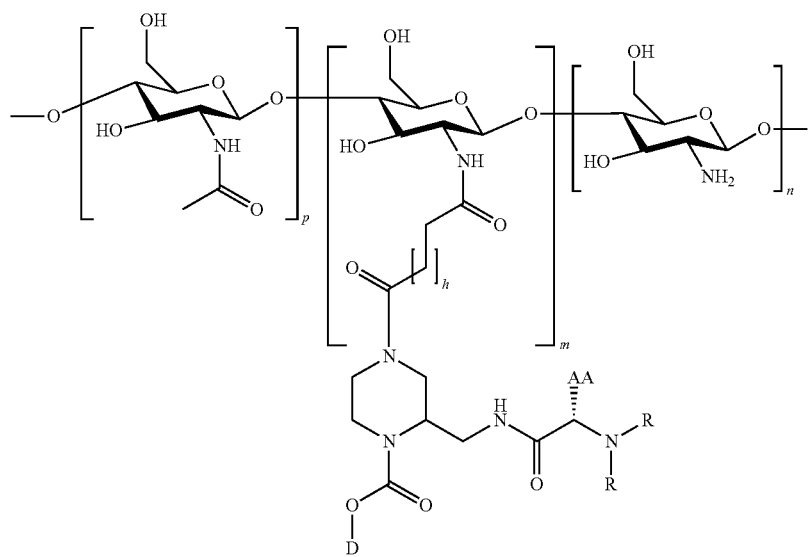

Where D is an opioid agonist as defined above; AA is a natural or unnatural amino acid side chain that is recognized by a digestive enzyme; R is independently hydrogen, methyl, ethyl, substituted alkyl, or substituted aryl, or a natural or unnatural amino acid, or a polypeptide comprising up to 10 natural and/or unnatural amino acids; adjacent R groups can be joined to form a cyclic or heterocyclic structure; h represents a number of substituted or unsubstituted methylene units and can be an integer from zero to ten; n, m, and p, can independently be an integer from 1 to 1000; each R' can independently be hydrogen, methyl, ethyl, substituted alkyl, or substituted aryl, acyl, or substituted acyl.

Further non-limiting examples of macromolecular trypsin enzyme-labile hydrocodone, oxycodone, hydromorphone, and oxymorphone prodrugs that operate via this mechanism can include the following:

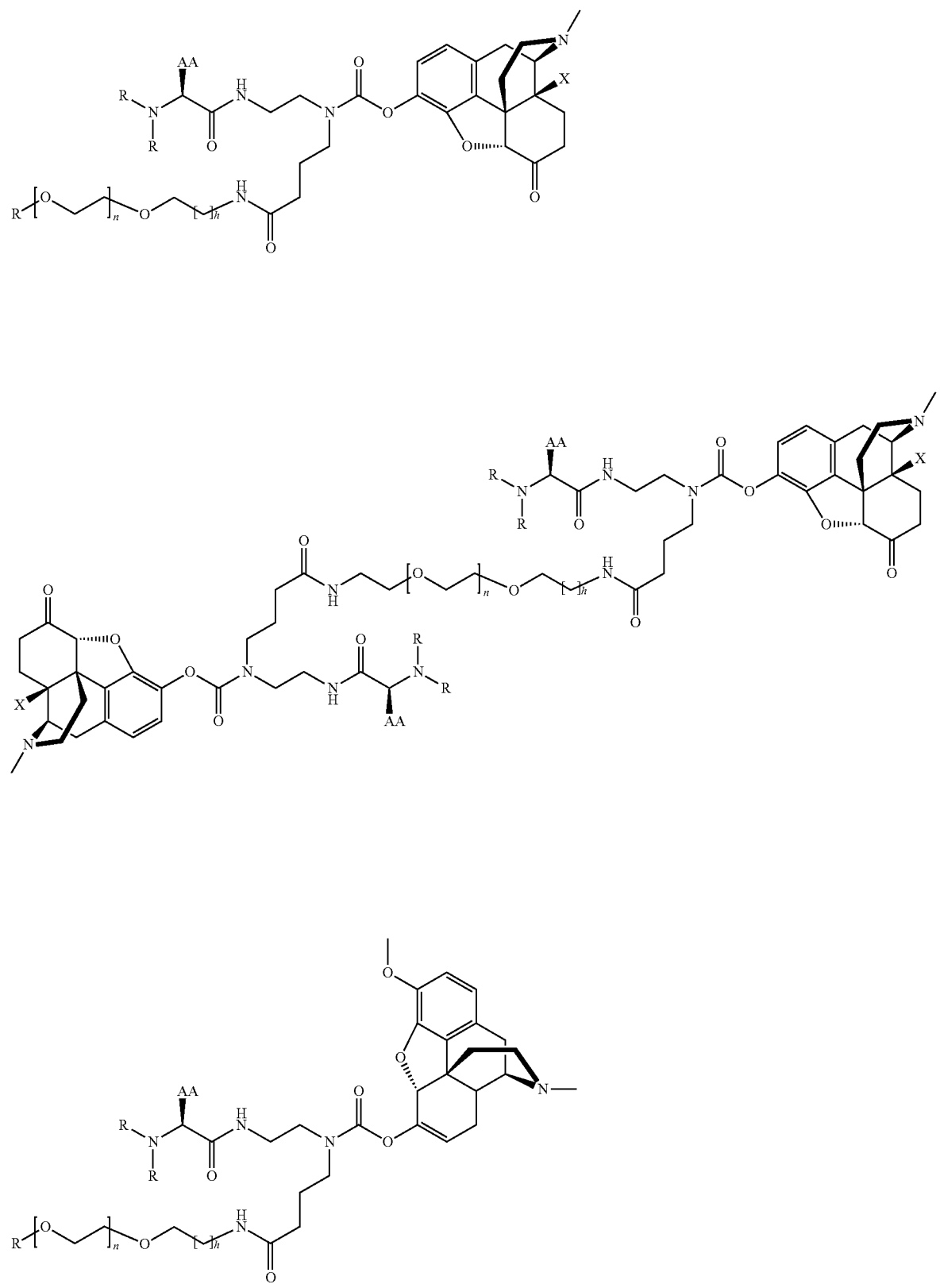

-continued
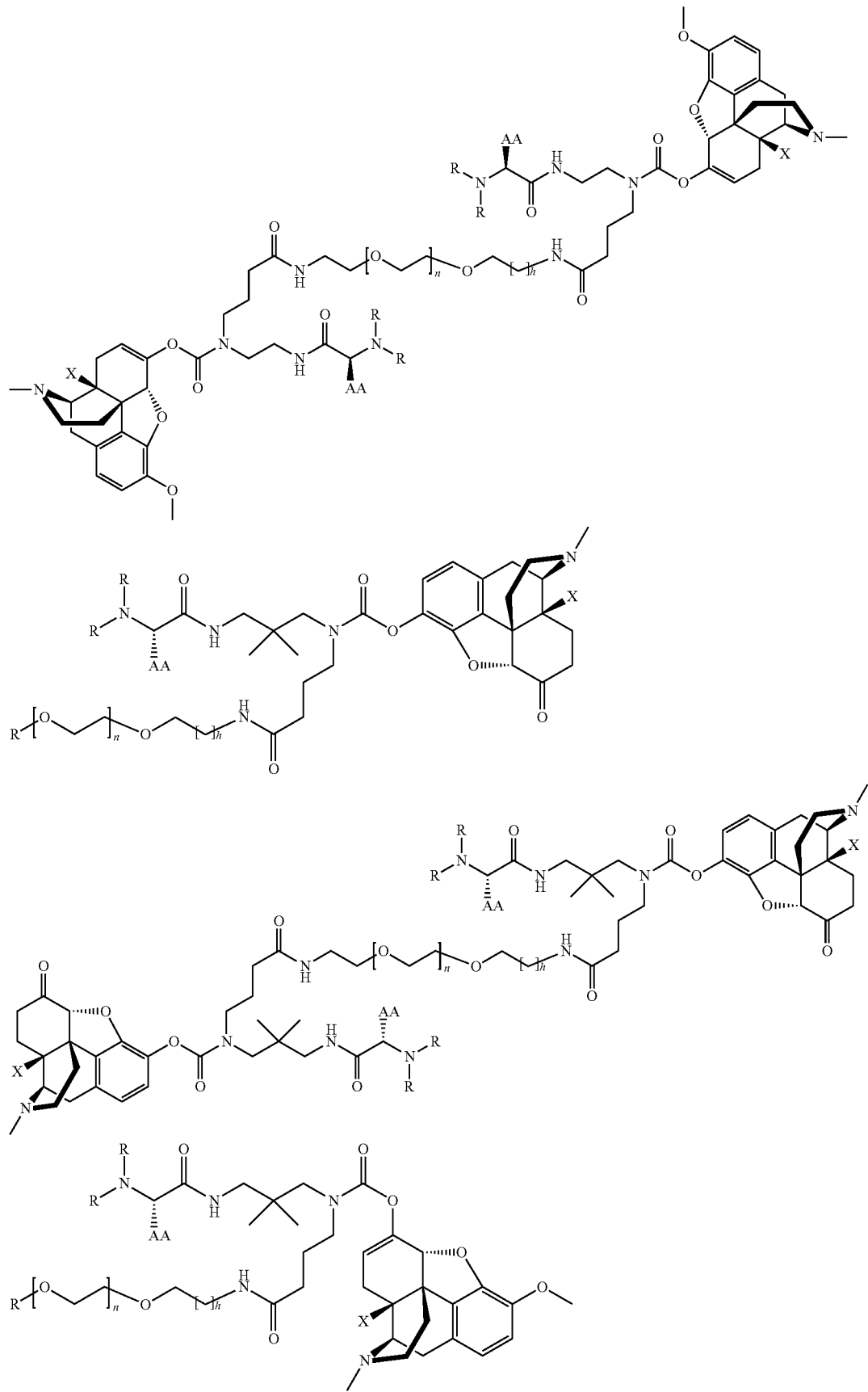

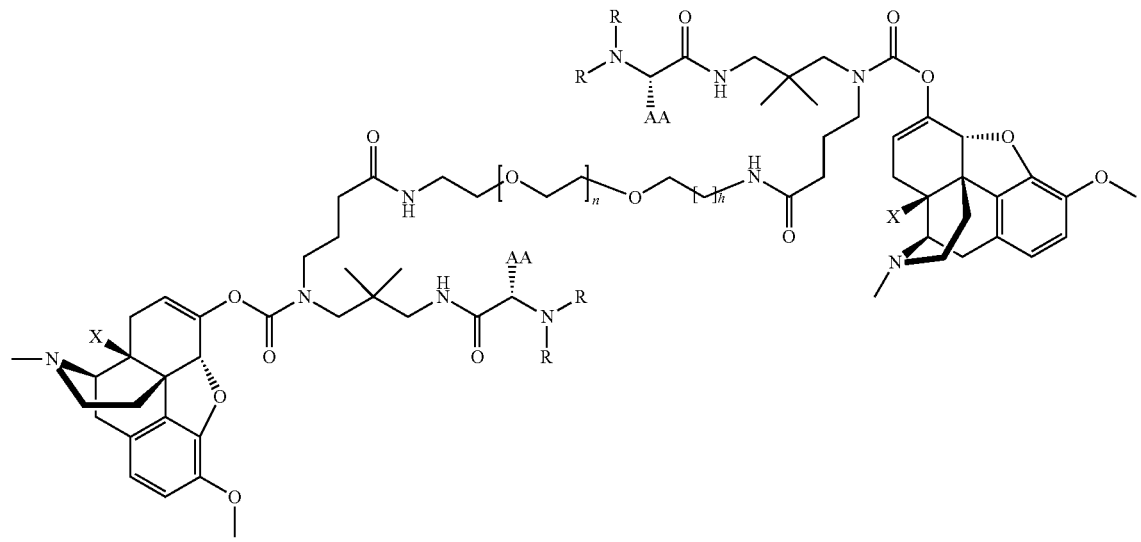
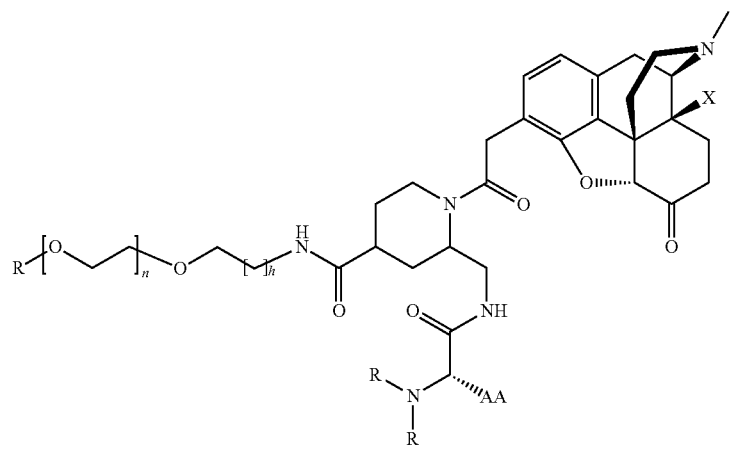
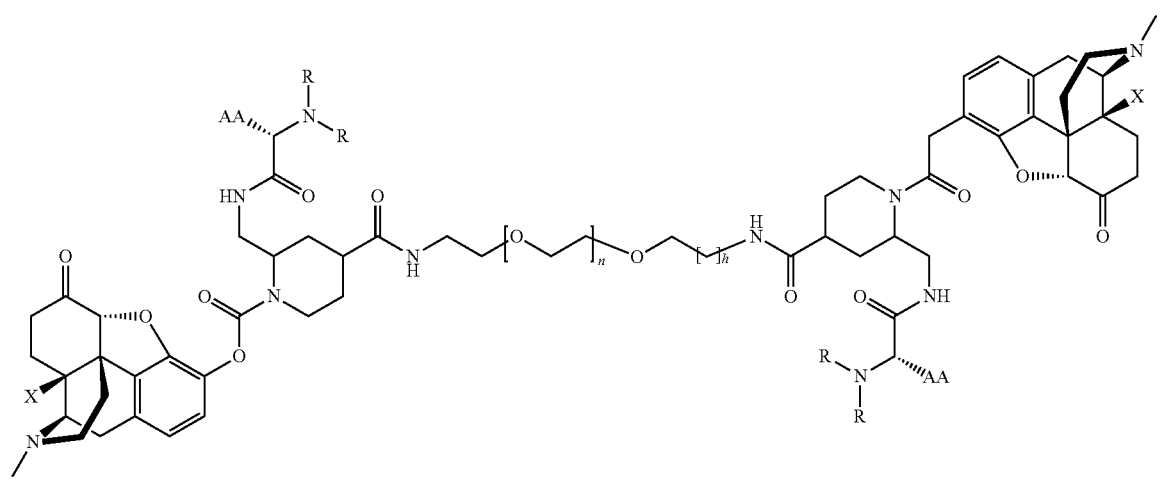

-continued
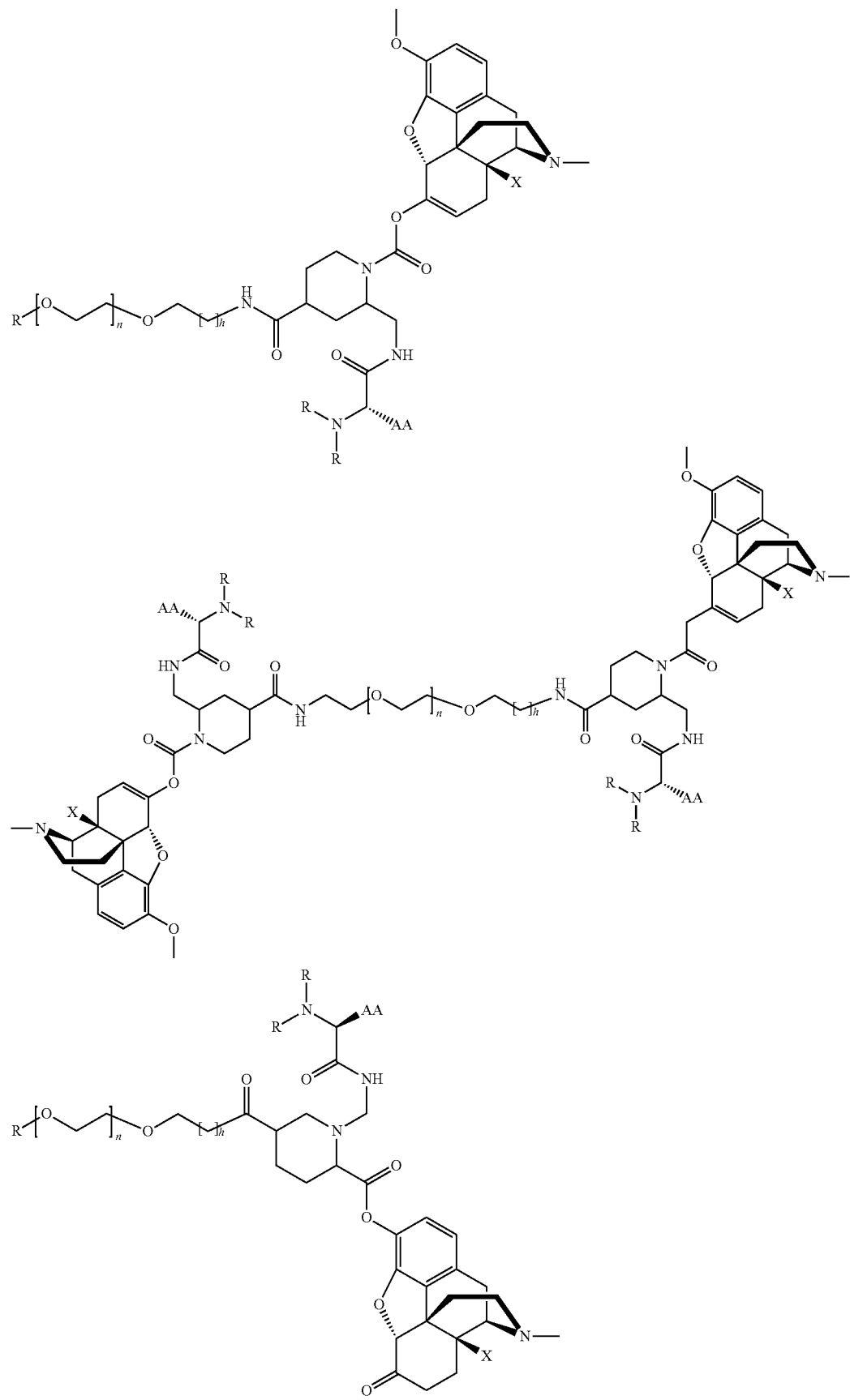

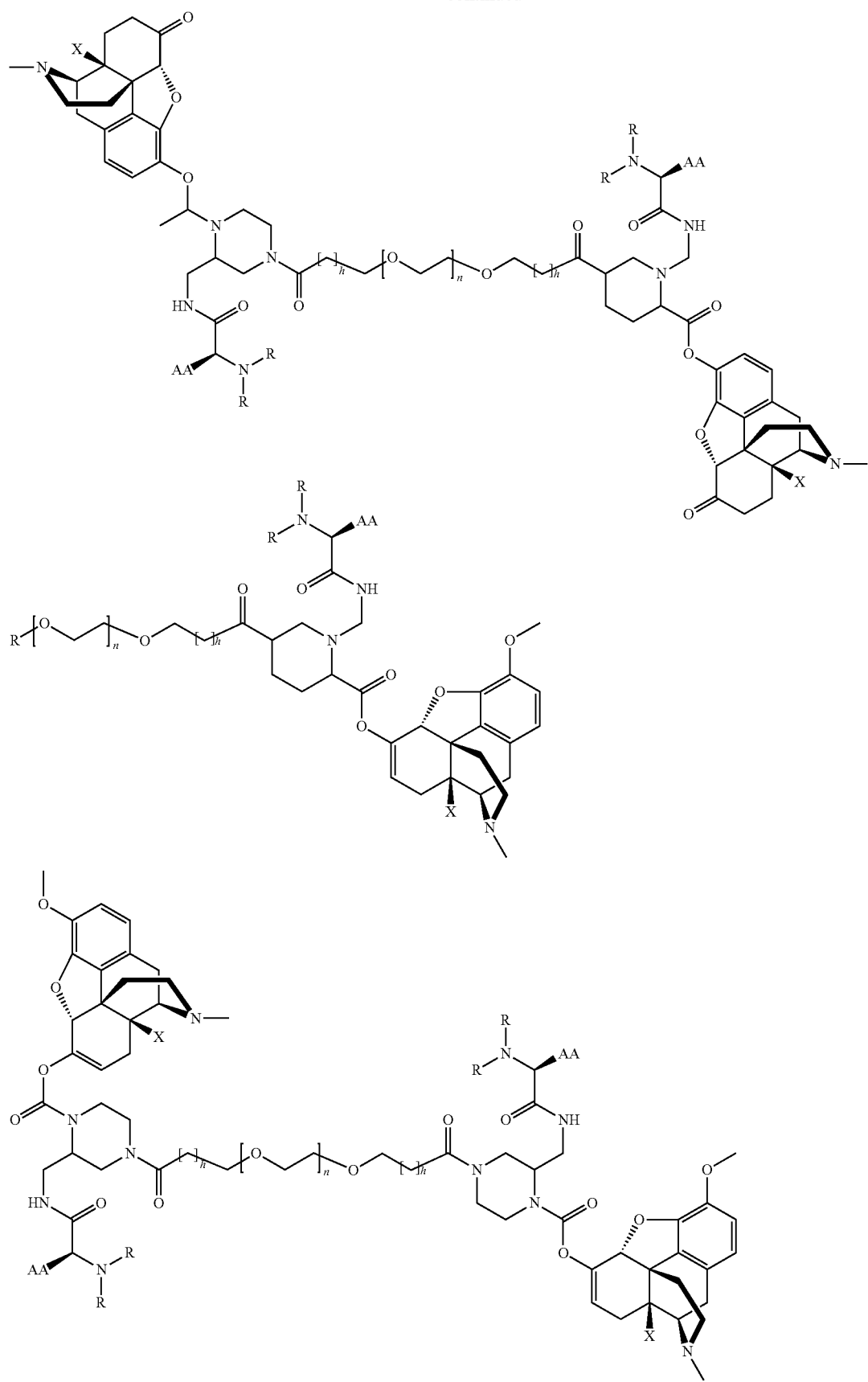

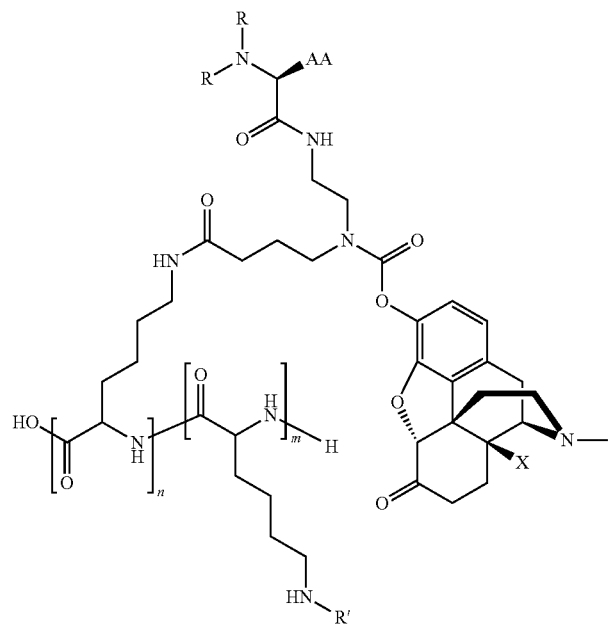
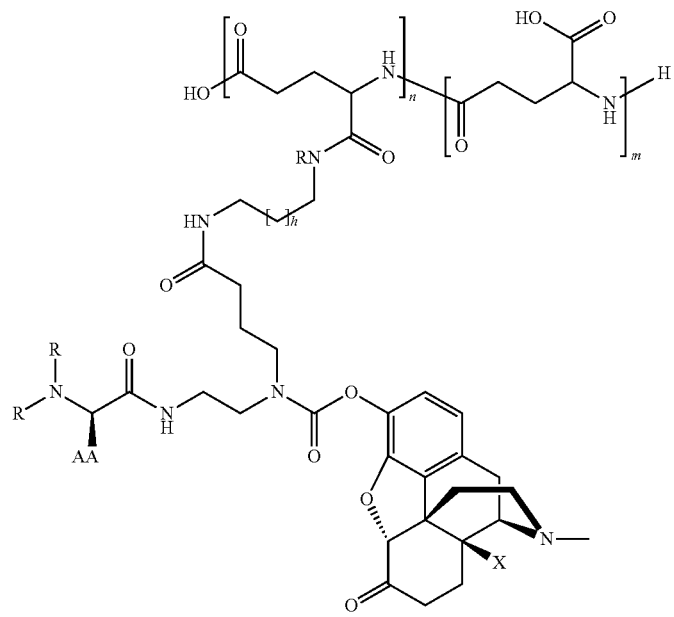

-continued
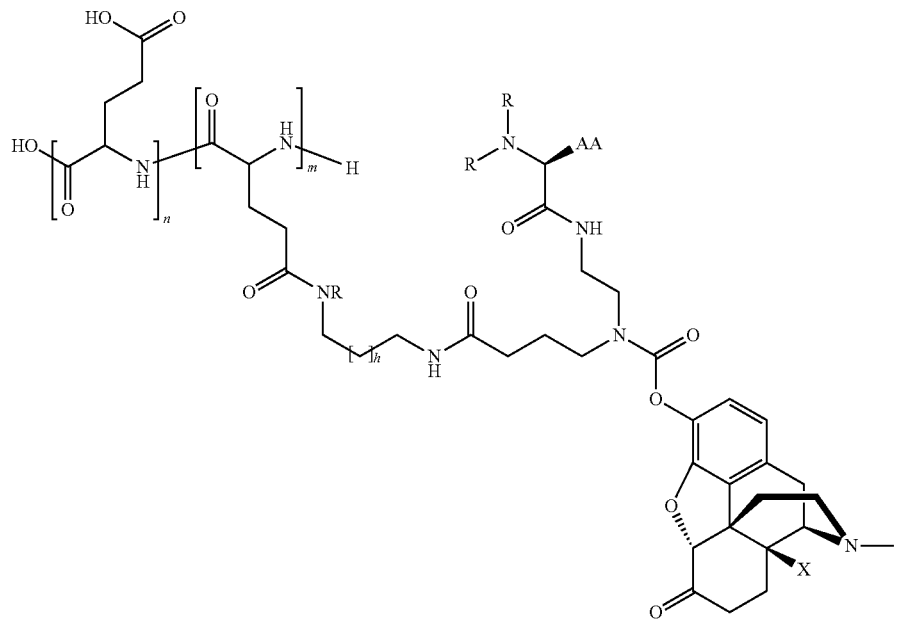
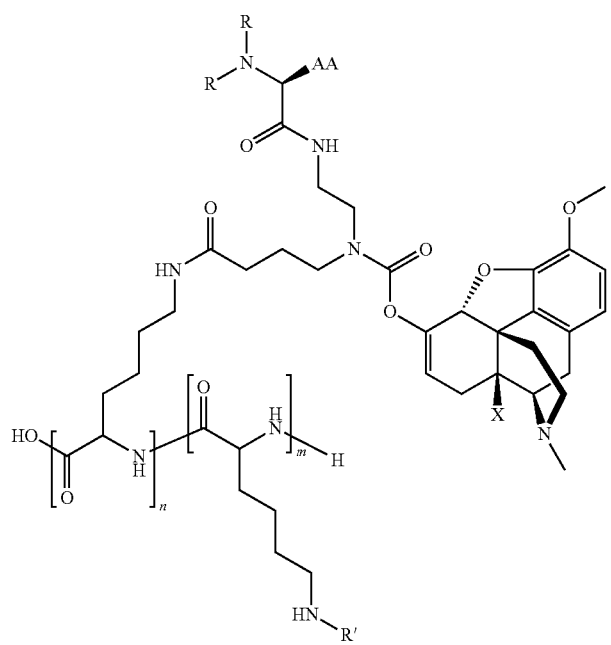

-continued
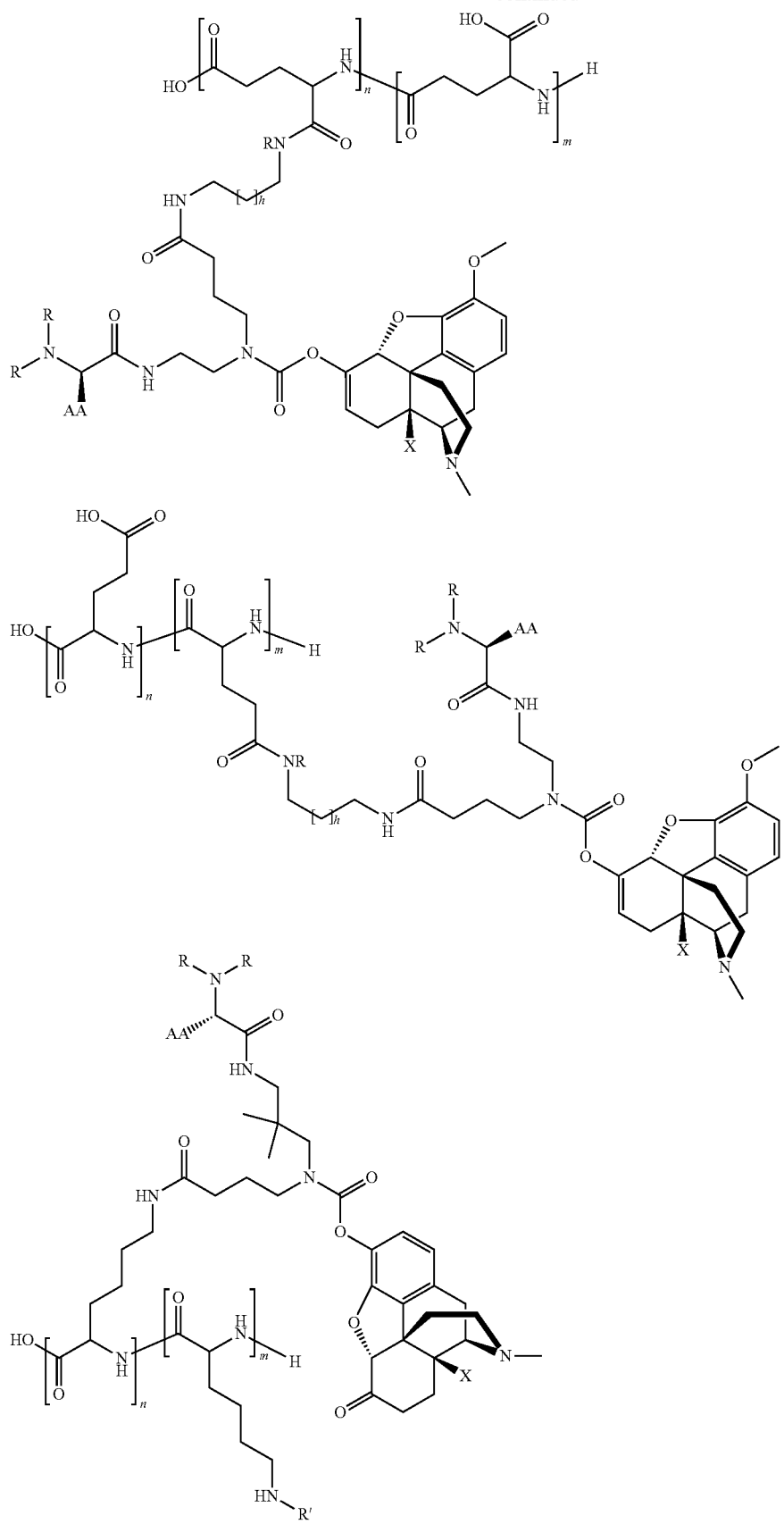

-continued
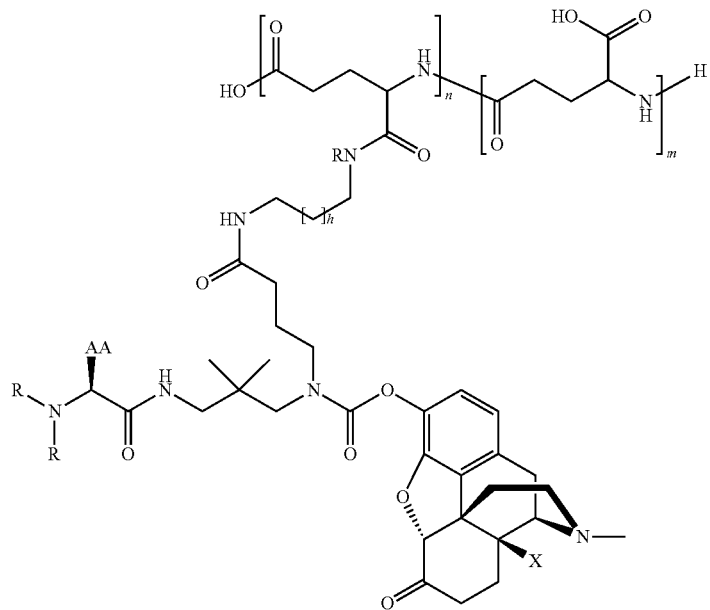
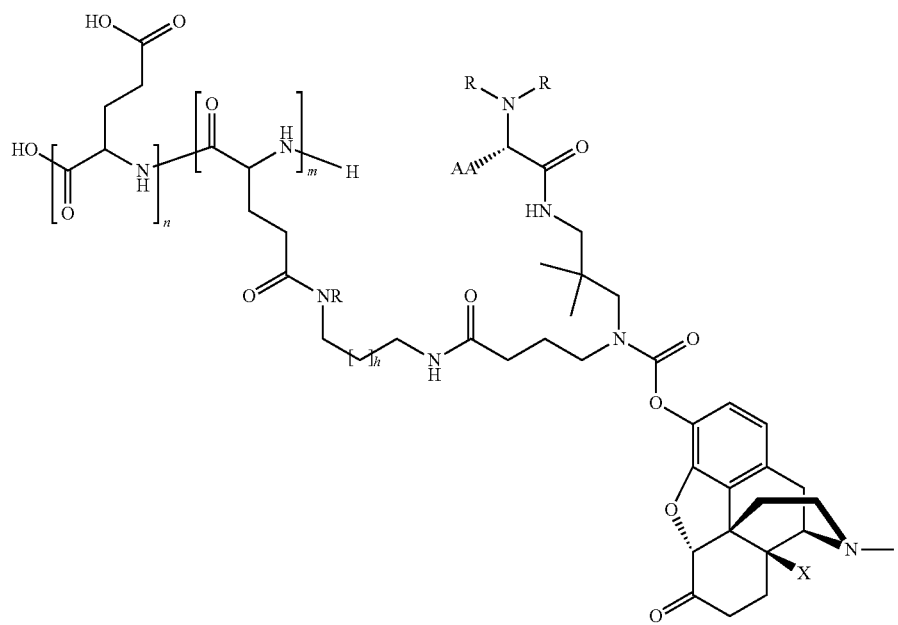

-continued
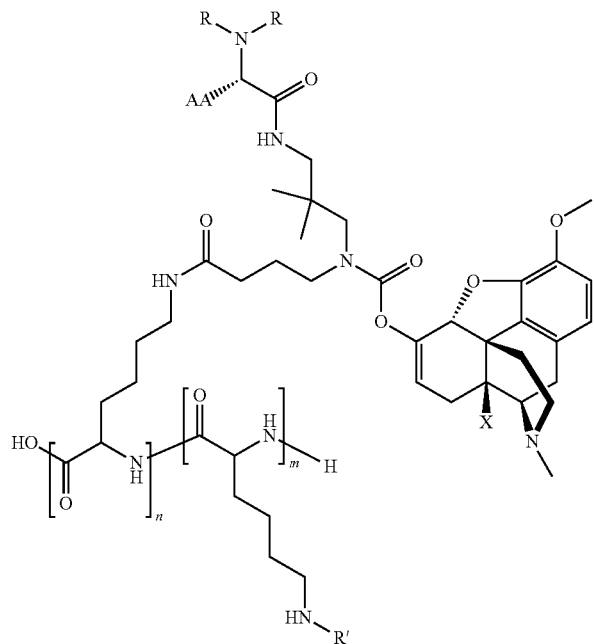
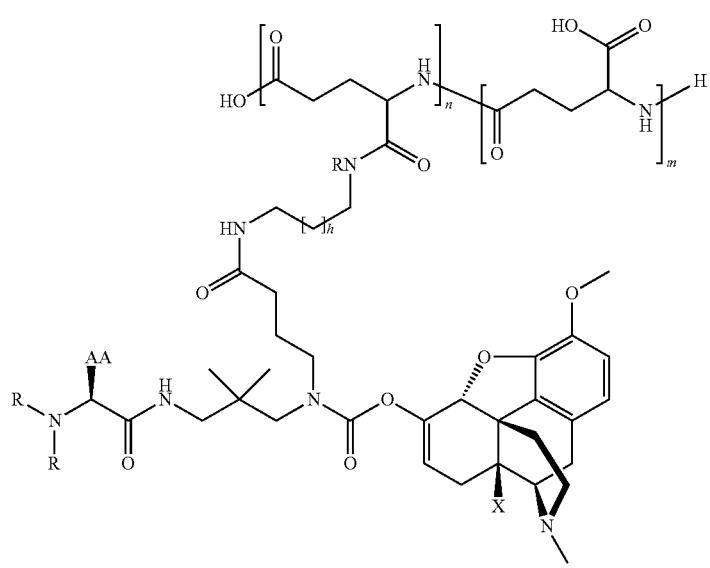

-continued
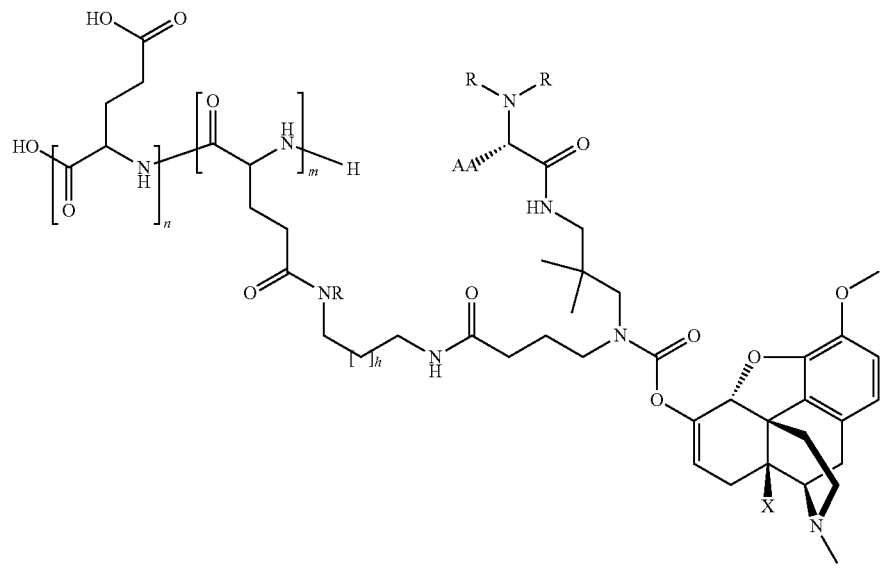
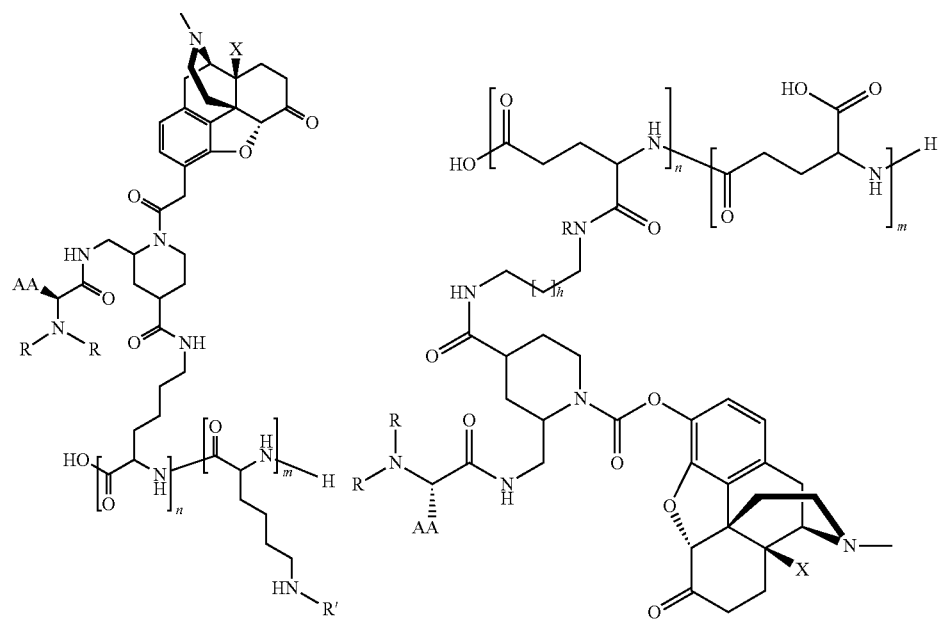

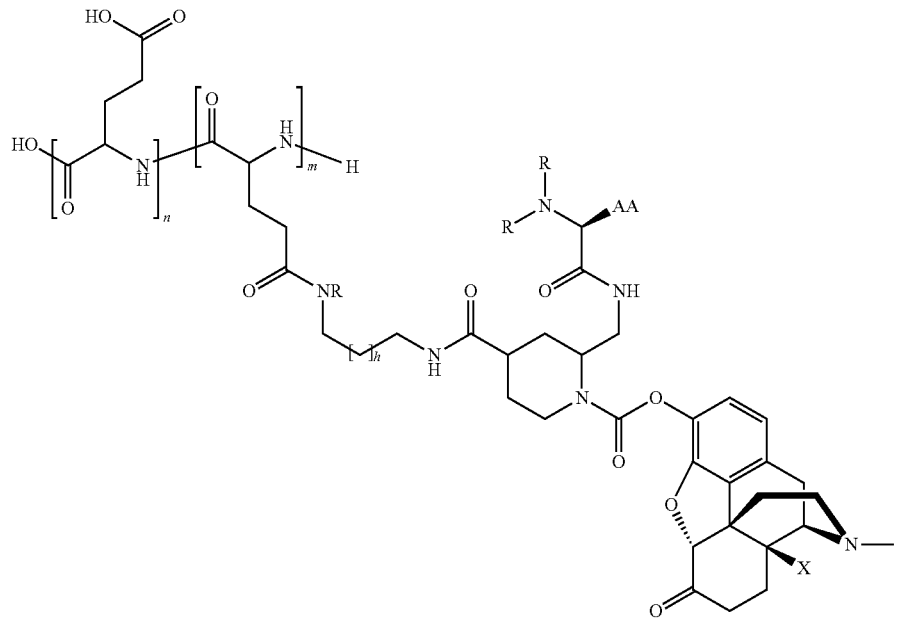
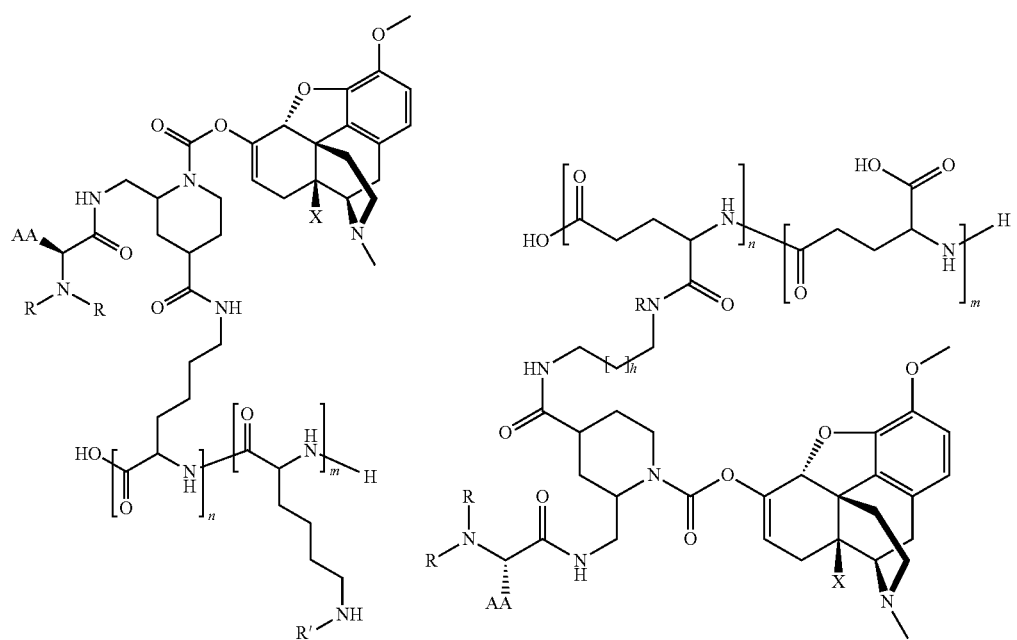

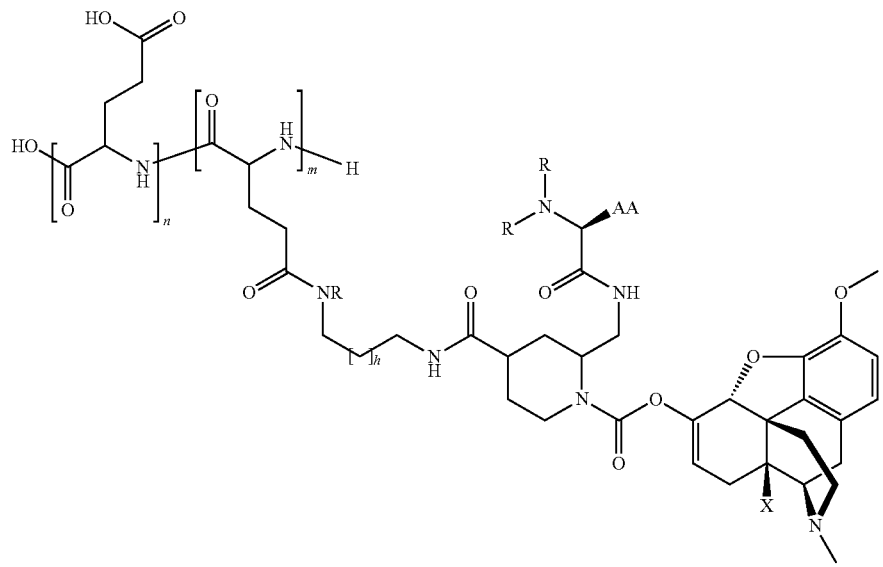
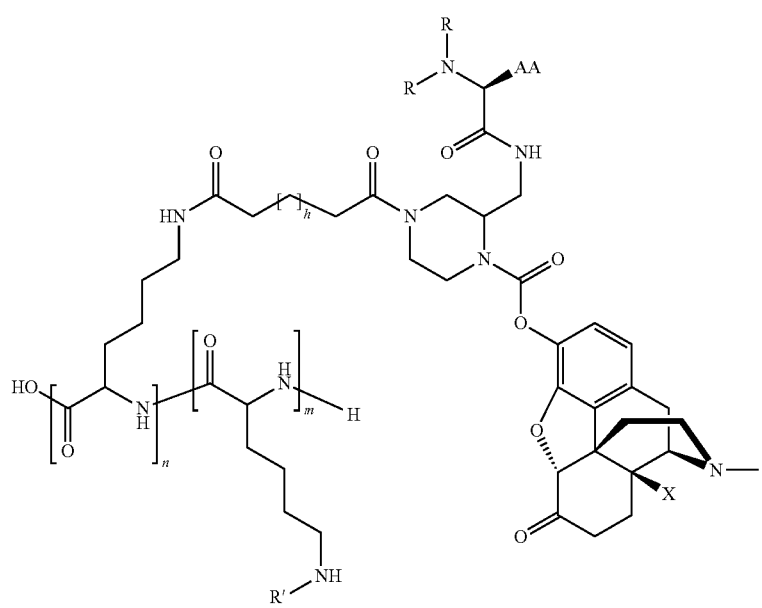

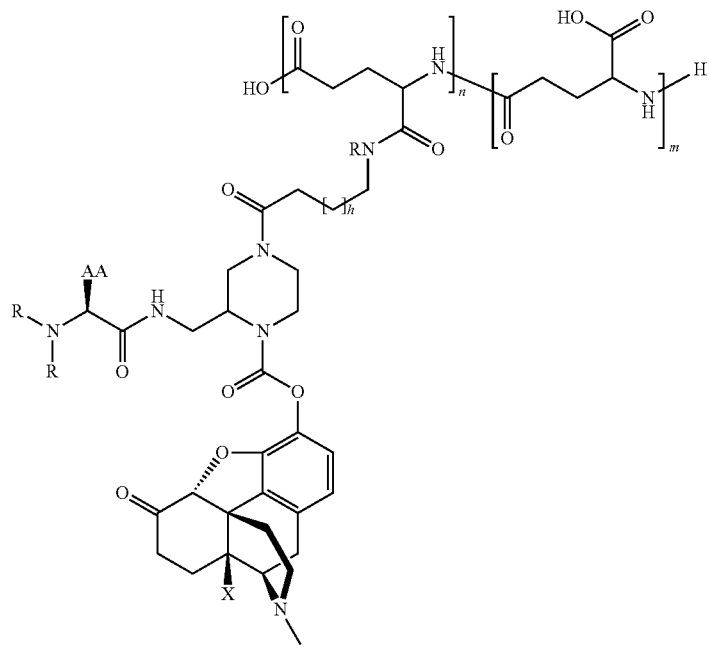
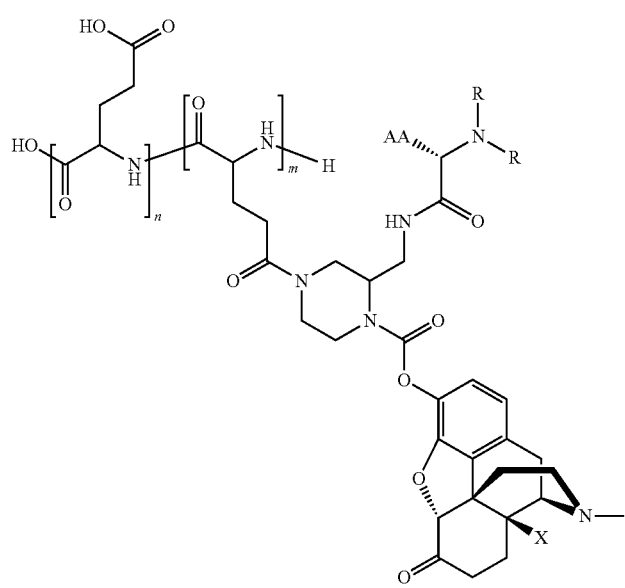

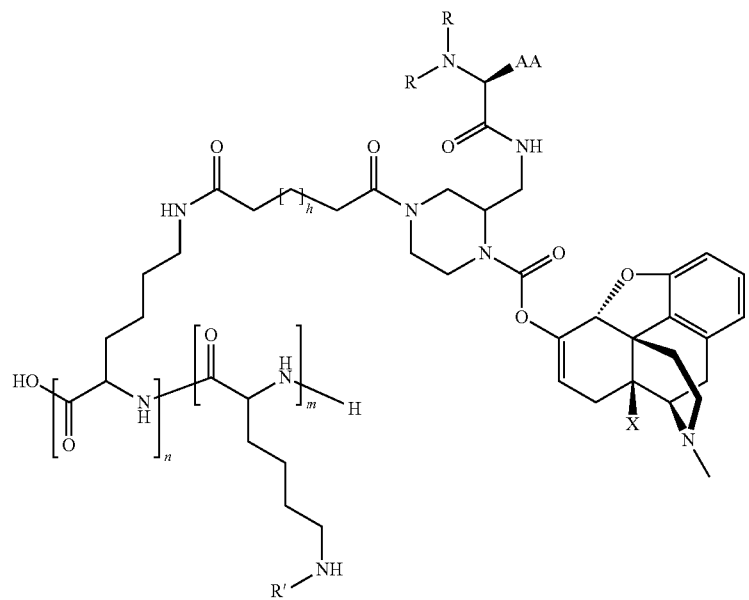
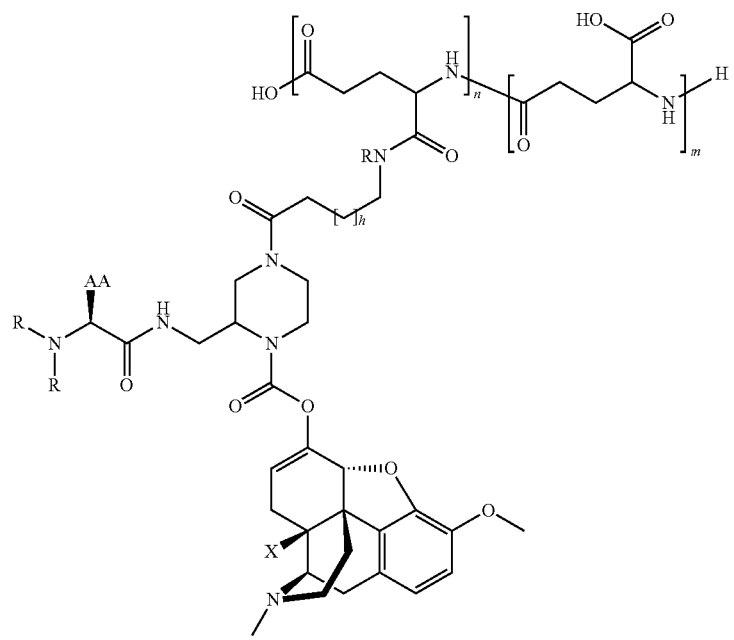

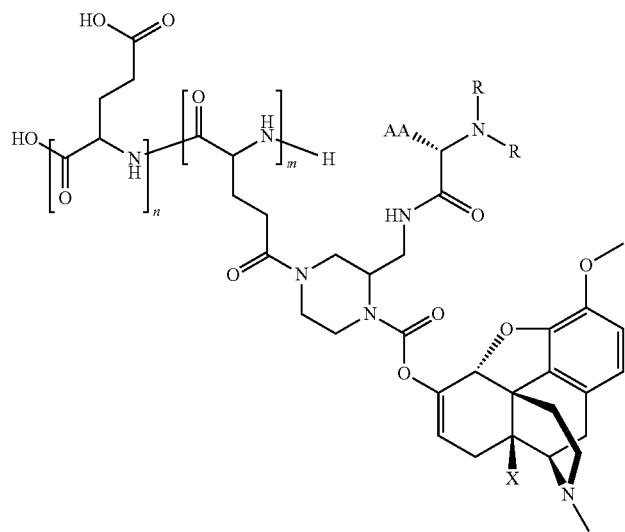
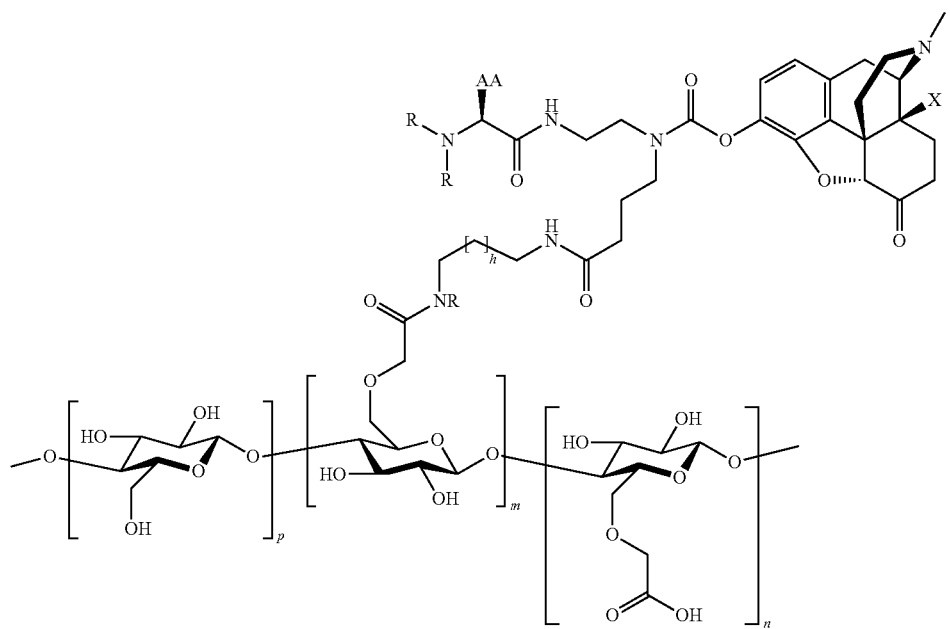

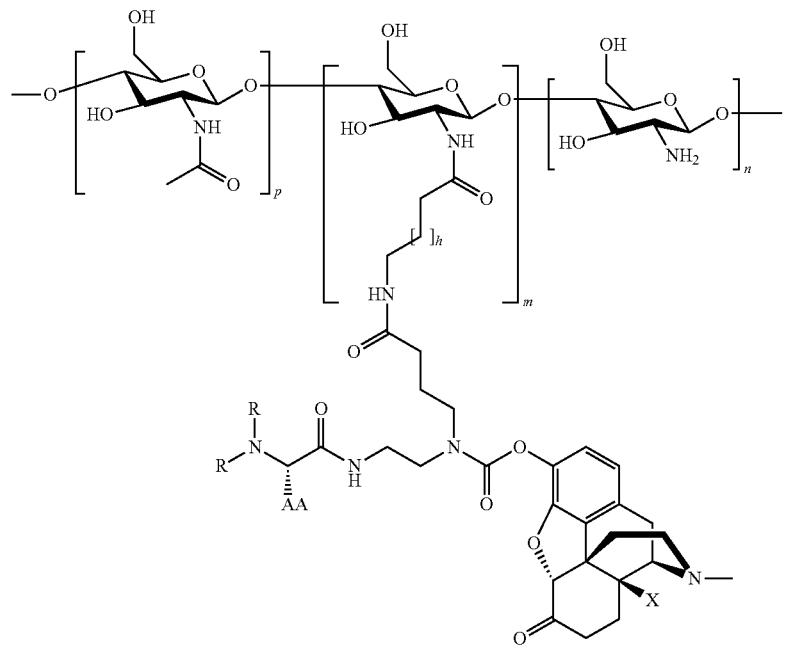
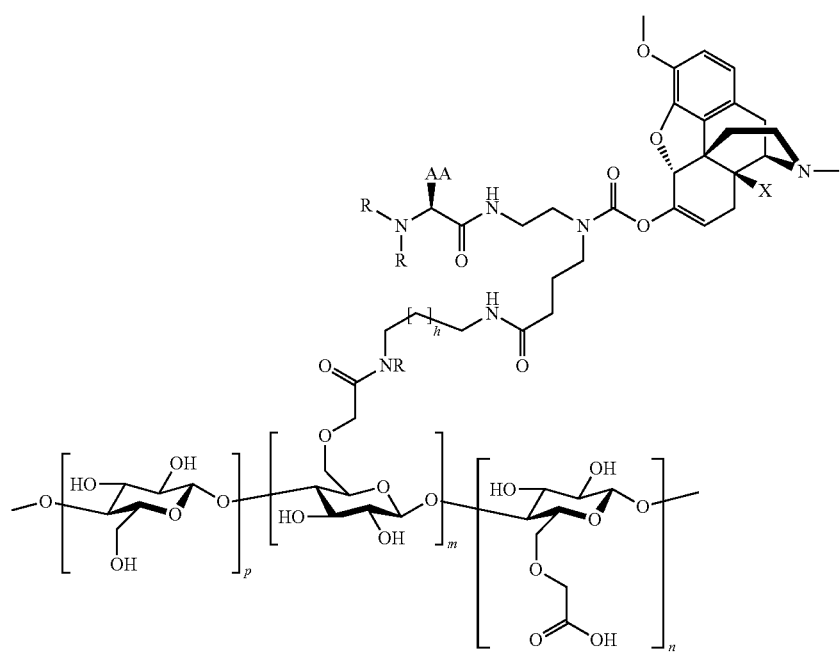

-continued
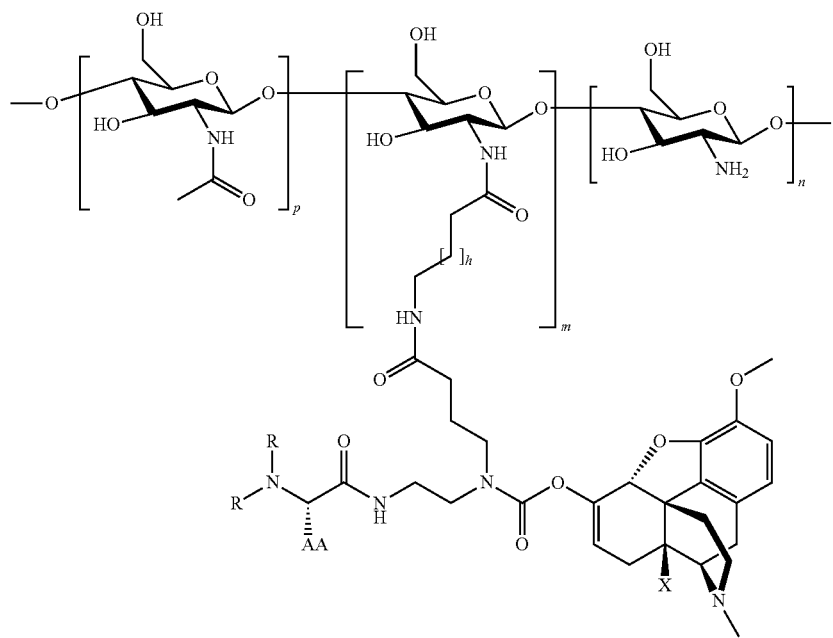
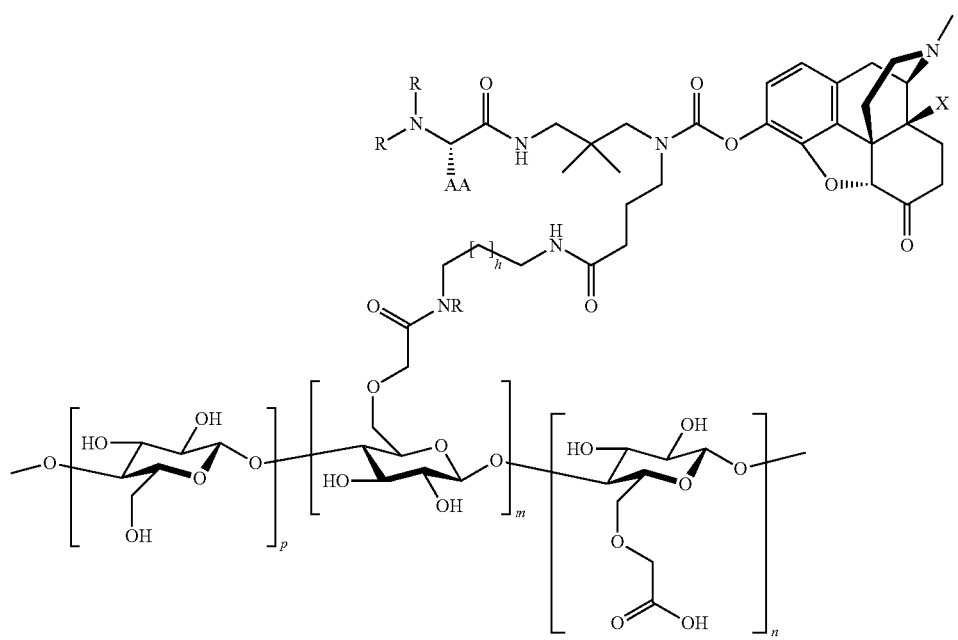

-continued
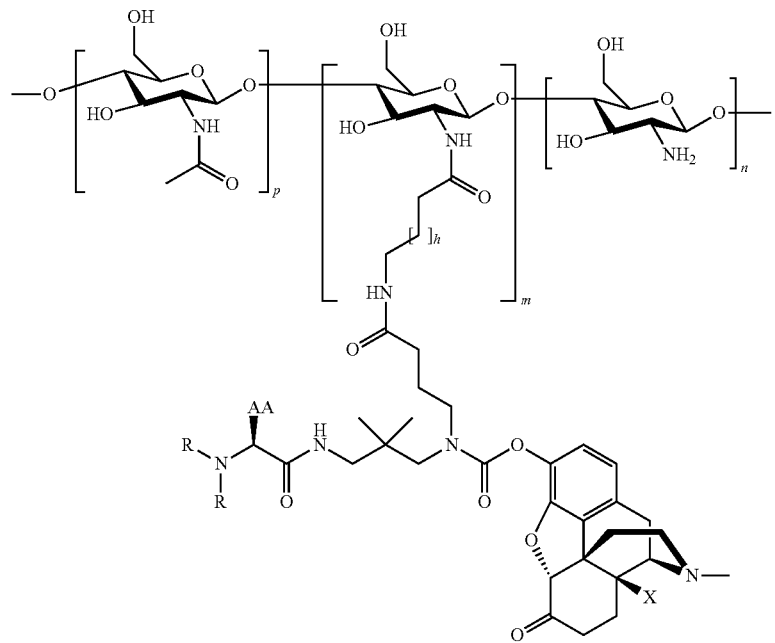
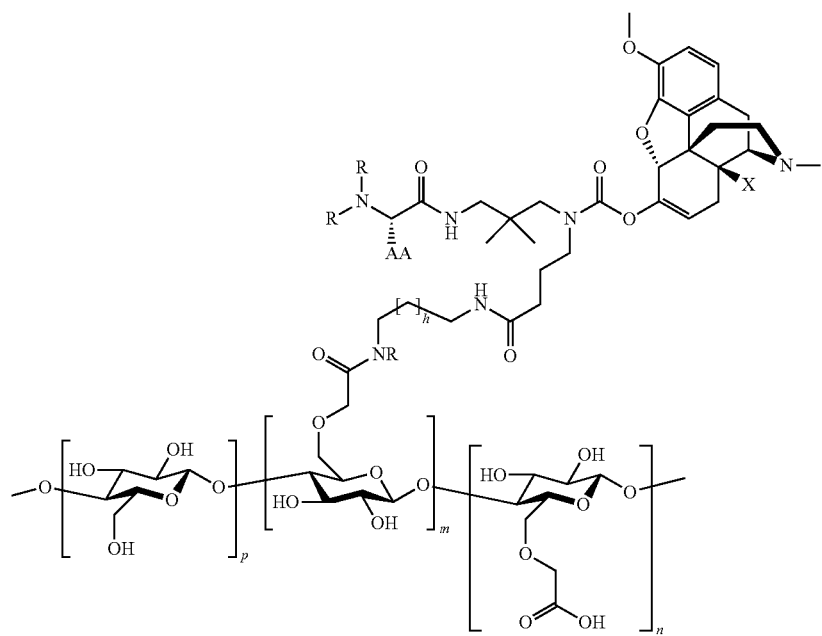

-continued
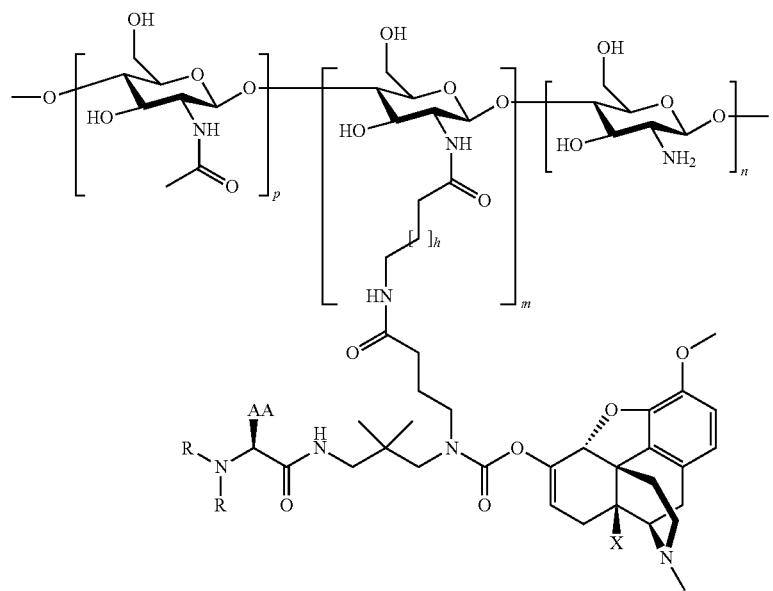
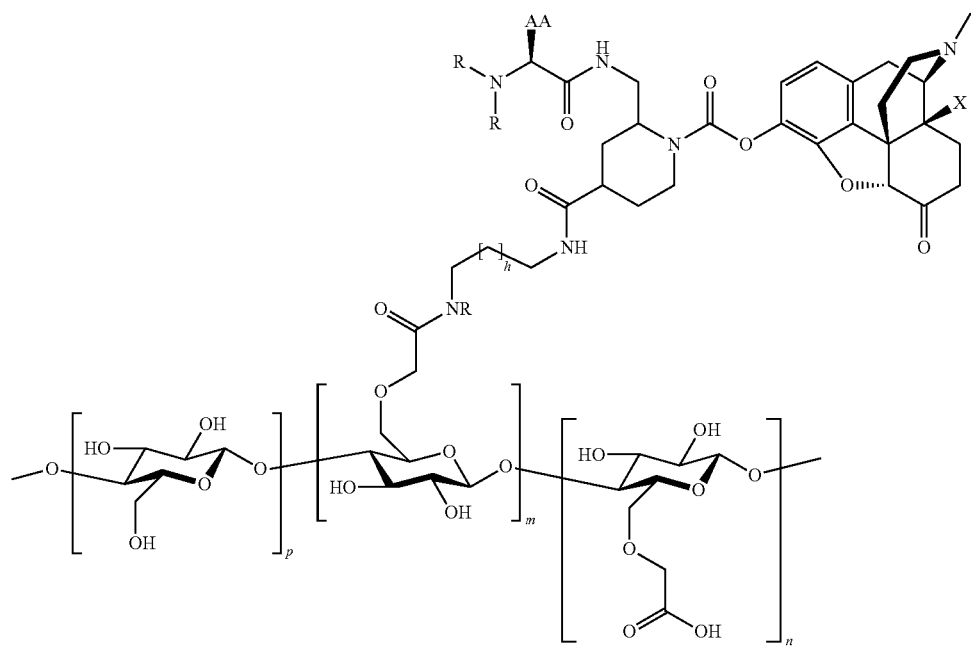

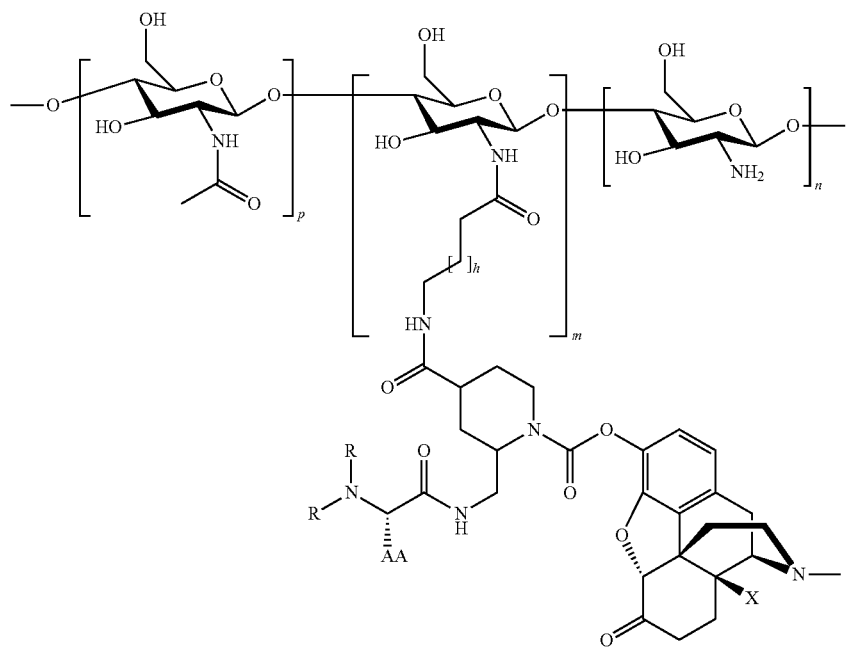
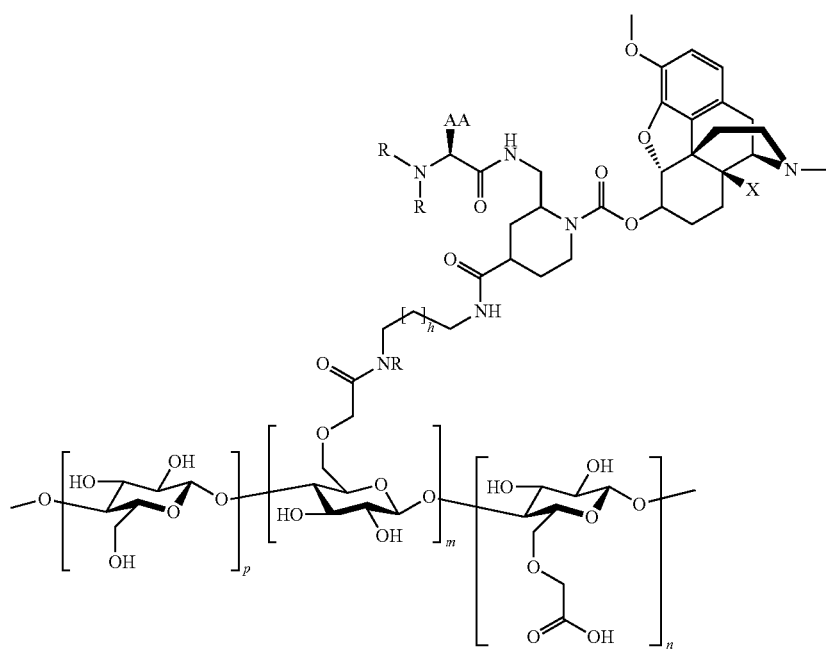

-continued
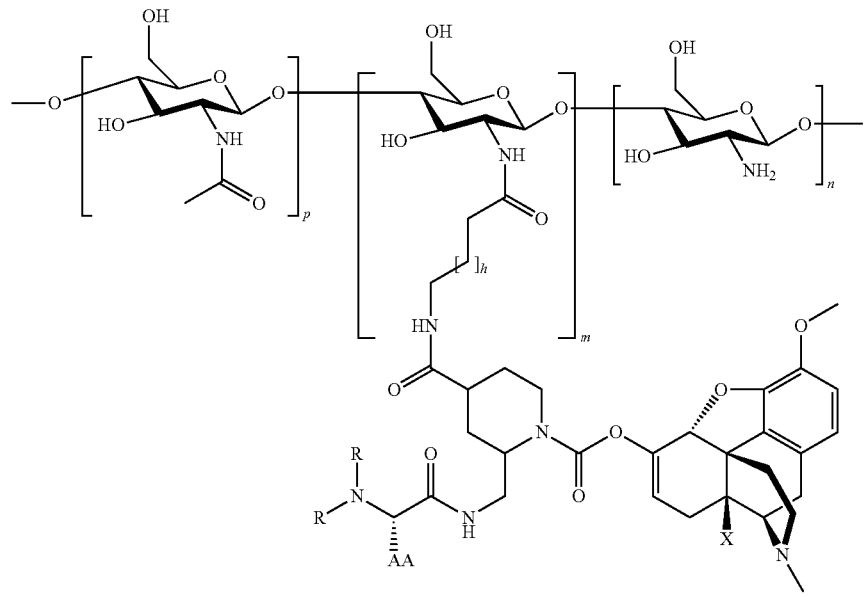
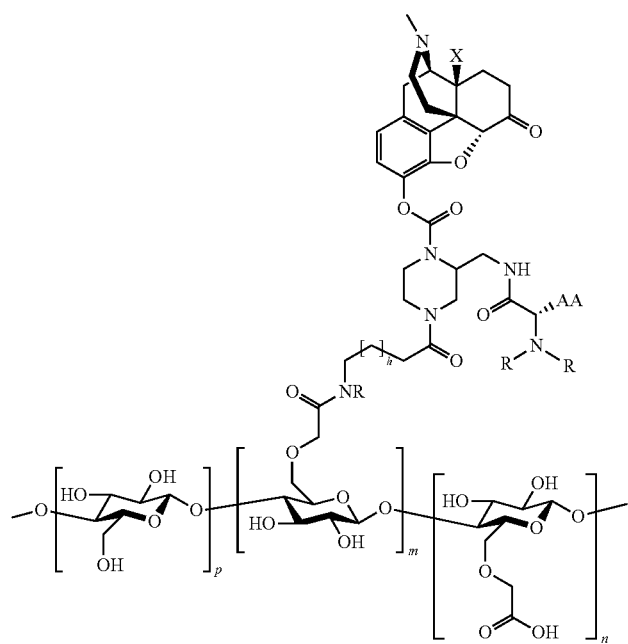

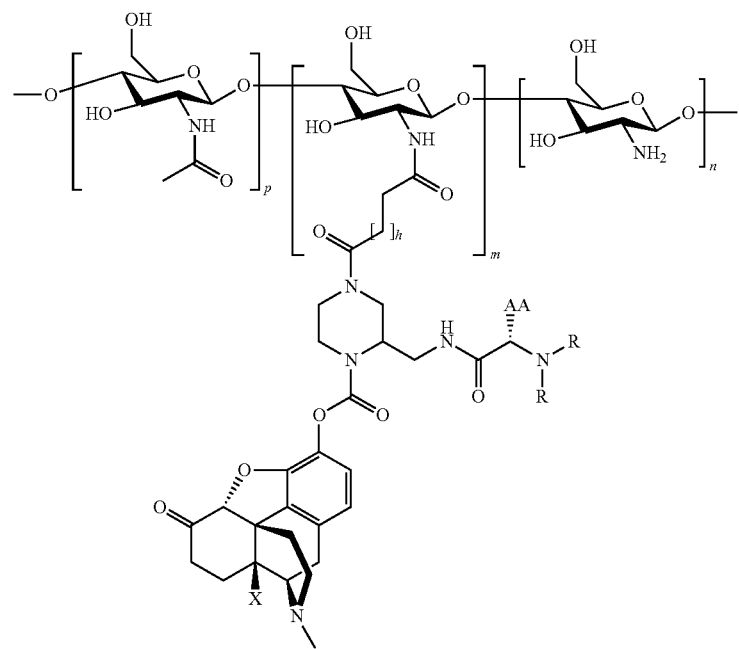
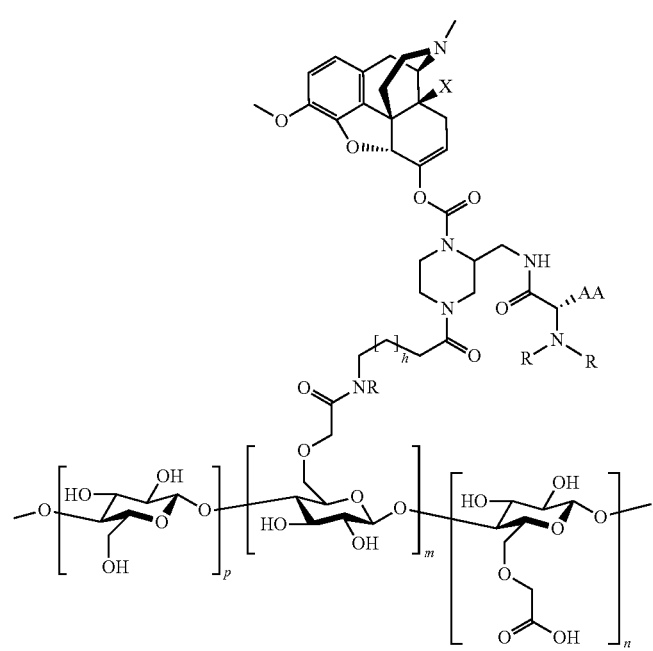

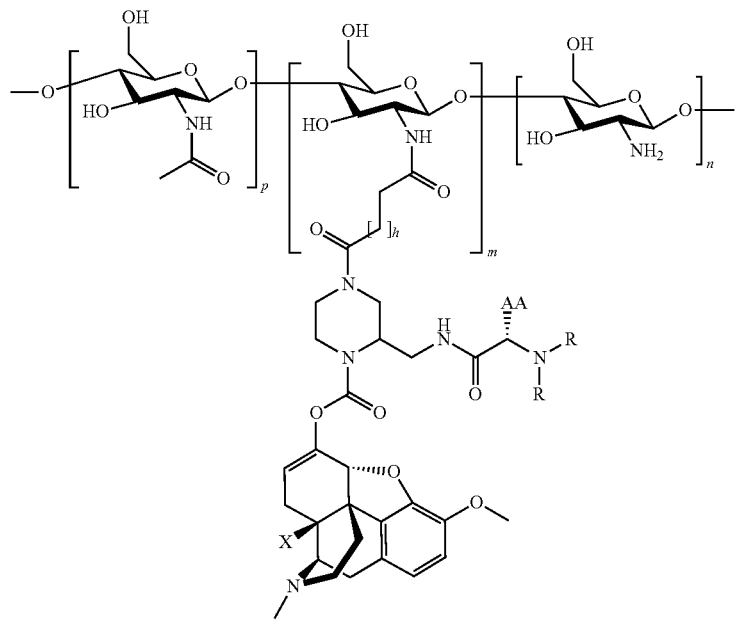

Where X is H or OH; AA is a natural or unnatural amino acid side chain that is recognized by a digestive enzyme; R is independently hydrogen, methyl, ethyl, substituted alkyl, or substituted aryl, or a natural or unnatural amino acid, or a polypeptide comprising up to 10 natural and/or unnatural amino acids; adjacent R groups can be joined to form a cyclic or heterocyclic structure; h represents a number of substituted or unsubstituted methylene units and can be an integer from zero to ten; n, m, and p can independently be an integer from 1 to 1000; each R' can independently be hydrogen, methyl, ethyl, substituted alkyl, or substituted aryl, acyl, or substituted acyl.

Further non-limiting examples of macromolecular trypsin enzyme-labile hydrocodone, oxycodone, hydromorphone, and oxymorphone prodrugs include the following:

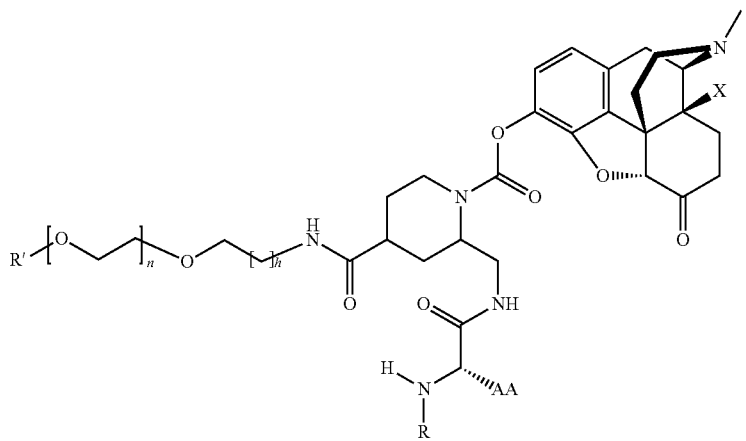

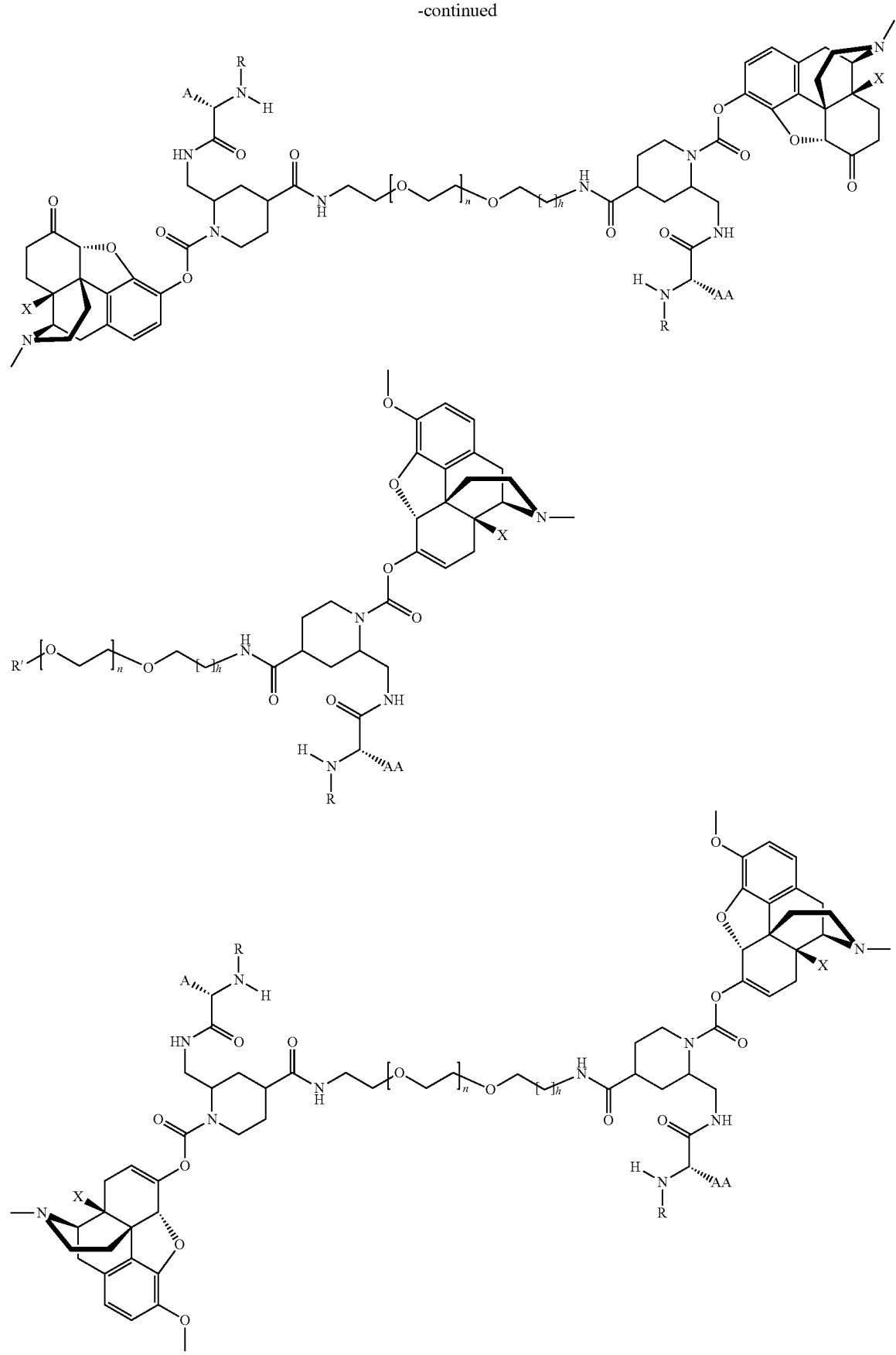

231

Where X is H or OH; AA is lysine, arginine or a lysine or arginine mimic; R' is hydrogen or methyl; R is a acetyl, a substituted amino acid, or a substituted di- or tri-peptide; h is an integer between 1-5; n is an integer between 10-100.

In yet another aspect of the invention, the GI enzyme-labile opioid prodrug is an enolic or phenolic ester and the release of the opioid agonist drug molecule from the macromolecular GI enzyme-labile opioid prodrug occurs via the two-step process depicted below. Cleavage of the GI enzyme promoiety reveals an internal nucleophilic amine. Subsequent controlled release of the opioid drug is then mediated as the appended nucleophilic amine undergoes an intramolecular cyclization-release reaction, whereby the parent phenolic or enolic opioid is released. This is depicted below whereby the digestive enzyme can be trypsin; AA can be the side-chain of lysine or arginine; and P is a polymeric addend:

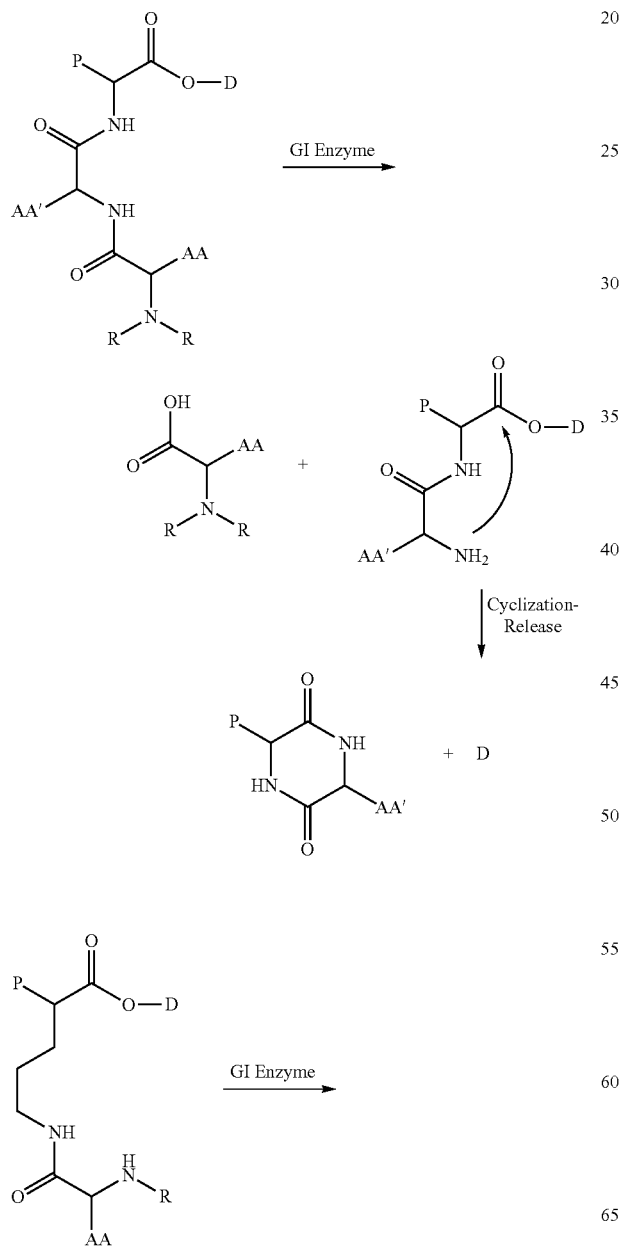

232

-continued

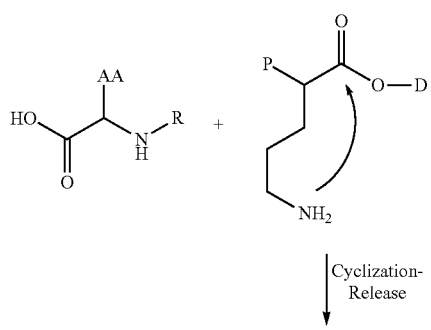

Macromolecular GI enzyme-labile opioid prodrugs that operate via this mechanism can be described by the general formulae:

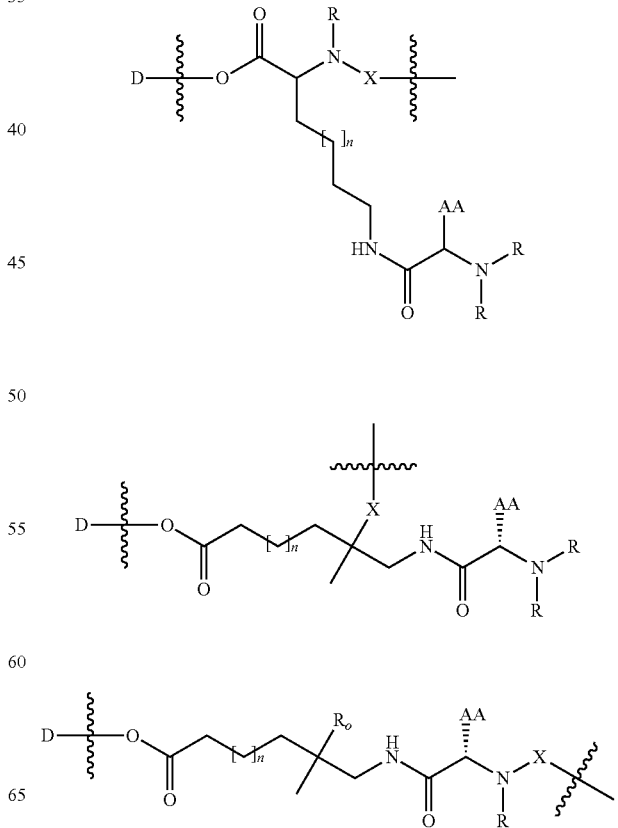

233
-continued

234
-continued

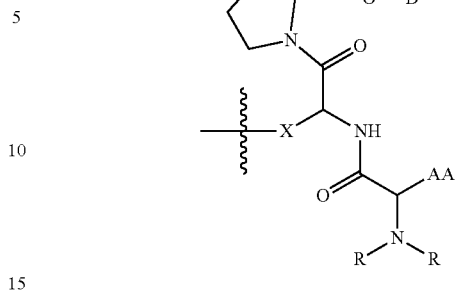

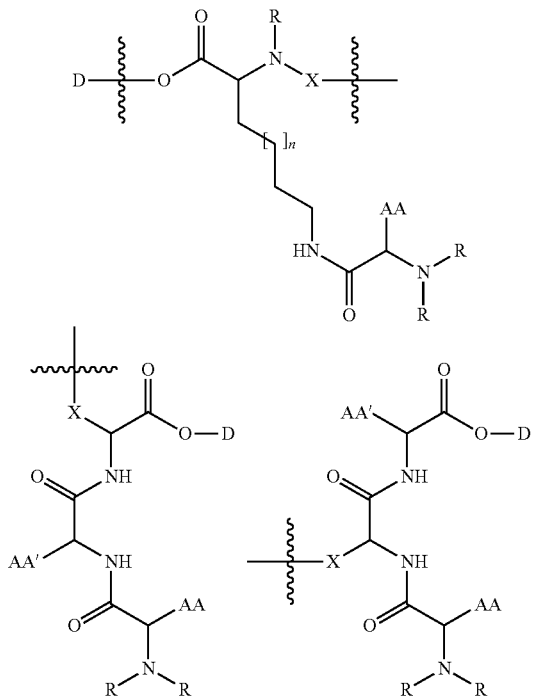

Where D is an opioid agonist as defined above; AA is a natural or unnatural amino acid side chain that is recognized by a digestive enzyme; AA' is a natural or unnatural amino acid side chain; R is independently hydrogen, methyl, ethyl, substituted alkyl, or substituted aryl, or a natural or unnatural amino acid, or a polypeptide comprising up to 10 natural and/or unnatural amino acids; adjacent R groups can be joined to form a cyclic or heterocyclic structure; n represents a number of substituted or unsubstituted methylene units and can be an integer from zero to five; o represents an integer from zero to 16; and X is a linker as defined herein.

Further non-limiting examples of macromolecular trypsin enzyme-labile hydrocodone, oxycodone, hydromorphone, and oxymorphone prodrugs that operate via this mechanism can include the following:

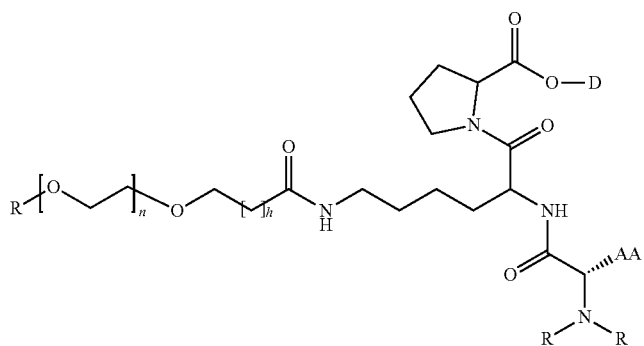

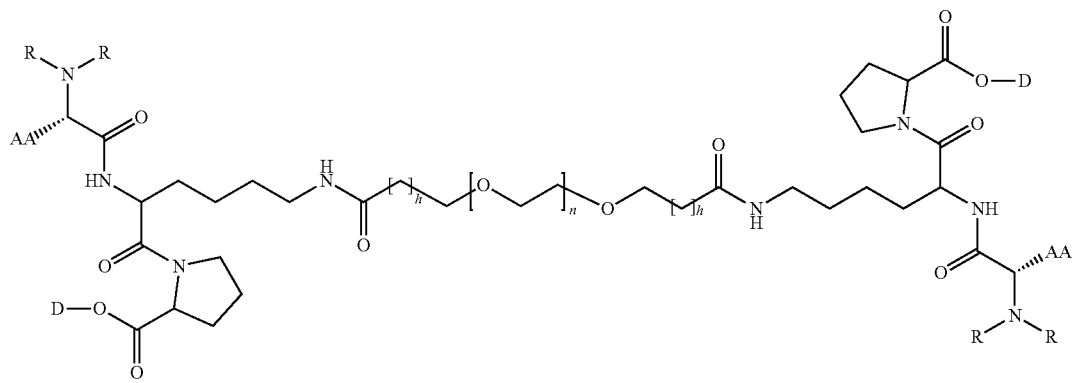

-continued
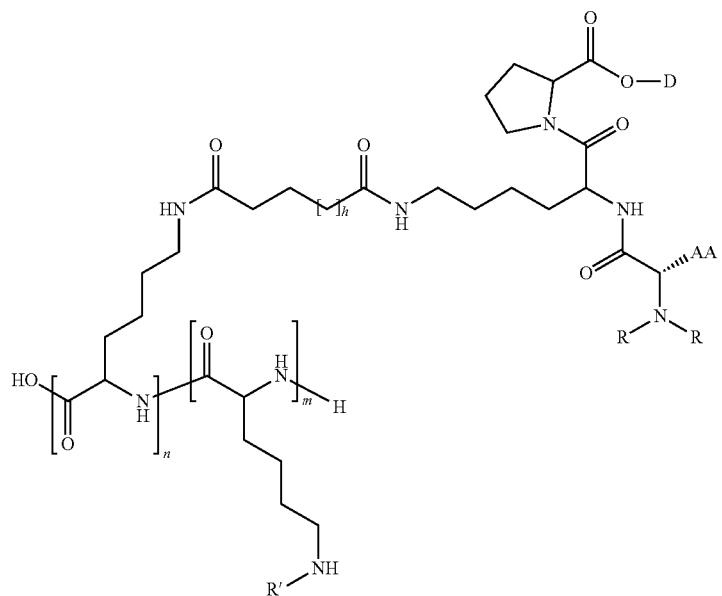
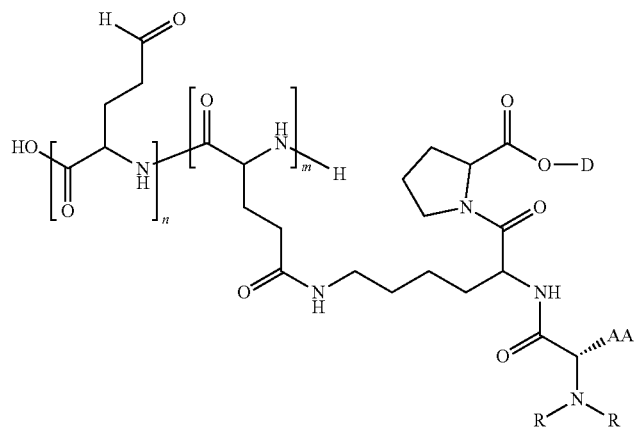
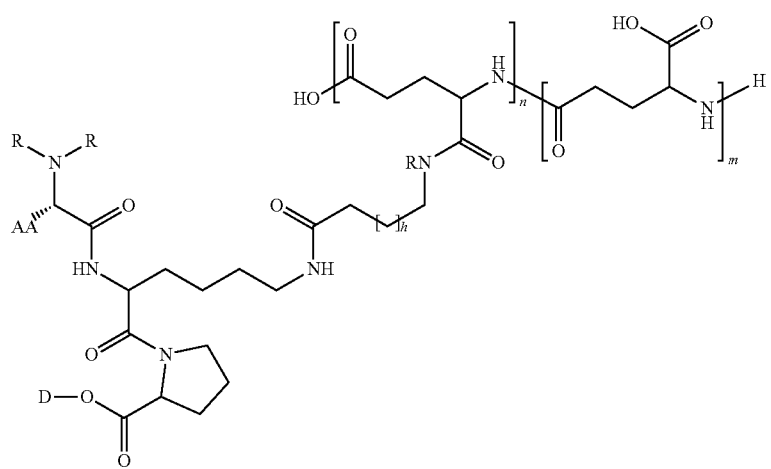

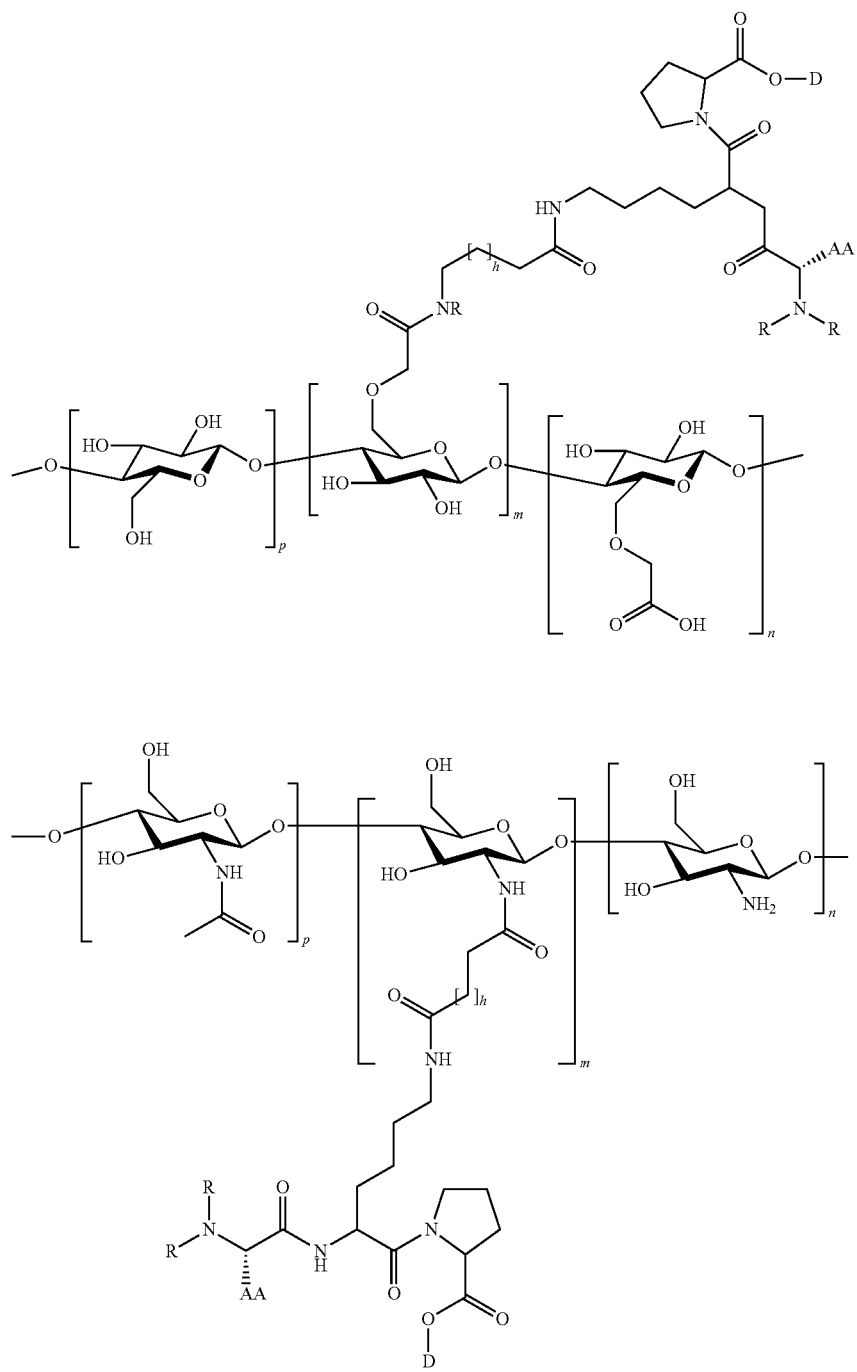

Where D is an opioid agonist as defined above; AA is a natural or unnatural amino acid side chain that is recognized by a digestive enzyme; R is independently hydrogen, methyl, ethyl, substituted alkyl, or substituted aryl, or a natural or unnatural amino acid, or a polypeptide comprising up to 10 natural and/or unnatural amino acids; adjacent R groups can be joined to form a cyclic or heterocyclic structure; h represents a number of substituted or unsubstituted methylene units and can be an integer from zero to ten; n, m, and p, can independently be an integer from 1 to 1000; each R' can independently be hydrogen, methyl, ethyl, substituted alkyl, or substituted aryl, acyl, or substituted acyl.

Further non-limiting examples of macromolecular trypsin enzyme-labile hydrocodone, oxycodone, hydromorphone, and oxymorphone prodrugs that operate via this mechanism can include the following:

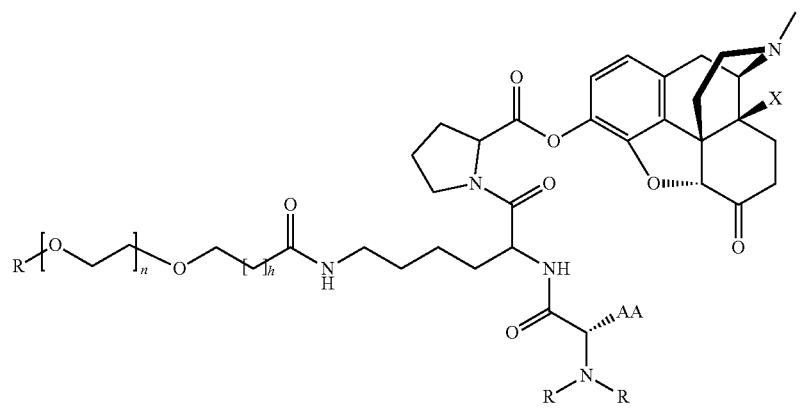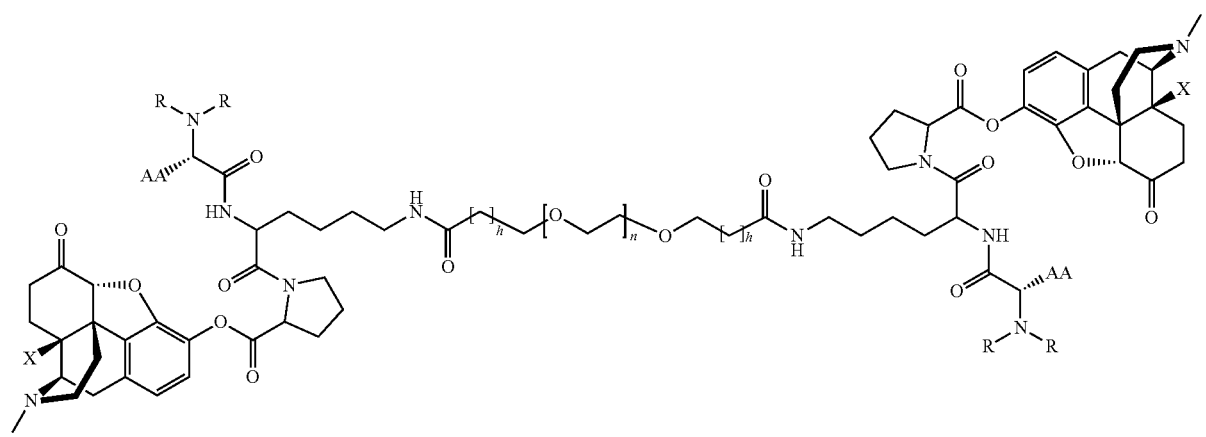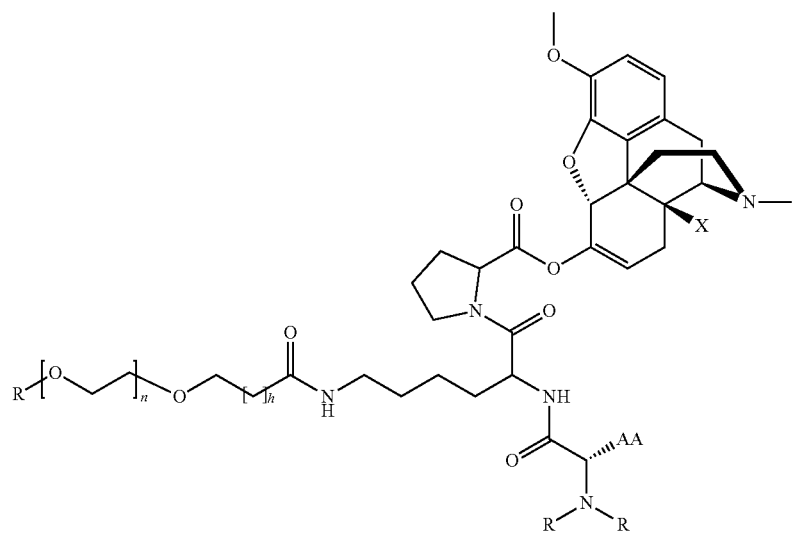

241 242
-continued
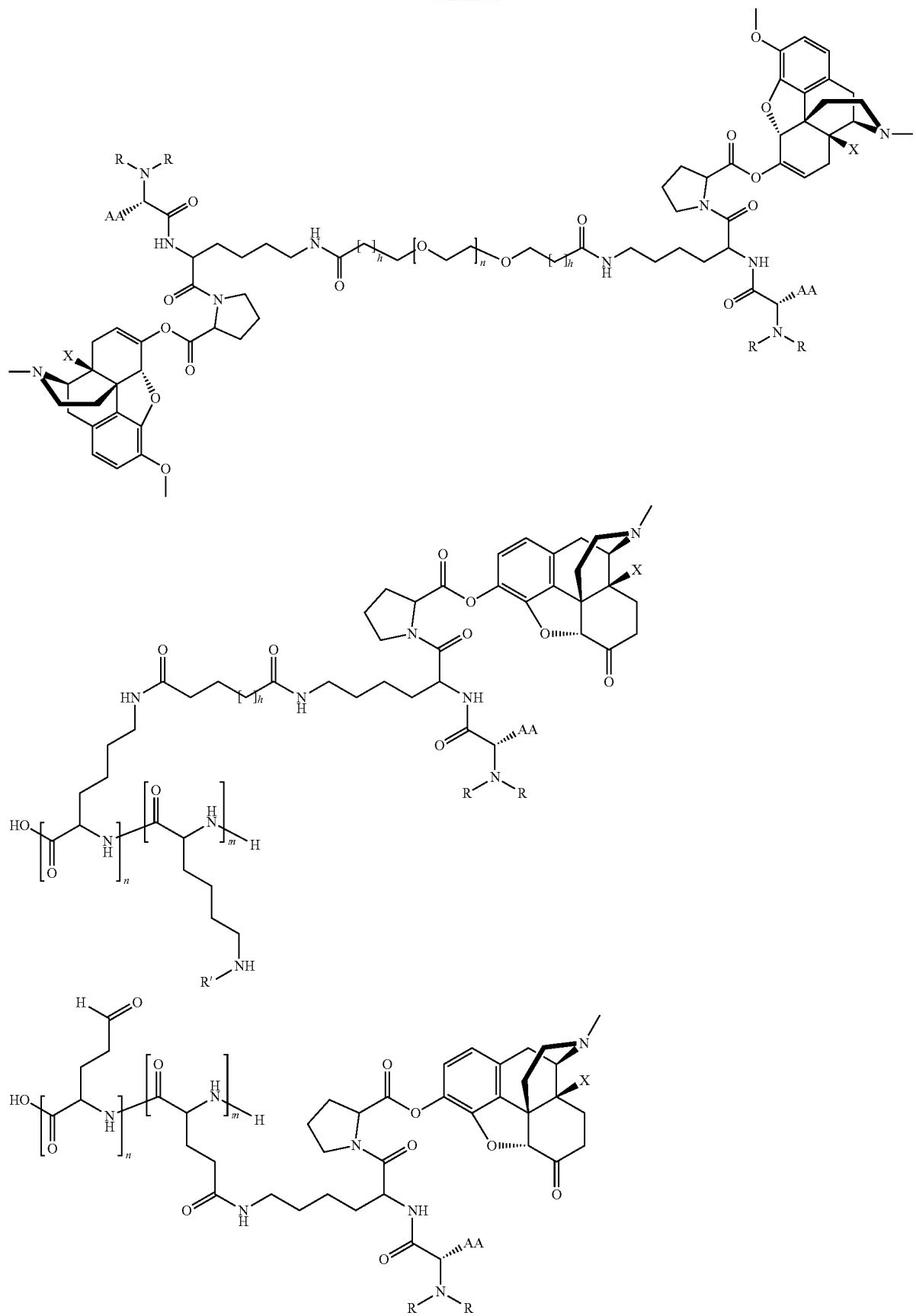

-continued
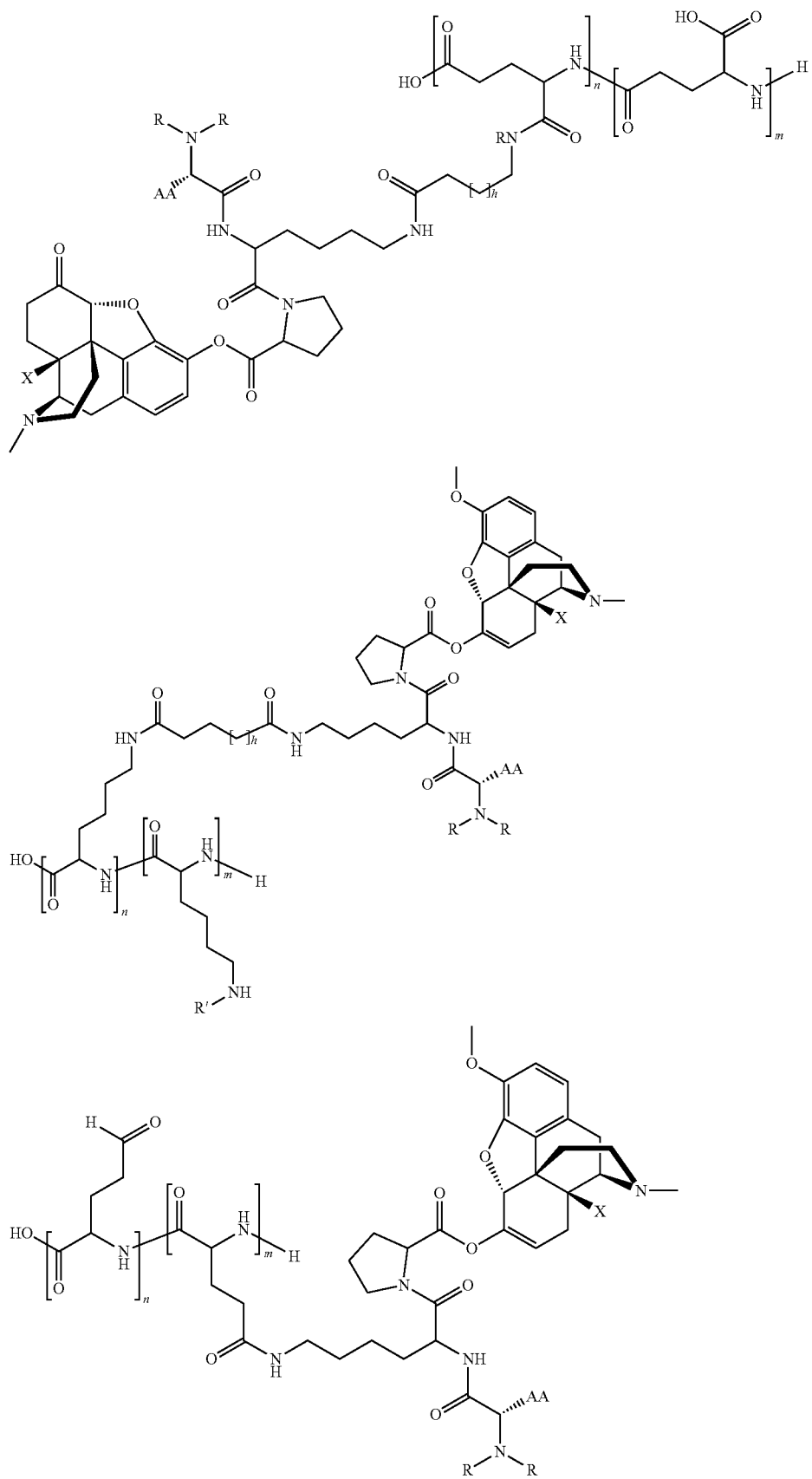

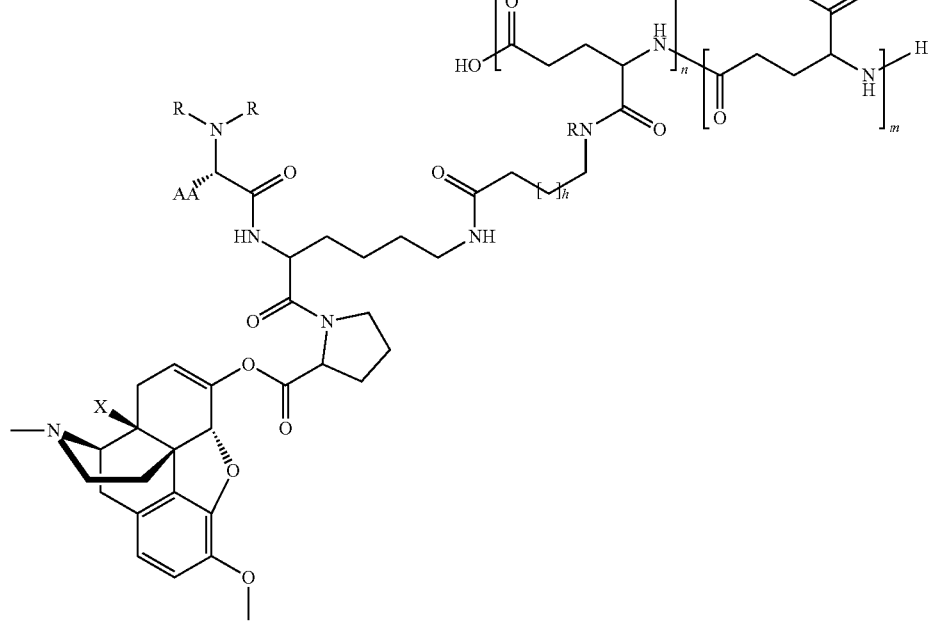
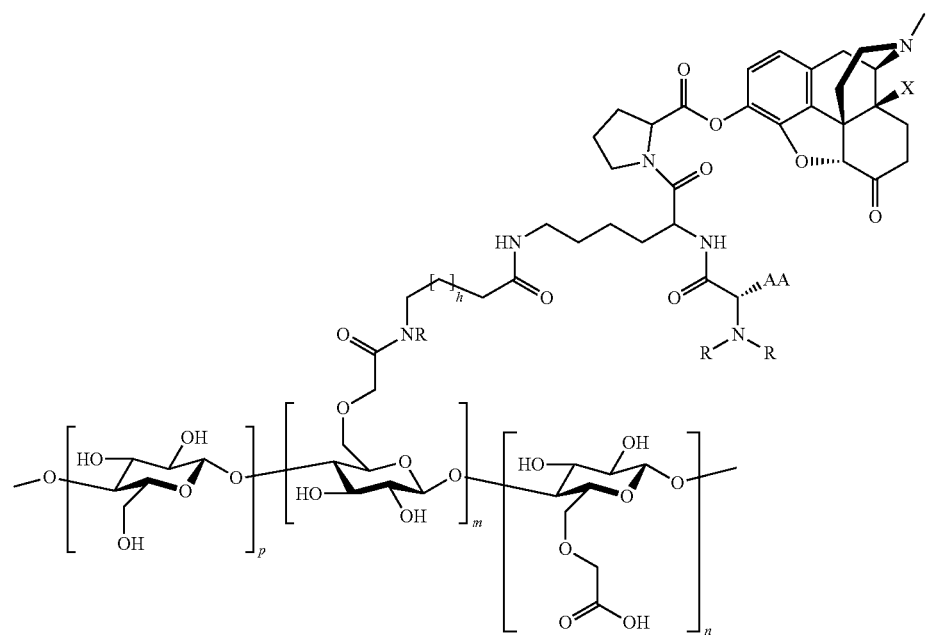

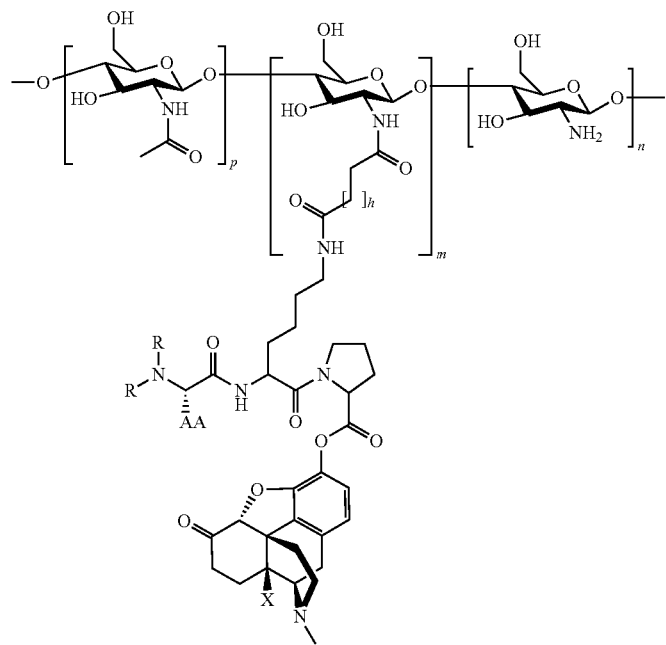
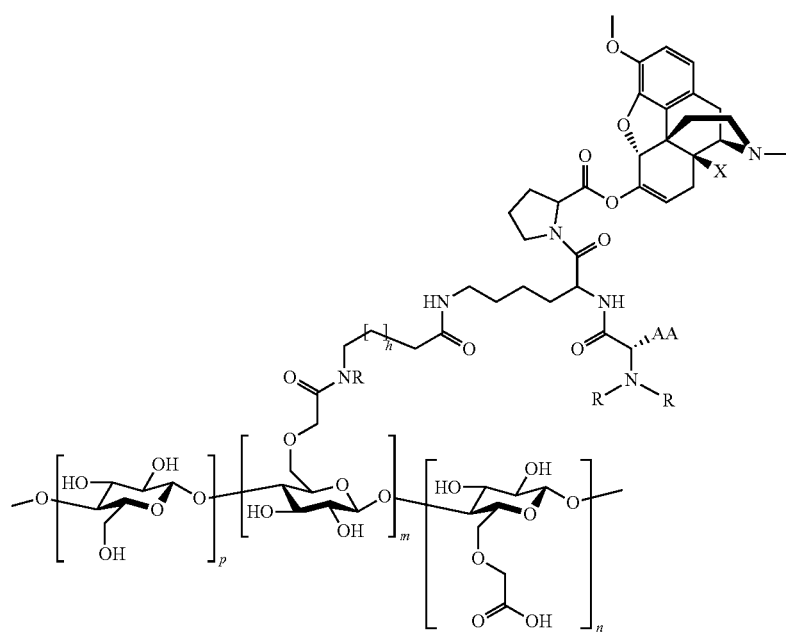

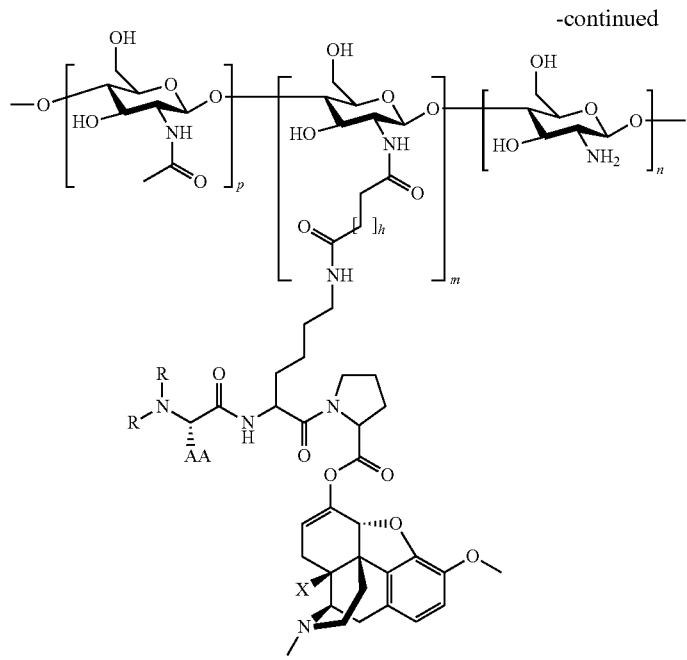

Where X can be H or OH; AA is a natural or unnatural amino acid side chain that is recognized by a digestive enzyme; R is independently hydrogen, methyl, ethyl, substituted alkyl, or substituted aryl, or a natural or unnatural amino acid, or a polypeptide comprising up to 10 natural and/or unnatural amino acids; adjacent R groups can be joined to form a cyclic or heterocyclic structure; h represents a number of substituted or unsubstituted methylene units and can be an integer from zero to ten; n, m, and p, can independently be an integer from 1 to 1000; each R' can independently be hydrogen, methyl, ethyl, substituted alkyl, or substituted aryl, acyl, or substituted acyl.

In yet another aspect of the invention, the GI enzyme-labile opioid prodrug is an enolic or phenolic ester and the release of the opioid agonist drug molecule from the macromolecular GI trypsin-labile opioid prodrug occurs via the two-step (r=0), or multi-step (r≥1), process depicted below. Cleavage of the terminal amino-acid residue of GI enzyme promoiety reveals a terminal lysine substrate which is subsequently recognized and cleaved by trypsin. This process iterates n+1 times until the opioid is released via the cleavage of the final lysine-ester residue that is directly attached to the opioid molecule. This is depicted below whereby AA is the side-chain of lysine or arginine and P is a polymeric addend:

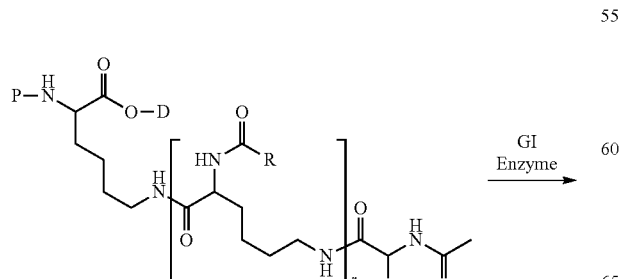

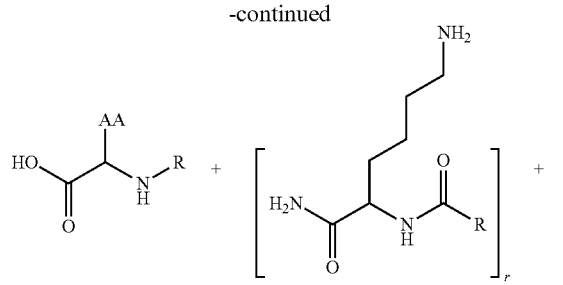

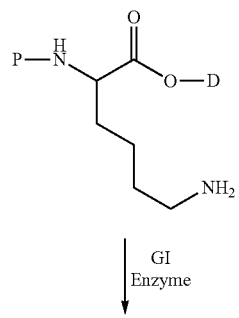

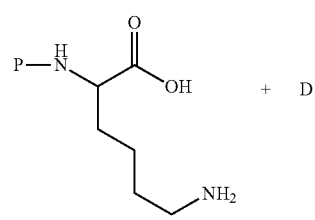

Macromolecular GI enzyme-labile opioid prodrugs that operate via this mechanism can be described by the general formula:

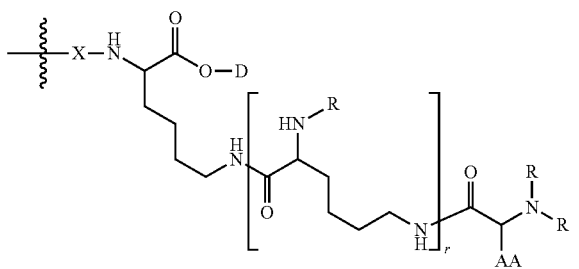

Where D is an opioid agonist as defined above; AA is an amino-acid side-chain that is recognized by a digestive enzyme; R is independently hydrogen, methyl, ethyl, substituted alkyl, or substituted aryl, acyl, substituted acyl, or a natural or unnatural amino acid, or a polypeptide comprising up to 10 natural and/or unnatural amino acids; adjacent R groups can be joined to form a cyclic or heterocyclic structure; r is an integer from zero to ten; and X is a linker as defined herein.

Further non-limiting examples of macromolecular digestive enzyme-labile hydrocodone, oxycodone, hydromorphone, and oxymorphone prodrugs that operate via this mechanism can include the following:

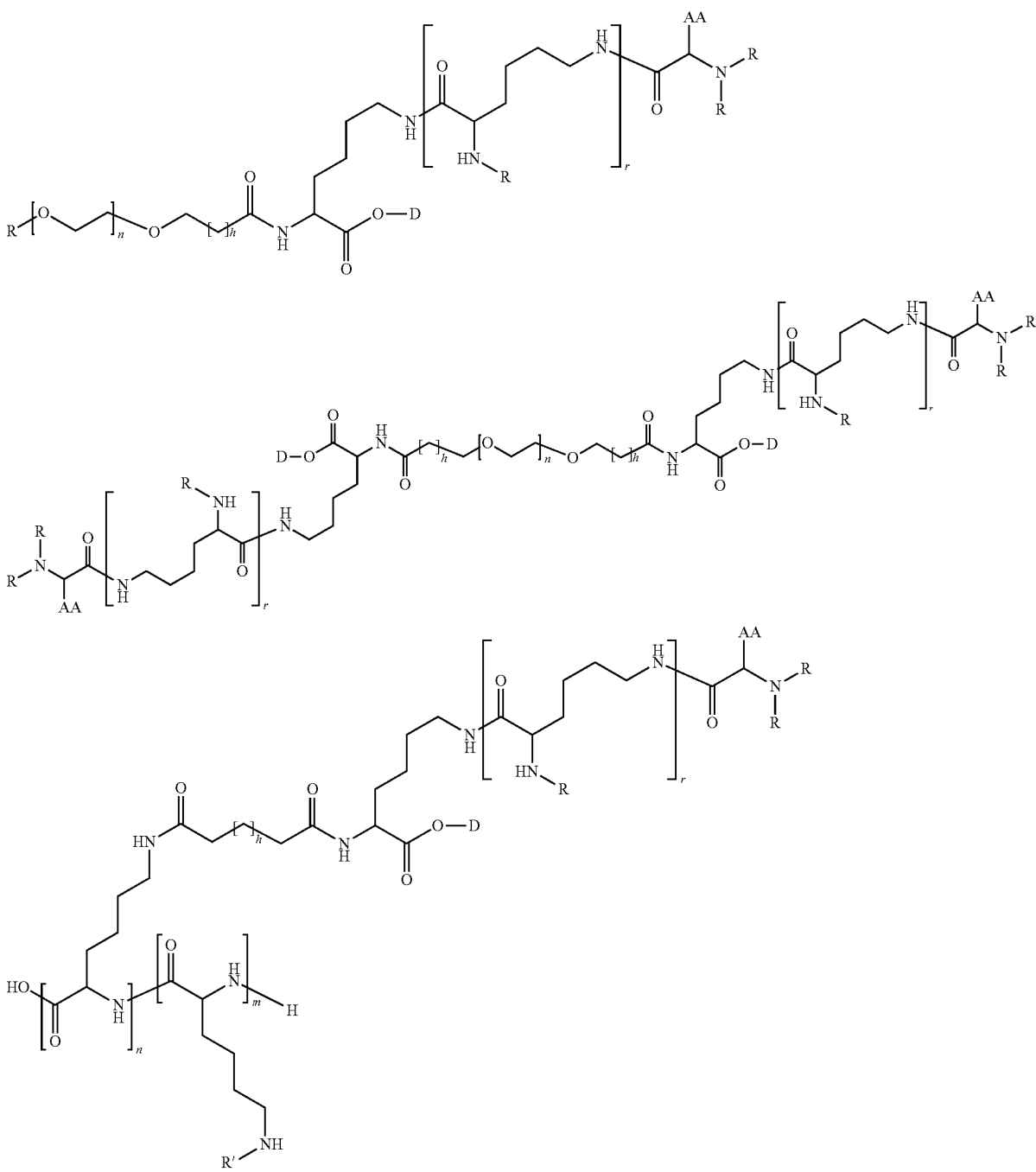

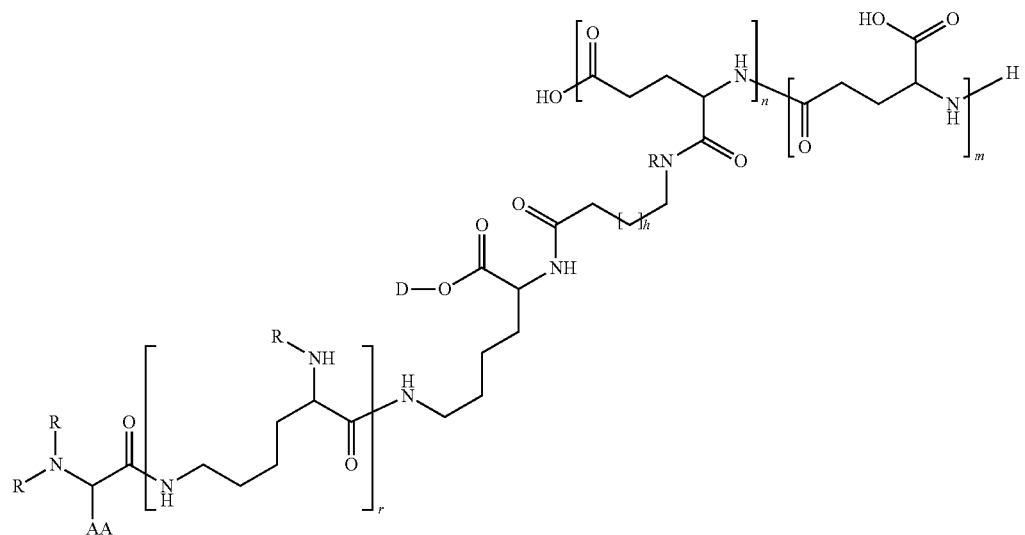
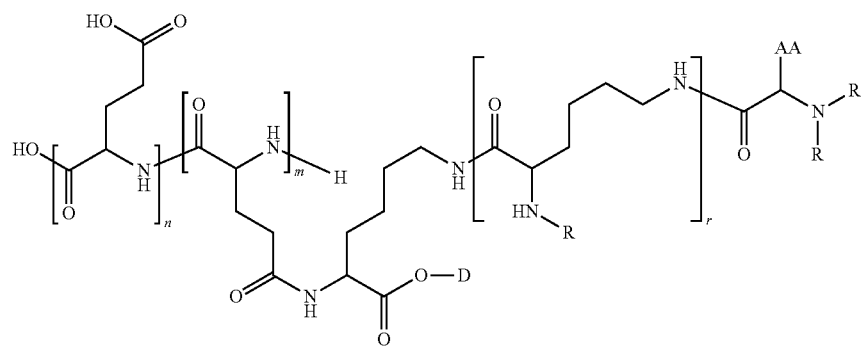
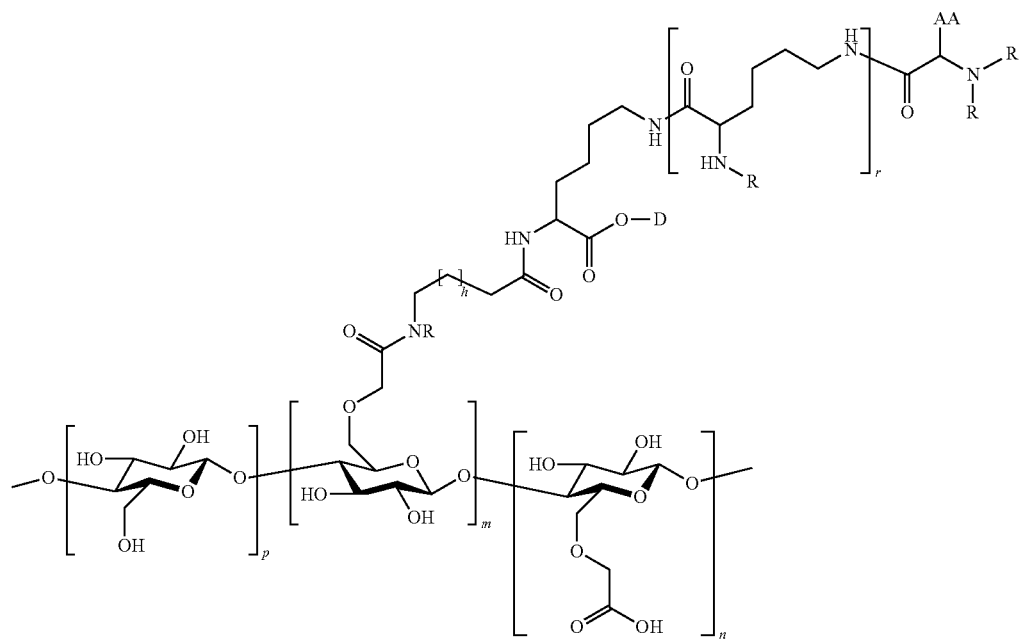

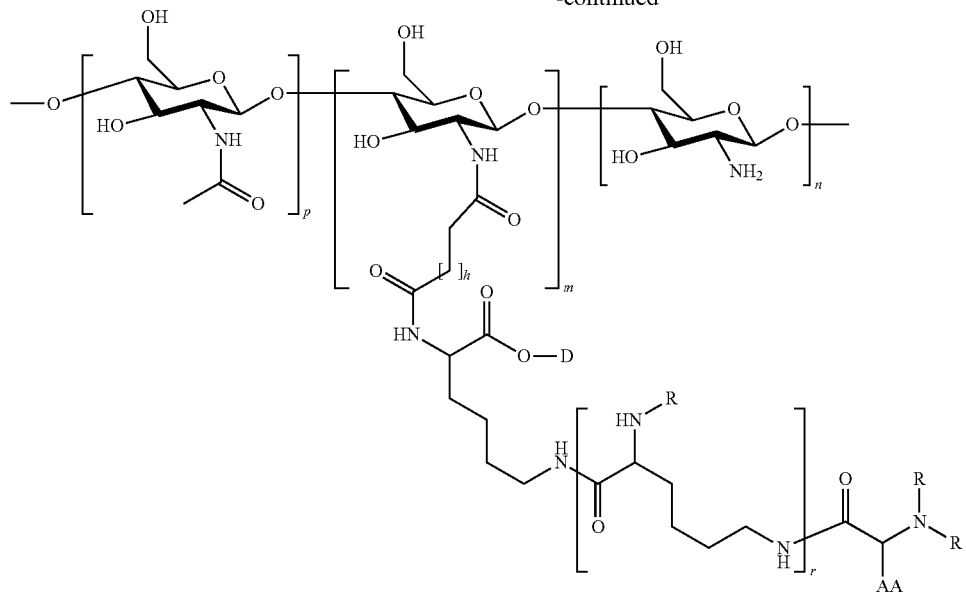

Where D is an opioid agonist as defined above; AA is an amino-acid side-chain that is recognized by a digestive enzyme; R is independently hydrogen, methyl, ethyl, alkyl or substituted alkyl, aryl or substituted aryl, acyl or substituted acyl, or a natural or unnatural amino acid, or a polypeptide comprising up to 10 natural and/or unnatural amino acids; r is an integer from zero to ten; adjacent R groups can be joined to form a cyclic or heterocyclic structure; and h is an integer representing a number of methylene, or substituted methylene, units from zero to ten; n, m, and p, can independently be an integer from 1 to 1000; each R' can independently be hydrogen, methyl, ethyl, substituted alkyl, or substituted aryl, acyl, or substituted acyl.

Further non-limiting examples of macromolecular trypsin enzyme-labile hydrocodone, oxycodone, hydromorphone, and oxymorphone prodrugs that operate via this mechanism can include the following:

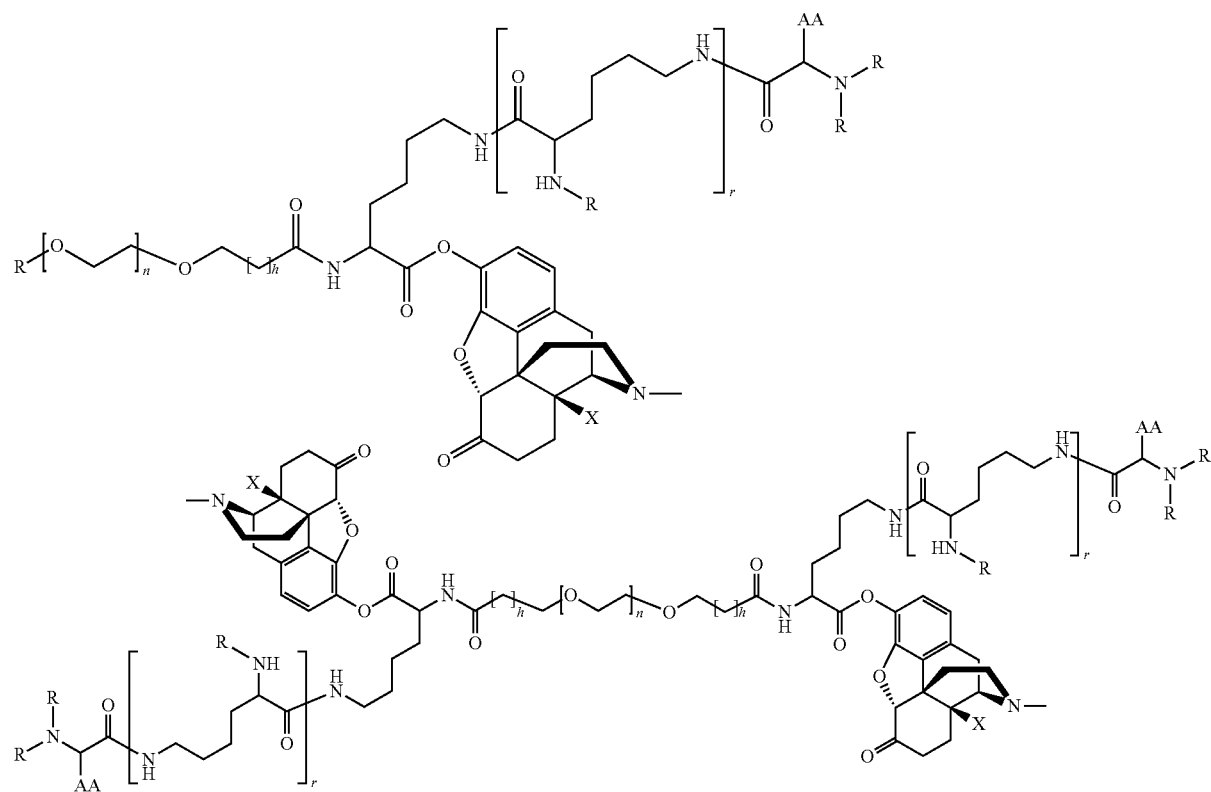

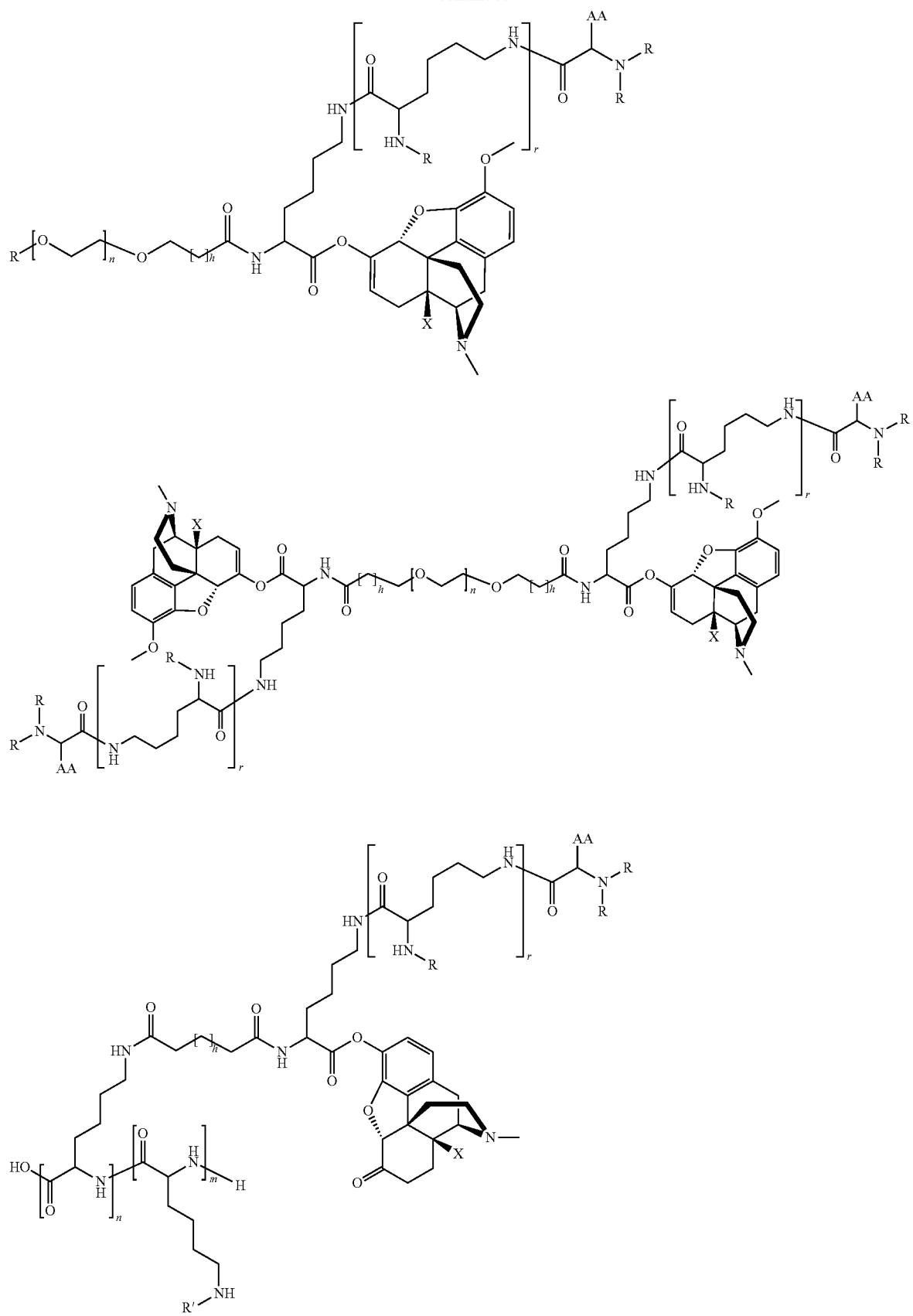

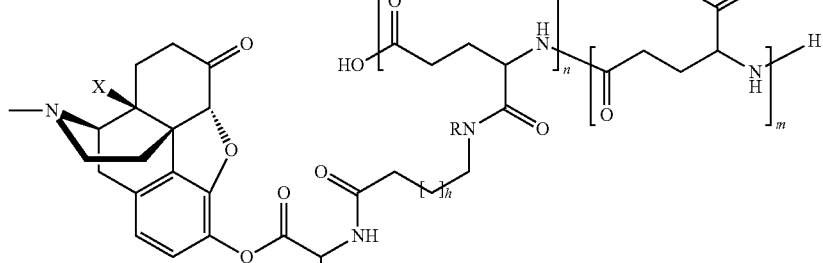
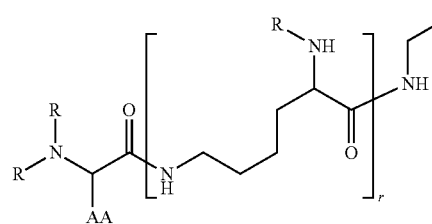
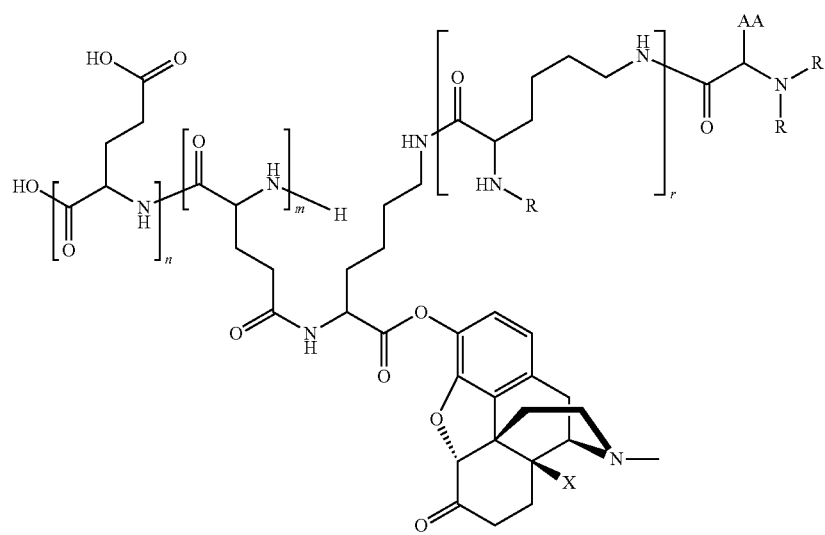

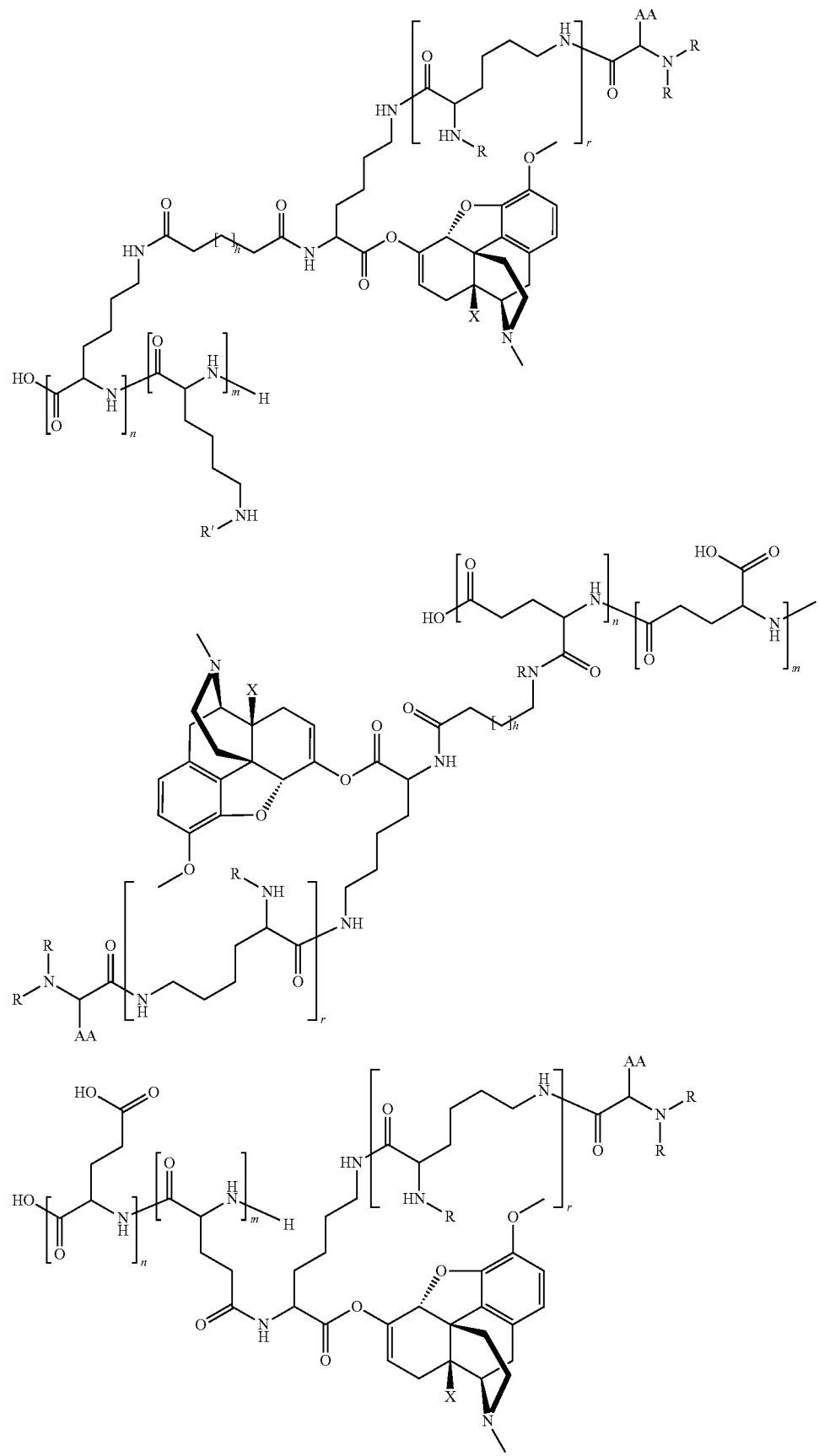

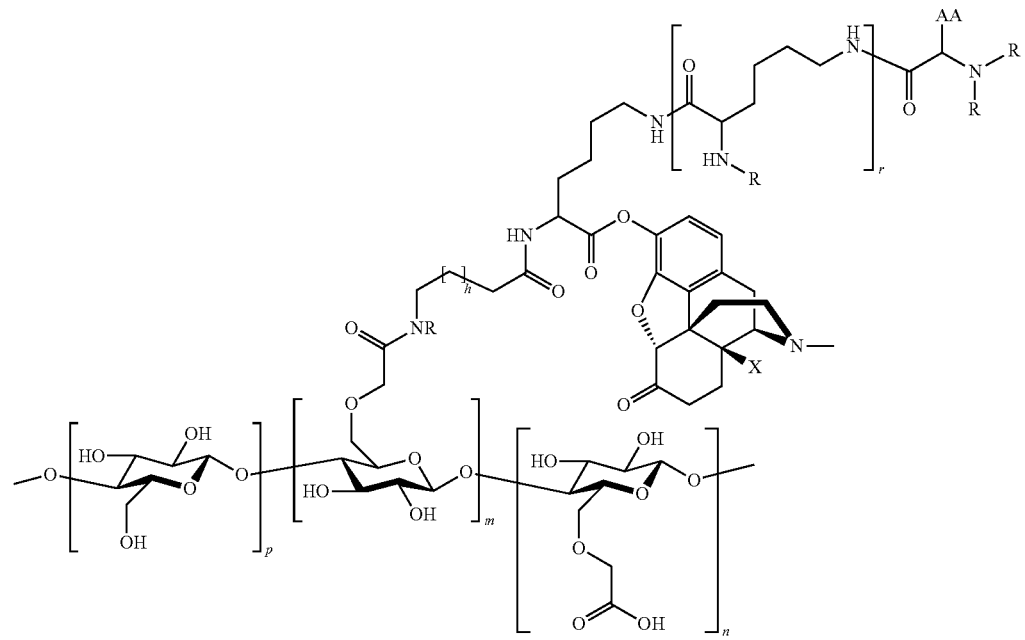
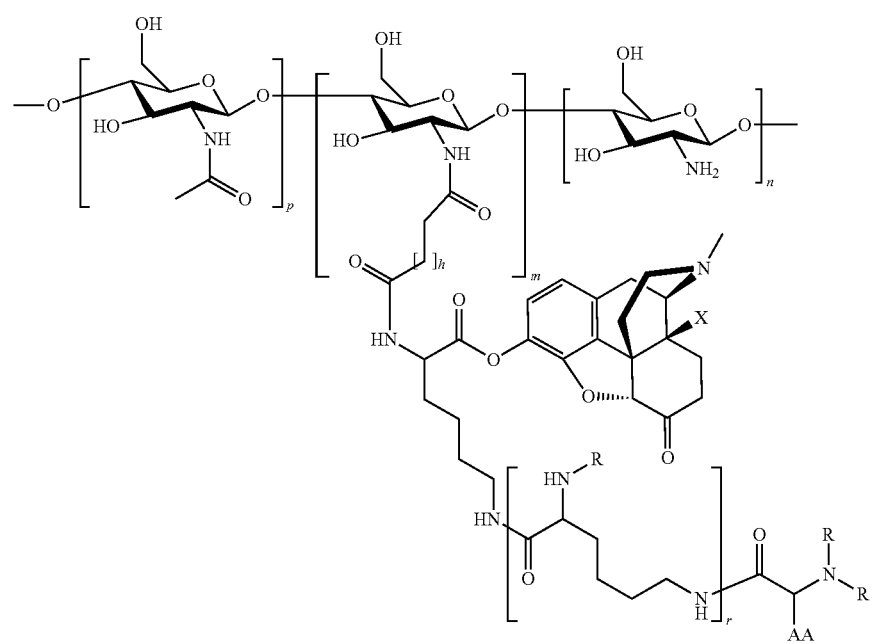

-continued

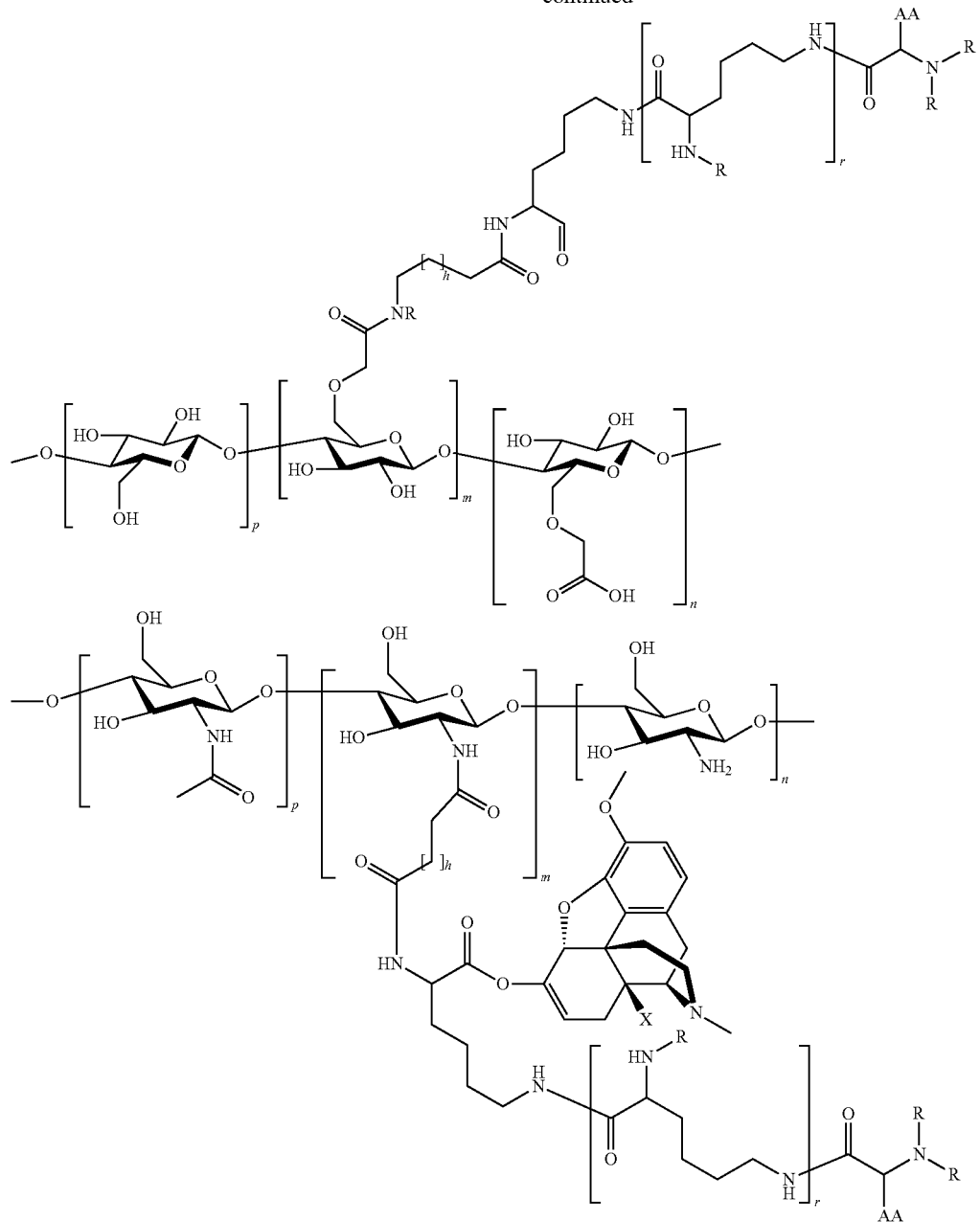

Where X is H or OH; AA is an amino-acid side-chain that is recognized by a digestive enzyme; R is independently hydrogen, methyl, ethyl, alkyl or substituted alkyl, aryl or substituted aryl, acyl or substituted acyl, or a natural or unnatural amino acid, or a polypeptide comprising up to 10 natural and/or unnatural amino acids; adjacent R groups can be joined to form a cyclic or heterocyclic structure; r is an integer from zero to ten; and h is an integer representing a number of methylene, or substituted methylene, units from zero to ten; n, m, and p, can independently be an integer from 1 to 1000; each R' can independently be hydrogen, methyl, ethyl, alkyl or substituted alkyl, or aryl or substituted aryl, acyl or substituted acyl.

The macromolecular GI enzyme labile opioid prodrugs of the invention are not required to have, and preferably do not have opioid activity. Thus, in one aspect of the invention, a macromolecular GI enzyme labile opioid prodrug in accordance with the invention will retain from about 0% to about 30% of the centrally-mediated opioid activity of the unmodified parent opioid compound. Such activity may be determined using suitable in-vivo, or in-vitro assays, depending upon the known activity of the particular opioid parent compound. For example, a functional opioid receptor based assay, or an in vivo hot-plate or tail-flick analgesia assay can be used to assess the level of agonist activity of the polymer conjugates of the invention. Thus, a macromolecular GI enzyme labile opioid prodrug of the invention will possess centrally-mediated opioid agonist activity of about 0%, 0.25%, 0.5%, 0.75%, 1% 2%, 5%, 10%, 15%, 25%, or 30% relative to that of the unmodified parent opioid agonist, when measured in a suitable model, such as those well known in the art. Preferably, a macromolecular GI enzyme labile opioid prodrug of the invention will have <1-10% of the centrally mediated opioid agonist activity of the unmodified parent opioid compound.

In another aspect of the invention, the macromolecular GI enzyme labile opioid prodrugs of the invention are not required to be, and preferably are not orally bioavailable and/or are not absorbed from the GI tract following ingestion, and/or do not readily traverse the blood-brain barrier (i.e. do not penetrate the central nervous system—CNS). Thus, in one aspect of the invention, a macromolecular GI enzyme-labile opioid prodrug in accordance with the invention will retain from about 0% to about 30% of the oral bioavailability or CNS penetration of the unmodified parent opioid compound. Oral bioavailability and CNS penetration can be determined using suitable in-vivo assays. Thus, an opioid-polymer conjugate of the invention will possess bioavailability of about 0%, 0.25%, 0.5%, 0.75%, 1% 2%, 5%, 10%, 15%, 25%, or 30% relative to that of the unmodified parent opioid, when measured in a suitable model, such as those well known in the art. Preferably, a macromolecular GI enzyme labile opioid prodrug of the invention will have <1-10% of the oral bioavailability or central penetrance of the unmodified parent opioid compound.

Non-Limiting Examples of Macromolecular Opioid Antagonists

The invention also provides compositions comprising a GI enzyme labile opioid agonist prodrug attached to a polymer having the general formula below:

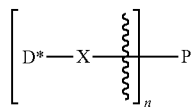

where D* is an opioid antagonist, X is a functional linking group as defined herein, and can be an ester, a thioester, an amide, a carbamate, a carbonate, or a urea; n is an integer between 1 and 1000; and P is a polymer. The polymer P can be any of the polymers described above, such as, for example, a PEG, a polypeptide, a polysaccharide or a biopolymer. The polymer and linker X are selected such that they are chemically stable to the chemical conditions in the GI tract, and to specific and non-specific actions of digestive enzymes in order to prevent or minimize the release of the opioid antagonist following oral ingestion by subjects. The polymer is chosen to prevent or minimize the absorption of the macromolecular opioid antagonist polymer conjugate from the GI tract following ingestion by a subject.

The particular linkage and linkage chemistry employed will depend upon the functional groups present on the subject opioid antagonist for attachment to a polymer or the chemical conversion of a functional group present on the opioid antagonist to a suitable attachment functionality. The presence of amenable functional groups present on the opioid antagonist molecule can be readily determined by one skilled in the art based upon the guidance presented herein.

The opioid antagonist polymer conjugate is designed to release the appended opioid antagonist upon chemical tampering by potential abusers. Chemical tampering methods aimed at hydrolyzing the opioid agonist molecules from macromolecular GI enzyme-labile opioid agonist prodrugs, or chemically destroying the macromolecular GI enzyme inhibitors of the invention, will also efficiently liberate the opioid antagonist from opioid agonist polymer conjugate. As a result, chemical tampering efforts aimed at oral and/or non-oral routes of abuse will be effectively thwarted by the presence of the opioid antagonist polymer conjugate. Suitable opioid antagonists include, but are not limited to, buprenorphine, cyclazocine, cyclorphan, naloxone, naltrexone, nalmephene, 6-amino-6-desoxo-naloxone, levallorphan, nalbuphine, naltrendol, naltrindole, nalorphine, norbinaltorphimine, oxilorphan, pentazocine, piperidine-N-alkylcarboxylate opioid antagonists such as those described in U.S. Pat. Nos. 5,159,081, 5,250,542, 5,270,328, and 5,434,171, and derivatives, mixtures, salts, polymorphs, or prodrugs thereof.

The opioid antagonist-releasing substrates may be linked via an ester, or suitably chemically-labile functionality as described above, to the amine, phenol, alcohol, or ketone functionalities found in naltrexone or naloxone as illustrated below.

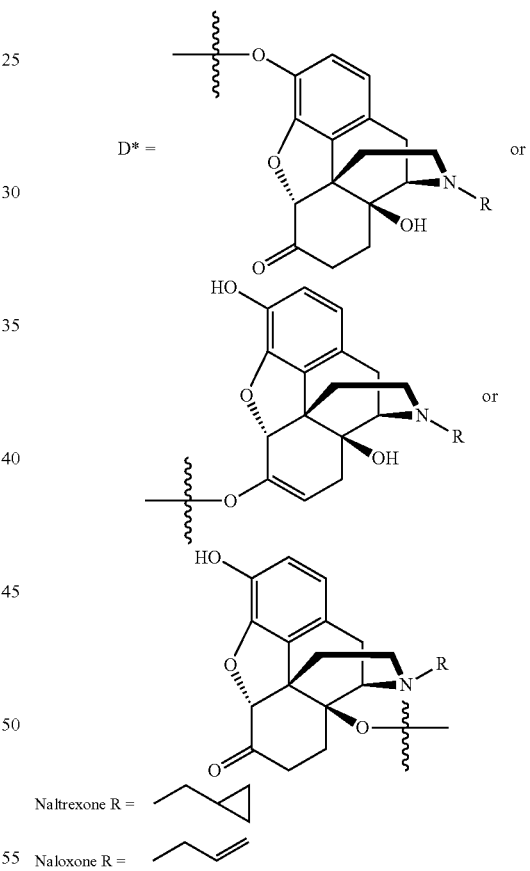

Non-limiting generic examples of macromolecular opioid antagonists comprising chemically releasable opioid antagonists are shown below:

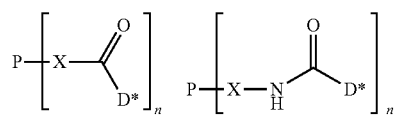

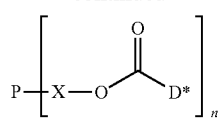
Wherein D* is an opioid antagonist as defined above and can preferably be naltrexone or naloxone, and P is a polymer as defined herein, and X is a linker as defined herein.
General mechanisms of chemically-mediated opioid antagonist release are shown below:
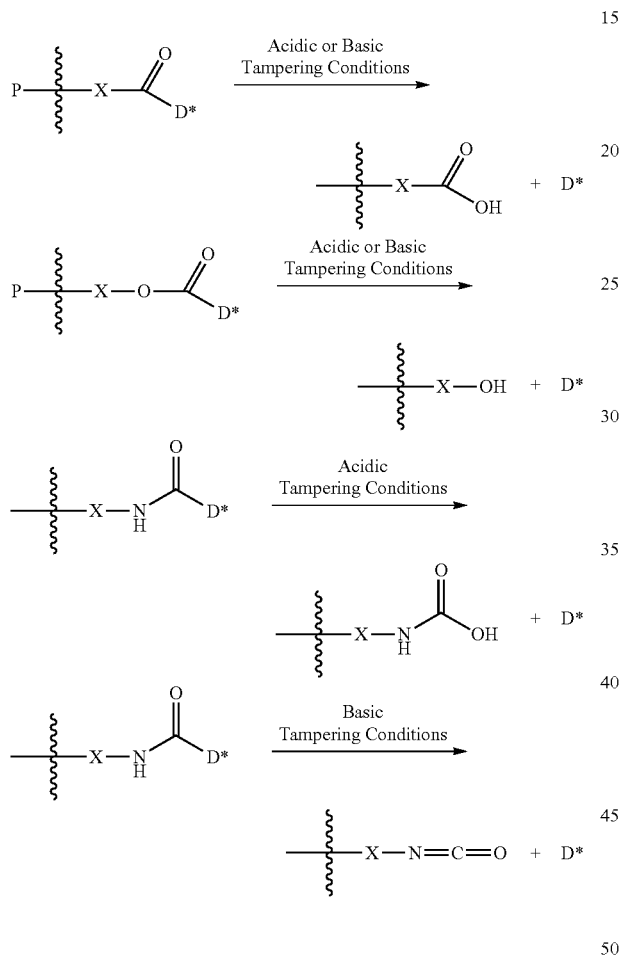
Non-Limiting Examples of Opioid Antagonist Releasing Subunits
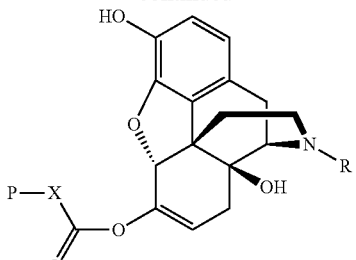
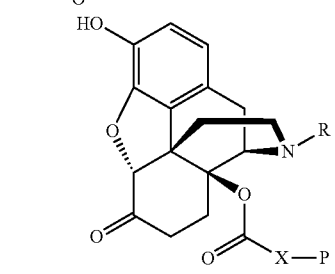
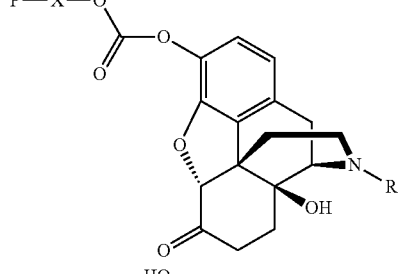
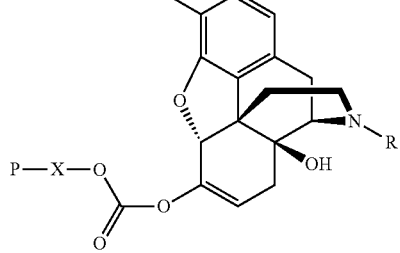
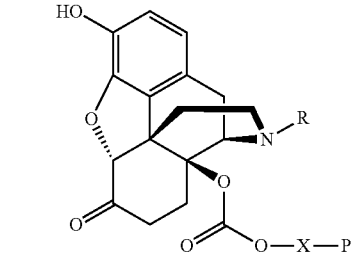
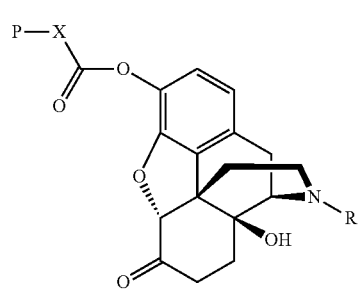
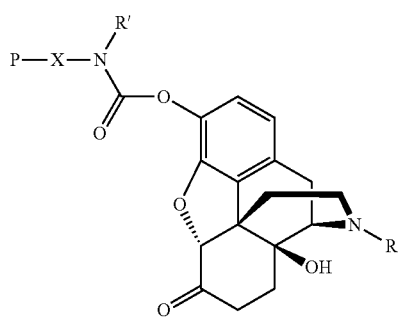

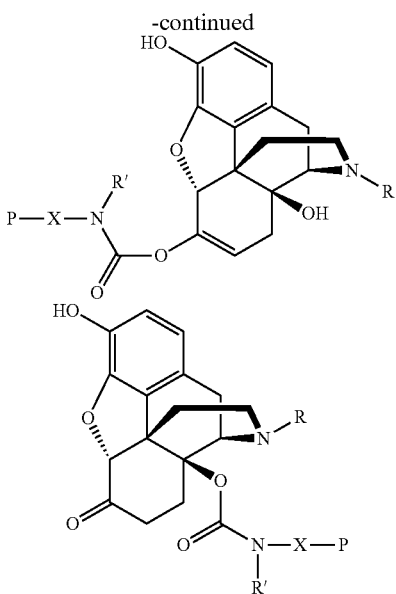

Wherein R is cyclopropylmethyl or allyl, R' is hydrogen, methyl, alkyl, aryl, substituted alkyl, or substituted aryl, acyl or substituted acyl; and X is a linker as defined herein.

Further non-limiting examples of macromolecular opioid antagonists of the invention are shown below:

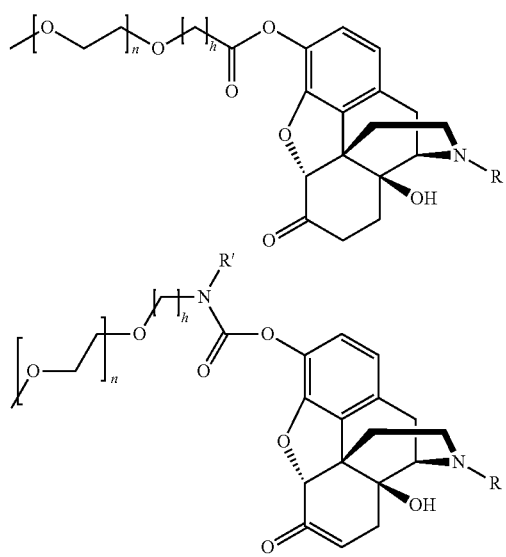

Wherein R is cyclopropylmethyl or allyl; R' is hydrogen, methyl, alkyl, aryl, substituted alkyl, or substituted aryl, acyl or substituted acyl; h represent a number of unsubstituted or substituted methylene units and can be an integer from zero to ten; n is an integer from 1 to 1000.

General Synthetic Approaches

The macromolecular GI enzyme labile opioid prodrugs of the invention can be synthesized using techniques and materials known to those of skill in the art, such as described, for example, in Smith and March, MARCH'S ADVANCED ORGANIC CHEMISTRY: Reactions, Mechanisms, and Structure, Fifth Edition, (Wiley-Interscience, 2001), Vogel, A TEXTBOOK OF PRACTICAL ORGANIC CHEMISTRY, Including Qualitative Organic Analysis, Fourth Edition, New York, (Longman, 1978), Carey and Sundberg, ADVANCED ORGANIC CHEMISTY $3^{rd}$ Ed., Vols. A and B (Plenum 1992), and Green and Wuts, PROTECTIVE GROUPS IN ORGANIC SYNTHESIS $2^{nd}$ Ed. (Wiley 1991). Starting materials for the compounds of the invention can be obtained using standard techniques and commercially available precursor materials, such as those available from Aldrich Chemical Co. (Milwaukee, Wis.), Sigma Chemical Co. (St. Louis, Mo.), Lancaster Synthesis (Ward Hill, Mass.), Apin Chemicals, Ltd. (New Brunswick, N.J.), Ryan Scientific (Columbia, S.C.), Maybridge (Cornwall, England) and Trans World Chemicals (Rockville, Md.).

The procedures described herein for synthesizing the compounds of the invention can include one or more steps of protection and deprotection (e.g., the formation and removal of suitable protecting groups). In addition, the synthetic procedures disclosed below can include various purifications, such as column chromatography, flash chromatography, thin-layer chromatography (TLC), recrystallization, distillation, high-pressure liquid chromatography (HPLC), dialysis, size-exclusion chromatography, and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS), and multi-angle light scattering (MALS) can be used as well. Methods of protection and deprotection, purification and identification and quantification are well known in the chemical arts.

In general, the synthetic methods use a polymer having a functional group, where the functional group present on the polymer can react with a functional group on the GI enzyme labile opioid prodrug, and/or the GI enzyme inhibitor, thereby providing a covalently-bonded macromolecular GI enzyme labile opioid prodrug and/or macromolecular GI enzyme inhibitor. The functional group of the polymer can be, for example, a carboxylic acid, an ester, an aldehyde, an alcohol, an amine, an isocyanate, and the like. Representative general syntheses of polymer conjugates of GI enzyme labile opioid prodrugs, and/or the GI enzyme inhibitors are illustrated below.

Thus, for example, the polymer and the opioid can be bonded using a coupling reagent to form an ester linkage, or an activated agonist, such as an opioid whose phenolic or enolic group is activated as a para-nitrophenyl carbamate, or related activated derivative, that can be reacted with an alcohol-containing or amine-containing polymer to form a carbonate or a carbamate linkage, respectively.

The opioid-polymer conjugate product can be collected and purified using methods known in the art. In general, compounds as described herein can be purified by any of the means known in the art, including chromatographic means, such as high performance liquid chromatography (HPLC), preparative thin layer chromatography, flash column chromatography and ion exchange chromatography, size exclusion chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969. The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Preparation of Macromolecular Trypsin Inhibitors

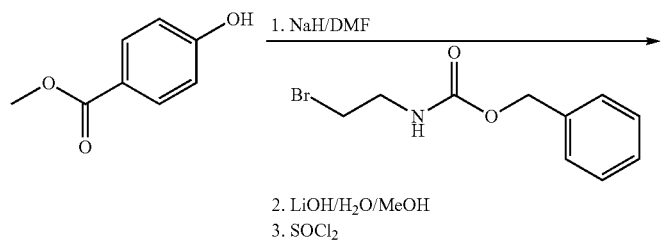

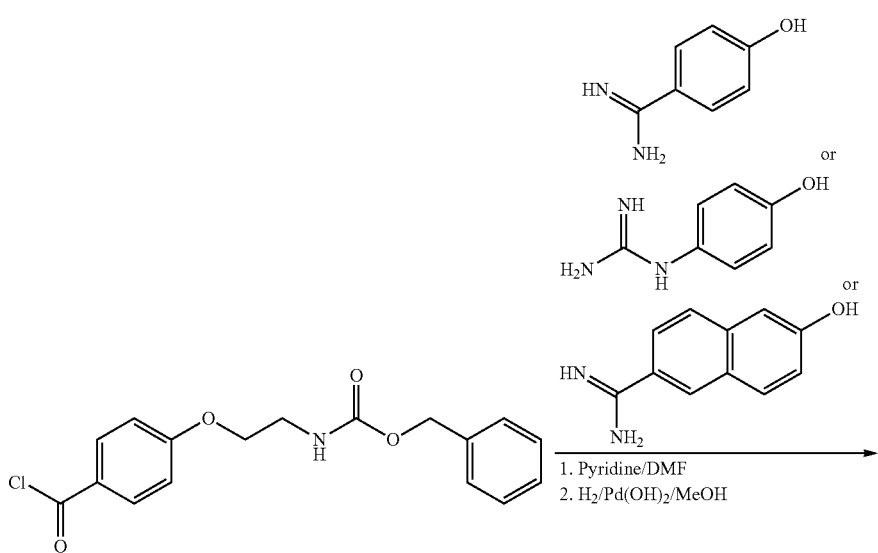

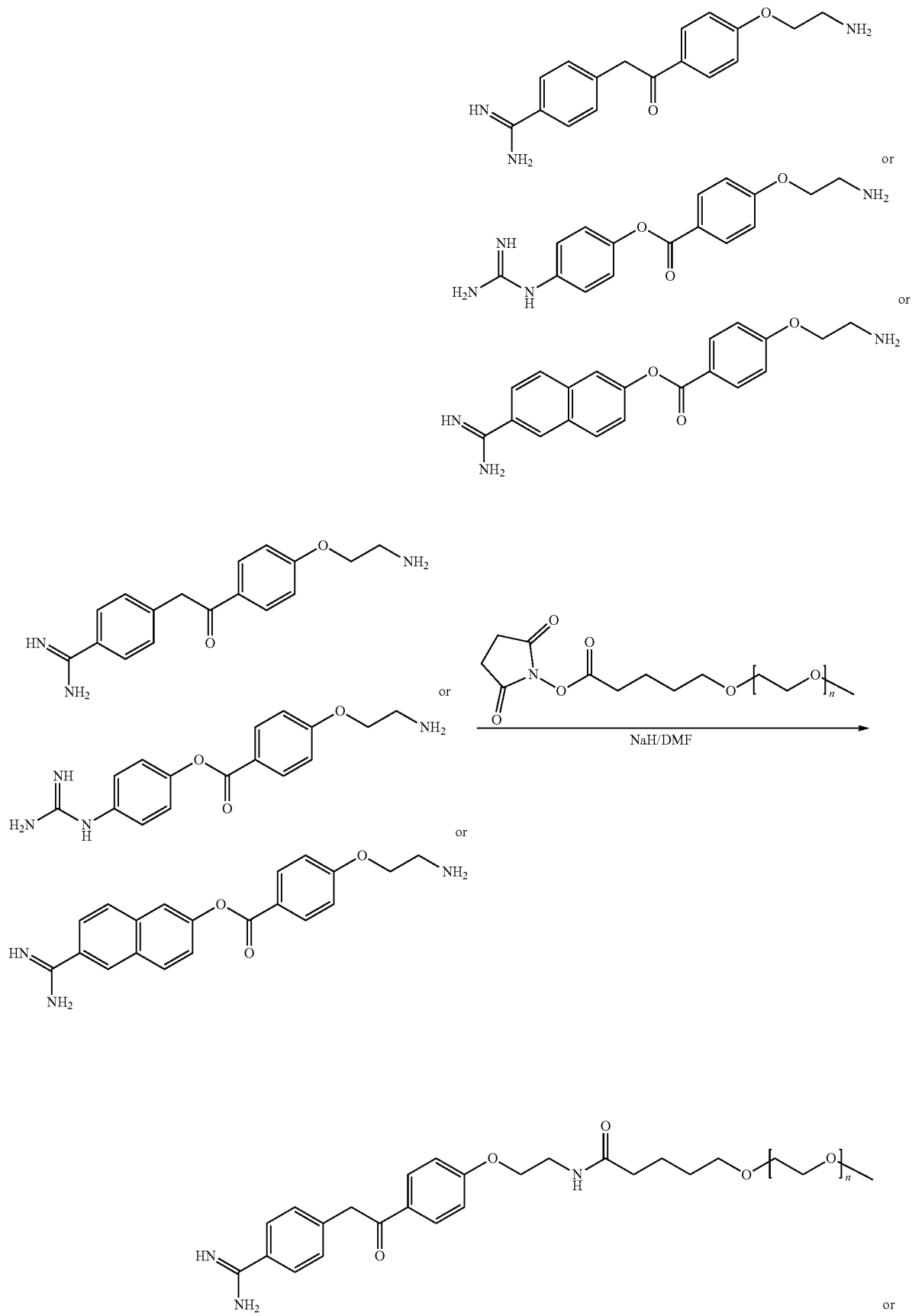

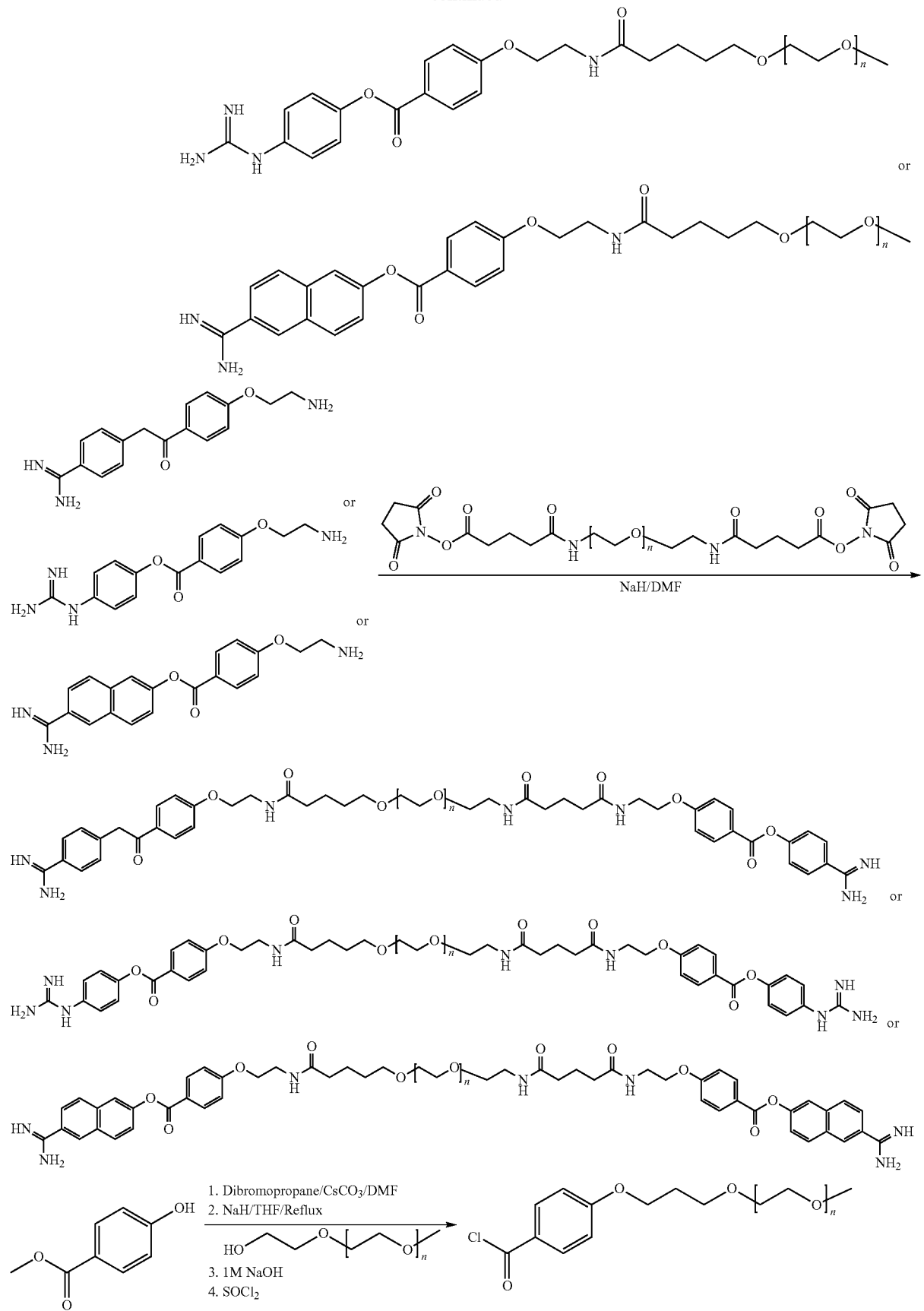

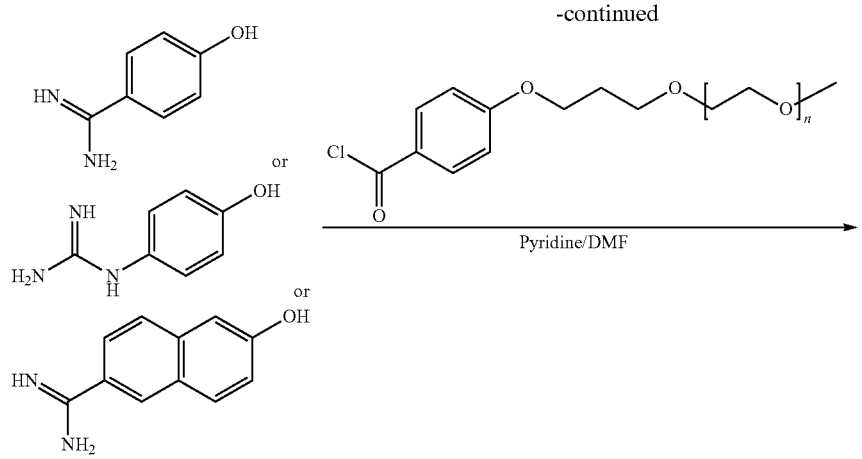
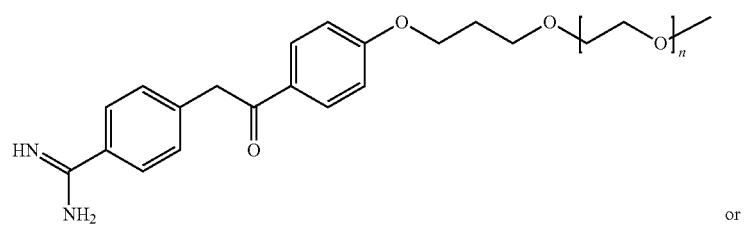
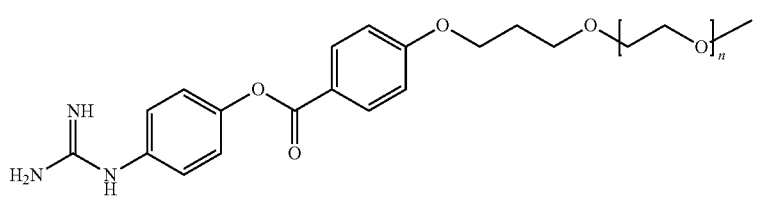
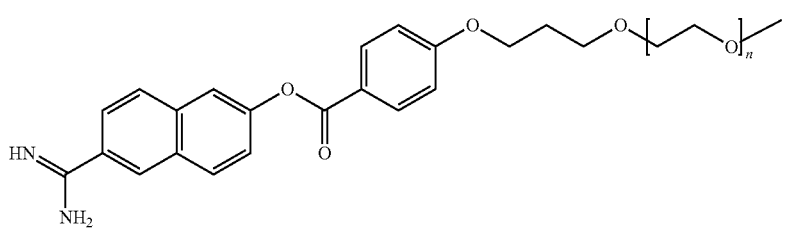
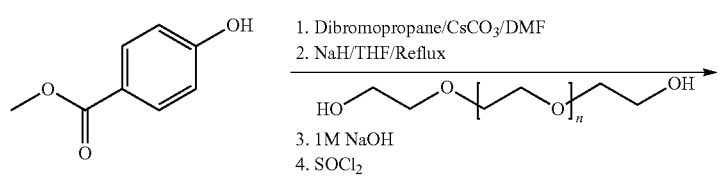
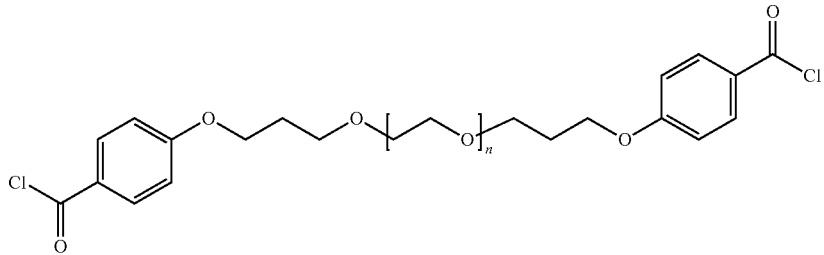

281 282
-continued
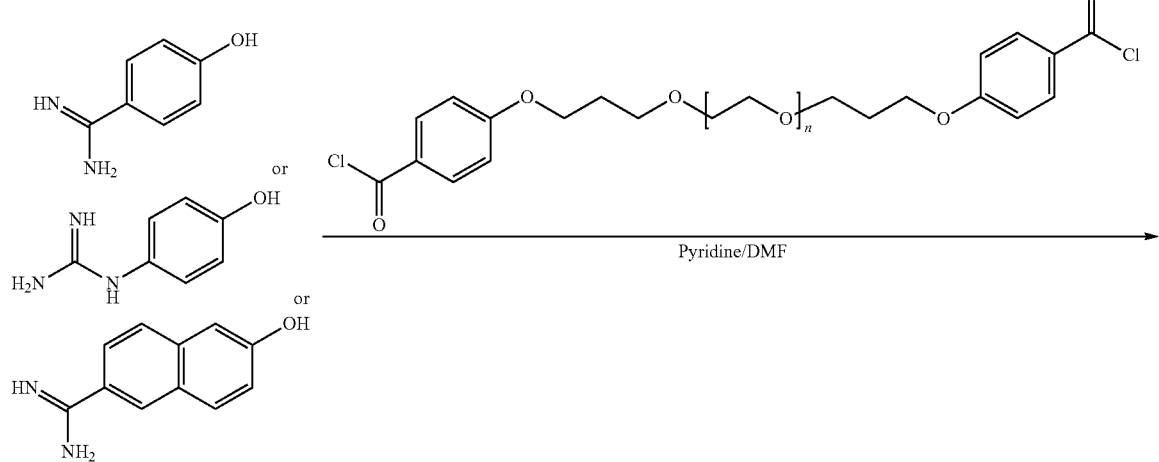
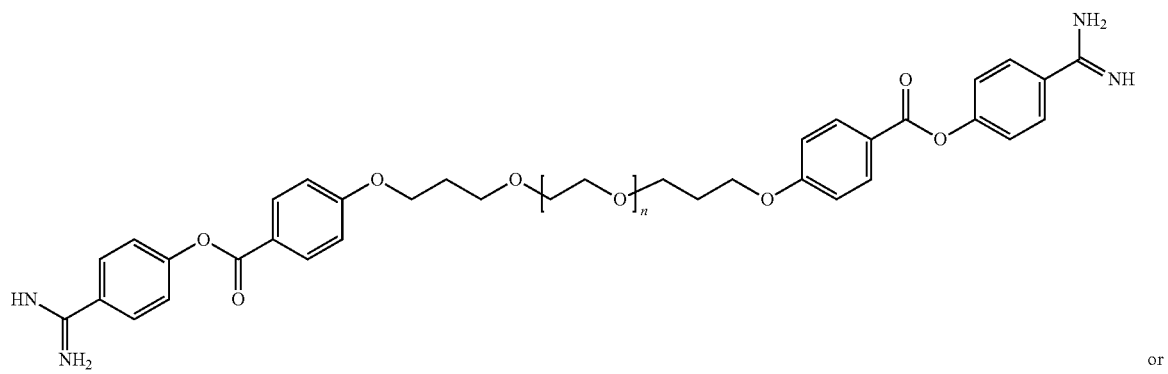
or
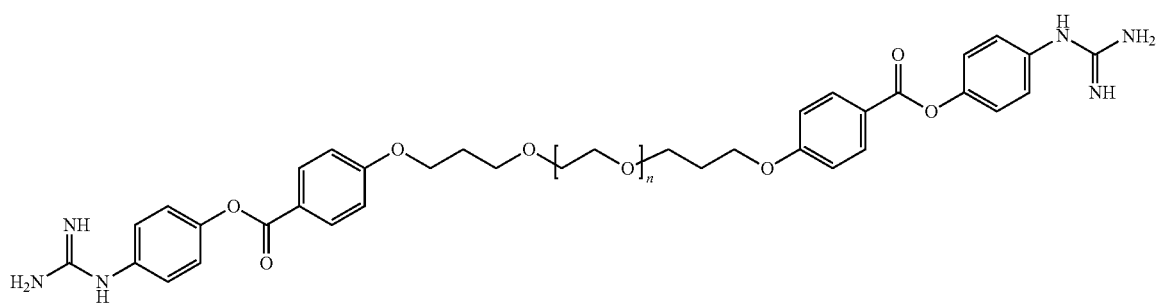
or
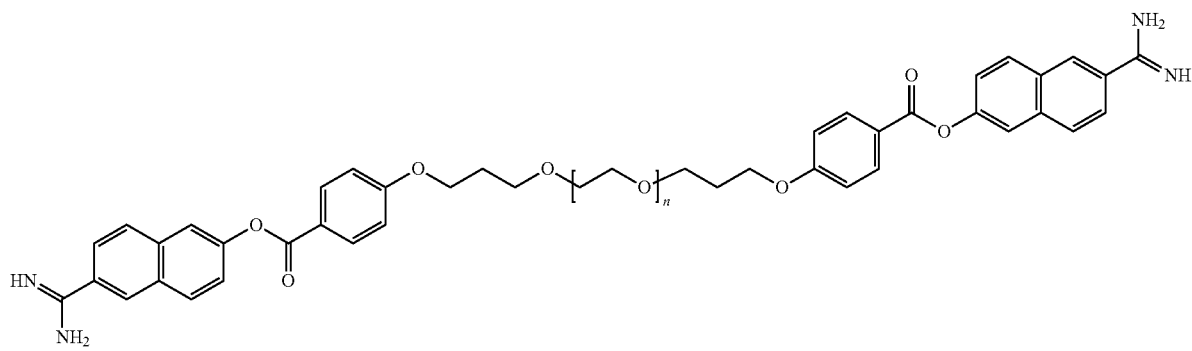

Preparation of Macromolecular Trypsin-Labile Opioid Prodrugs
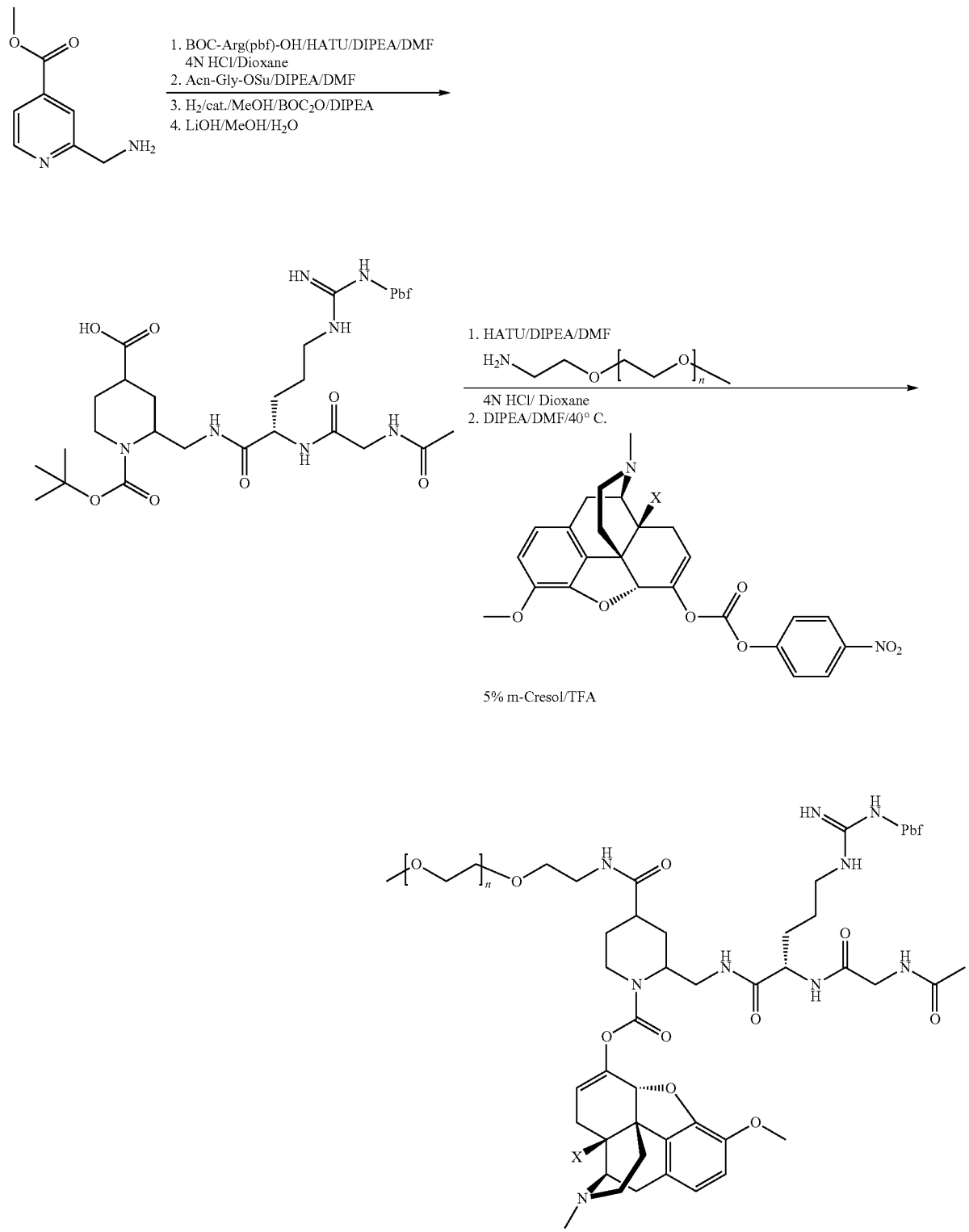

-continued
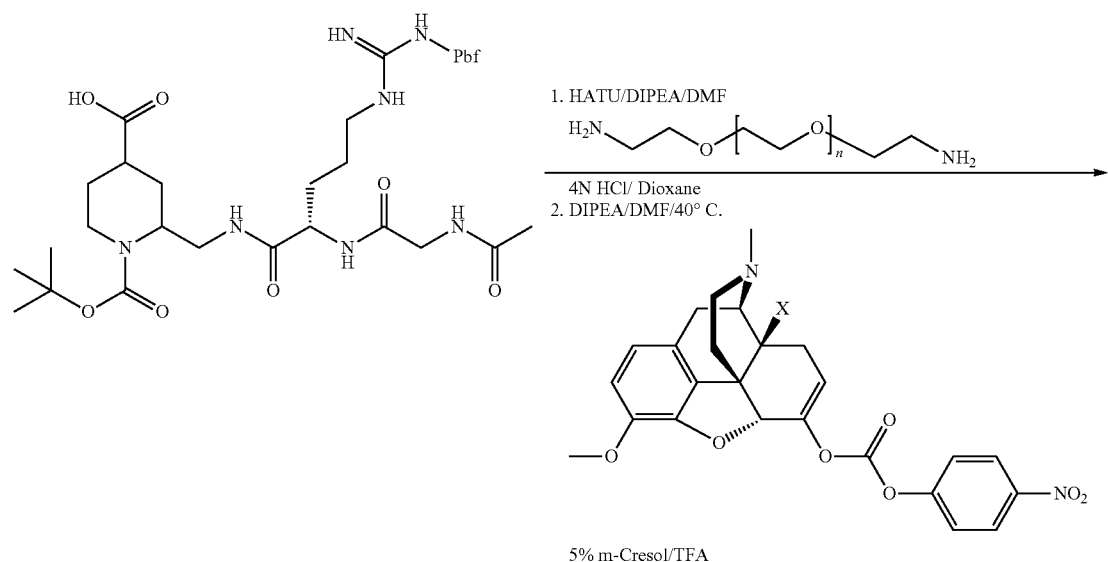
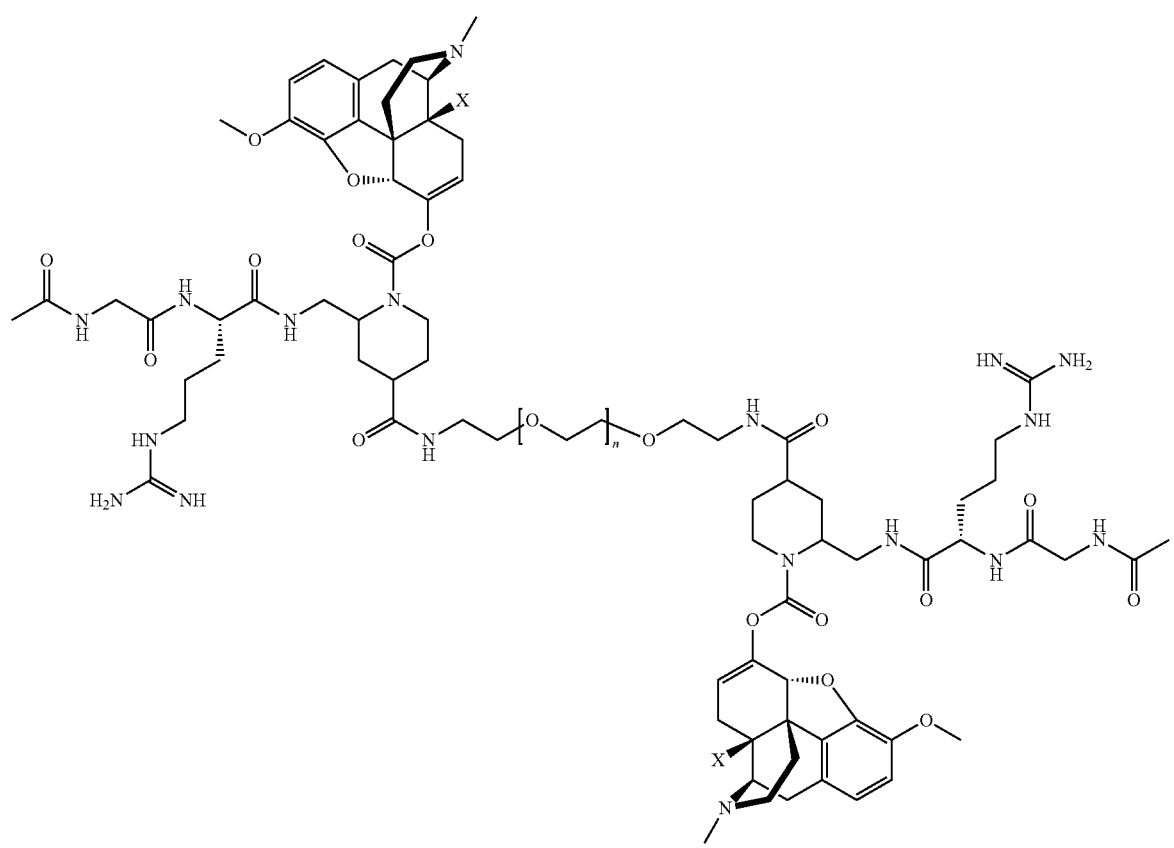

-continued
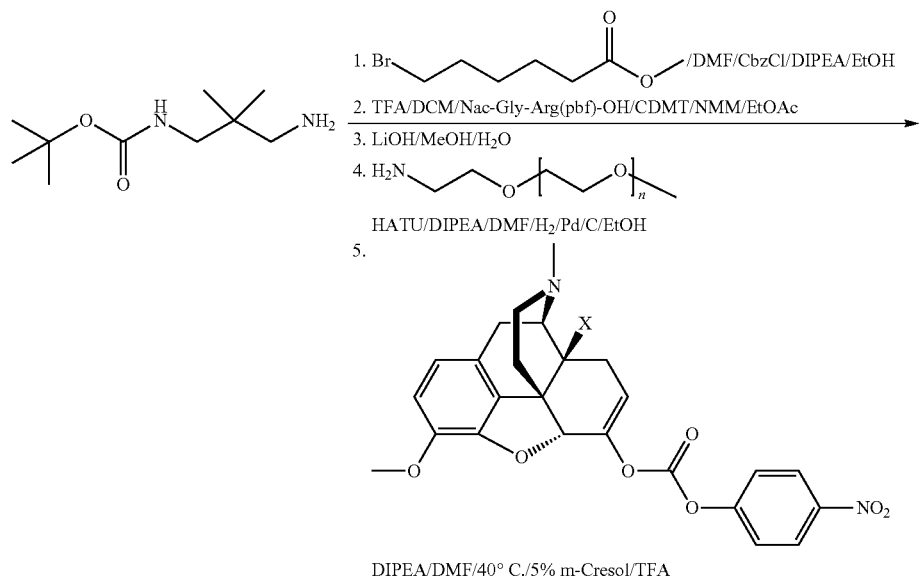
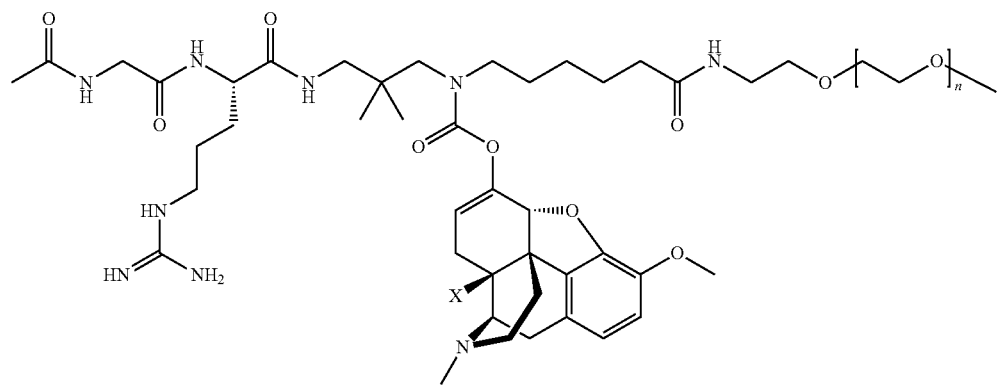
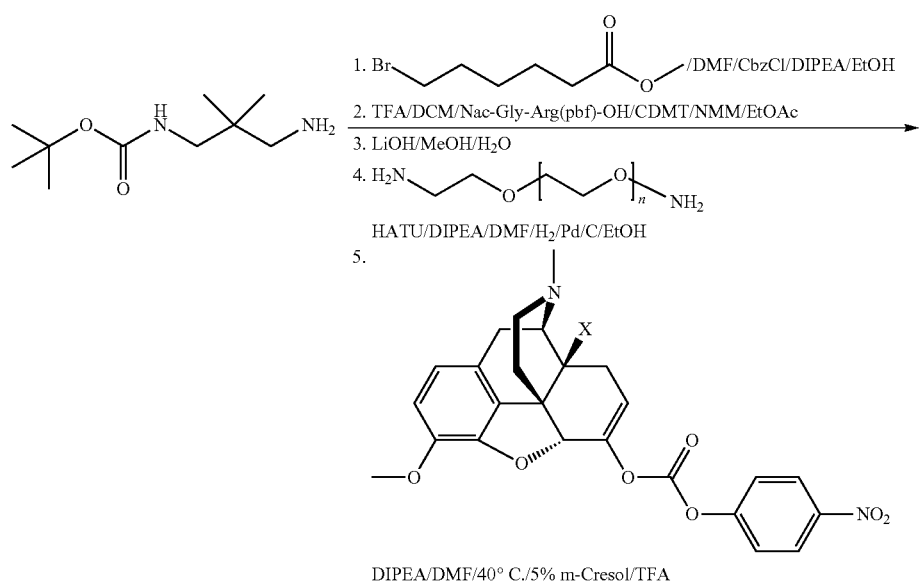

-continued
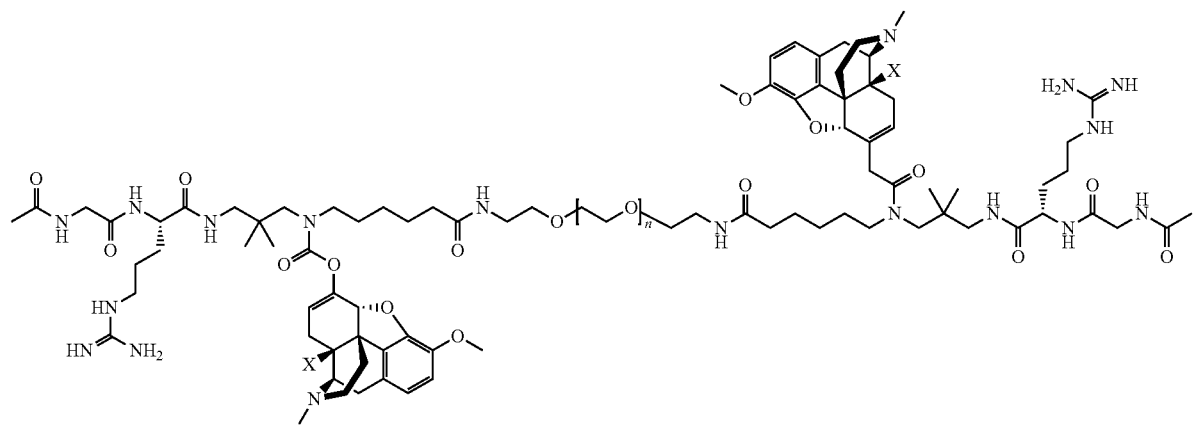
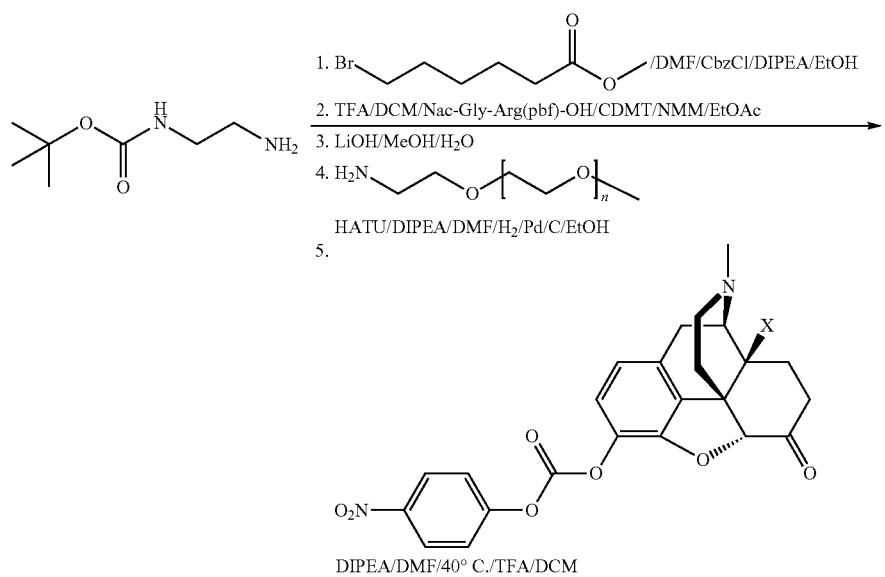
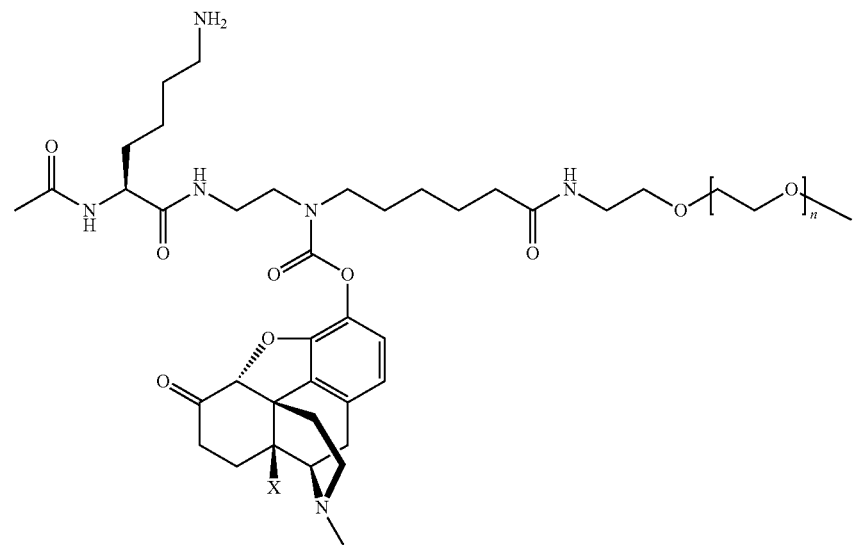

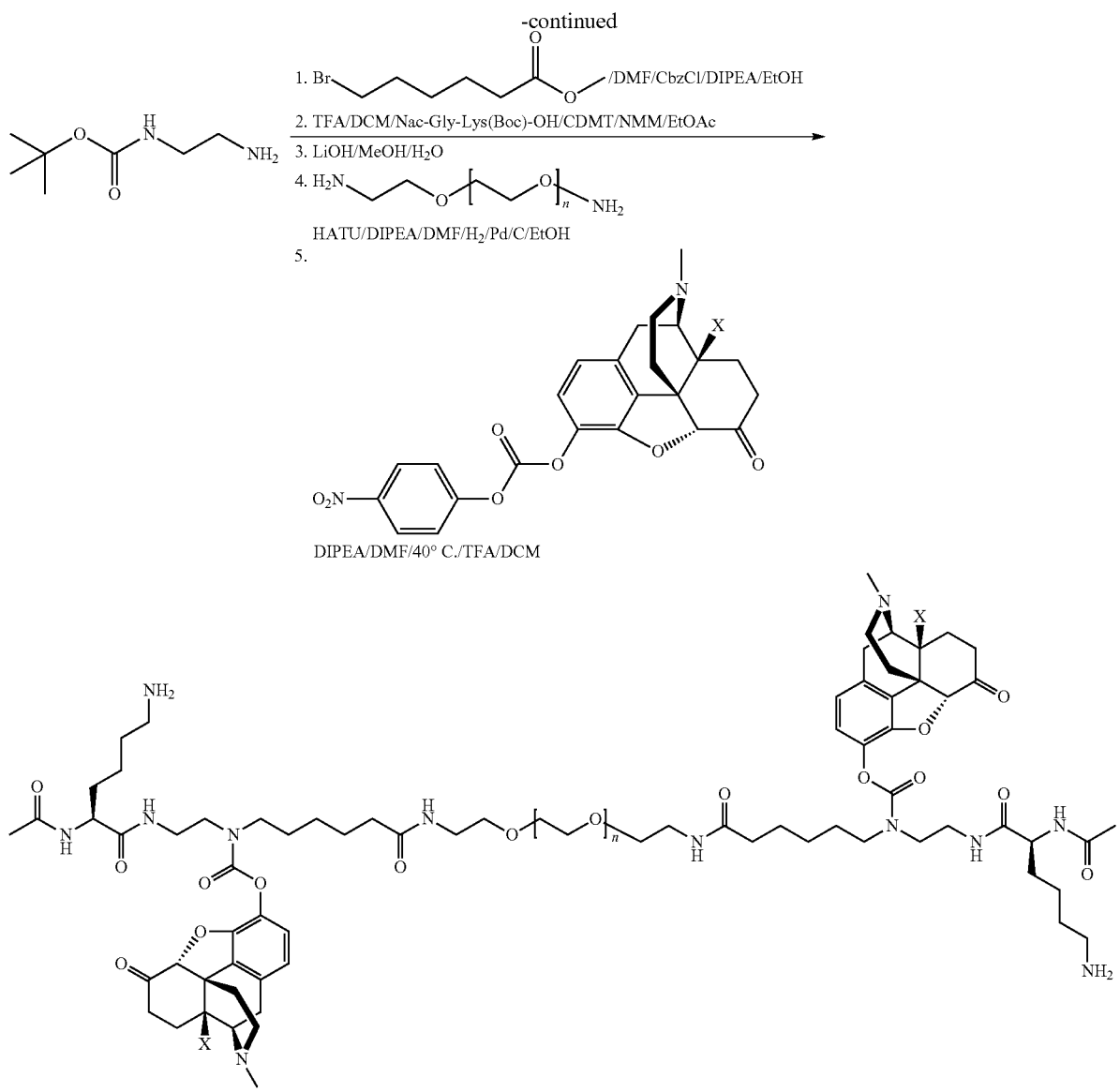

Preparation of Macromolecular Opioid Antagonists

Representative synthetic routes useful for the preparation of opioid antagonist polymer conjugates are depicted below in Scheme X. The syntheses utilize well-established phenol-ester and phenol-carbamate forming synthetic strategies published in the art (see, for example: U.S. Pat. Nos. 8,802,681, 8,685,916, 8,217,005, and 8,163,701, 8,685,916, 8,569,228, 8,497,237 and U.S. Patent Application Nos. 2014016935) are also employed. Purification of the resulting macromolecular opioid antagonists can be accomplished using standard purification procedures involving normal or reverse phase HPLC, crystallization, trituration, etc. The chemical identity of the macromolecular opioid antagonists can be established by LC/MS and/or NMR analysis.

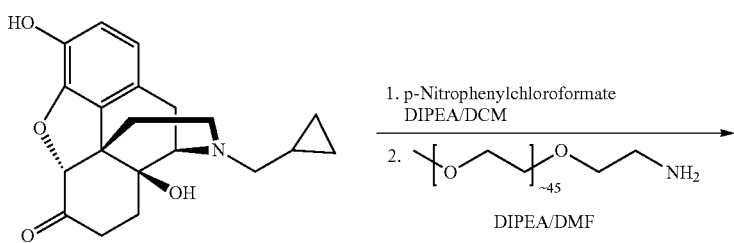

-continued

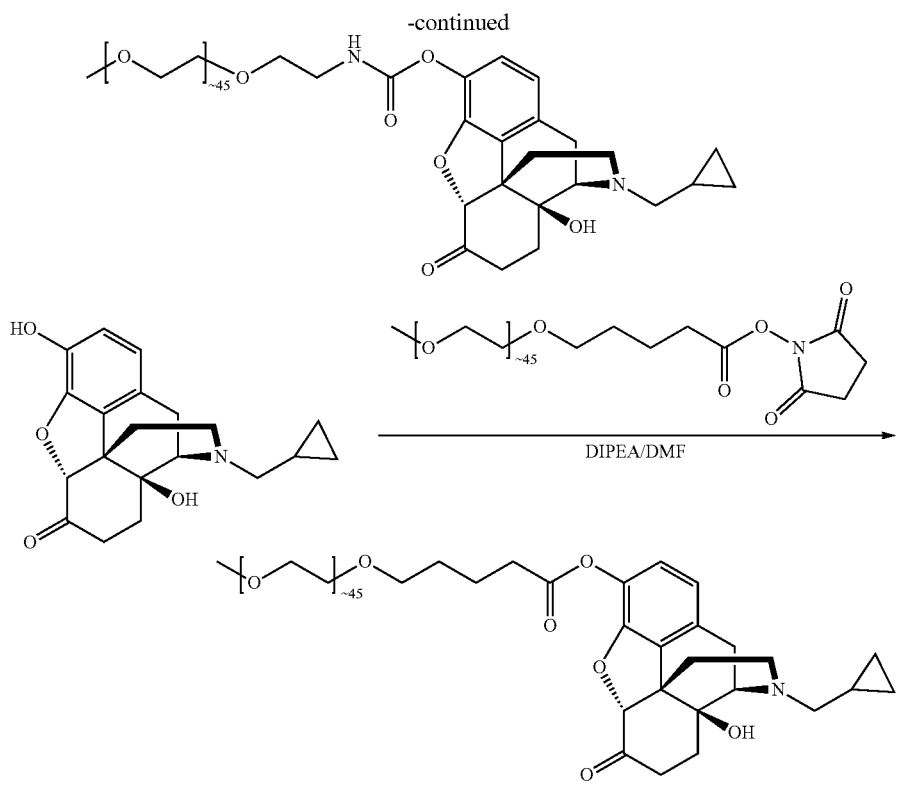

Combinations of Macromolecular GI Enzyme-Labile Opioid Prodrugs with GI Enzyme Inhibitors In an aspect of the invention, macromolecular GI enzyme-labile opioid prodrugs are combined, or co-formulated, with small molecule, or macromolecular, GI enzyme inhibitors into a pharmaceutically acceptable dose formulations as shown below on TABLE 2:

TABLE 2

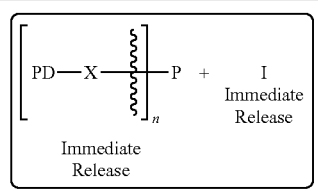
(I)

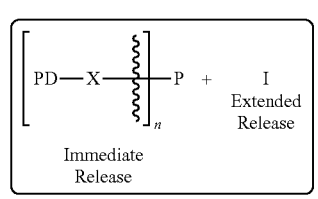
(II)

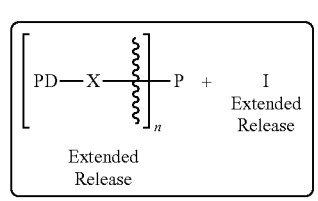
(III)

TABLE 2-continued

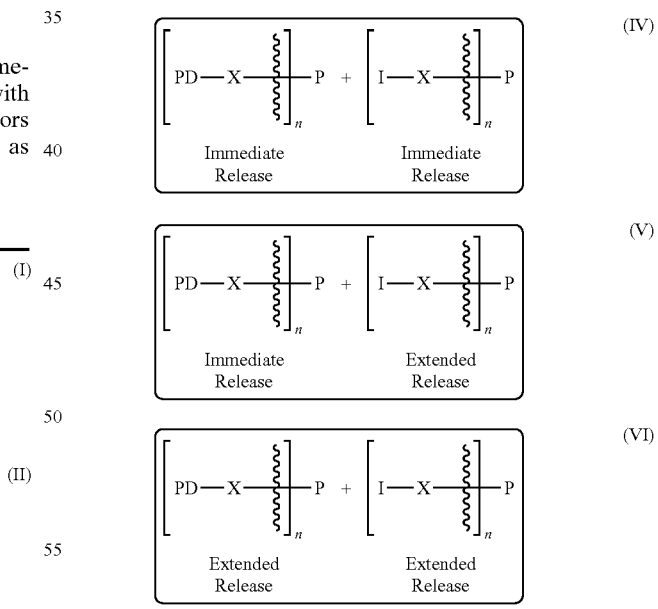

wherein PD, X, P, I, and n are as previously defined for each component, respectively.

In some embodiments graphically represented by formulation (I) above, dose forms that are suitable for oral administration are made by combining a macromolecular GI enzyme-labile opioid prodrug and the small molecule GI enzyme inhibitor in an immediate release matrix.

In some embodiments graphically represented by formulation (II) above, dose forms that are suitable for oral administration are made by combining a macromolecular GI enzyme-labile opioid prodrug with a small molecule GI enzyme inhibitor whereby the macromolecular GI enzyme-labile opioid prodrug is formulated in an immediate release matrix, and some or all of the small molecule GI enzyme inhibitor is formulated in an extended release matrix.

In some embodiments graphically represented by formulation (III) above, dose forms that are suitable for oral administration are made by combining a macromolecular GI enzyme-labile opioid prodrug with a small molecule GI enzyme inhibitor whereby some or all of the macromolecular GI enzyme-labile opioid prodrug, and some or all of the small molecule GI enzyme inhibitor, is formulated in an extended release matrix.

In some embodiments graphically represented by formulation (IV) above, dose forms that are suitable for oral administration are made by combining a macromolecular GI enzyme-labile opioid prodrug and a macromolecular GI enzyme inhibitor in an immediate release matrix.

In some embodiments graphically represented by formulation (V) above, dose forms that are suitable for oral administration are made by combining a macromolecular GI enzyme-labile opioid prodrug with a macromolecular GI enzyme inhibitor whereby the macromolecular GI enzyme-labile opioid prodrug is formulated in an immediate release matrix, and some or all of the macromolecular GI enzyme inhibitor is formulated in an extended release matrix.

In some embodiments graphically represented by formulation (VI) above, dose forms that are suitable for oral administration are made by combining a macromolecular GI enzyme-labile opioid prodrug with a macromolecular GI enzyme inhibitor whereby some or all of the macromolecular GI enzyme-labile opioid prodrug, and some or all of the macromolecular GI enzyme inhibitor, is formulated in an extended release matrix.

In further embodiments, any or all of the formulation options described above may optionally contain a macromolecular opioid antagonist.

Macromolecular GI enzyme-labile opioid prodrugs, small molecule GI enzyme inhibitors, and/or macromolecular GI enzyme inhibitors described herein may independently be present in a unit dosage form of the invention in a mass range of from about 0.1 mg to about 2000 mg; from about 1 mg to about 1000 mg, from about 5 mg to about 1000 mg, from about 5 mg to about 25 mg, from about 10 mg to 100 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, from about 950 mg to about 1000 mg, from about 1000 mg to about 1050 mg, from about 1050 mg to about 1100 mg, from about 1100 mg to about 1150 mg, from about 1150 mg to about 1200 mg, from about 1200 mg to about 1250 mg, from about 1250 mg to about 1300 mg, from about 1300 mg to about 1350 mg, from about 1350 mg to about 1400 mg, from about 1400 mg to about 1450 mg, from about 1450 mg to about 1500 mg, from about 1500 mg to about 1550 mg, from about 1550 mg to about 1600 mg, from about 1600 mg to about 1650 mg, from about 1650 mg to about 1700 mg, from about 1700 mg to about 1750 mg, from about 1750 mg to about 1850 mg, from about 1850 mg to about 1900 mg, from about 1900 mg to about 1950 mg, from about 1950 mg to about 2000 mg, from about 2000 mg to about 2050 mg, from about 2050 mg to about 2100 mg, from about 2100 mg to about 2150 mg, from about 2150 mg to about 2200 mg, from about 2200 mg to about 2250 mg, from about 2250 mg to about 2300 mg, from about 2300 mg to about 2350 mg, from about 2350 mg to about 2400 mg, from about 2400 mg to about 2450 mg, or from about 2450 mg to about 2500 mg.

The mass ratio of the macromolecular GI enzyme-labile opioid prodrug to the co-formulated small molecule GI enzyme inhibitor, or to the co-formulated macromolecular GI enzyme inhibitor, can be from about 1:100 to about 100:1, preferably from about 1:50 to about 50:1, more preferably from about 1:10 to about 10:1, and even more preferably from about 1:5 to about 5:1. Thus, for example, the mass ratio of the macromolecular GI enzyme-labile opioid prodrug to the small molecule GI enzyme inhibitor, or the macromolecular GI enzyme inhibitor can be 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and the like.

The following are non-limiting examples of mass ratios of the macromolecular GI enzyme-labile opioid prodrug to the small molecule GI enzyme inhibitor, or to the macromolecular GI enzyme inhibitor. The mass ratio can be: about 20: about 1; about 19.9: about 1; about 19.8: about 1; about 19.7: about 1; about 19.6: about 1; about 19.5: about 1; about 19.4: about 1; about 19.3: about 1; about 19.2: about 1; about 19.1: about 1; about 19: about 1; about 18.9: about 1; about 18.8: about 1; about 18.7: about 1; about 18.6: about 1; about 18.5: about 1; about 18.4: about 1; about 18.3: about 1; about 18.2: about 1; about 18.1: about 1; about 18: about 1; about 17.9: about 1; about 17.8: about 1; about 17.7: about 1; about 17.6: about 1; about 17.5: about 1; about 17.4: about 1; about 17.3: about 1; about 17.2: about 1; about 17.1: about 1; about 17: about 1; about 16.9: about 1; about 16.8: about 1; about 16.7: about 1; about 16.6: about 1; about 16.5: about 1; about 16.4: about 1; about 16.3: about 1; about 16.2: about 1; about 16.1: about 1; about 16: about 1; about 15.9: about 1; about 15.8: about 1; about 15.7: about 1; about 15.6: about 1; about 15.5: about 1; about 15.4: about 1; about 15.3: about 1; about 15.2: about 1; about 15.1: about 1; about 15: about 1; about 14.9: about 1; about 14.8: about 1; about 14.7: about 1; about 14.6: about 1; about 14.5: about 1; about 14.4: about 1; about 14.3: about 1; about 14.2: about 1; about 14.1: about 1; about 14: about 1; about 13.9: about 1; about 13.8: about 1; about 13.7: about 1; about 13.6: about 1; about 13.5: about 1; about 13.4: about 1; about 13.3: about 1; about 13.2: about 1; about 13.1: about 1; about 13: about 1; about 12.9: about 1; about 12.8: about 1; about 12.7: about 1; about 12.6: about 1; about 12.5: about 1; about 12.4: about 1; about 12.3: about 1; about 12.2: about 1; about 12.1: about 1; about 12: about 1; about 11.9: about 1; about 11.8: about 1; about 11.7: about 1; about 11.6: about 1; about 11.5: about 1; about 11.4: about 1; about 11.3: about 1; about 11.2: about 1; about 11.1: about 1; about 11: about 1; about 10.9: about 1; about 10.8: about 1; about 10.7: about 1; about 10.6: about 1; about 10.5: about 1; about 10.4: about 1; about 10.3: about 1; about 10.2: about 1; about 10.1: about 1; about 10: about 1; about 9.9: about 1; about 9.8: about 1; about 9.7: about 1; about 9.6: about 1; about 9.5: about 1; about 9.4: about 1; about 9.3: about 1; about 9.2: about 1; about 9.1: about 1; about 9: about 1; about 8.9: about 1; about 8.8: about 1; about 8.7: about 1; about 8.6: about 1; about 8.5: about 1; about 8.4: about 1; about 8.3:

about 1; about 8.2: about 1; about 8.1: about 1; about 8: about 1; about 7.9: about 1; about 7.8: about 1; about 7.7: about 1; about 7.6: about 1; about 7.5: about 1; about 7.4: about 1; about 7.3: about 1; about 7.2: about 1; about 7.1: about 1; about 7: about 1; about 6.9: about 1; about 6.8: about 1; about 6.7: about 1; about 6.6: about 1; about 6.5: about 1; about 6.4: about 1; about 6.3: about 1; about 6.2: about 1; about 6.1: about 1; about 6: about 1; about 5.9: about 1; about 5.8: about 1; about 5.7: about 1; about 5.6: about 1; about 5.5: about 1; about 5.4: about 1; about 5.3: about 1; about 5.2: about 1; about 5.1: about 1; about 5: about 1; about 4.9: about 1; about 4.8: about 1; about 4.7: about 1; about 4.6: about 1; about 4.5: about 1; about 4.4: about 1; about 4.3: about 1; about 4.2: about 1; about 4.1: about 1; about 4: about 1; about 3.9: about 1; about 3.8: about 1; about 3.7: about 1; about 3.6: about 1; about 3.5: about 1; about 3.4: about 1; about 3.3: about 1; about 3.2: about 1; about 3.1: about 1; about 3: about 1; about 2.9: about 1; about 2.8: about 1; about 2.7: about 1; about 2.6: about 1; about 2.5: about 1; about 2.4: about 1; about 2.3: about 1; about 2.2: about 1; about 2.1: about 1; about 2: about 1; about 1.9: about 1; about 1.8: about 1; about 1.7: about 1; about 1.6: about 1; about 1.5: about 1; about 1.4: about 1; about 1.3: about 1; about 1.2: about 1; about 1.1: about 1; or about 1: about 1; or about 0.9: about 1; or about 0.8: about 1; or about 0.7: about 1; or about 0.6: about 1; or about 0.5: about 1; or about 0.4: about 1; or about 0.3: about 1; or about 0.2: about 1; or about 0.1: about 1.

The amount of the optional macromolecular opioid antagonist included in the dose formulation options described above can be selected to release between 0.1 to 100 mgs of bioavailable opioid antagonist in the event that the dose form is subjected to chemical tampering.

A dose unit form of the invention, or composition of the disclosure, can be designed to provide an analgesic effect to a subject for a defined period of time. The amount of opioid agonist delivered by prescribed doses of the invention can be based on the currently defined doses, and resulting systemic exposures, of opioid agonists used for effective opioid-based treatment of pain in subjects.

Pharmacokinetics and Pharmacodynamics

Currently, all orally administered opioid agonists, partial agonists, inverse-agonists, and the emerging "biased" opioid agonists used to treat pain demonstrate linear pharmacokinetics in subjects. Linear or "dose-independent" pharmacokinetics are characterized by ADME parameters that obey first-order kinetics, PK parameters (e.g. CL, V, F, and half-life) are constant, AUC values that are directly proportional to dose, and normalized Concentration vs. Time profiles being superimposable for all doses administered. In contrast, compositions or formulations of the invention are designed to demonstrate non-linear, or dose-independent, pharmacokinetics whereby at least one of the ADME processes are saturable, at least one PK parameter is dose independent, and the resulting AUC values are disproportional to the dose administered. Specifically, compositions or formulations of the invention are designed to demonstrate reduced systemic exposures (e.g. Cmax, AUC) of the delivered opioid agonist when doses in excess of the recommended doses are ingested by subjects. The non-linear behavior of compositions or formulations of the invention results from progressive inhibition of GI enzymes (e.g. trypsin) in the lumen of the small intestine that are required for the release of the opioid agonist from the macromolecular GI enzyme-labile opioid prodrug as increasing doses are co-ingested. The extent of the non-linearity of the pharmacokinetics demonstrated by compositions or formulations of the invention can be "tuned" by adjusting the extent of GI enzyme inhibition exerted by the intended dose. Commonly, this will involve increasing or decreasing the potency, and/or the amount, of the macromolecular GI enzyme inhibitor contained in the intended dose form.

Formulations

Also embraced within this invention are pharmaceutical compositions comprising one or more compounds described above in association with one or more non-toxic, pharmaceutically acceptable carriers and/or diluents and/or adjuvants (collectively referred to herein as "carrier" materials). The compounds of the present invention are intended for oral administration, preferably in the form of a pharmaceutical composition adapted to such a route, and in a dose effective for the prevention or treatment of pain.

In another aspect of the invention, the compositions can comprise a further prodrug or drug. Such a prodrug or drug would provide additional analgesia or other benefits. Examples include opioid antagonists, acetaminophen, non-steroidal anti-inflammatory drugs (NSAIDs) and other analgesics. Other examples include drugs or prodrugs that have benefits other than, or in addition to, analgesia (e.g. laxatives).

In certain embodiments, compounds disclosed herein and/or pharmaceutical compositions thereof can be used in combination therapy with at least one other therapeutic agent. The compounds disclosed herein and/or pharmaceutical compositions thereof and the therapeutic agent can act additively or, more preferably, synergistically. In some embodiments, compounds disclosed herein and/or pharmaceutical compositions thereof are administered concurrently with the administration of another therapeutic agent. For example, compounds disclosed herein and/or pharmaceutical compositions thereof may be administered together with another therapeutic agent (e.g. including, but not limited to, peripheral opioid antagonists, laxatives, non-opioid analgesics and the like). In other embodiments, compounds disclosed herein and/or pharmaceutical compositions thereof are administered prior or subsequent to administration of other therapeutic agents.

Thus, in one aspect of the invention, the oral dosage form can contain one or more macromolecular enzyme-labile opioid prodrug, one or more macromolecular enzyme inhibitor, and one or more macromolecular opioid antagonist, and a non-opioid drug. Such non-opioid drugs would preferably provide additional analgesia and/or anti-inflammatory effects, and include, for example, aspirin, acetaminophen, non-steroidal anti-inflammatory drugs ("NSAIDS") such as, for example, naproxen, ibuprofen, ketoprofen, N-methyl-D-aspartate (NMDA) receptor antagonists, such as, for example, a morphinan such as dextromethorphan or dextrorphan, or ketamine, a cycooxygenase-II inhibitors ("COX-II inhibitors"); and/or glycine receptor antagonists.

For oral administration, the pharmaceutical composition can be in the form of, for example, a tablet, a capsule, a soft gelatin (softgel) capsule, a hard gelatin capsule, a suspension or a liquid. The pharmaceutical composition is preferably made in the form of a dosage unit designed to deliver a particular amount of an opioid agonist, a GI enzyme inhibitor, and, optionally, a macromolecular opioid antagonist and/or another active ingredient. Examples of such dosage units are tablets or capsules.

The amount of compounds disclosed herein and/or pharmaceutical compositions thereof that will be effective in the treatment or prevention of diseases in a patient will depend on the specific nature of the condition and can be determined by standard clinical techniques known in the art. The amount of compounds disclosed herein and/or pharmaceutical compositions thereof administered will, of course, be dependent on, among other factors, the subject being treated, the weight of the subject, the severity of the affliction, the manner of administration and the judgment of the prescribing physician. The daily dose can be administered in one, two, three, four, five, six, seven, eight, or more doses per day.

For therapeutic purposes, the compounds of this invention are ordinarily combined with one or more excipients appropriate to the oral route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, water, lubrisol, labrafac, plant derived oils or waxes, polyethylene glycols, etc. and then tableted or encapsulated for convenient administration. Such capsules or tablets may contain a controlled-release formulation as may be provided in a dispersion of active compound in hydroxypropylmethyl cellulose, polylactic acid, polyglycolic acid, or combinations of polylactic and polyglycolic acids of various molecular weights and mass ratios.

Further provided are anhydrous compositions and dosage forms comprising active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations. Anhydrous compositions and dosage forms provided herein can be prepared using anhydrous or low moisture containing ingredients and low moisture or low humidity conditions. An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms can be tablets, capsules, granules, or bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid oral dosage forms such as for example, capsules or tablets. The tablets, pills, capsules, troches, and the like, can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene lauryl ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil or liquid polyethylene glycol. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

In all embodiments, tablet and capsule formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of non-toxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD&C dyes, and mixtures thereof. Flavoring agents include natural flavors extracted from plants such fruits, and synthetic blends of compounds which produce a pleasant taste sensation.

For a solid dosage form, the solution or suspension, in for example, polyethylene glycol, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol or alcohol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing compounds provided herein, in a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In certain embodiments, the compositions are lactose-free compositions containing excipients that are well known in the art and are listed, for example, in the *U.S. Pharmacopeia* (USP) 25-NF20 (2002). In general, lactose-free compositions contain active ingredients, a binder/filler, and a lubricant in compatible amounts. Particular lactose-free dosage forms contain active ingredients, microcrystalline cellulose, pre-gelatinized starch, and magnesium stearate.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Advantages of controlled-release formulations include extended activity of the drug, reduced dosage frequency, enhanced opioid delivery efficiency, optimized overdose protection when doses in excess of the prescribed doses are co-ingested, and increased patient compliance. In addition, controlled-release formulations can be used to affect the time of onset and/or the duration of action or other characteristics, such as blood levels of the active opioid delivered, or the duration of trypsin inhibition, or the occurrence of side (e.g., adverse) effects.

Controlled-release formulations of the invention can be designed to initially release an amount of drug (active opioid) that promptly produces the desired therapeutic effect, and gradually and continually release of other amounts of drug to maintain this level of therapeutic or prophylactic effect over an extended period of time. Further, the formulations can be designed to release GI enzyme inhibitors (either small molecule or macromolecular variants) over an extended period of time in the lumen of the GI tract in order to appropriately assert and maintain the appropriate level of GI enzyme inhibition in order to achieve the desired level of overdose protection (i.e. non-linear pharmacokinetics). In order to maintain this constant level of drug in the body, the drug must be released from the dosage form at a rate that will compensate for a variety of biological processes such as partitioning, dilution, metabolism, absorption, and excretion. Controlled-release of an active ingredient can be stimulated by various conditions including, but not limited to, pH, temperature, enzymes, water, or other physiological conditions or compounds.

The active ingredients can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber, epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

In some embodiments, the dosage form is comprised of beads that on dissolution or diffusion release compositions and/or compounds disclosed herein over an extended period of hours, preferably, over a period of at least 6 hours, more preferably, over a period of at least 8 hours and even more preferably, over a period of at least 12 hours and most preferably, over a period of at least 24 hours. The beads may have a central composition or core comprising compounds disclosed herein and pharmaceutically acceptable vehicles, including optional lubricants, antioxidants and buffers. The beads may be medical preparations with a diameter of about 1 to about 2 mm. Individual beads may comprise doses of the compounds disclosed herein. The beads, in some embodiments, are formed of non-cross-linked materials to enhance their discharge from the gastrointestinal tract. The beads may be coated with a release rate-controlling polymer that gives a timed-release profile.

The time-release beads may be manufactured into a tablet for therapeutically effective administration. The beads can be made into matrix tablets by direct compression of a plurality of beads coated with, for example, an acrylic resin and blended with excipients such as hydroxypropylmethyl cellulose. The manufacture of beads has been disclosed in the art (Lu, Int. J. Pharm. 1994, 112, 117-124; Pharmaceutical Sciences by Remington, 14$^{th}$ ed, pp 1626-1628 (1970); Fincher, J. Pharm. Sci. 1968, 57, 1825-1835; Benedikt, U.S. Pat. No. 4,083,949) as has the manufacture of tablets (Pharmaceutical Sciences, by Remington, 17$^{th}$Ed, Ch. 90, pp 1603-1625 (1985).

In still other embodiments, polymeric materials can be used (See "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, New York (1984); Langer et al., 1983, J Macromol. Sci. Rev. Macromol Chem. 23:61; Levy et al., 1985, Science 228: 190; During et al., 1989, Ann. Neurol. 25:351; Howard et al., 1989, J. Neurosurg. 71:105). In some embodiments, polymeric materials are used for oral sustained release delivery. Such polymers include, for example, sodium carboxymethylcellulose, hydroxypropylcellulose, hydroxypropylmethylcellulose and hydroxyethylcellulose (most preferred, hydroxypropylmethylcellulose). Other cellulose ethers have been described (Alderman, Int. J. Pharm. Tech. & Prod. Mfr. 1984, 5(3) 1-9). Factors affecting drug release are well known to the skilled artisan and have been described in the art (Bamba et al., Int. J. Pharm. 1979, 2, 307).

In still other embodiments, enteric-coated preparations can be used for oral sustained release administration. Coating materials include, for example, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In yet other embodiments, drug-releasing lipid matrices can be used for oral sustained release administration. For example, solid microparticles of compositions and/or compounds disclosed herein may be coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379, 700. The lipid-coated particles can optionally be compressed to form a tablet. Another controlled release lipid-based matrix material which is suitable for sustained release oral administration comprises polyglycolized glycerides as disclosed in Roussin et al., U.S. Pat. No. 6,171,615.

In yet other embodiments, waxes can be used for oral sustained release administration. Examples of suitable sustained releasing waxes are disclosed in Cain et al., U.S. Pat. No. 3,402,240 (carnauba wax, candedilla wax, esparto wax and ouricury wax); Shtohryn et al., U.S. Pat. No. 4,820,523 (hydrogenated vegetable oil, bees wax, caranuba wax, paraffin, candelillia, ozokerite and mixtures thereof); and Walters, U.S. Pat. No. 4,421,736 (mixture of paraffin and castor wax).

In still other embodiments, osmotic delivery systems are used for oral sustained release administration (Verma et al., Drug Dev. Ind. Pharm. 2000, 26:695-708). In some embodiments, OROS® systems made by Alza Corporation, Mountain View, Calif. are used for oral sustained release delivery devices (Theeuwes et al., U.S. Pat. No. 3,845,770; Theeuwes et al., U.S. Pat. No. 3,916,899). In other embodiments, an oral sustained release pump may be used (Langer, supra; Sefton, 1987, CRC Crit Ref Biomed. Eng. 14:201; Saudek et al., 1989, N. Engl. J Med. 321:574).

In still other embodiments, the dosage form comprises compounds disclosed herein coated on a polymer substrate. The polymer can be an erodible or a non-erodible polymer. The coated substrate may be folded onto itself to provide a bilayer polymer drug dosage form. For example, compounds disclosed herein can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense the compounds over a sustained release period. Representative biodegradable polymers comprise a member selected from the group consisting of biodegradable poly(amides), poly (amino acids), poly(esters), poly(lactic acid), poly(glycolic acid), poly(carbohydrate), poly(orthoester), poly (orthocarbonate), poly(acetyl), poly(anhydrides), biodegradable poly(dihydropyrans), and poly(dioxinones) which are known in the art (Rosoff, Controlled Release of Drugs, Chap. 2, pp. 53-95 (1989); Heller et al., U.S. Pat. No. 3,811,444; Michaels, U.S. Pat. No. 3,962,414; Capozza, U.S. Pat. No. 4,066,747; Schmitt, U.S. Pat. No. 4,070,347; Choi et al., U.S. Pat. No. 4,079,038; Choi et al., U.S. Pat. No. 4,093,709).

In other embodiments, the dosage form comprises compounds disclosed herein loaded into a polymer that releases the drug(s) by diffusion through a polymer, or by flux through pores or by rupture of a polymer matrix. The drug delivery polymeric dosage form comprises a concentration of 0.1 mg to 2500 mg of active agents homogenously contained in or on a polymer. The dosage form comprises at least one exposed surface at the beginning of dose delivery. The non-exposed surface, when present, is coated with a pharmaceutically acceptable material impermeable to the passage of the drug(s). The dosage form may be manufactured by procedures known in the art. An example of providing a dosage form comprises blending a pharmaceutically acceptable carrier like polyethylene glycol, with a known dose of compositions and/or compounds disclosed herein at an elevated temperature, (e.g., 37° C.), and adding it to a silastic medical grade elastomer with a cross-linking agent, for example, octanoate, followed by casting in a mold. The step is repeated for each optional successive layer. The system is allowed to set for about 1 hour, to provide the dosage form. Representative polymers for manufacturing the dosage form comprise a member selected from the group consisting of olefin, and vinyl polymers, addition polymers, condensation polymers, carbohydrate polymers, and silicone polymers as represented by polyethylene, polypropylene, polyvinyl acetate, polymethylacrylate, polyisobutylmethacrylate, poly alginate, polyamide and polysilicone. The polymers and procedures for manufacturing them have been described in the art (Coleman et al., Polymers 1990, 31, 1187-1231; Roerdink et al., Drug Carrier Systems 1989, 9, 57-10; Leong et al., Adv. Drug Delivery Rev. 1987, 1, 199-233; Roff et al., Handbook of Common Polymers 1971, CRC Press; Chien et al., U.S. Pat. No. 3,992,518).

In other embodiments, the dosage form comprises a plurality of tiny pills. The tiny time-release pills provide a number of individual doses for providing various time doses for achieving a sustained-release drug delivery profile over an extended period of time up to 24 hours. The matrix comprises a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, gelatin, and a hydrophilic colloid. The hydrophilic matrix comprises a plurality of 4 to 50 tiny pills, each tiny pill comprises a dose population of from 10 ng, 0.5 mg, 1 mg, 1.2 mg, 1.4 mg, 1.6 mg, 5.0 mg, etc. The tiny pills comprise a release rate-controlling wall of 0.001 mm up to 10 mm thickness to provide for the timed release of drug(s). Representative wall forming materials include a triglyceryl ester selected from the group consisting of glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills are disclosed in Urquhart et al., U.S. Pat. No. 4,434,153; Urquhart et al., U.S. Pat. No. 4,721,613; Theeuwes, U.S. Pat. No. 4,853,229; Barry, U.S. Pat. No. 2,996,431; Neville, U.S. Pat. No. 3,139,383; Mehta, U.S. Pat. No. 4,752,470.

In other embodiments, the dosage form comprises an osmotic dosage form, which comprises a semipermeable wall that surrounds a therapeutic composition comprising compounds disclosed herein. In use within a subject, the osmotic dosage form comprising a homogenous composition, imbibes fluid through the semipermeable wall into the dosage form in response to the concentration gradient across the semipermeable wall. The therapeutic composition in the dosage form develops osmotic pressure differential that causes the therapeutic composition to be administered through an exit from the dosage form over a prolonged period of time up to 24 hours (or even in some cases up to 30 hours) to provide controlled and sustained release. These delivery platforms can provide an essentially zero order delivery profile as opposed to the spiked profiles of immediate release formulations.

In other embodiments, the dosage form comprises another osmotic dosage form comprising a wall surrounding a compartment, the wall comprising a semipermeable polymeric composition permeable to the passage of fluid and substantially impermeable to the passage of compounds disclosed herein present in the compartment, a drug-containing layer composition in the compartment, a hydrogel push layer composition in the compartment comprising an osmotic formulation for imbibing and absorbing fluid for expanding in size for pushing the drug composition layer from the dosage form, and at least one passageway in the wall for releasing the composition. The method delivers compounds disclosed herein by imbibing fluid through the semipermeable wall at a fluid imbibing rate determined by the permeability of the semipermeable wall and the osmotic pressure across the semipermeable wall causing the push layer to expand, thereby delivering the compounds disclosed herein from the dosage form through the exit passageway to a subject over a prolonged period of time (up to 24 or even 30 hours). The hydrogel layer composition may comprise 10 mg to 1000 mg of a hydrogel such as a member selected from the group consisting of a polyalkylene oxide of 1,000,000 to 8,000,000 weight-average molecular weight which are selected from the group consisting of a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer comprises 0.0 mg to 350 mg, in present manufacture; 0.1 mg to 250 mg of a hydroxyalkylcellulose of 7,500 to 4,500,000 weight-average molecular weight (e.g., hydroxymethylcellulose, hydroxyethylcellulose, hydroxypropylcellulose, hydroxybutylcellulose or hydroxypentylcellulose) in present manufacture; 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylated hydroxyquinone, butylhydroxyanisole, hydroxycoumarin, butylated hydroxytoluene, cephalm, ethyl gallate, propyl gallate, octyl gallate, lauryl gallate, propyl-hydroxybenzoate, trihydroxybutyrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laurate, salts of fatty acids, salts of alicyclic acids, salts of aromatic acids, stearic acid, oleic acid, palmitic acid, a mixture of a salt of a fatty, alicyclic or aromatic acid and a fatty, alicyclic or aromatic acid.

In the osmotic dosage forms, the semipermeable wall comprises a composition that is permeable to the passage of fluid and impermeable to the passage of compounds disclosed herein. The wall is non-toxic and comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from the group consisting of hydroxypropylcellulose or a hydroxypropylalkylcellulose such as hydroxypropylmethylcellulose. The total weight percent of all components comprising the wall is equal to 100 wt %. The internal compartment comprises the drug-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of compounds disclosed herein to a subject over time. The dosage form comprises a passageway in the wall that connects the exterior of the dosage form with the internal compartment. The osmotic powered dosage form can be made to deliver drug from the dosage form to the subject at a zero order rate of release over a period of up to about 24 hours.

The expression "passageway" as used herein comprises means and methods suitable for the metered release of the compounds disclosed herein from the compartment of the dosage form. The exit means comprises at least one passageway, including orifice, bore, aperture, pore, porous element, hollow fiber, capillary tube, channel, porous overlay, or porous element that provides for the osmotic controlled release of the compounds disclosed herein. The passageway includes a material that erodes or is leached from the wall in a fluid environment of use to produce at least one controlled-release dimensioned passageway. Representative materials suitable for forming a passageway, or a multiplicity of passageways comprise a leachable poly (glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of compositions and/or drugs from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in Theeuwes et al., U.S. Pat. No. 3,845,770; Theeuwes et al., U.S. Pat. No. 3,916,899; Saunders et al., U.S. Pat. No. 4,063,064; Theeuwes et al., U.S. Pat. No. 4,088,864 and Ayer et al., U.S. Pat. No. 4,816,263. Passageways formed by leaching are disclosed in Ayer et al., U.S. Pat. No. 4,200,098 and Ayer et al., U.S. Pat. No. 4,285,987.

In order to decrease dosing frequency and augment the convenience to the subject and increase subject compliance, the sustained release oral dosage form (regardless of the specific form of the sustained release dosage form) preferably, provides therapeutic concentrations of the compounds disclosed herein in the patient's blood over a period of at least about 6 hours, more preferably, over a period of at least about 8 hours, even preferably, over a period of at least about 12 hours and most preferably, over a period of at least 24 hours.

The pharmaceutical composition of this invention may be prepared by uniformly mixing predetermined amounts of the active ingredient, the absorption aid and optionally the base, etc. in a stirrer or a grinding mill, if required at an elevated temperature.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in a conventional manner using one or more physiologically acceptable carriers, diluents, excipients or auxiliaries, which facilitate processing of compositions and compounds disclosed herein into preparations which can be used pharmaceutically.

Examples of Species

Representative non-limiting examples of species of the invention are provided below:

Compound A

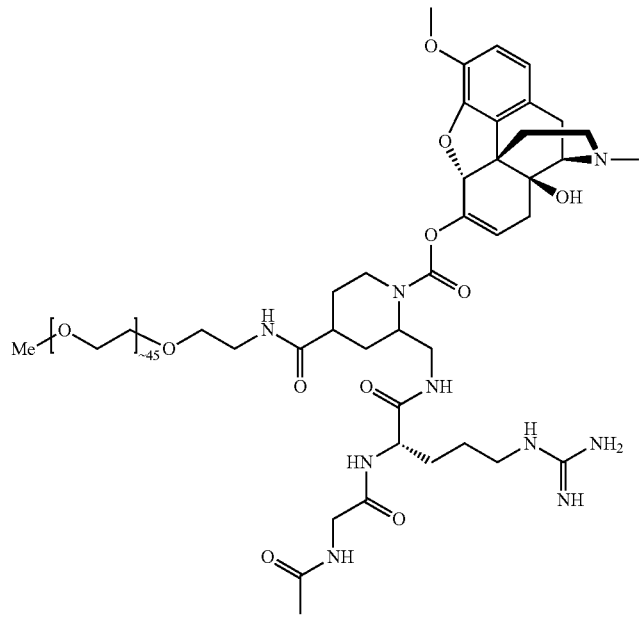

Compound B

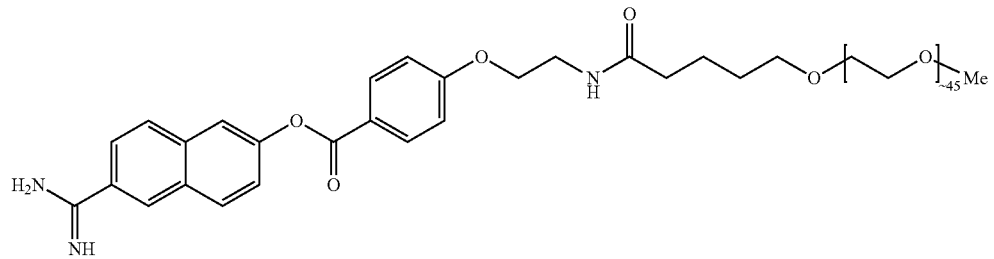

All printed patents and publications referred to in this application are hereby incorporated herein in their entirety by this reference. While the preferred embodiment of the invention has been described, it will be appreciated that various changes can be made therein without departing from the spirit and scope of the invention.

What is claimed is:

1. A macromolecule of formula:

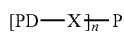

wherein:
PD is a gastrointestinal enzyme-labile opioid agonist prodrug, wherein the opioid agonist is selected from the group consisting of morphine, hydromorphone, hydrocodone, oxycodone, codeine, levorphanol, meperidine, methadone, oxymorphone, dihydrocodeine, tramadol, and pharmaceutically acceptable salts thereof;

X is a linker group that covalently joins PD to a polymer, wherein the linker group is independently at each occurrence absent or an ether, an ester, a thioester, an amide, an amine, a carbamate, a carbonate, a thioether, or a urea, wherein the nitrogen atom of the amide, the amine, or the carbamate, is substituted or unsubstituted, and the nitrogen atoms of the urea are each independently substituted or unsubstituted;

P is a polymer, wherein the polymer is a polyalkylene glycol; and n is an integer from 1 to 2.

2. A composition comprising the macromolecule of claim 1, wherein the macromolecule is formulated in an immediate release matrix.

3. A composition comprising the macromolecule of claim 1, wherein the macromolecule is formulated in an extended release matrix.

4. The macromolecule of claim 1, wherein the opioid agonist is released from PD in the presence of the gastrointestinal enzyme.

5. The macromolecule of claim 1, wherein the polyalkylene glycol is polyethylene glycol.

6. The macromolecule of claim 1, wherein the gastrointestinal enzyme-labile opioid agonist prodrug is:

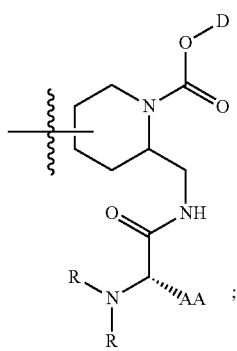

wherein D is the opioid agonist, less the oxygen atom to which D is bound and a hydrogen atom;

AA is a natural or an unnatural amino acid side chain that is recognized by the gastrointestinal enzyme; and R is independently hydrogen, methyl, ethyl, substituted alkyl, substituted aryl, acyl, a natural or an unnatural amino acid, or a polypeptide consisting of from 2 to 10 natural and/or unnatural amino acids; wherein, adjacent R groups can be joined to form a ring.

7. The macromolecule of claim 1, wherein the gastrointestinal enzyme-labile opioid agonist prodrug is:

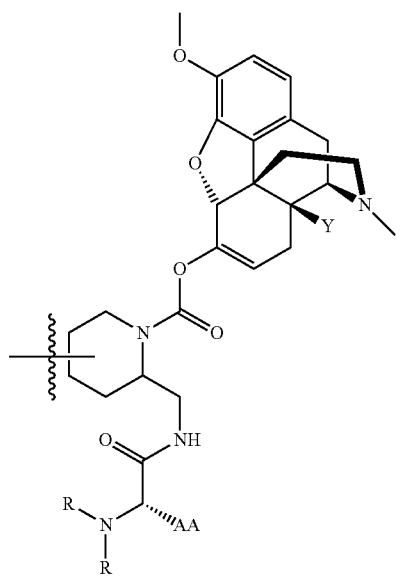

or

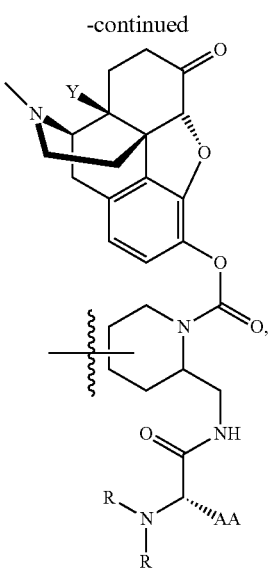

wherein Y is H or OH;

AA is a natural or unnatural amino acid side chain that is recognized by the gastrointestinal enzyme; and R is independently hydrogen, methyl, ethyl, substituted alkyl, substituted aryl, acyl, a natural or unnatural amino acid, or a polypeptide consisting of from 2 to 10 natural and/or unnatural amino acids; wherein adjacent R groups can be joined to form a ring.

8. The macromolecule of claim 1, wherein the gastrointestinal enzyme is trypsin.

9. The macromolecule of claim 4, wherein the gastrointestinal enzyme is trypsin.

10. The macromolecule of claim 1, wherein the molecular weight of the polymer is from about 1,500 to about 50,000 Da.

11. The gastrointestinal enzyme-labile opioid agonist prodrug of claim 6, wherein:

D is

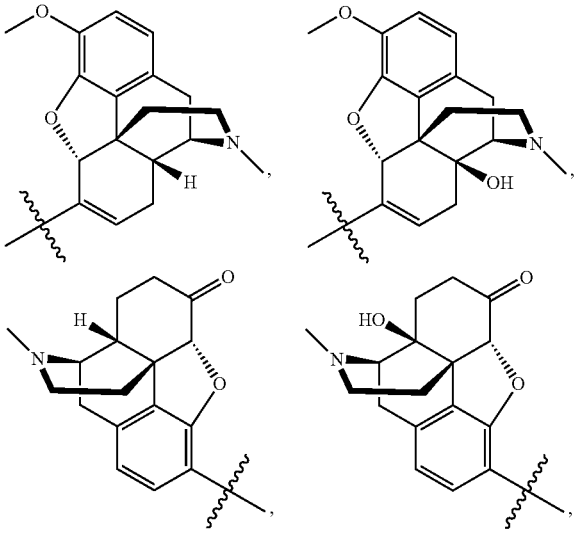

313

-continued

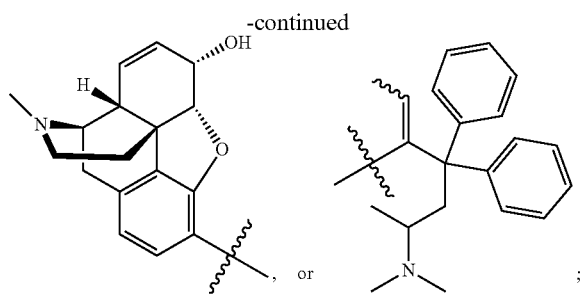, or

AA is a side chain of lysine or arginine; and
R is independently hydrogen, methyl, ethyl, or a natural or unnatural amino acid.

12. The gastrointestinal enzyme-labile opioid agonist prodrug of claim 11, wherein the gastrointestinal enzyme-labile opioid agonist prodrug is:

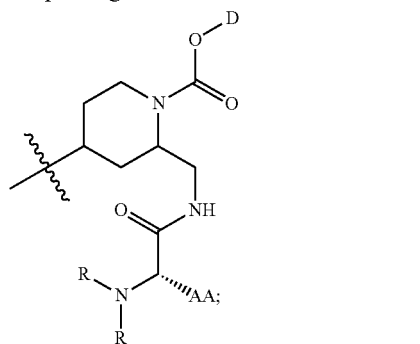

wherein R is independently hydrogen or N-acetylglycine.

13. The macromolecule of claim 1, wherein the macromolecule is:

314

-continued

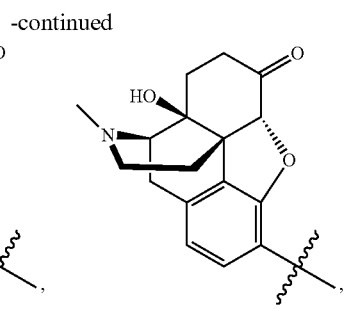,

AA is a side chain of lysine or arginine; and
p is an integer from 10 to 200; or
a pharmaceutically acceptable salt thereof.

14. The macromolecule of claim 1, wherein the macromolecule is:

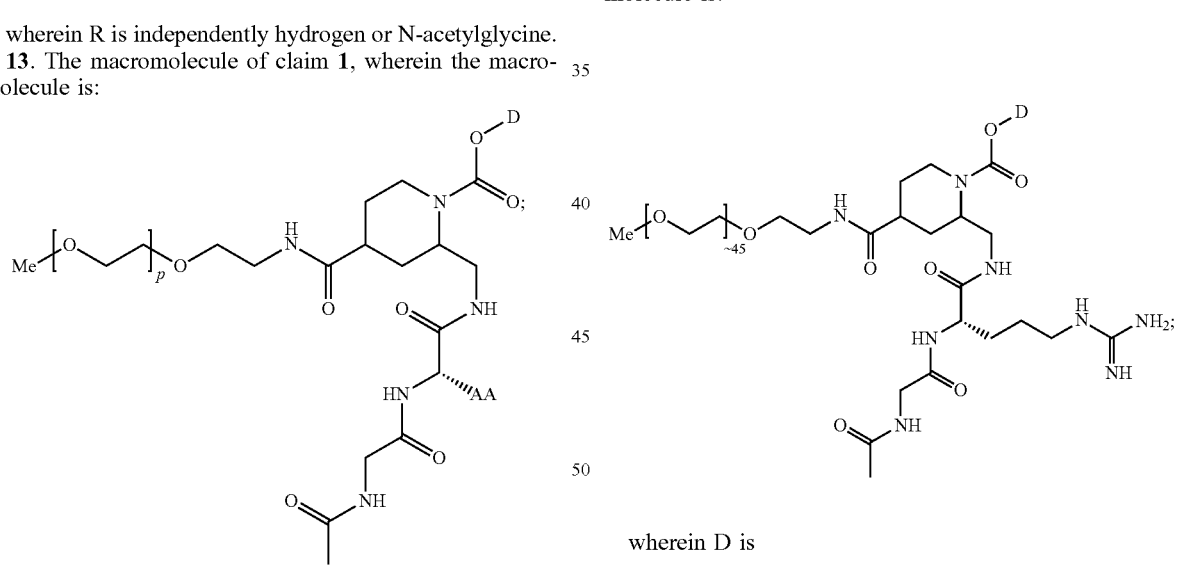

wherein D is

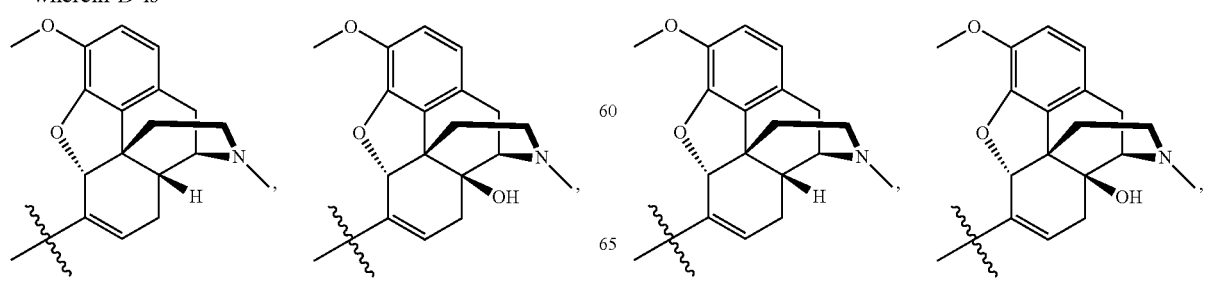

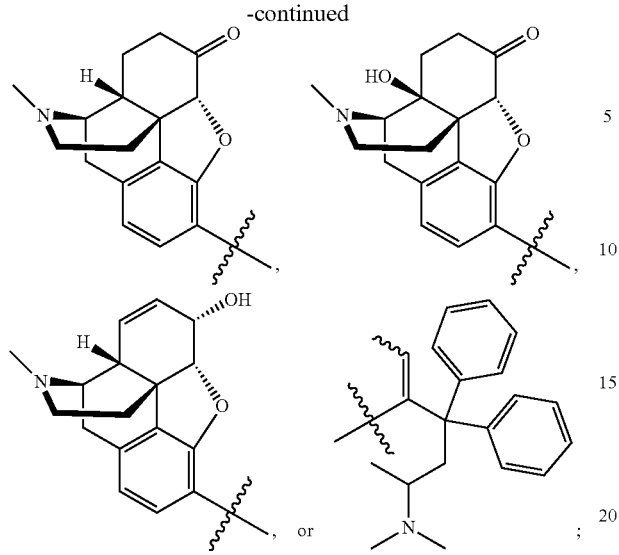
or a pharmaceutically acceptable salt thereof.
* * * * *